(12) United States Patent
Andersson et al.

(10) Patent No.: US 7,892,736 B2
(45) Date of Patent: *Feb. 22, 2011

(54) SELECTING ANIMALS FOR PARENTALLY IMPRINTED TRAITS

(75) Inventors: Leif Andersson, Uppsala (SE); Michel Georges, Villers-aux-Tours (BE); Geert Spincemaille, Zwevegem (BE); Carine D. A. Nezer, Neupre (BE)

(73) Assignees: University of Liege, Liege (BE); Melica HB, Uppsala (SE); Seghers Gentec N.V., Buggenhout (BE)

( * ) Notice: Subject to any disclaimer, the term of this patent is extended or adjusted under 35 U.S.C. 154(b) by 1120 days.

This patent is subject to a terminal disclaimer.

(21) Appl. No.: 11/357,733

(22) Filed: Feb. 17, 2006

(65) Prior Publication Data

US 2006/0288433 A1 Dec. 21, 2006

Related U.S. Application Data

(63) Continuation-in-part of application No. 09/868,732, filed as application No. PCT/EP99/10209 on Dec. 16, 1999, now Pat. No. 7,255,987.

(30) Foreign Application Priority Data

Dec. 16, 1998 (EP) .................................. 98204291

(51) Int. Cl.
    C12Q 1/68 (2006.01)
    C12N 15/00 (2006.01)
(52) U.S. Cl. ............................................ 435/6; 800/21
(58) Field of Classification Search ........................ None
    See application file for complete search history.

(56) References Cited

U.S. PATENT DOCUMENTS

| 7,255,987 | B1 | 8/2007 | Andersson et al. |
| 7,732,137 | B2 | 6/2010 | Andersson et al. |
| 2006/0037090 | A1 | 2/2006 | Andersson et al. |
| 2006/0288433 | A1* | 12/2006 | Andersson et al. ............ 800/14 |

FOREIGN PATENT DOCUMENTS

| AU | 779393 | 12/1998 |
| EP | 98204291.3 | 12/1998 |
| WO | WO 98/03682 | 1/1998 |
| WO | WO 00/36143 | 6/2000 |
| WO | 2004063386 | 7/2004 |

OTHER PUBLICATIONS

Moore et al., Multiple imprinted sense and antisense transcripts, differential methylation and tandem repeats in a putative imprinting control region upstream of mouse Igf2, Proc. Natl. Acad. Sci., Nov. 1997, pp. 12509-12514, vol. 94.
Pandya et al. (American Journal of Human Genetics 1994:55(3) Suppl:A161).
Witkowski et al. (Biochem., 1999 38:11643-11650).
Andersson-Eklund et al., "Mapping Quantitative Loci for Carcass and Meat Quality Traits in a Wild Boar × Large White Intercross," J. Anim. Sci., vol. 76, 1998, pp. 694-700.
Kovács and Klöting, "Mapping of Quantitative Trait Loci for Body Weight on Chromosomes 1 and 4 in the Rat," vol. 44, No. 2, Feb. 1998, pp. 399-405.
Johansson et al., "Comparative Mapping Reveals Extensive Linkage Conservation—but with Gene Order Rearrangements—between the Pig and the Human Genomes," Genomics, vol. 25, 1995, pp. 682-690.
Reik et al., "Imprinting in Clusters: Lessons from Beckwith-Weidemann Syndrome," Trends in Genetics, vol. 13, No. 8, 1997, pp. 330-334.
Catchpole and Engström, "Nucleotide Sequence of a Porcine Insuline-like Growth Factor II cDNA," Nucleic Acids Research, vol. 18, No. 21, 1990, p. 6430.
Andersson et al., "Genetic Mapping of Quantitative Trait Loci for Growth and Fatness in Pigs," Science, vol. 263, Mar. 25, 1994, pp. 1771-1774.
Knott et al., "Multiple Marker Mapping of Quantitative Trait Loci in a Cross Between Outbred Wild Boar and Large White Pigs," Genetics, vol. 149, Jun. 1998, pp. 1069-1080.
Jeon et al., "A Paternally Expressed QTL Affecting Skeletal and Cardiac Muscle Mass in Pigs Maps to the IGF2 Locus," Nat. Genet., vol. 21, Feb. 1999, pp. 157-158.
Nezer et al., "An Imprinted QTL with Major Effect on Muscle Mass and Fat Deposition Maps to the IGF2 Locus in Pigs" Nat. Genet., vol. 21, Feb. 1999, pp. 155-156.
Van Laere, et al., "A regulatory mutation in IGF2 causes a major QTL effect on muscle growth in the pig," Nature, Oct. 23, 2003, pp. 832-836, vol. 425.
De Vries, et al., "Gamatic imprinting effects on rate and composition of pig growth," Theoretical and Applied Genetics, 1994, pp. 1037-1042, vol. 88.
Evidence in Support of the Opposition by Monsanto Technology LLC to Australian Patent Application Acceptance No. 779393 (Appln No. 27952/00) in the name of University of Liege, Melica HB and Seghersgentec N.V., dated Oct. 10, 2005 with Application for Extension of Time.
Statutory Declaration of Bruce Stephan Wellington dated Oct. 7, 2005.
Dechiara et al., Parential imprinting of the mouse insulin-like growth factor II gene, Cell, 1991, pp. 849-859.
Statement of Grounds and Particulars in Support of Opposition, dated Jul. 15, 2005.
Notice of Opposition, dated Apr. 19, 2005.
Notice of Acceptance for Patent Application No. 27952/00 dated Jun. 12, 2004.

(Continued)

Primary Examiner—Michael Burkhart
(74) Attorney, Agent, or Firm—TraskBritt, P.C.

(57) ABSTRACT

The present invention relates to a method for selecting a domestic animal having desired genotypic properties comprising testing the animal for the presence of a parentally imprinted quantitative trait locus (QTL). The invention further relates to the use of an isolated and/or recombinant nucleic acid comprising a QTL or functional fragment derived therefrom to select a breeding animal or animal destined for slaughter having desired genotypic or potential phenotypic properties. In particular, the properties are related to muscle mass, fat deposition, sow prolificacy, and/or sow longevity.

9 Claims, 49 Drawing Sheets

OTHER PUBLICATIONS

Armarger et al., "Comparitive sequence analysis of the INS-IGF2-H19 gene cluster in pigs," Mammalian Genome, 200, pp. 388-398, vol. 13.

Baylin and Bestor, Altered methylation patterns in cancer cell genomes: Cause or consequence? Cancer Cell, May 2002, pp. 299-305, vol. 1, No. 4.

Bell et al. Isolation of the human insulin-like growth factor genes: insulin-like growth factor II and insulin genes are contiguous, Proc Natl Acad Sci USA., Oct. 1985, pp. 6450-6454, vol. 82, No. 19.

Caricasole et al., "Transactivation of mouse insulin-like growth factor II (IGF-II) gene promoters by the AP-1 complex," Nucleic Acids Research, 1993, pp. 1873-1879, vol. 21, No. 8.

Hirooka et al., A whole genome scan for quantitative trait loci affecting teat number in pigs, J. Anim Sci., Sep. 2001, pp. 2320-2326, vol. 79, No. 9.

Lucentini et al., Gene Association Studies Typically Wrong, The Scientist, 2004, vol. 18.

Wacholder et al., Assessing the Probability That a Positive Report is False: An Approach for Molecular Epidemiology Studies, J. Natl. Cancer Institute, 2004, pp. 434-442, vol. 96, No. 6.

Zhu et al., Use of DNA methylation for cancer detection and molecular classification, J. Biochem. Mol. Biol., Mar. 2007, pp. 135-141, vol. 40, No. 2.

PCT International Search Report, PCT/EP2004/00149, dated Aug. 10, 2004.

* cited by examiner

Fig. 6

```
Contig 1 (500 bp)
GGGTGGGCAGCTTCCTCCCAGACCGCAGGAGGCCCAAGTTCCCTGGCCCTGCCCACCCAGGGCCAGCTGAAGC
AGGTCAGAGACACCCGCTCCTGTCCCTCCTGTCACCTAACCCAACAGGCCGGGGCCCAGGGACACAGGCCACA
TGGCATCTCCCCCCATGCCCCTGCCCCAAGGCGCCCAGCAGGTGAGGCTGGAGCAGAGTCTGGGTCCTGCGGG
CCAGACCGAGGGCAGGACAGCTGGGCATCTGTCCTCACAGTCCCCGCGCTTTGTCGGGAGGCGGCAGAGCCTC
ATCCAAGACGCCCGCAAGGAACGGGAGAAGGCGGAGGCCGCGGCTGCCGCGTCCGAGCCCGGGGAGGCCCTGG
AAGTGGGGGCCCTTGCCGAGCGGGACGGGAAGGCCCTGCTGAACCTGCTCTTCACCCTGAGGGCCACCAAGCC
CCCCTCGCTGTTCCGGTCCCTGAAAAAATTCTAGGTGAGGGGGCGGGCCAGGGCTCCCCGGG
Contig 2 (943 bp)
TGCTCCTCACACCCCGGGCGGGGCTGCTCTTGGGGCCATCCTCCCCATGGGCCCAGCACCCACTCTGGCCTTC
ACACCTGCCGTCTTCTGGGAAGTCCTCTGGTTCCCAAGGAAAGTTTCTGAGCTGGACAAGTGCCACCACCTGG
TCACCAAGTTCGATCCTGAGCTGGACCTGGACCACCCGGTGAGCCGGTGCCTCCCCTCCCCGGCCGCCATGTC
TCCCATCCCCAGGGGTGTCCCCACACTCAGGGCCGGGACTGGGCGTGAACCCCGGGTTGGGACGGATGTTGGC
CTGCTGTGTGGCTCCTGGCGGAACAGAGAGGCCTGGCTGGGTGCCACCCCCAGGGCCCCCGCCGATGACACGG
GCCGCGTCTGGGCTGGGCGGGCAGGGCGGCCAGGC
AGGGCAGCCTCCGATGGCGTCCCCGGCTGTCACCAGGGCTTCTCGGACCAGTTGTACCGCCAGCGCAGGAAGC
TGATTGCCCAGATCGCCTTCCAGTACAGGCAGTAAGTCCCTCCAGGGCCTCAGCCTGGGGGCCCAGACCTCAG
CCTGGGCCTCACGCCAGACCTGGGGGTGGAGGGAAGGGAGGTTGTCTTTGTCACCAACGCCACCACCTTCACT
GTCACCATGGTCACCGACTCTGGGTCCCCAAATCACAGCTGAGGAAACTGGGGCACAGAGTGGTTAAGCATCT
TGCTGAAGCCACACAGCTGGCGGAGCATTTGGCCCCGGCCCCTCCTGCGGCTCCCACACGTGCTCCCTGAGGG
GCCCGGGACTGACAGCTGTCCCCTCCTCAGAGGTG
ACCCTATTCCCCGCGTGGAGTACACAGCCGAGGAGATTGCCACCTGGTGAGGCCCTGTGACAGCGGCTGGGAG
GGGCGGGAGTGGGGGAAGGGACAGGAAGACCTCAGAATTCCCGCGTGGAACGTGGTGGCCTCTATCATGA
Contig 3 (1500 bp)
GGGGAGGGGATGCTCAGACCCGCTCTGGGAAGAAGAGAGCCTCAGAAGAAATCCCTTCCCAAGGGTCACGCGG
TGGAGCCCAGGGGCCCGCTAGGGGCCGATTCCCACAGCTCGTGCTGCCACCTGCTGGCGCTCCCAGGAACTGC
GGAGGCGGTGGGGGCCCTGGATGGGTCCGGCAGTGGGCTCGCAGGAGACCCCTGGAGGGGCTGCGGACACCCC
AGCTGCCACTCACAAGGTGCCCAAGCGGCGGTGGCAATGGGCTGAGCCTCTCCCCCCCTCCTCCTCCGCAGGA
CATTGGCCTCGCATCCCTGGGGGTCTCGGACGAGGAAATTGAGAAGCTGTCCACGGTGGGTTTCTCCCCCTGC
AGGGCCCTGGGTTCCAGCCAGGCCCTCCTGTCCAA
GGGGTGTCGTCCTCACGCTGTGACCGCCCGGGAGCCTGGATCGGTTCTGCCTGGGTGGGCGGTGCCCGGGCCA
CGGGCAGCAGGGGCAGCGGTGCGGGCCCCAGCCGTGTCTGAGCCCCCTTGCCGCCTGTCCCCACCAGCTGTAC
TGGTTCACGGTGGAGTTTGGGCTCTGCAAACAGAACGGCGAGGTGAAGGCCTACGGGCTGGGCTGCTGTCCT
CCTACGGGGAGCTCCTGGTGAGGCCTCCCCCACGCGCTGGGGCCTGGGTCCCGGGGAGGTGACCCCTGCGG
TGCCTTGTGGATTCCAGCTCTCGGGAGGCTGGAGCGAGGGGCTGCCCTCCTGGGGGCACCAAGAAAGCTGGTC
TGCGCCCCTCTCCACACACCTGTGCCTGGGCCCTG
GGGGGACCCCTGCTGGGGGATGTGGGTGCACAGCCAGGGCCACCAGGGAGTCAGGACACGGGGCTCCCTTCCC
TCGGGTCCCTGAGACCCCTGGCCTCCCGCCAGCACTCCCTGTCCGAGGAGCCCGAGATCCGGGCCTTCGACCC
CGACGCGGCGGCCGTGCAGCCCTACCAGGACCAGACCTACCAGCCCGTCTACTTCGTGTCTGAGAGTTTCAGT
GACGCCAAGGACAAGCTCAGGTGGGCCGGGGCCCGGGGCCCCAAACTGGAGGATCCAGCCTGCAGCCCCGCC
TATGAGCCCATTTCCCAGCAGAGGGAGCTGCTGCGGACCCCACCGTCACAACCCCCCTCCCACAGCTGGAACC
CCAGAAAGCCTGCGGAGGGGGGACCTGCAGGGCTG
TGGCCAGGTCAAGGCCAGGTCGAGGCCAGGCTTTTAGGGGTGAAGTCTGACTTTGTAAGAGGGGGTGCAGGGT
CCTTCCCAGCCTCCTCCCCTCCGAGCAGCTGGGGGCGGGCGGGGTGCGATGAAGGCAGAGATGACGCAGCC
ACCCGTTCACCCTCAGGAGGCGCCTCCTGTCCAGCCAGGCTCCTGTTGTCACAGGGGAAACTGAGGCCCCAGG
TGTGTGTGTGGGGGGGTGATTCTCACACACAAGCTTAGGGACAGGGACATAACGGCCTCTCCAGGGCACACAG
TCTGGAGG
Contig 4 (3024 bp)
TTAANTCCANGTTGGCCCGACAAGTTTTCCCCATTTGAAAAGGGGCCAGTTAAGCCCCAACNCAATTAATTGG
AAGTTAGCTCCCCTCATTAGGCTCCCCAGNCTTTACNCTTTATGTTCCGGTTCGTATTTTTGTGGGAATTGTA
GCGGATACAATTTCTCTCAAGNAACCAGCTATGCCCATGATTACGCGGTACAGTAGTTCATCAGTCCCCCCCG
CCCATGGGACAGCGAAGGGAACCAGTATGTCGTGGGGCCGGGTCTAAAGGGGTCACCACCAGGGAGGGGCAGG
GGCTCCAGGAGGCAGGGCCACTGAGCGGTACCTGGTGGGGGGAGGTGGTGGGGCCACACCCAGGAGTCCTGTG
CCCCCCCCACTCCCGCCGTTGGACATGAGAAGCAGGGGCCAGCCTGCGGGTCCCTGAGTTCAGCGCCCCCCCC
CCCCACCGCCGCAGCAGCCCGGGTCTCAGCAGGCTGCTGTGCTGGGGGCGGGGCGCTTATGGRGCCGGGAG
CAGCCCCCCCCACGGCTTCAGAGCATCTCTGGGGCCTCAGGGATGGACCGGGGTCTGCRGGCAGGTGTCCTC
TCGCGCCCCCCACTCCCTGGGCTATAACGTGGAAGATGCGGCCCAAGCCCGGKCGGTTTGGCCTTTGTCCCCAG
CCAGTGGGGACAGCCTGGCCCTCAGGCCGCTCGTTAAGACTCTAATGACCTCAAGGCCCCCAGAGGCGCTGAT
GACCCACGGAGATGATCCCGCAGGCCTGGCAGCAGGGAAATGATCCAGAAAGTGCCACCTCAGCCCCCAGCCA
```

Fig. 6, contd.

```
TCTGCCACCCACCTGGAGGCCCTCAGGGGCCGGGCGCCGGGGGGCAGGCGCTATAAAGCCGGCCGGGCCCAGC
CGCCCCCAGCCCTCTGGGACCAGCTGTGTTCCCAGGCCACCGGCAAGCAGGTCTGTCCCCTGGGCTCCCGTC
AGCTGGGTCTGGGCTGTCCTGCTGGGGCCAGGGCATCTCGGCAGGAGGACGTGGGCTCCTCTCTCGGAGCCCT
TGGGGGGTGAGGCTGGTGGGGGCTGCAGGTGCCCCTGGCTGGCCTCAACGCCGCCCGTCCCCCAGGTCCTCAC
CCCCCGCCATGGCCCTGTGGACGCGCCTCCTGCCCCTGCTGGCCCTGCTGGCSCTCTGGGCGCCCGCCCCGGC
CCAGGCCTTCGTGAACCAGCACCTGTGCGGCTCCCACCTGGTGGAGGCGCTGTACCTGGTGTGCGGGGAGCGC
GGCTTCTTCTACACGCCCAAGGCCCGTCGGGAGGCGGAGAACCCTCAGGGTGAGCCGAGGGGGYGTCCCGGGA
GCGGTYGGGGGAGTTTTTAAGGAGGAAATTGGTAAAAGTGACCAACTCCCTGGGAGCTGAGCCCAGAGACACC
CCTCCCACGCCCYGGTCCCGCTCGAGAAGCCCCCCTTCCCTCCCCTCCTCCCG
AGGCGGCTCCAGGGAGGAATCTTACGGAGTCAAGGCCCGGGTGCCGCTGGTCTCCGAGTGACATGGCCGTGGT
GTCCCRTCTGCCGGCCCACATGCCCGTGAGAGAWGCCCCATCCCCCTGGGAGGGGGCCCCGTGCCGGGCAGGC
GGCGGGAGGCCCAGGACCGGTGGCTGCTGCGGCTTCCACTCCAGGGTGGGCGGGGTGGGGGGTGGCTGTCTCT
GTGTGACCGGCTCTCCCCGCAGCAGGTGCCGTGGAGCTGGGCGGAGGCCTGGGCGGCCTGCAGGCCCTGGCGC
TGGAGGGGCCCCCGCAGAAGCGTGGCATCGTGGAGCAGTGCTGCACCAGCATCTGTTCCCTCTACCAGCTGGA
GAACTACTGCAACTAGGCCGCCCCTGAGGGCGCCTGCTGCTCCCCGCACCCCAAAACCCAATAAAGTCCTGAA
TGAGCCCGGCCGAGTCCTGTGGTCTGTGTGGCCTGGGGCGGGGCCCTGGTGGGGGAGGGGCCAGAAGGCTGT
GGGGGGCCTGCCTGCGACCCCTCTCTGCTCTCGCCACATCGGCTGCTCTAAGCTTCCTCCACATGCATCGGGT
GCCCACAGGCACATGGGCACCGGGGGACCAGGGCCCAGGGCAGGGCCCTTCAATGTGGCGAGCTCTGGTTTTC
AGGGCTCCAGACACCCCCTCCTGGGTGCCCACTGCTGCACAGGGTCACTCTGAGGGTCACAGGGCACCCACCC
AGACTGCTCTTGGGCACACAAAATAGCCCAGGGGCTTCTTGGGCTGGCTGCRGTCTGGGAGGTCAGAGAGTGA
CCCCGCGGGACCAAGACCTGGCCAGCCTGCCAGTCGCCCAGGCCAAACCAATCTGCACCTTTGCTGAAGGTTC
CACCCGGGCCAGCACTGGGGGCGGCCGGGCCTAGAGCTGGGCGCCCGGGCCCCAGGGACTGCACACCCGCCAG
AGGTGGGCCTGAGGGGTGGCAGCAGGCTCTCCGCCTGGGACCCAGCCAGCTGGGCAGCTCACCTCTCAACACG
AGGCTCTCACCTGTGTCGTCCCCTCCCCACGGCCACACAGACACCCCTCGGGGAGAAGTCACAGGCCCCCAGCA
GGCCCCGCCCCTGGAGAGGAGGCCAGGGCTGGGCAGGCGGGTGGCCGGCCGGACACTGGACCCGGAAGGGGGG
TAGGCGGCTGGGATGAGTGGCGAGCTGTCCATGGGAGCACCCAGCGGCCCCATTGGCACCAGTACAGGCAGGG
GCACCTGCAGCAGCTGAGGTACGTGGGGTCCCCGGACTGGTTGGTGTCCGGCTGCCCTCTGGGAGGCAGCGGG
CTGAGCTTGTGGTCCTGCCAACCAGGGAGACCCGTGACCACCCTGCTGCTTCCCCTCCCCCCCAGGGCCAGCA
GACTCCTTTGGGACTCGGGGCCCCTGAGCCGCCCCACTCGCAGGACTCACGGGGTGTGCGGTCCTGGGTGAG
TGGGGGCTTGGGAGAGGGTCACTCTTGTCCGTCGGGTGGGGAAGGCTGAGAGTCATGGTGTGACAGCGCCCTC
GGCCTGCCGGGTGGGGGGTCTCCCTTCTCCCGAGCCCAGATCCCCGGGTAC
Contig 5 (1730 bp)
CGTCACCCGCAGAAGCCAGGCCCACAGGCCTTGGCTCAGCCCCTCCACCCAGGCCCACGTTCCGCCCCTTCTG
GGAACTGGAGGACAGCCCGCCTCGCCCTCGGACCTGGCTTCGTTTGCCCTGGCATCTGGCAGTGGCCGGCAG
CTGCGTTCAGCCCTGGATGACACCCTGGCGTGAGCGGTGGGTCCCCGTGCTGAGGGCAGCCCCCACACACGTC
CTGCTCACTTGCCTTGTGTCTGCTCCGCATCCCGTCATCACACATGCCATGCTGGGGCACCGTAGCGCCTTGC
CCTGTGTGGCACTGTGGCACTGTGTTCCTGATGGGAAGACTGAGGCTGGGGTCAGGCCCGCTGCTGCCCACCC
TCTAAGGACATTCTGCCGGTGCAGCTGCCTCCAGG
CTGGCCCCCGGATTGCATCTGCTTCTGGCACGGATGAACTGGCACCTCTGCCTGACCATTAGGGCTGTATTT
GCCTTCTCCTGTTGGCAGTAAATATTTACTGTCCCTCCCTGTTCCTCCAGGCCCGANCCAGTTCCTGAGGGGC
ATGGGAGGTGGACACAAAGGTGCCCAAGCAGCCCCCTGCTCTTGAGGGCCCAGTGTCTGGTGGGGGCCAGCCT
GGGAAGGAGGAGCGAGACTAGGAACCAGAGGCCTGTGTTCCTGGAAAAGGCCCCCTGGCAGAGTTCCGGCTGG
TGTGTGTCCAGCTAGGCTGTGAGTCTTCAAACTGGGGAGCCCGGCCCCTGGACCCAGGCAGGGCTGCACCCCT
GGTGCCAGTGCTTCACTGGGTGGGCACCTGTCCCC
ACCAGGCAAGGTGGTCCGAGCGGTCATTCACAGACAGAACCAGCAGAGGGCGCCAAAGCCCCACTTTTGACAA
ACTCCCCTTCGCCCTGAGCCGAAAGTCCAGGCGGCAGGTGGACCTCTCTGCAGGGCTCTGCCACCCCTGCTGC
CGCTTGCCAGCACTCACAGGGGCTGCGGGGGGTGCCCAACAGGCCGGCTACCCTGAGCTCTGGAGGCGATGGA
GTTTAGGAGGGAACGAGGGGACTCCTGGGGGTGACTTTCTTCAGCGCCCACATTGCGGCCCAGCAAACCGAGG
CTGGAGGAGGCCGGGCACCTGTGCCCAGCTGGAGCCTTTGCTGAGGGTCTCCAAGGCCTGGGGAAATTGAGGC
TGGGGGCTGGGGGGTGTCACTGTCGGGCCAGGAGG
CCCCTCGCTCTGATTGGAGCCGCCTCGGCCACTTGAGCCAGGAGGCTCACATGAGGCGGGGGCTGCAGGGACA
GGACCCTCGGGGCCCGGGAGGCCTTGGAGGGGGTCCAGCTGGGCCAGGGTTCGTTCTTTCCCGGGTCCATGTC
CACCGCCCTCCCGCTGCTGGGAGGAGAGGAGGTCCAGGGCAGAAAGAATGCGTGGGGATGGGGGGGTGGTCAG
GGGTCTGGGAGCTGTGGAAACAACAAACAGACAGCGAGGTCCTGGGGCGCCCGGCCCCCGCCCCCTCCGGCA
CTGTTGTTTCTGGCCGGGGTGCAGGGACAGCGAGGCAGATTCCTTCGAAAGTGGAGACTGGCGGGGGGCCCCT
CGGGTCCTCAGCTCACCCCCTGAGCTAGCCCGCCC
ACTCGGCTCCAACCTCCCGCAGGCCCCTGGCACGGTCTCCAGGAGTCCACTGAGGGGTCCCCAAAGCTGCCAC
CAGGAGCTGGGCCTGGGTCTGTCACCACCCCACCCCACCCTCCAAGTCTGAGATATG
Contig 6 (4833 bp)
ATGTGAGCTGCACAGCATGAGCCCTCGGCCCCACTGCTGTGGCCTTGCGGACATTGAGGTGTGTGCCGCCCAG
GGCGACCACACCCTGGCCTCTCAGGGTGCCCGTACAGAGGCGGCTGGGTCGTANGAGGTGCGGGGCTCTGGGG
ACCGCTGGTGAGTTCAGGACGGGGGTCATGCCACCTCCTCTCTGAAGGTTTGGTGAGGTGGCCCTTCTCTTAT
CGTGATGACAATACTGATTTCTGGAAGAGCCAGGTGTTTTCTGAGGCTGTGGTTGCACTTCTCCACGTGGCCA
CAAGGTGCCGGGCTCGGGTCAGATTTGAGAAGCCCTGCGGGAGCGGGTGTCATGCGCCAGATTCAGCTTGCCT
```

Fig. 6, contd.

```
CCTGCGGGTCTGGGGTCAGGACGTGGTCCCCAGCAGTCTGCTCCAGAGCCTGTCAGTGATGTGTGGGATTTTA
CCGCTAGAACACAGTTTCCTCTGATTCTCAGAAACCAGCAGATGCTTTAGGAGGGGCGTGCAGGTTTCACCTG
TGCTGCANNGCCCCCTGCCACCTGGTCGGAGCCNCAAGACGGCATCTAAAGATCAGTTCCTCATCATCAGTTC
CGCAGTGCTGGGGTGGGGGCAGATGAGAACCTCAGGGCTGGGCGCAGAGGTGGGGAGCCCGCCTGGACCCCGA
CACTGCAGGGGGGCCTCCCCCTTGTAGGAAGAACAATGTCGCTTTGCCACCCAGCCCTCTCCCCAGGGTGCCC
CGAACTGTTGCTCCTAAGACCTCTGGGCTGTGTGCTGTAATTCTATAAGTGGCCACCAGGTGTCAGCAGGAGG
CCACTTAAGCATCCATGTGGCGGAAACCTGGAGCTGGGGGTTCCTAAGGGTCCCTCGAGTGTCTCCTGAATAA
ATAGGCGCTGACCTGATCCCCAGGAAGGGATAACCCTCTCCCAGGCCTAAGAGGCAGTGGGGCAATGAGGTTT
ATGTGTCCACTGTACCCCCAAATTGTCTCTTCCTTCCCTCTACCCTGTGTCCCCACCGTGGACGATACACGGA
GTGCGAGGCTGCGGGTCACAGCCCTCACAGCCCCAAAGCTGCAGGTCCTGCCTCAGGGGCACCGCAGCTTGGC
TGGTCCCCCTTGGGTCCTCCCCACCCTGACCCGTCCTCTGCTCCCCTCCCTTTGCTTAAATGCTCTGCGTTTC
AAGGTTCTGATGGAATAAAATAGCCCTGCACTGGTGTGTTCCTCTTTGGGGCTGTGCCAGAAGTGGGAATTCA
GACCAGGGCAGAGCTCAGATTCCACATACTGTGTTAGGGATGGCAGGTGCCACATTTCCAGGAGTTTCATTGG
TGGTTTGTAAATGCTACTTCCGTTTCAGCCCCTCAGCTGCCCACCTCCTCAATTTAGGGACCCCCCCCTTTGG
CGGGTTGCCCATGGAACCACATCATCTGGCGTGGGTGAGCCCTTTATCCTCCCTGGCCCCACTGGGAGGGTT
TGGGGAAGTCCCAGCTAAATTTCTCCGTAGGGACCTGGAAGGAGCCCTTGTGACATCTGGGCACAGATAAGAG
GTAGGGGGCACAGGCCGTGAACACTTGAAGCTGCAGAGCCCAGAGCAGAGCCAGCAGGAGCAAGTGACTGCTC
CCCACCCCAAGAACTGTGGGCTGCGTCACACACTCCCCACTGTGTGCCCTGGACCTGACAGGGCCTTTAGCCT
CCCTGCATCCCTCCCCACCCAAGAACCCAGTGAGGCACCCCACTTGCCCCTCCTTAGTGTTGTTATGGCTCTG
GGGCATCTGCATTTTGTTTAGGACACCCCCAGCTAGATTTAAGTCCCCCCAAGTGTGACTCTTTCCTCCACTG
AAAACCCTGTCCTCCCACCAAAGGGCCCTATCCCTTTAGCTGAGCCAAGGAAATTCAGGAGGGGCCTTGAATG
ACAAAGGAAGAGGGGGAGAGTTAAACCCCAACACTGGCTGGCAAGCTGGGTGGGGTGGACACCCCAGGGTGCA
GGGGTGCAGTGAAGGTAGCGGCTGGTGGCCTTCTGGAAACTACATGTGACTTTGCCATTAGGTGAGTCTTTGC
TTTGCCCCTGCTCTATCTGCAGGCTTATGGAAGAAGTTTAAATTCCCAGGGACACTTGGTCTAACCAGGCAGC
GCTTGTATCTGGGCCCTTCCCCAGCTGCTGACCACTCTGAGTCTGCGCCTTAGTTGGAGTTTTGGCCAAGCTC
AAGAGGCTGTGGACCCCAGTCATCCCACCCAGGGGTGCCTGTGGGCAGGACGCTGCTGCCTGCCATTTGCTGC
AGTATTGTCACTGTCCGGCACCACACACATGGTGCAGGGGTGGTATCAGGTGCCACTGGGGAAGGGAGAAAA
CTCCCAGGTGAGTCCCCTGCCTCTGGAAGCAAGATGGACATGACCGCACTGTGTTGCAGCTGCATTGGGAGGC
CCCGAAGAAAGATTTTTCTGATCTTTCTCGAACCCTGCTTTTCCCCATCATGCCCCGCCCCCATTTTACCCGT
GCCACGCCCACTGGTGTGCCGGGGTGTCAAGTGACTGACAAGTGTCAATCTACTGAGGCCCTGCCCACTCTCC
ACCCCCCCACATAGTCCCACCTCCCAGCTGGCAGGGAGAACTTCCAGCTAATGCCCATGCCCACAAATGTCTT
TCTGTCAGCCTAGAGCTGGACCAAATCTCCACCCTGTAACATGCTGTGCCCTGGCGTGGGAAGGTGCCAGAGC
CAGTTGCCCCAGCAGCCCCAGAACCACTAAGTTGGCACAAAGCTACCCAAATTTGGAGGGGCTTGGGGAAGGG
CATGGAGGGGATGAGGAGGTGAGGGGCAAAACTAATTTCAGTTAGCATTTGAGCAGGTGCCACGCTCAGCGTG
GAGAGGCTCTCTTGCTTCTAGGGACCCATTATGATGCACACGCTAAAAGCGCCCTTCACCATCTCTCCAGCCT
CAGCTTTGTCCCCCTCCTCCTCAGCGGCAACCCGGCTGGAGGGTCTGGCCACTACAGCCAGAGCGCCCCC
TACTTTGGTGGCGACTGCTACTATTGGCCCAACCAGCGGATCACCGGCCAGGCAGTTTCGGCAGAGAGTCTGG
GGCACCAGTGACTCCCCCGTCCTCTTTATCCACCACCCAGGAGCTTCAGGGACTACACAGCGACTAGAGGGCA
GGTAACTGGTCTGCCCTCCCTAGGGCTGCCCCCTCAGAGTGTGTGAGAAAAGCTGCATTGAGTGTTTGGGTGC
AGGTGGGCTGGGGGCTTGGGGCAGCCAACAGGAACGGCGGGACCTCTGCTTCCAGAGGACCCCAGATCCTGGC
AAGCTTCGACTTTGGAGGGGACAGGAAAGACAGGTGGAGAGGGGACACTTCCCTCTTCTGTACAGACGCCCAC
CCGGAGCCACAGAGGCTTTTGCAAGGAAAATAGGTTTTCCCTCACTAATGCAGCAGGCAAAATGGGAGGGGCA
GGGGTGGAGGGTAGTGCCCCCGCCCCCAGCAGGAGGGCACAGCTGTTTCTGCAAATGTAAAAAAGCAGGGTTT
TTCTGTGTGAGAAGTTCCCTCTTGCTGCATGTCCCCACCCCCGCCACCAAAGACAAACAGGACACTGTGCAGA
GGGGCCAGAGCCCCGAGATTTTGGAGTTGTTTTTATATGCATATATACCATTTTGAAAGCAAAGCTTCCCTCT
CCCCTACTCCCTACATGTCCCCCTTCACCAAAAAATCCCACCACGTAACTGGAAAGGGGAGTGAGAAGGACGA
CGAAGGGGCACTGTCCCCTCCCGTCCCACAGCGGGACTTAAAACGTACAGCTTTTCGCCTCCGGACAGTGTGC
CGCCCCCTGGCCCCCGTCACGCTCCCCTGCCCGGGGGCTGAGTGTGGGCCAGGGCCTGTCTCCAGGCATGC
ATTATTTTGTGCATGAAGGTTTTGTCCCGCCCACCCAGGCTGGTGTTGGGGGGAAGGGGTTCATTGCTCCAAA
GAAGCCCATCTCCCCCCTCAGCCACCTTCAGCCGCCTTCGCAAGGCAGAGCTGTGTCCTCTGCTGTGTGCCTG
GCCCCCTCCTTGCTTCTATTCAAGGTGGAAGTGTTGGGGGGAGGAGAAGAGTTTTTATATTGTGTCTGTGATC
CCCCGAGGCAGGCCATTTGTGTGCGGCCCCCCAGCCCCCAGGCCCAGGCAGATGGGCCAGCCTGCCCGACAGA
AGGGTCTCCTGCTTGCTTGGCTGCAGGGAAACCCAGCTCTGGGTGAACCGTGGGCACCTTCCTTCCTCCATGCC
CTGTATTTAAAGAAGGAGAGCTGGGGGGCCAGAGGCACAGGGAGGGGAGCCACGGCCCCAGGTCTGACAAGAT
GACCTGCGGGCCTCTCCACCCAAGAGTCGGGTGGGGGGCGGATTTGGTTTGAAAAGAGAACAAATAGGAAC
ACACTCTTTATTTTCCCCAGGGGCCGAAGAGTCACCCCTGAACTTGAGGACGAGCAGCCGGATTCCAGCCCCC
AGCCCCAGGGCCCCACATCTCCTCGGGCTCAGCCGCGCGCCCCAGCTGCCCCCCAGCCTGAGCTGCAGCAGGC
CAGGGCTGCCCGAGACCCCAGCCCCCAGGTGAGCTGCTGCAGCCTGTGGCCCAGGAGATCTCCGCCGGCTCAG
AACTGAGGCGGGCAGCCCACCCAGCCCACAGCGGTGAGTGTCTCCAGACCCCAGGGCAGGGCCCGGTGTCCCC
CGGCACAGAGAGCTGTGCTGCAGGCCCAGACCTCCCAGGCCGTTTTAGTTCCCATCTCCCCTTGGGGGAGGGG
TGGGGCTCAGAGGGGCTGGGGTGCATCCGCAGAGCTGGGGTGCAGGGCTCCAGGTGCCTCTCTCCCAGGCGGC
TGGCCCGGAGGGGGG
```
Contig 7 (2014 bp)

Fig. 6, contd.

```
CTGGTTTCGCACTCCTCCGGGGACTGTTGAAGTACCCGAGAGCGCNCGCGGAGCGCCGGGGCGAGCGGGGGTG
GCCGCCGGGGGTGCTCCCGGGCCCCCGGACCGAGCCAGGGACGAGCCTGCCCGCGGCGGCAGCCGGGCCGCGG
CTTCGCCTAGGCTCACAGCGCGGGAGCGCGTGGGGCGCGGCCGCTGCCGGGAGTCCGCCTGCCTCCTCGGAGG
CGGCCGACCGGGGAGCCTGGGGGACCCCGAGCGCCCGGGGAGCAGCGCCCCGACACGCCCCGGGCCGCTCTCG
GCTTCCTCCCTTCCAGCCGGCGCCCGCGCGGCCGGGCTTCGGCACCGGGGCGCTCTCAGTGGCAGGAGAAGCG
TGCGCTCCCGCGGGGTGGGGGACCCGCAGGAAACC
CGCACCGCCTGGAGCCGCCGCCGCGCGGCCAGCGCTCGCGTCCCCGGGGAGGGCGCCACTGCTCCGCGCGCG
CGTCCCCCGACGCCCCGCGCGCTTCCCCGGCCGGCCCGGGATCCTAACCTCTCTCTCGGTCGCAGCCCCGCAT
CCCCAGGGCTCCAGGCCCCCGGCGACTTGCCCGCTCCTCCCAATTGCAGACACGACTTTTTCTGGGACCTCCC
AAAGGACAGCCTGGCTCCAGGGTCCCCCAGATACATTCACCATTTCTCCAGATCACAAGTGGGTTTTTCGGGC
ACTAACTTCCAGAGACCTCAAAGCACATGAGCCCCTACTGGCTTTCCCAGGTTTCCACTAGTGGCCTCGGTCC
CCACCTCACTGGGGATTGTCTCCCAGGCTCTTCGC
GGTGTGATCCCACCCATTCGCGCCCAGGTCCCGCAGTGCCAATCCCTCCTCTAGAAAACTTAAACACTGACTC
CTGGTCTCGGGGTGAGGCTGCCCAATGTGCCTGACTCCCCAGAAGGTATACCAGTGTTTTTCTGGCATTTGGG
CACCGTTCCCCCAAAACACGTGAAGCTCTTTTCCCGCGTCCCCATAATTTTGGACGCCAGGGGCACCCAAGCT
TAGCGCCCCTGTTTGGCTCCCCCACACCGCGAAGCCCTGCTCCCTGGGGTTCACGACAGTTTGGGACTTTATC
TGCCAAGTTCCACAAACTGATTGGCCCCAAGCTGGGGTCCCTAAATTGTACACAAAGAACCCCAGCCCCCCCC
CCCAACTCCAGTACAGGAAGCGATGGCCCCAGGGA
CCCTCGGAGTTGGAACGTGGCTTCCTAAGCCTTCACCAAAATTGAGGCTTTCCGCGCATGGCGCGCTGATGCC
CTTGCTGAATCAGAAGCACTCTGCCCTCTGATTCCTGCTTTCCACAACCCTGAGAGCATGATTTCTGGTCCCC
CAAACTCACTGAGCAAAAATCTTTTTGTGGGGGCTGCAAAGATAGGAGGCATTTCTCTCCGGAGCTCTCCAAA
CTCCCTTGCCTATAATCAAGTTCCCTAAAACTTAGACAGAGCTTCCCAGGCCCCAGAGGCACACAGAGCCATT
ATTGGAGCTGCGTTTAATGATGACAGGGACCATGGGTCATGCAGCTCCCCCAAGTCACAAATGCCCCAGGTAT
CCTTGGCTCCAGCCAAGCCCAAAGCAAACTCTTGC
ACAGATCCCATATCTTGTTATGTCAAGCGCTTTGCGTGTCCCAGTAAACAAATAGTCTGAGTGTTTTCTCCAC
CTCATAACATTCGGAATATTAAAAAATTCCCTGGGCCCCGGAGCTGACAGACAAGAATCCGGGCTTCCTAAA
ATTCAGAACTGATTCCCAAATCCCAGGCCAACGCCAGACCCTCTCCCAATCTGGAGCCCCTCCGACTGGACAC
ACTGGACTCCTAAGTATTACGCGCTGTCCTCCAGGCACCCCAAATGCATTCAAAGTGACGCTTTGGTCACAGA
AAGGCACTGATTTCTTGGGCTCCAAAGCAGCCCATGCACCCCCGAGTCACCCCAAACTTAGTCAGCATTTCCC
GGGTCTCCCTCCGCACTGCAAACTCCCAACTGCGG
ACACCGGTTCTTCAGGACCCACCGCCTAGACGGTCTTAATCCCTTTTCCCCCAGACCTAGATTC
Contig 8 (371 bp)
AGATTCAAAAACTATTTTTCTGGGGCCTCCAAATTGAGGTGCTGCCTGCCAGTCCTCCAAAATAAACTGAGGG
GTTTTTGTTTGTTTGTTTTTTGTTTGTTTGTTTTTTTTTACCTTCCACGAAACAATCCAACTTTTTTGGA
CCATTGATTTATGGGTCCCCTGACTTTATGACCCTTGCCCCAAGTCCCCCTAAATGTAGGCCATTTTCCACGG
GCCTCCCAAAATGAAATTGCCCAGATCCCGCCGAAAAAAATATCCCCGGGTCCTGGAAATCCCAGGTATTACA
GGCCTGCGGCTGACACCCCTCCTTGCTACTAACCAGGTTCCCTGAAGTTTAGAGATCACTACCTAATGAACAA
ATCCAC
Contig 9 (2415 bp)
CCAAAACTGGGGCCCTATCTTACTAGGGTTCCCTAAATGCAGACAGCGCCCGGGAAAATAGGGGCGTTTTTTT
TCCTGTTTGCCAAAAATAAACTAATTGAAACCAATTTTTAGAATTAAAATCTAAAATGACCTTGATTTTCTGC
GTTCTCCAAATGTACTTTTCACAGCCCAGGTTGCCCCCAGTTTAGACGGTGTTGCTTGAATCTCTAAAGCACC
CTGAGGATTTTTCCCGAGGAAGCCACCACAACTACGGAATTTACTGTCCTTCGGGGCCACAAGCCTCCAGGCC
ACCAACTTGGATTTCTAAACCGTGGAAATCAGCCTCCACTTCCCTCCGCCACCCCGAGGGTCTGCTCAGACCC
CCCAAACGTGCCCGCTGTTCTTCTCCCCCCAAATT
TTATTTAGAGAATATGCCTCTCTCGGGTTCTGCCAAGTTTCCCGCTGAGACTTCCTCGGTCATCCCCAAATCC
TCTTCCCCACAGTCCGGGAGCCCCCACAAGCTTACCGACCCACATGCTGGGGTCCCCAACTTAAACGCGATC
CCCTGTCCCCCAGATTCACCGAGTGATTTCCCTGGTCCTCAGACTGGGACTCTTTTACTGGAGTCTCGAATTT
AGCCATTAATCACAGTTCTCCACTCCGACGCAGGCTCCCTTGGGTCCCCACGTCGGGGACATGGGTTCTCTTG
CCTGCAAATCAGGCTGCTCTGACTTGCATTCAGGCCTTTGGGCATTGTTCCCCGCCCGCCGCGGTCTCGGTTC
TCCCCCCATCCCGCGCACGACGGGCACTGGGTCTG
GGCCTCTTGGTGTCTCCTACAAGTCCCCGGAGCTCCTCGGACTTGGGAACTGTCTCTTGCGTTCCCCAAATAC
ACTCGGCCCGGCAGTGTGTCCGCCAGGACGTAGGCAGAGCTTCTCCCGCGTCCAGGAAAACGACTGGGCATTG
CCCCCAGTTTCCCCCAAATTTGGGCATTGTCCCTGGGTCTTCCAACGGACTGGGCGTTGCCCCCGGACACTGC
GGACTGCCCCCGGGGTCTCGCTCACCTTCAGCGCGTCCACCGCCCGCTGCAGAGCGCTCGCTCTCCGTCTCTC
GGCTCCCAGCGCGCTTGGGGACGCAGCCTCCGGGCCTCCAGCCTTGCGGTGAGCTCCCCGTCGCCTCGCGTGT
CCCGGCCCGGCTCCCAAACCCACTCGCCGCCGTCC
CGCTGGGGCTGGCACTGGCCTCCGGCGACTGCCGGGGACACGGGAGCGGAGCGCGGGAGCCTGCTGCAGGCCA
GCCCGTCGGCCGGGCCGCGCGCCCTGAAACGCGCGCGGCTTTCGTTTGCTCTTTGCAAAGGTCACAACCGTGG
GGAAAACGCCTCGGCGGCCCCAAGCGGGGCAGGCAGGGCGTTGGAAGGAGGGACACGCGGGAGAGGAGCAC
CCCGCTGGGGCGGCGCAGCGCGGCGCCTCCAGCCGCCGGGCGGAGGATCCCGGGAGGCGCGCGGAGCGCGG
GCGAAGTGATTGATGGCGGAGCGAGGGGGCCAGCGGATCGCGGGCTTCCGCCGGCGGCGGCCCCTTCCCCTCG
GAGGGACTCGGGCGGCCCGGGTTTCTGGGGGCGGG
```

Fig. 6, contd.

```
CGGGGCGCGGGGGCTTGTGCGTGGTCTCCACTTGGTAAAAATCACAACGACTTTTTACGTCGCCCCGACTCTC
CAGGAGATGGTTTCCCCAGACCCCCAAATTATCGTGGTGGCCCCCGGGGCTGAACCCGCGTCTACGCAAGGCC
AACGCGCTGAGGACGGGGGAACCATTATCCGGATATTTTGGGTGGGCCCCCAAAGCGAGCTGCTTAGACGCGC
CCCGGTGAGCTCGGTCCTGCAGGTAGGCTTGGAGCGAGGTTCCCCGCCCTGCTCCTCTCTCTTCGGGCAGGCG
CGGCCAGGCCGGCCGGCCCTCCCCACGTACGGCACCTGGCGGCCGCCGAGACGACTCCCCGGTTCCCGCGCGG
CACCGGGGGGCGCTCGGGCTCTGGCTGCGGCTCGA
GGCGCTGCGCCTGCTCGGGCAGGTGGAGGCTTCACGCCGGGCCCGCGCCCAGGGACGACCCCTTACCCCGCAG
GTCCCAGCGGGACTCGGGGCCCCCGGATCCAGCGTCTAGCCACCTGTGCCCGCACCGCCGCGAGGGCTTGTGA
CACCTACCACCCTGGCCGCCCCCGCGTCCCCCGCGCACGAATGTAGGGATCCTGACACCCCGGAACCTAAGAC
GGGGCCCCCATACACTTTCGTACAGCGATTCGGGATTTCTCTCGAACTCTGCAGATCTGTATGGCAAAGTTGA
TGGCCTGCATTATTTTTCTGATAATTCAGCGAAAGATGGCGACCAGAGCTATGCGCGTCTGGGTTTTAAAGGC
GAAACCCAAATTAACGATCTGGTCAACGAACAGAT
ACAGCATACGTTTTT
Contig 10 (3753 bp)
AGATTCCAATGGGGATCCCGATGAGGAAGCCGCTGCTCGTGCTGCTCGTCTTCTTGGCCTTGGCCTCGTGCTG
CTATGCTGCTTACCGCCCCAGTGAGACTCTGTGCGGCGGGGAGCTGGTGGACACCCTCCAGTTTGTCTGCGGG
GACCGCGGCTTCTACTTCAGTAAGTAGCTCAGCGGGGCACGGGGGCGGGGCGGACACAGCAGGTGCTCCATCG
GTGCTGCCCCGGTACCTGTGCGGGTCCTTCGGGATGGATGGTGTGGGGGACGGGGGGCGGGGGGCGGCCAAGG
GAGGACCTCTCCTCCGAGGGTCTGAGACTTCAGAGCGGGGGCGCCCTGGCCCTGCGCAGTGATTGGCACCTGC
CATGTGCCTGGCTGGGGCTCACACCCCCTGACGTTCCTGCAGCGTGACTCGAAACGGGAAACCGAAGGGACGG
GTGGCACGGGGTGGGGAGGCAGACCGTGAGTGGCAGGCGTGCGAGGGGTTCTTTCGGCGGGGTGGCCCAGGC
AGGCCCCACAGGATGACAGCCTGTCCCCTCCTGCTCCTCCTTGACCTGCCCACAGCCAGGGCTGCAGGCACTG
ACATTCACCCATGGTATTGTGGTGCCTGACGTCTTGGCAGTGGGCATGGGTTCATGGACTGTTGGATTGAAAG
TGGAATAAGATGGGTTGAAAACCAATAAGAATAAAGGCGCGTGTGGCTGGCGGCATCTGCGAGAGGTGACCGC
TGCCCTCCCTGGGGTTGGGCTTTGGGTGGGTTCCCATGGGTGGGGCGGGCCGCCATGCAGGGTGCCCGCCTGC
TGGCCTCAGAGTGCTTTGCCGTCCTCATCTTTCTCTCTGGCCCCCGTCCCGCTCCTGAGGCTGGCTGGCTGGG
CCCGCGGAGACCTCCGCTCCCGCCTCGTCTGTGCCCAGGGAGCAGGGTGGACCCTCCCTTGGGCTCTTGCCTG
CACCTCCCAGCAGGCTGGGCCTCAGTGTCCTTACCTGTAGGATGGGTCAGGGGCGTCCTGGAGAGAGTCCTCG
GGACAATGGGGAGGCTGGGGGCAGGCCCAGCCTGACCCTGAAGGTGGGAGTGTGTGCTCCCCCTGGGCTCAGC
CAGCCGCGCTTGGGGCCGGGAGGGGGTGGGGGACGTGGCTGGGGCAAGTTGTCAAGGGCCGCGAGGCTCACCC
CCGCCCATCGCTCCCCATGTGGCAGCCTCTTCTGCAGCCTCTACTTACCCACCCTCTGAAATGGGCTGAAAAC
ACCCATCTTGGCATGCCAAAGCTTCTCTGTAAAAAGCGTTGCTGCTTCTTGATGCTTCTGAGGCCCCTGCCTG
CCCTGGCCTCTGAGCCCTCTCTCTCCTGCCTCGTTTGGGGGCAGGGAGTGGCACCATAGAATCTGGTCGCTGGG
CCTGGGGAGCGGCCCCCTCGTGCCAGGCTTCCCCGAAAGGAGGGCTGGGCTGAGCTCCCGACCCTCTGGACCC
CTTACCAGGACCCCTTACCAGGGGCTTCCCCCCCCCCCCCCCGGTGGCGGCGGGCTGGGCTGGGGCCTTTT
CCTTGCAGCCGAGTCGGAGCTGTCGGAGGCGAGGGCGAGGACGGGAAGAGAGGAGGGCGTGGTTTCTGCTGGT
CCTCACTCCTCTCCTCCCGTCTTCCTCCTCCTCCTCCCATTCCCACCTGTGTCTCCGGGTCCCGGGGCCGCAG
GCTGCCCAGGCGCCTGCTGATCCATTGGGGACCGCACTCGGGTCCCCGCTGGCCTTCGGGTCAGGGCCACGGC
CCACCTATTTTCCAAACAGCCTTGGGTCGAGGCCCAAGAGGCTGGGCCCGGTTTAAGGACGGGGAGGGAGGCG
CCAAGAGGCCAGGGGCTGGTCCCGAGCACGCCCGCACCCGCTCACCCCCGCTGTCCCCTCTCCTTCCCCGGGG
GGCCCCTGTGCACCCCACTCTCACTTCTTCTGCTCGAGGCCACGAGGCTGGCTGTCCCCGCAAGGTGACCGGG
CGTCCTGTCTGGAGGGCGGGGGCCGGGCGGCTGGGGGCACCGTCCGTGCCCGGGGCCCCTGTGCTGACGTGC
CCTCCCCTTGGTCCTGTGGGACTTCCAGGCAGGCCGGCAAGCCGCGTGAACCGCCGCAGCCGTGGCATCGTGG
AAGAGTGCTGCTTCCGTAGCTGCGACCTGGCCCTGCTGGAGACCTACTGCGCCACCCCCGCCAAGTCCGAGAG
GGACGTGTCGACCCCTCCGACCGTGCTTCCGGTAAGGCAGCCCCTCTCTCGGCAGCGCCCCCCCCGGGGGGG
GGCTGTCTCCTCTGAGCCGGGGGACCGGGGCGCAGCCGGCTCTTGGGCTTCAAGTGCTGCCAGAGGGGCCTTC
CCCGCTGGGGACCCTGGCCAGAAGCCAGGGCAGTCTTCGCTCTGTCGCAGGGCAGGCAGGCAGGAGGACCCCG
CAGAGGTTGTTGTTCTGGGACAGGGGCTGGGGGGCCAGGCCCCCCCCTGACGGGCCCTTCCCCTCTCAGGACA
ACTTCCCCAGATACCCCGTGGGCAAGTTCTTCCGCTACATGACACCTGGAAGCAGTCCGCCCAACGCCTGCGCAG
GGGCTGCCGGCCCTCCTGCGCGCCCGCCGGGGTCGCTCGCCAAGGAGCTGGAGGCGGTCAGAGAGGCC
AAGCGTCACCGACCCCTGACCGCCCGTCCCACCCGAGACCCCGCCGCCCACGGGGCGCCTCTCCCGAGGCGT
CCGGCCATCGGAAGTGAGCCAAATTGTCGTAATTCTGCGGTGCCACCATCCACCTCGTGACCTCCTCTCGACC
GGGACCGCTTCCATCAGGTCCCCCTTCTGAGATCTCTGTACCCTTCTGTCTGCGGGCATCTCCGCCCGGGCC
CCGTGCCCCAACCTCCCCATGTCAGGCTAGTCTCTCCTCGGCCCCTTCCATCGGGCCGAGGGCATCCAAACCA
CAAACCCAATTGGCTTGGTCTGTATCTCCCCCCAAATTATGCCCCCAATTATCCCCAAGTTACATACCAAAAA
TTGAACCCCTCAACCACACCCACATACAATCAGCCCCCGTAAAACGAATTGGCATCTTTAAAACACCAGAAAA
GCGAATTAGCTTTAAAAAAAAAATAAACCCAAAATATCAATTAGCTGAAAAAAAAA:TACTAAAAATAAATTG
GCTTAAAAACAATTGGCAAAATAAAAGAATTTGGCCCCCCCCTTCCTTCTCTTTCTTTTCGGACCTTGAGTTA
AATTGGCTGTGACCCATCATCCAAGAGAAAGGAGGGACCCAAAATTTGCAGGTAGGCTTGTCGCCGCTCACAG
CCATCTCCCTCCTCCTGCCACACCCTCGCCGGCCACTGGCGGTGTGGCACCAAGGACCCAGTCCCGTCCTCTC
TCTAGTCCCATGACCGAGACCGCGGTGGAGTTGGCTGGGAGACCCCGTGAGATCAGAGGAGGGGAGCACGGAA
CCAGAAACCCAAACCTGCACAGGTACAACATGACTGGCCCCCGCACAGCCCAAGACCTCTCATCTCAGTCTC
CACTTAAAAAGCACCTGTACCCACACGCATCCCTGCAGAAACACACACACACACACACACACGCACGCA
CGCACACACGCGCGCACGCACGCGCACACACACACTCATGCGTATACACACACACACACGCACGCACGCGCAC
```

Fig. 6, contd.

```
CCACACACACACATGCATTCACACACACACACACTCGTGCATACACACGTGCGCGCGCACACACACACACA
CACACTCTCTCTCTGTGGGATCCCTGAG
Contig 19 (500 bp)
TGGCTCTGGCATAGGCTGGCAGCTGCAGCTCTGACTGGACCCCTTGCCTG
GGAACCTCCATATGCCGTGGAAGCGGCCCTAGAAAAGGCGAAAAAAAAAA
AAAAAAAAAAACAACCAAACAAACAACAAAAGCCAAAACACACAGAACTC
ACAGACACAAGAAGAGACTGGTGGTTGCCAAAGGTGGGGTCGAGGGTGGG
AAAAATGAGGAGAGGGGGCAAAACACACAAACGTGCAGCCATAAAATGGT
AAAGTCCCGGGGACCTCCGGTAGCGCGTGTGGGGACTCGGGTTGAGAACA
CACCGTGATGTGTATTCGCGAGTTGCTAAGAGTCCCTGTTGGAGAAACAA
ATGCGTATCGACGTGTGGAAATGAAAGTTAACCCGACCTGCTGTCGTGAT
CACTTTGCAACACATACAGACATAGAATCATTATGTTTTACCCCTGGAGC
TGACAGCGTTATACGTCCCCCAGCCTCAATTTAAAAACAGCGTTGCCGTG
Contig 20 (400 bp)
TTCATACTGTGCAATGCCAGCCTTAAATGCACAGAGGAGAGCATTAACTT
CTTTGCAGAATCACTGAAATGATACCACTCATGTTTTGCAACTTGCACTT
GGGCGTTATTTTATTGGTGCCGGAACAGCGGCGATGTGGCACCAAACTAG
CGCCGCTGTTTTTATTTCCCCTCGGTATCCGCGCTCTCGCTGTCTTCCCC
CCCTTCCGCTTGCAGCTGAGGAAAGGGCTGAGAGGAGGAAAGTCTGCATT
CACCCATCTCCCCCTGCCTCTGTTGTCATCCTTCACAGAAGTGGTGGCCT
GTGCGGGGAAGTCACTAAACCTAGGCAGGTGTCCCGTGGGGTCATGCTTG
TTACACCTTTGTGCACCTGGCCCAAGTTCTGGGTGGAGCGAGAACGTGGC
Contig 21 (559 bp)
AGCTAGCCCCCCCAGCCAGGGCCAGGCCTCTCCTGCCACCCGCCCAGCCA
GCATGTCTCAAGAGGAGGGGGCCTCTAAGGGATGAGGACCTGCTCCAGTC
GGAGACACGAAGCCCGCCGGCTCCTCCCCGAAAGTCCAGCTGCGGCTTT
CGAGCACGGCTGCGCCCTTCGTCAATCATTTCAGCCACAGAAGTGAAAGG
CGCTTTCGTGGCCGAGGCAGGCGGGACACAGAATGGAATCCCACCCCAGA
GCGAAGAGCCGCCGTGGGTGAAGCGCGTCTCTGGTGGGGACCGGGCCGGG
AACTTCACATGGGGGTCGCTGTCCCCATCTCCCCATCGTCATTACTGCAG
GGGCTCGGCCACACCCGGAGCTGCGGGGGCCAGTGCTGGACACTGGACCT
GGCCTCCGTCCTATGATGTCATGGGGGCGGGGCCAGCACAGGGCAGTGGC
CACACCTCGGGCCTCCCAGCACCAGCCAGGATGGCAGAGGGCCCCACCCC
ACCACGGGGCATGTACATCCCAGAGGACCAGCTGAGCAAGGCTTGATANG
GGCTTCAAC
Contig 22 (450 bp)
CGTGCAGGGACCCGTGCGGGCCTTCCTGTGGCCACAGAGAACAAACACAC
CATTATCTTCAGCCCCACCGCGCGGCCTGTTAATGGGTAAACTGGGGCAA
GGGGGCCCCTGCCTGAGGCCGGGGTGGGGAGCGCAAGGCATGGCCTGTGT
GCCCCAGCCCAGTCCTTCAGGGCGCTGCTGTCCTGCACCGGGGCCCCAG
GAAGCAGAGCACCCAGCTTCTCCCCTATTCTAGAACCAGCCCCCAGAACC
CTGGACCCAGACCCAGGCCCAGGGGATACTGACAGAGCCACGGCAAGGCG
GCCACTCCACACCCCACAGAGGGGCCAGCAAACCCCAGTCACTGCGCAGC
CCATGCCCAGGGGGCAGATGGGACACGAGAGCAGCCCTCATCCACAGCAG
GCAGGGGAGTGAACTGGTGCAAAACGGGGCGGTTCCACGAAAGTTAAGCA
Contig 23 (535 bp)
TGCCAGAGACCTCAGAGCTGGGCTCTGCCTTCCCGGGCTGACACGGAGGG
CTGTGGCTTCCACCACCCCAGGCCACAGCCAGCCTGCCCAAGTCCCTGAA
GTGTCCCCAGAGGTGGCCCTGCCTCCACGCCCAACATCAGGCCTGCTGCA
GCCCTGGACGGCCCCCTGTCCCCCGGAAGCCCTCGGGGCTCTCTCGCGTC
GCCTCTGGGGAACCCTCGGTAATGTGGCCCAGCCGTGCAGTGGCCGGATC
ATTTGCTCAGGGGGGCCCAAGGCAGGGGGGTGACACATCCGCAAGTACCG
CATATGCACAGGATATGGATTGGGTGTGGATTTAACCTTTTCGCAAATGT
CTCTGCCGGTACAAATATTGTTTCTAATCCTCTGCCTCCCTGAGCCGGTG
AGTCTGCCCGGGAGCTGCGGGGAGCTGGCTTGCTGAACCTGCCCTGGCCC
CCACCCCCAAGGGAGCCCCGGCCAGTGCTGAGGGCAGGAAGCTTGGGCA
CAGGCTGCAGAGGCCAGCGCTGGCCTCAGTCACCT
Contig 24 (868 bp)
TATTGAAGACCCTATCATGAGTTCCCAGAGCGGAGGGGTGGAAGCAGGGG
CCTACAGCCCACTCCCCATCACTCCAGACCCGTCCGGGGCTGGTGTCCCC
TGCCCCCTACTCCTGTCTCTGGTGGGCGGACGCTCGAAGGAGGCACTCTG
GCCTGGAGCCTGGAGGGTCCCTGAACTCCCGCTGCCACCTGGGCCCTCGG
GCTCCTCCTGCGCTGGGACCCGCGGTGGTGGGAAGCAGCCCTGCTCAGTG
GGAGGAGGCAGGGCTGTGGCCGCCCCGCACGGCCCTGGGGGGACGCACG
```

Fig. 6, contd.

```
CAGGACGCANGTGGGCGTGTGTGAGTCCGTCTACACGTCCAGCCAAGGGC
GGCCGCGACCGGCCAGGGTGGGCAGCCCCAGCCTCAGCAGGGCGCTCTCT
GGGGCTCAGGCTGCGCCGACGGGAGATGAGGGGTGAGGCGCAGTCTGGGG
CTGCTGCCGCAGAACCTCGCCCAGCTGGCAGCTGGGCACAGGGAGACCTG
TACTCCCAGAACCTGAGGCTGGACGTCCGAGACCCGCGTGCCGGCCTCTT
GGGTGCCTGGTCAGGGTCCTCTTTCTGGTTTGTGGGCAGAACCTCCTCAG
CGCGTCCTTGCATGGGGTGCTAATCACGGAGTAAGGAGCCAGAGAATGAG
GCACGGAGTATCCAGTGTTAACCCTGGAGTATGGAGACGGGAGTACTAAT
TGTGGAGCATGGCTCTAAGGAATGGAGTATTCGTCACGGAGAACGCGGGG
CCGGGTGAAATACGGAGAGCGGCGTACGGACAACGGGGACGGGGTATCCG
AAGGGGAGGATGGAGTATCGGCCGGAGGGTGGAGAATGGACACTAGAGGA
TGTATANNGGGCGTCAAT
```
Contig 25 (500 bp)
```
ACCAGTTTCGATGAGCAATCCCAGCGGCGTAACATTATGGCTGCAGCCTG
GTCAATGCCGGTGGAGTTTGAACCTCACGCGTGGCGATTGTGGTAGATA
AATCGACATGGACCAGGGAGTTGATTGAACATAACGGTAAATTTGGCATC
GTTATCCCGGGCGTTGCAGCAACTAACTGGACGTGGGCGGTGGGAAGTGT
GTCGGGGCGTGATGAAGATAAATTTAATTGCTATGGCATTCCGGTTGTGA
GAGGCCCGGTATTTGGTTTGCCTCTGGTCGAGGAAAAATGTCTGGCGTGG
ATGGAGTGTCGATTGCTACCTGCGACTTCTGCGCAAGAAGAATACGACAC
GCTGTTTGGCGAAGTAGTATCAGCAGCGGCAGACGCACGGGTATTTGTCG
AAGGCCGCTGGCAGTTTGATGATGATAAGCTCAATACGTTGCATCATTTA
GGTGCTGGGACGTTTGTTACCAGCGGCAAGCGTGTTACGGCGGGTTAAGC
```
Contig 26 (900 bp)
```
ATGTTTGATGTCCGCGCGTGCTGTAAAAATTTACGCTGCTCGCGTTCTTT
GGCTTCGTCCACCACCGGAAAACGGACAAAAATTTCCGTCATACCTTTTT
CTTTCAGGCGGAAGCCAATGTCGTAATCTTCAGTAAGACTCTGCACGTCG
AAAGCAATACCGTCACCGTCAGCTAACAGTGCGGTCACGGCGCGGCGGCT
GAAACAGGTGCCGACGCCTGCGCTGGGCACTTGTCCGGCGAGGGCTTCAC
GCACCGGAACATCTTTGCCATGCAGCTCTGAAAACTCATCAATGTAAGTC
ATGCTGGTGAAGTGCGTCCATTCGCGTTCGAACGGATACACCGGGATCTG
AATCAGATCTTTACGCTCGACCAGATAGTTGAACAGACGCAATTCCATCG
GTGAAATCACATCTTCGGCGTCATGCAGAATAAAACCAGCAAAAGCGAAA
TTGGCGCTACGCTCAAATTGGGTGATGGCGTCCAGCACGTTGTTCAGACA
GTCGGCTTTGCTGGTGGGGCCAGGACGCGCGCAGACTACCTTATGCACAT
TCGGGAAGCGAGCGCACACTTCGTCAACATCACGCTGAGTATCGGGGTCG
TTGGGGTAGGTGCCAACAAAGATATGATAGTTTTCGTAGTCGAGCGTGGT
CGCCGCCAGCTCGGCCATATTGCCGATGACGCCCGTTTCATTCCACGCCG
GAACCATAATCGCTAACGGTTTTTCATCTGGTTTATACAGTTCGCGGTAA
CTCATTCGCGGGTAGCGGCGATAAACACTCAACTTGCGTTTAATGCGGCG
TACCCAGTATACGACATCTATAAAAAAATCGTCCAGCCCGCTGATGAACA
TGATGACCGCTAACGTTATCGCGATTACTTTTAAGCCGTATAGCCAGGTA
```
Contig 27 (500 bp)
```
AGCTGGATGCCCCCAGCTGTGGTCCCTTCCCTTCCCTCAGGGCAGGTTCT
GTCCCTCTTGCAGCCACCGTCACTGCTGTGGACAGGTCTGCACACCCGCC
GTCCACCAAGAGCGTGGCAGGTCCCTGGGCACGGGCCGGCTCCTGACGCA
CCATGTGTTCAAGGCAAGAGCACTGGACAGAGGGTCCAGACGTCCCCTTG
TCCTGCTCAGGCCTGGGCGGGGCAGCCCTGGCGGGAGAGGCCCTGGGCA
TCAGAGCCTCTGTGGCCTGGAGCTTGGCGCCCTGCCCTCCCCACCTCCGT
CCTGCTCCTCGCCGCGCTGCACGGACCCTCTCCCGGCCCCCCAGGCTCATT
ACTCTTAAGGACCCTAGCCCCCTATGCTGAAATGCTGTACCTCGTGCTTG
TTTTCATCTGTTTATTACCTTATCTTCATTCCTGCTTGATGATATCTGGT
TATTCTTTATTGATTATATATATCTTGTTCGTGTTTTTATAGGACACTGT
```
Contig 28 (450 bp)
```
AGTGCGGTCGGGCCGTCCTGACGCTCAACACCGTATTTCCACGCGACCGC
GGATTCAACCTGGTCACACGGACGCCATGTAGACATGTTCGGGGTTACGC
GCAGAGAAGCGACCTGCTCAACCGGCTGGTGAGTCGGGCCGTCTTCGCCC
AGACCGATGGAGTCGTGGGTGTAAACCATCACCTGACGCTGTTTCATCAG
CGCAGCCATACGTACGGCGTTACGTGCGTATTCCACGAACATCAGGAAGG
TGGAGGTGTACGGCAGGAAGCCACCGTGCAGGGAGATACCGTTAGCAATC
GCGGTCATACCGAACTCGCGAACACCGTAGTGGATGTAGTTACCCGCAGC
ATCTTCGTTGATTGCTTTAGAACCAGACCACAGGGTCAGGTTAGACGGCG
CCGGGTCAGCAGAACCGCCGAGGAATTCCGGCAACAGCCGGACGAACGCT
```
Contig 29 (450 bp)

Fig. 6, contd.

```
TCAGGCCAATCTGTCTGGTCTCCAATGGGGACAATTTGGTTCTTTAGGCT
TCTGTCCAATGGTCCGAATGGCCCACTCCCCGGGCGCCGGCCAAGGGTCC
TCTGTGCCTCGGGTGGGCTGGCACGGACCGCCCCCAGGGTCGTGCCAGCC
CCGTCACCGGGGCCCAGAAGCTTCGGGCCTCTAGCTGGCTAGTCGGGCTG
CTGTGCAGGGGGGCTGCGCTGGGGGCAGAGGCGGGGGTGAGGTAAACCTC
CCAGCCGCCCGGGGTCCCTGCCGCAGCCCTAGGCGCCGAGACGGTGGCTG
GGTCGGTACCGCCAGACCCGAGGGCCTCGGGGCCCGGGTGACCCCAGCTG
TCGCACACGCTCGCAGCTCTCTTGCTCATCAGGGCTCATCCCTCTGGACC
TCTCCTACTGCCCCACCTCACCCCGCCTGGACCCCATGAAGCCCCGCGGA
Contig 30 (600 bp)
TAAAACTAGCTCTAGTAGAAACATTTTATTTAAAAATAAAAAACCTGACT
ACGTCGGGAGTTCCCGTTGTGGCTCAGTGGTTGACGAATCCGATGAGGAA
CCATGAGGTTGCGAGTTCGATCCCTGGCCTCGCTCCGTGGGTTGAGGATC
CGGCGTTGCCGTGCGCTGTGGTGTAGGTTGCAGATGAGGCTCGGATCCTG
CGTGGCTGTGGCTCGGGTGTAGGCCGGCGGCTACAGCTCTGATGAGACCC
CTAGCCTGGGAACCTCCACATGCCCTGGGAGTGGCCCTAGAAAAAGGGCA
AAAGACAAAAAAACAAAAGAAAAAGGAAAATAAAATAAAAAAGACTATGT
AAATGAAATTAACGACTGCCTAGGGTGGGATTTACAGCATGGGAAGTACA
GCATGGCCGTGACAGTGCAAGGGTGAGGCGGGAAAATGGAAATAGGTTAG
GTGAGTTTCTCCTGCTATTTGTGATGTGGTCTGCTATCGCTTGAAGACGG
ACTGCAGTGAGATAAATATGTACAGTAAGCATCCGAAAAACCGCCAGAAC
GGCAAAACGAATGACTCCAAGTAAGAACCCAAAAGAGAAAAGGAAATAAT
Contig 31 (450 bp)
GCGCGGGCGTTCCGGCTGGGGTATTTAACGTGGTCACCGGTTCGGCGGGC
GCGGTCGGTAACGAACTGACCAGTAACCCGCTGGTGCGCAAACTGTCGTT
TACCGGTTCGACCGAAATTGGCCGCCAGTTAATGGAACAGTGCGCGAAAG
ACATCAAGAAAGTGTCGCTGGAGCTGGGCGGTAACGCGCCGTTTATCGTC
TTTGACGATGCCGACCTCGACAAAGCCGTGGAAGGCGCGCTGGCCTCGAA
ATTCCGCAACGCCGGGCAAACCTGCGTCTGCGCCAACCGCCTGTATGTGC
AGGACGGCGTGTATGACCGTTTTGCCGAAAAATTGCAGCAGGCAATGAGC
AAACTGCACATCGGCGACGGGCTGGATAACGGCGTCACCATCGGCCGCT
GATCGATGAAAAATCGGTATCAAAAGTGGAAGAGCATATTGCCGATGCGC
Contig 32 (450 bp)
GGTGGATGCTGGCGATAGCGTCATCCTCGCTTATGCCGTGCAGCGGGCAA
GGATAAAGCGCGCGATAAACATGACCCGGCATCAGCCCCATGCCCGCAGA
GTACGGATTCACCTTGCCGGTCAGCGCCAGCGTGTAATGCGTGCGCCCGT
GATACGCGCCGCTAAAAGCGATGGTGCCGCTACGTTTGGTGGCGGCGCGG
GCGATTTTTACCGCGTTTTCCACCGCTTCGGAACCGGTCGTAACCAGCAG
CGTTTTCTTGGCGAAATCGCCCGGCACCTTCTGATTCATAATCTCGCACA
GCTCCAGATACGGCTCGTAAGCCAGCACCTGGAAGCAGGTGTGCGACAGT
TTTTTCAACTGCGCTTCCACCGCGGCCACCACCTTCGGATGCAAGTGCCC
GGTATTGAGCACCGTAATCCCGCCCGCGAAATCAAGATACTCACGGCCTT
Contig 33 (500 bp)
ACGTGAGGTTTGGGGGAGGAAAGCGGGGGACGAGCAGCCCGAGAGGAGTG
GGGGCTGGCCTGTGGCTGATGAAACTCTGAGAAGGTTAAGAGCCCCCATT
TTTGTCTTCCTCTTTTTATTATGGAAAATTCCAAATGGATGCAAAAGTC
CCAAACCTAACTGGACATCTTCTTGGTACCAGGAACGGTCAGGCACTTAT
GATGCACCGAGCCCCGAGGGAAAAACCCTGCCGTCCTGGAGCCCACGGTC
CAGCAGGGCACACAGGCCCCAGCCCGCAAGCGGCACGGCTGAGTCAGTGA
ATGGCGTGCCCTCTGGTCAAGGACGGGCACTCTGGACCCCAGGGAAGCCT
CTGAGGAGCCCCCTTCACAGCGTCAAAAACTGTTAACAGGGCCATGTTCG
CACCCCCCCACACACGTGGTTCAGAAGCAGACCCCAGGCATCGTAATATG
TCATCCGTGAGTTCCCTGTGTGCCACCAACAGAAAGCCCATCGTCACGTT
Contig 34 (400 bp)
CGGCATCGATGTACATGGTACGCAAGGCACTCGTAAGGCCCCGAGCCTCT
AGGCCTTGTCATTGTCACGTGCTGCTCGCGGGATCAGCAGCCAGGCTTG
TGACCCCGGCCACTTTGACAGATAAGGACACAGAGAGGCCACAGCACTGG
TGTGAGGCCCCACAGCCAGCAGCCCAGGGCAGGGAGGACTGGGTCTCACC
TGCCTCAGCTGGGCCCAGCCTCCCTGGGAGTCCCGGAGTCTCCCCAGCTT
AGGAGTGTCCCTGGAACCCTCTTCTCTCCCCTTCCCGCCCTCACCCGGAC
CCCCTGCCTCCCCCCACCAACCCCTCCCCCTCCTTCTTTCACCTTGAG
CTCCCCTCTGAGGACCTCTACTGTTCCTGCTTATCCTCCCCTTTGAGCCA
Contig 35 (500 bp)
TGGCGGTGAACTATGTCGTGCGTGAAGAGCATTTGTGGTCGGTAGCGCGT
```

Fig. 6, contd.

```
TATATGCGGGAAGTTTAGGCGAACTGGACAGCCTGGGTTTATCCGGTAGC
GAAATCCGCTTTCACGGTAAAACGCTGCTAGCGCTGGTGGAAAAAGCGCA
GACATTGCCGGAAGATGCCTTACCGCAGCCGATGCTTAACCTGATGGACA
TGCCGGGTTATCGTAAAGCGTTTAAAGCGATTAAGTCGCTGATTACTGAC
GTGAGCGAAACGCATAAGATCAGCGCCGAATTGCTGGCATCGCGTCGGCA
AATCAACCAACTGCTGAACTGGCACTGGAAACTGAAACCGCAGAACAATT
TGCCGGAGCTGATTTCCGAGCTGGCGTGGTGAGCTGATGGCGGAAGCATT
ACACAATTTATTGCAGGAATATCCGCAGTAAAATCTTCCGAAGCCGCACT
GGGCGCGCTCAGCGCCACATCCGGCTTCGGCAAACTACAAATCCAACACC
Contig 36 (500 bp)
GATTTCACAAGCCTGACCCACGCGGAAATGCGCTAACAGCGTAAAGTCGT
GCGGCCAGAATTTTTTCGTCTCTTCGCTTTGCGTCAATTCAAAAGTCAGC
GCTACGCCATCAGCATCTTCATGATGTGATTTCAGCGTCCACGGCAGGTT
GCGGGCAAAACCGTGCGCAGGCAGACCTTGTTGTGCCGCCGGACCAAACC
ACGGCCAGCAAACCGGTACGCCACCGCGAATAGCGACGCCATTTTTGAAC
GGTGTGTTGTTGCTCAACCACAGAACTTCTTCTTCACCCGCAGGTTTCCA
CGAGAGAAGGTGTGCGCCCTGTAATGCAAAAGAGGCTTTTACCTGGGGAT
GATCGACCACAATGAGGTCCAGTTCATCCAGTTTACGACGGGAGAGGACA
GGGGAGATTTGTTCGATGACCGGAAGGGCAAAATTTTCTTAATCATGAC
GCAGTCCTTTAACTTCATTTTATCAGGTAAAAAAAAGAGCGACCGAAGTC
Contig 37 (300 bp)
ACCTGATCAGGCTCTGCACTGTGTTCATCAGCGGAGCCGAGATATTTGAC
CGCCCCATGCATAACGGAAAGGCGTGGGTAAACCCCGGGCGCGTTCCTT
TATCAAGATGACGTTCGAATATTCCGGCAGGTGCAGTTTGTTTATTCCAG
AAAGGCGTTGAGCGCGTATGAATATAATTCTGTGGGATTTGAAGCATCCT
TTTCCCTCCTTCGGTGAATGCGCTGAAAACGGCTTATTCCAGCCGGTTCA
GGGTACGCCTGATAATTTGCATTTTAAATACCATTTATTGGGTACTTTTT
Contig 38 (450 bp)
ATCCTTTTGGGGTCTGGCAATTACGCAATAAAGAAGGCCCCCATGCGATT
AAAGTCACCGGCCCACTGTCGTCTAATCATGGAGAAATTGTCCATCAGTG
GGGTCTCGATGGGCAGGGGATTGCTCTGCGTTCCTGGTGGGATGTTAGCG
AAAACATTGCCAGTGGTCATTTAGTGCAAGTGCTACCGGAATATTACCAG
CCAGCGAACGTCTGGTCCGTTTATGTTTCAAGGCTGGCGACGTCAGCGAA
AGTGCGGATAACGGTAGAGTTTTTACGCCAGTATTTTGCCGAGCACTACC
GGAATGTTTCACTGTTGCATGCCTGATTTATGATTCAATTATCGGGTTGA
TATCAGTTTAAAACCTGATTTTCTCCTTTCTAAGCCGCTACAGATTTGGT
AGCATATTCACCTTTAATCGCGCATGATCTAAAGATAATTGAAGAGGTTA
Contig 39 (450 bp)
AATGTACTGGCAAAAAGCCAATGGCGAAGCGTGGGGAACGTTACATGCTC
TGCTGGCGGATATTAATAGTCAGGGTCAGGTGCAGATGGCGATGAACGGC
GGCATCTATGATGAAAGCTATGCGCCGCTCGGTTTGTACATCGAAAACGG
TCAGCAGAAGGTGGCGTTAAATCTCGCTTCAGGTGAAGGGAATTTCTTTA
TCCGTCCTGGCGGCGTGTTTTATGTCGCGGGAGATAAAGTCGGCATCGTT
CGTCTGGATGCCTTCAAAACCAGTAAAGAGATTCAGTTTGCGGTGCAGTC
AGGGCCAATGTTGATGGAAAACGGTGTAATTAATCCGCGTATTCATCCCA
ACGTCGCCTCAAGCAAAATTCGTAACGGTGGTTGGGATTAATAAACATGG
GAACGCCGTGTTTTTGTTGAGCCAGCAGGCAACAAATTTTTATGATTTTG
Contig 40 (400 bp)
GACATTAATCATTTCAAAATCAAAGCCCCGGTTTTCCATCGCCCGTTTGG
TGGCGTGGCACTGAACGCAATCGTTACGAGTGTAAATAGTAATGCGCATG
ATTCGTATTTCCGTTTAAAATGAAGATACGGCGCGATGATACGCGTCGGG
TTGTCTCTCTGTTGATACAGAGATACTAGATGTAGTTGAAAAAAGATTCA
ACCACACAATATATAGCCCAGTAGGGGTCGAAATTACCCTGGATATGAGC
GTGACGGGGTAGGGGATTTTTGTGATTCACCAGGCAAAAAGAAACCCCG
AAGACAGGCTTCGGGGTCAAAGACGCGTATTTATTATCATTTTTGCACTA
CGATTTGCGCATGCTTAACAGTGCGCCGATTAAAATATCTACCGCAGCTG
Contig 41 (500 bp)
GCAAAATCACGTCCGCGACCTGGCGTTGTCGCTGGGCCATATTGGCAAAG
GAGCTGGATTGCGGTGCCTGCAAAGTGCCCTGAATAATGCCATTGTCCTG
TACCGGGAAGAAACCTTTCGGAATGAACACCCACAGCAGCACGCTAAGCA
GCAGCGTGCTGAGTGCCACGCTTAAGGTCAGCCACGGATGATTCAGCACT
TTCGCCAGTCCACGACCATAGGCGGCGATTATCCTGTCGAACATTTTTTC
CGAGGCACGGGAGAAGCGGTTCTGTTTACGCAACGACTCCTGGCTGAGCA
TCCGCGCGCACATCATCGGTGTCAGGGTCAGCGACACCACCGCTGAGATC
```

Fig. 6, contd.

AAAATCGCTACCGCCAGGGTAATAGCAAATTCGCGGAACAGTCGCCCGAC
GATATCGCCCATAAACAGCAGTGGGATCAACACCGCAATCAGTGAGAAGG
TCAGCGAGATAATGGTAAAGCCGATTTCACCTGCGCCCTTGAGCGCCGCC
Contig 42 (400 bp)
AGCTATCTACGGCAAAAGGCACGGTAGTCAATTTCGTTGTTAAATACATC
AAGCGTTTGGCGCCGAAATACCATCTGCCAGATGCCATTTCATTTCGTAG
CGCACTGCATAACGGCTACCGGATGCAGTACGTCAAACCCGAACTGGGGC
CGGAAGGATTTAGCTTTTCTGCAATACACCGGCGGCACCACTGGTGTGGC
GAAAGGCGCGATGCTGACTCACCGCAATATGCTGGCGAACCTGGAACAGG
TTAACGCGACCTATGGTCCGCTGTTGCATCCGGGCAAAGAGCTGGTGGTG
ACGGCGCTGCCGCTGTATCACATTTTTGCCCTGACCATTAACTGCCTGCT
GTTTATCGAACTGGGTGGGCAGAACCTGCTTATCACTAACCCGCGCGATA
Contig 43 (450 bp)
GATTAGCGCCAGATGCTCGCCATCGAAAAGTTGAATCAACCCCAGCTGCG
GGTAATAAGTGCGCGTACGAACAAATTCAGTATCCAGGGCTATCGCCGGA
AAGGCACGGACGGCTTCACACAAAGAAGCCAGCGCATCGTCCGTGGTAAT
CATTTGGTAATTCAAATTGTTTTCTCTTTAGTGGGCGTCAAAAAAAACGC
CGGATTAACCGGCGTCTGACGACTGACTTAACGCTCAGGCTTTATTGTCC
ACTTTGCCGCGCGCTTCGTCACGTAATTCTCGTCGCAAAATTTTTCCGAC
GTTAGATTTCGGTAACTCATCACGAAACTCCACCAGCTTCGGTACTTTGT
ATCCCGTGAGCTGACGGCGGCAAAAAGTCACCAGTGACTCTTCGGTAAGC
GATGGATCTTTTTTCACTACGAAGATTTTCACCGCTTCACCACTGGAGCC
Contig 44 (750 bp)
GAGCAGCCCGCGTGATGACAGGCATGCGCCCGCGTCGGCTCTCTCTCTCT
GGTGCACTGAGTCACAGGATGGCGGCGGTGGGCGCGGTGGTGGAAGCGGT
CCTGGAGGGCTCGGGAGGGAGGATGCGCTCAAGCTGGCTCCCCGTGGGGC
TGGCCCGGAGTAGCCTCCGTGAGGGCACCGTGTCTGCTCCCAGAGCCCGC
TCCCCGGCCTGCCCTGCCTCCCTTCCCTGCCCCAGTTCCCCCGGAGCCCC
TGGATCCCGATGGGAGGCGCCCCTGGGGAGAGGGGACCAGGGAGGGGCCC
AGAGCTCTGAGGCCACCAGACCTGGCCAGGACCCTTCGTGGGAAGAAGAG
GTGGGCCCCAAAGGCACCTAGAGAGAGGGAGGCTCTGCTGGCTGGGGGGC
CTTCCAGGCGGGGCTTCCAGGCAGGGCCAGTGTCCTGGGGGCTGGAGGGA
GTCCCTGCTGCTGGGGGGCGGCAGGAGCACCTGGGGCGTCTGGGAAGAG
AGCGGGAGGAGACTGGAGCCAACTGGGGGGACAGAGGAGGGGTCCAACCC
CAGCGGTGGTGTTGGGGGTGCTGGTGGTGGAGGCCCTGAGAGGCTGTGCT
GGGGGGCAGAGCGGGTGCTGGGAGGGGAGAAGGGGTCCCCAGGGCTCATG
GGCCCTTCGCAGCAGTGGCAGTTGGGGTGGGTGGCTGTCTCTAGGGCTGT
ACCACGGTGGGTGCCTGGAGAAAGAGGTCCTACCCCTAGTCTTTGCTGCA
Contig 45 (300 bp)
TGGGGACCCCACTCCAGCCCCACTGAGTGACGCGCCCCCCTGTGGTCCCA
CCGCCAACCCTGCCTCACACCAGAGGGGCTGTGGCCACACCTTGTCCACA
GCCTGTCCCTGAGACCACGAGCCCCCGGGCTCAGCCCCCTCCTCACCCCT
GGACCGAGGAGAAGCCCCCACCTGGGCTCAGCTCTTGGAGCTAAACTTCC
AGGAAGGTTCTGGTGCCCTCGGGTCTTAGAGCATGGTGGGGAGGGGGATG
CTGGTGGGGCGCAAGCCCTCCCCACATTTCGCACTCGACCCGGTGGGNG
Contig 46 (300 bp)
CCGGCTAGAAGCCACGAGAGCCCCAGGCCCCGCCCGACGTCTCTCCTGC
AGGGATTCGGCAGCCCTGGGGCCACAGGGCCTGAGCAGACCTTGGGGTTC
CGGTGTGACTCCAGCCAGGGTCCCTACTGTGTAGGCACCAGGGCAGAGTC
AGCCCTGGGACCATGGCCACAGCTGCTCCCGCCTGAGCCGGGCCCCCGC
CCAGGCTGGGCCCCCTCAGTGCACTGTCCCAAGCCAGCTGCTCTCCCCAC
CTCCACCTTCTCCATCCAGGTCCTGCCCCACGGCCTTTGCTCAGGCCCAG
Contig 47 (500 bp)
TTGACTGGCACTAGCACGAGCTCTGTACCCGGGGATCTGGGCTCGGGAGA
AGGGAGACCCCCCACCCGGCAGGCCGAGGGCGCTGTCACACCATGACTCT
CAGCCTTCCCCACCCGACGGACAAGAGTGACCCTCTCCCAAGCCCCCACT
CACCCAGGACCGCACACCCCGTGAGTCCTGCGAGTGGGGCGGCTCAGGG
GCCCCGAGTCCCAAAGGAGTCTGCTGGCCCTGGGGGGAGGGGAAGCAGC
AGGGTGGTCACGGGTCTCCCTGGTTGGCAGGACCACAAGCTCAGCCCGCT
GCCTCCCAGAGGGCAGCCGGACACCAACCAGTCCGGGGACCCCACGTACC
TCAGCTGCTGCAGGTGCCCCTGCCTGTACTGGTGCCAATGGGGCCGCTGG
GTGCTCCATGGACAGCTCGCCACTCATCCCAGCCGCCTACCCCCCTTCC
GGGTCCAGTGTCCGGCCGGCCACCCGCCTGCCCAGCCCTGGCCTCCTCTC
Contig 48 (500 bp)

Fig. 6, contd.

```
GGGGTTGCCGCAGGCTGCTGTGTAGGTCGCAGACGCAGCTTGGATCTGGC
GTGGCTGTGGCTGTGGCTGTGGCTGTGGCATAGGTCAGCCACTGCGACTC
CGATTTGACCCCCAGCCCGGCAACTCCCACATGGCACAGGTGCAGCAGGG
AAAATAAATAAATGAAATAAAAATAGGTGAAGACAGTGGATTTCATCTCT
TGGGGTTGCGGTAAGCTCTACACAATAGGGAGTTTACCATTTTACCTGTT
TCAAGTGGCACTGAGTCAGCTCACAGTCCTGAGGGCCCACAGATGCCGTC
TGCCTGGGAGATTGTTCCTCTCACCACACTGCCCCTCTGTCCCCACTAAA
TACTCACTGCCCTCCCCGTCCCAAGGGCCCCTGCCCCACCCTCTGCTTCC
TGTCTCTGAACTTGCTGGCCACCAGCGACCGTCTGGTGACCTCACTCTTC
GGCCCCATTTGTCGCACACCCCACCTGGCCTCTCCCCGGCATGGGCAGAN
Contig 49 (600 bp)
GGGATATTTGGGGGCATATTTGGGGGGGAGATCCCCACAAGGCATTTGGG
GTTTGTGGTTTGGAATGCCCCCGGGCCCGATGGAGGGGGCCGGGGAAGAA
TCTAAGCCTTACTTGGGGAGGGTTGGGCCCCGGGGCCCCGGGCCGGAAAT
GCCCCCAAGACAGAAGGTGTACAAAATTTCTCAAAAGGGTGACCCTTAAT
GAAACGGGTCCCGGTTGGAAAGAGGTCACCAGGGTGGATTGGTGGCACCG
CAGAATTTACGACATTTTGGCTCTCTTCCAATGGCCGGACGCCTGGGGAT
AGGCGCCCCGTGGACGGCGGGGTCTCGGGTGGGACGGGCGGTCAGGGGT
CGGTGACGCTTGGCCTCTCTGACCGCCTCCAGCTCCTTGGCGAGCGTGCG
AGCGCGGCGGGCGCGCAGGAGGGCCGCGCAGGCCCCTGCGCAGGCGTTGG
GCGGACTGCTTCCAGGTGTCATAGCGGAAGAACTTGCCCACGGGTATCT
GGGGAAGTTGTCCTGAGAGGGGAAGGGCCCGTCAGGGGGGGCCTGGCCC
CCCAGCCCCTGTCCCAGAACAACAACCTTTGCGGGGTCCTCCTGCCTGCC
Contig 50 (179 bp)
ATCTTCATATTCATGCAGAAGACACTCTCCTGCCTTTCTATCTTGGGGAA
AAGGACGATGTCACTTATGCAATAAAGCCCACTTGCTGGCCGGGGCTTGA
CATTATTCCTTCCTGTCTGGCTCTGCACCGTATTGAAACTGAGTTAATGG
GCAAATTTGATGAAGGTAAACTGCCCACC
Contig 51 (500 bp)
CTCGGGCTGCTTCCAGGGGGCCTTGGGGAGCCATAGAATGCTATGGAGCA
AGAGAGTGCTATGGTCAGACGACTTTGGGGGAAGGTCTGGGAGAAGAGGG
GTGACTGGCCACTGTGATAAAGAGTGGGCGCTTCCTTGAGATAACACGGT
GGGCAGCCGAGGTGGACCTGTGCAGGTGGAGAAGGCCTCCTGCCGCGGCC
AGTACGTGGCTCTGGGCTGCCGGACACGAGAAAGCCCACCTCCACGGCTG
CCTCCAGGCGGCCCTTCCTCTCTTCACACCGCCGGGCCATGCCCAGGTGC
AGGTGCCATCAGAGGGTGCTCAAGAGAAGCTCTGGGCTGGGGTTGTCCCA
GGTCCCGGAAGCCCCGTGTCCCAGGGGCCACCTGAGGAAGCGTGGGCGCA
CAGAGACTGTCCCTCGGTGCTCAGAGAGGGTCCCGTCCCCACGGCAACGA
CGCCCAAGGCGGAGGTGGTCAGAGGTCTTGGGAGGGAGGATGGCCGCGCA
Contig 52 (900 bp)
TGTGTTGCACCTGTTGCTGCCTGTCGACTCTAGAGGATCAATACTCCTTA
CATAATTAAGGAGAACAAAATGGAACTTAAAAAATTGATGGGACATATTT
CTATTATCCCCGATTACAGACAAGCCTGGAAAATGGAACATAAGTTATCG
GATATTCTACTGTTGACTATTTGTGCCGTTATTTCTGGTGCAGAAGGCTG
GGAAGATATAGAGGATTTTGGGGAAACACATCCCGATTTTTTGAAGCAAT
ATGGTGATTTTGAAAATGGTATTCCTGTTCACGACACCATTGCCAGAGTT
GTATCCTGTATCAGTCCTGCAAAATTTCACGAGTGCTTTATTAACTGGAT
GCGTGACTGCCATTCTTCAGATGATAAAGACGTCATTGCAATTGATGGAA
AAACGCTCCGGCATTCTTATGATAAGAGTCGCCGCAGGGGAGCGATTCAT
GTCATTAGTGCGTTCTCAACAATGCACAGTCTGGTCATCGGACAGATCAA
GACGGATGAGAAATCTAATGAGATTACAGCTATCCCAGAACTTCTTAACA
TGCTGGATATTAAAGGAAAAATCATCACAACTGATGCGATGGGTTGCCAG
AAAGATATTGCAGAGAAGATACAAAAACAGGGAGGTGATTATTTATTCGC
TGTAAAAGGAAACCAGGGGCGGCTAAATAAAGCCTTTGAGGAAAATTTC
CGCTGAAAGAATTAAATAATCCAGCGCATGACAGTTACGCAATGAGTGAA
AAGAGTCACGGCAGAGAAGAAATCCGTCTTCATATTGTTTGCGATGTCCC
TGATGAACTTATTGATTTCACGTTTGAATAGAAAGGGCTGAAGAAATTAT
GCGTGGCAGTCTCCTTTCGGTCCATAATAGCAGAACAAAAGAAAGAGCTC
Contig 53 (450 bp)
CCAGCCACCAGCTGGACCCTCCCGGAGAGGGCTGCCTCCTCTTTCCCGC
CCAGACGCCCCCAGCAATCTGTGGCCAAGAGGGAGTGATACCGAAGATG
GCCACATGGGGCGCCAGCCCACAGGGAACCCCAGGAAGGCGCTGGACCG
TCAGGAGTCAGGGCTGCTGTGCACCCATGTGGCCTGGGGACTTTCCACAG
CCTGGTGGAGATGGCCGGGCACACCGCTGCCTCGGGGGAACGTGCACACG
```

Fig. 6, contd.

```
GGTGGTACATGTGGCCGGAGCCCAGGGCACAGGGTGAGGGGAGAAGGGAG
CATGCGGGTGCAGACTCGGAGCCCGCGCGTGAGGTGCTGGGTCCTCAGGA
CACGCTCTGGGAGTGGAGGACCCCCATCCACGCCCTCACCCAGTGTGTGC
CCGCCTGCTCCCCCGGAAACCCTCACAGACACGAGGGCACACCCAGCCCC
Contig 54 (1133 bp)
ATGGCGCTCATTAGAATTCGACCTCGGTACCTTGGGATCTTTTGACCCCT
ACCTCACGCCATCTACAACATTTACCTCCGAATGAATGAGAGACACCAAA
AGCAAATTCATAGAAGAGAAAAAAAGGTAACCTGGACTTTAAAAATGTAA
ACTTCTGCTCTTTAAAAGGCAGTGCTAATGAAGTTCAAATACAAACCACA
GACCATAAGAAAATACTTGCAAATCTTGTTCTGACAAAGACTAGTGTTCA
GAACATACGACGATCAGGGAGAGGAAAACCAGCAATCCTATAAAACTGGA
CAAAGAATTGGGGGGAAAAAAAACCCACTTGGCCAAGAAGTTGGTAAATA
AGGCCATGAAAACATGCTCAACATCATGAGTCATTAGAAAAATGCAAATT
AAAATTATAATGAGATACTACTACACAGCTATTTGAATGGATAAAAAATG
TTTTAAAAACTGATTATACCCAGGTTTGGCAAGAACATGAGAAACGAGAT
TTTCACACACGATTGGTGGAAAACAGAAATGGTCCACCCACTTTGGAAA
AGAGCTGGGCACTTCCCTCAAAAGTTAAACATACATCCAGGACCTCACAC
AGGCTTTCCACCACAGGTGTTTATTCCAGAGACATGAAAGCGCTCATCCA
CACAAAGACTCGTAAATGAAGGTTTATAGCACCGTTTGTGGCCCGAACTG
AGAAAACCCAAATGACCTTTAACCAGAGAATATCTAAACAAAATATCCAT
TCACATTAATCACCCATAAGAAGGAACGGGCTATGGGGACGGGAACCGTA
TTGAAGAGGGTCAAAATACATACGCAGCATCAAAGAAGCCTGCCCAAAGG
ACACACACTGCAGGGTTCCATGGACTGAAACTCGAGAAGGTGAAAACTCG
CCAGCAGTGACAGAGAGCAGGTCCGAGATCAACCTGATGTGGAGGAAAGT
GAACCCTCGTGCGTTGTTGGCAGGACTATAAACTGGAGCAGCCCCTACGG
ACAACAGTAGCCCGGGCTCCTCCTCCATCTCCCTGGGGAGCCTGAGCC
TTGAGACGCTGGGGCAAGTGCACGGCATGCTGCCTCACGTGGGGCCCCGG
TGAAAACACGTGGCAGCTGGGGAAAGAATCGTA
Contig 55 (735 bp)
TACTGCCTGTCTCTATGGACTTGACTCCTCTCGGGACTTCATGCGAGGGA
TCTTACAGAATTTGTCCTTTTGCATCTGGCTTGTTTCACTGAGCATCGTG
TCCCCAAGGTCCATCCATGTTGCAGCCTGTGTCAGGATTTCCTTCCTTTT
CAAGGCTGAATAGTACTCCACTCTGCGGATGGACCACGTTTTGATTATCC
ATACTAGTAAATCCATACTAATAACTTGTTCACTGAAGCCCACAGCTTAT
GCTACCTTCCGTGGGCTCCTCCCTGCCCTGTCTCTACGCCTTCTGCTATA
GCCCCATCCCCTCTCATCCAGGCCACGCCTCCTGTCCCTGGACACTGTC
CCAGAAGCCAACTGCCCTCTGACTGCTGCTCTCGCGTGACGGAGGACAAG
GCAGGCTCAGGGGTCCACGGGCTGGGGCCCCAGGGCTCCCCATGGCTGGT
GCCCCTTCCTGATTCCAGAAGTACAGTGGCAGCACCAGCTTTCCAGCTGC
CCCACCTTCTGTCCGCAGGCTGCTCGGGTGGGGGCAGGTGGGCAGTGATG
TCACCTGCTGTAACCACCCTACCGTCGCTCATCCCTGTCCAGGAGGTCAC
GGTGACCTTGGCAAACATTCTGAACAACACACACCTCCCTCTGCTTAGAG
GCCGGGGGCCTCCCCGGGTGACTGGGGGCACAGGCTGACCCCAGCCTGTC
TCTGTTCTCTGAAGGACATGATAAGTACTGCAACA Contig 56 (500 bp)
AGGAAGAACAGGAAACAACGGGGTTGAGGAGAAGAAACGGGTGTCTGGCA
GGGGCACGTGCCAACGGTCCACCGGGTGCTGCCGCGCTGCGGCCTGGCGC
CAGAGGGGGCAGCTCCGCCCCTCGGGCCGCGCCCTGCCGCTTGTGCTGGC
TCGCGGCTGGGCTCTGCTTGGCTGGGTTACAGCTGGGTGCAGCCGCAGGC
TGTGGTGGGTGCCGCCGGGTCAGCCAGCCCGGCCCCACCCGGCCCGTCTC
GCCGGCCTGGCCCGGGCAGCCCTCCTGCAGTCGAGGAGTCGCCCTGACGG
GCTGATTGGTCCACAGCCTCAGATGCAAACCAGCCCCACGTGCCTGGAGC
CAGCCAGCCCGGGACACCCTGGTGGAGGCAGGAAGGCAGCAGCCTGGAGA
GCCGCGCCGGATGATGCTGCGGGGAAACCGGGCTCCCGCCGGGGCGCCC
TGGCTCTGGCCAGGCTTGGCTTGAATGCTGACGTGAGCGGTGGCCCTATA
Contig 57(500 bp)
TGGCGTTGCAGTGGCTCTGGCGGAGGCCGGCGGCTACAGCTCCGATTGGA
CCCCTAGGCTGGGAACCTCCATAAGCTGTGGGTGCAGCCCTAAAAAGCAA
AAACCCCAACATATATATATATATATATATAATTATGGTAAAATACA
CATAAAATAGAATTTACCTTCTTAATAATTTTCAGTGCACAATTCAGTGG
CACTAAGCACATTCATGCGGCCGTGTCACCTGCTCCAGAACTTTCCATCT
ACCCAAACGGACTCTCCGCCCCATGGAACACGCCCCTGCCCCTCCCCCG
GCCCTGCCCCGCCAGCTCCTCCCTGTGTCTGTGGATCCGGCTCCTCCAGG
```

Fig. 6, contd.

```
GACCCCGTGCGTGGGCTCACAGAGTGTGTGTCCCTCTGTGACCGATCGTC
GTGTCCCCGAGGCCCGTTCTGTGGCAGCTGCGTTATGACCGACTACCTTC
GAATGCTCAGTGACTGCCGTGCATTGGACACGCAGTCCGCTACCCTTTTC
```
Contig 58 (550 bp)
```
TGCTTTCTGTGCCCCCCTCCAGCTTGGGACCCCAGCAGGGCAAGGGGTGT
ATAGGGCTTAAGGAGGCAGGGGGCGTCTCCTCCCGCTGGCTGCCCAGAGC
ACCCCCAGCCCCGCCTGCCCCTCGTCCATCTCCAGCCTGTCCTTTCCTGT
GCCCTCCCTGTCCCGGGCGGGCCGCACACTGGCTTCCACCTCCCCACCCA
ACTGGCGGCCCGGTCCTTCCTGCTGAGGCACCCCGAGGTCCCCGCTGCTG
GGGACCAGCTGGCAGGTGGGTCCCACTGCTTTCTCAGCGTGGGCTTTGGA
GGGGGGATCTGCACATACCATCCCTTCAGGCCCCGTGGGGAGCCTGGGGA
CCATCCGGGACCCCTGTGGGCAGGCCCAGAGGACTGCCAGGAAGAGACCC
AGGGGACCAGGCAGCTCCCAGGCCTCTCAGCTTCAGGCCAGGGGAGCCCA
CCCCCAGGTGGCAGGTGAAGCCAGGCCCCCAACCCACAAAACTGCCCGCA
GGGAAGTAGGAGGGACAGGAGGAGGGGAGGCCAGGCCCGGGCCGCCCTTG
```
Contig 59 (800 bp)
```
TGAGGAGCGCAGGCCCAGGCCTGAGTGTGCCCAGCTTACACCCCTGGCAG
CTTCGTCCCTCCTGGCCCTAACCCCCATCCTACCCCAGCAGCAGGGGCTC
CCCCGGTGGGGCCTGGTGAGCGTCTGACTGGGGTTTGGAGTCAGGTCTGC
TCCAGGCTCAGCCCCCATCCCCAAGGGTGCCCTGCAGCACTGCTGCCCAC
CCCCTAGCGCCCCCAGACCTTCGCCCCTCCAGCCTGGATGTACCCACGGA
CCCTGAAAAGTGGGGCTGAGCAGGTGCCCTGGCTGGAGTCCCCCTGACTT
GGGGCTGGCCAGGCTGCCCTGGAGGGGCTGTGGGGGCACAGCCTGCCCCA
GGGGCCCGCTGGGCACTGGCTCTGGAGCTGACGACAGGCAGGCCCTCTCT
TCCTGGCGGGGCCACACCCTGCCCTGGGGTTTGGGGCCAAGGCGGGCACG
CCCCATGTCAGGCGGGGGCGAACCAGGTAATTACAGCCTGGCAGCCCGCT
CCCCAGACCCCCAGCCCCGGAGGGCCCCCACCCAGGCTGTGCCACCAAGA
CCTGGCATCCAGGGCCCAAAGCAGGTCAAGGGCAGCTGCTACAGATTCTT
TTAAGTTGAGACAGAATCGACACATGACAAGTTCCTGGTTTTAGGTACTT
CGCTGCCGGGGCCGCCAGTCAGTTTAGTGACCCAGCACACCCCACACAGG
TACAATTGCTCTTCTCAAAAGAGGCCCCTGAGAGAGCGCCTGTCTTGGCT
CAGGGGTAATGAGCCCAATGGGTATCCATGAGGTTGCGGGTTCCATCCCC
GGCCTCGCCGCGTTGGTTA
```
Contig 60 (500 bp)
```
GGCTCAGGAAGCGCAGGGGCAGCGTGTGGGGCGACGGGAACCATGGGGGT
CTGTCTTCCCGCCTCTCCTCAAGCCCACCGCCCTGCTGCCCACCTCCGAC
TCTGCAGCCAGCATGCCGGCTAGAGCCCCTGTGCACCCAGCTGGTGGCCT
CTGGCTAAGGGCAGTGCTGGCTGTGGACGCGTGTCCCCTCCCCAGCAGCC
CAAGGGTCCCATCTGCCAGGCTGGTGGCTGAGGTCTGCCCTGTGTGGTCC
TTGCAAAAACCCCGCCCTCTCCTGCCCCTTGAGGCGTGAGGGAGACGCGG
GCTGGGCGGATGCCCTCGGGCACAGCCGCCCGCGGTGGCGCCCTGTCGAG
GAGGGGGCTCCGACGTGCCCTGACGGCCCTGGCCGGGCGGAGAGGGTGAG
GCCACCTCCTGGCCACGTCCACCCAGCTGCCACGCCGCCTAGCCAGTGGC
CCGGGGCCAAGTCAGCAGAGCCAGGCTTCCGACAAGCAGAGGCTGTAGGC
```
Contig 61 (700 bp)
```
GATGAGGAAGCCGCTGCTCGTGCTGCTCGTCTTCTTGGCCTTGGCCTCGT
GCTGCTATGCTGCTTACCGCCCCAGTGAGACTCTGTGCGGCGGGGAGCTG
GTGGACACCCTCCAGTTTGTCTGCGGGGACCGCGGCTTCTACTTCAGTAA
GTAGCTCAGCGGGGCACGGGGGCGGGCGGACACAGCAGGTGCTCCATCG
GTGCTGCCCCGGTACCTGTGCGGGTCCTTCGGGATGGATGGTGTGGGGGA
CGGGGGGCGGGGGGCGGCCAAGGGAGGACCTCTCCTCCGAGGGTCTGAGA
CTTCAGACCGGGGGCGCCCTGGCCGTGCGCATTGATTGGCACCTGCCATG
TGCCTGGCTGGGGCTCACACCCCCTGACGTTCCTGCAGCGTGACTCGAAA
CGGGAAACCGAAGGGACGGGTGGCACGGGGTGGGGAGGCAGACCGTGAGT
GGCAGGCGTGCGAGGGGTTCTTTCGGGCGGGGTGGCCCAGGCAGGCCCCA
CAGGATGACAGCCTGTCCCCTCCTGCTCCTCCTTGACCTGCCCACAGCCA
GGGCTGCAGGCACTGACATTCACCCATGGTATTGTGGTGCCTTGACGTCT
TGGCAGTGGGCATTGGGTTCATGGACTGTTTGGATTGAAAAGTGGGAATA
AGATGGGGTTTGAAAAACCCAATTAAGAAATAAAAGGGCGCCCTGTGGGC
```
Contig 62 (300 bp)
```
TTTGAAAAATTTTGAGTCAGTGCAGAATTCGCATCTATTCCGCATTCAGG
CTCTCCTGTTCTCACCTTGCCTTAGTGCGGATCTTCTATAACCACCACAG
TGACGTTTTCAAGGTACTTTATTGAATAATAAGAAAAAAGTGCACACAAT
CATGTAGTTAACTTTCTGTGCTCTTTGCCAGTTTGAAGGGACCCTCTTTT
```

Fig. 6, contd.

TTTCCTTTTTAGGGCTTCGCCGACGGAAGTTCCCGGGCTAGGGGTTGAGT
CAGAGCTGCAGCTGCTGGCCTACAGCACAGCTCTTGGCGGCGATGGATCC
Contig 63 (450 bp)
TCCTGGGCCACAGGCTGCAGCAGCTCACCTGGGGGCTGGGGTCTCGCTCT
GCGGATGGACCCATGAAGGCCGGAGCCAGGTGGGGGCCGAGACGGCAGGG
CAAAGGGTCTGCACACACAGCGTCCCCCCGACCCGGCTTCTCTGGGTTCT
TGGGGGGTTGGCGAGGCTTCTCTCAGTCTGGGTTTCCTGGGGAACTTTCA
AGAACTGGGAAGTCTTCCAGAAAGTTGGGGTGAGGGGAGGTACCCCCAAA
GTGCTGCTCCTGTCCCCATCCCCCACCCCGCTGTCCATCGGCGAGACCCC
GGACCGCCGTCTCCCTGCCGAGGTGTGGGGTCCCCCCCTCTGCCGGCCAG
GCTGGGCAGGGGTGAGCGCCCCCTGCTCTGCACTCGGGACTCAGCCTGGG
GAAGGCGGGCCCCAGGAGGTCCTGGCCTGGACGGCAGTGACCTTCCACCG
Contig 64 (500 bp)
TGTGCATCCAACCCCAGTGGCCACGGGGGGTGACCCTCGGCCGGTCAGCC
GCCCGCGTCTCCCACGGAACCGGGCCTTGGCCTGAGGCAGAAGGACCCAG
GACTCCATCCCTGCCCCGGACTCTGCCGGAGGGTGCGGTCTGCACAGAGA
CCCTCTGGGGGTGAGGCCGGTCGGGGCTGGGGTTGAGATGGGATGGTCAG
GGCGGCCCCGCGGGCCTGCAGGAGGCTGGGTGAAGGAGGGGCCCAGCT
CAGACGCCCCCAAACCTAGCTTGGGAGAGCTGCAGCCCCGCCCCGTCAAT
CGCGACAGCCTGCCCACAGAAGGCATTCAAATGAGAGACAAATATTTGGG
CTTGAAGACTATACCCAGCCACGTCTCTTTGGGAGCCCAAGCTGCTCCCA
GGCCCTCATTTGGGTATTAATTGGTTTTCGTTTAGAGATTTGCATGCTTA
TCAATGGCCACTGGGCGGCTGGGCCTGGATGCGGTCCCAGGCTTTGTATG
Contig 65 (661 bp)
TCCCACGACCTGCCCCTCCAGGGCCACATCTGGCGACACCGTCGCAAGAG
TTGGACCGGCCTGGTGTGGCCACAGCCTCAGGCCTTGTCTGGCCGCCCAG
GCCGGCTCCAGGCTCCAAGGAGCTCCTGCCTGCCCTCCGGAACCCCAGCA
CCCCGGGCCCGCTTCCCCACCAGACCTGTTTTTCCAGGTCAAGGTCACAG
CTAATTTGGGCTTAAACTGGACAAGGAGGCCTTATCTGGAGCAGGCTCCC
GGCCCTTTGGCCTCTGCCCTGGTGGGGAGGCCTTCCCAGAGGCTGTGTGT
TGGCGCTGACCGTGCAGCCCTGAGCTTGAACCCGGATAAGGAGGGACCCC
ACCTGGGCTGGAGCCAGAGAGCCCTCGTTCCCCAGCTCCGCAGGGTTCTC
ACAGTCCCGCCCCTGCCCTGGGGACCCTGGACGTCCCCAGCAGGTGAAAG
GTCCAGATGCCCTCTGACTAGAGGCTCCTCCGCTGTCAGACATGCTCCCT
TCCCGCACCGAGGACGAGACCTCAGCAGCCCTGCGTGGCCTCGGGTGCGG
ACCCCAAGGCGTCTCTGAGTGTGTTCTAATGGGGAGCCGTGGGGCCTCAA
CAGTGGGGGTGGCACTTGGAGGGGAGCCTCCCCACAGCTGCCCCAAGATG
GGCCCTGGACT Contig 66 (500 bp)
TTTGTTGGATGAATGAAATCATGAGAAAGTGATTGGACCGCCCCGTTCGT
CCAGCTGCTTGCCAGCTGCTTTGTAAAGATGACCTCTCACCTTCTCAGAG
GCCTGGCCGGCCCGAGGTGGCAGTCAGCTGAGATGCCATGCTTGTTTGGC
ACGTGGGAGGCCCCTGTCCACGGCGTGGGTGCCTCTTGTGTCTAATCAGG
GTCAGGGGGAGCAGCAGGTGCAGGGCACATGTGGGGCCGGGGCCGATGTC
TGGGGAGGGCGGGAGGAGGGGGTGTGCGGAGGCCGTTGTGGCGGTGCAGG
GGACAGACCCCAGCGAGACCCTCCCTGGCCAGGCACCAGGACAGGTGATG
GGGGGCCGCCTCCGGGGCGTGTGACAGAAGCCTCTCAGAGGAGGCCCTCC
CACGGTCTCTGGACCATCAAGGGACCGGGGGCGCTGGGCCTGGGGGTCAC
ACCCAGCTGGCCGGCCAGCCCGGGTGGGGTCGGAGGCCCGGGCAGTTCAC
Contig 67 (550 bp)
GGGCAGGAGGGGCCCGGGGCTGGTGCGGAGGGTGGAGGTGGTGCAGGAGG
GTGTGAGGCAGGGCTCACTGAGCGTGCGCGGCTGGCTGTGCCCTAGAGTG
GTTAGCACGTGCCCCCACCCTCCAGTGTCGCTCTGTTCACCTGTGCCTGG
CTCACAGGTGTGGAAACTGAGACTCGGGTGTTGCATGAGCTTCCAGGATG
AGAATCAGCAGGCTTCCCAGGCAGGGCTGTGTCCGGGGCTCTGGGCTCTT
ACCAAGGAGGGGACACCCAGGGACAGCCCTGCTTGGGGGTGTCGGGCTGG
CCAGGCTGGGTGGTCCTTCCTGTGGCTGGCAGCCCTTGGCAGTCACCCCC
TTACCCTCAACTGCCCCTCAGCTGAGACACGACCTCCCTGCAGAGCCCTG
TCCACCCAGACACTCACTCGCCTCCTCCAGGAAGCCTTCCAGGGCTGCCT
CGCCCTGGTCTCAGCAGGAGACAGAGAGAGAGGGTGGGCCCAGGAGCAGA
GGCAGGCAGCCAGAGGGGAAGCCCAGGGGCCCTCACTCACCCCTGGGGCC
Contig 68 (500 bp)
TTTGCATTCAGCTCGTACCCGGGATCCTTCCCGGGGGCTCTGGGGGTGGG

Fig. 6, contd.

```
GGAATGGGGGTCAGAGGCAGCTGTCATCTGCCTGTCCTACCTGCTCTCAC
AGGCTGGCCCTGGAGCCCTGGCCTCCTCCTAGGGGCACATCAGGTTTTGG
GGGAGGCCCAGCCCACCGTCCCACCTCCAAGACCACAGCTGGGAGCCTGC
CCCCCAAGCCTAGACCTAGTGGGGCTCCTGCCAGCCAGGCCCCCACCTTC
ATGCTGCCACCCACCAAGGTGGGACAGTGCAGCCAGGACATCCAGCTTCT
GGAGCTGCCCGAGGCTCAGCACAGGCTGGTACCCTAGGGAGCAGGTCACC
CAGGGCCGCCTGGCGAGGCCTGCGGGGACGGGGGGTAGGGTGGGCAGCAA
AAGAACCTCTGAGCTGGGCCGGGCGGGGTCGGTGAGGGCCCGGGGCCGCG
GGCTGTGTGCGTGGCCCCTGAGCCCGTGCAGACGCAGACCCTGGGTGGGT
Contig 69 (550 bp)
TGTGCTGCTGTGGCTGTGGTGTAGGCCGCCAGCTGCAGCTCTGATTCGGA
CTCCTAGCCTGCGAACCTCCATATGCTGCTCTAAAAAGACAAACATAAAA
TAAAATGGGTGCGCTGTTAATTTGAACACTCTGCCTCCTCCAGAGACGAG
GCCGAAACAGGCCTCTCTGAAGGTCCCACCTGGCAGGGAGGAGGAGGCCA
GCCCCGTGGGGGGCAGAGAGAAGCCCGATGTCCCCAGACACACACGCACA
GGGACCGTGGCCCCGGCTGCCAGCCCCGCGGGGGGAGGGCAAGGCCAGAG
ACTCCCAGCAGCCCACAGGACCTTGGTGGCCACAGGACACAAACACAGGT
GACGGTGGGTGAGGCCTGGCCTTTCCCCCCCTGGGCACGAGCACAGGACA
CACAAGAGCCCCAGCGTGCTGACCGCCACGCCAAGGAGCCTGGATGAAGC
TGGACACCGAGAGTCCACACTGTGTGATTAGGCTGACGTGAAGTTTAAGA
ACAAGCGGGTGGCTCAGCGCTTGAAGGCCAGAACAAGGCCGGGAGGGCAG
Contig 70 (1300 bp)
ATGTCAGGATAGTAACCTGGGGTGCTGCAGTGACAATGCCAGATCCTTAA
CCACTGTGCCACAAGGGAACTCCTTGACCTAGAATCCTATACCCACTGCA
AATATATTTCAAAAAAGGTAAAGTCCTGAGCAGAAAAGCAAAAATGGGAT
AATTCATTTCTGGAAGACCTTCCTTGTTAAAGGAAGTTTTTTGGACGTGA
TGAAGGTAGAAACTCGGAGGCACACAAAGAAAGAAAGAAAGAGCAC
TGGAAACGGAGCAAATAAAGGTAAAAATAAAGTTCATCTCTTTCTCATTT
TTTAATTGCTCCAAAAGATAGCTGACCTCTAAAGTAAAAAATAGTGGAAA
TGTAGCATATGTCTCTAGCGTAATTTAAAGTATAACTTATAGCAATGATA
GCCCAAATAAAGGAGGAATTGAGAATATACAGTTGCTGTGTTCCCATTGT
GGCTCAGCAGTAATGAACCTGGCTAATATCCATGAGGATGCAGGTTCAAT
CCCTGGCCTCACTCAGTGGGTTAAAGGATCCAGGGTTGCAGTGAGATGTG
ACGTATGTCACAGACGTGGCTCGGATCTGGCATTTCTGTGACTGTGGCTG
TGGTGTAGGCCAGCATCTGCACCTCCGATTTGACCCCTAGCCTGGGAACC
ACCATATGCTGCTGGTGTGGCCCTAACAGACACAAAATAAAATAAAAATA
AAAGAGAGAGAATATACCATTGTAAATTTCCTCACATGACACAAAGAG
CAATGTGATATTATTTGGTATATGGTGATTGATTCAAGATGTATATCATA
ATATTGATTCAAGATGTATATATTCCTTTTCTAAAAAAGAGATTTATACA
ATAAGGCAAGAGTGAAAATAAAGTGGAATGCTAAAGAATAGTTAATCCAA
AAGAAGGCAGAAAATGGGGAAAAGCACATATAACAGATGGAACAAATAAA
AAGAGCTAATGAGATTGTAAAATTTAATCCAAACATACAGATAATCCCAT
TAAATTTAAACACTCTCAACACATTGATTAAAAGAAATTGTCAAATTGAA
TAAACAAAGCAAGACCCAACTAGATGCAGACTATGAAAAACCCACTTCAT
ATAAAGACATGGGTAGGTTTAGAGCAGAATGATGGGGAAACCATGTCACG
CAAACATTTGTCAAAATAAAGCTGGTGTGGCTGTATTCATCTCAGACACA
GCAGACTTCAGAACAAGAAACACTGCAAAGGATGAAAGAGATACTGCATA
ATGATAAAGGGATCAATTTTCCAAGTGCAGGCTCCAAACAACAGAGGTTT
Contig 71 (500 bp)
ATGACCTCATACTGAATCGAGCTCGGTATCAGGGGATCTCTCAGCTGGGG
GGGAGGGCAATGGGGCATTTGTCTGAGGATGCCCCAGGGCAGGCCCATTG
GCTGGTTTGGTGCCCATGCCCCCCCCACACCCCGGCAGTGCCCCCTGCTG
AGCCTGGGACCCCCTCTGGGAGTTAGGGATTGGGGGTGGGAACCAGGCTT
TGCAGTAATTCCAGCCCCCAGGGCCCTTCCCTCCCCGCCCTCAGGACCCC
CAGCCCCGCCCCACACAGTCTCCACTGTGACAGCCTCACCCCTTGGGTCA
AGTCCTGTCCTCTCCGGCCCCGCTGGGCAGTGGAGCCAGCTAGGTGAGA
GGCACAGGCCACTAGGGCGGTGGCACTGCTGAGGACAGAGGGGCCTGGG
TGGCCTTGGACGAGGCCCAGCGACGCTGAGACAGTGAGCCAGGCTCCAGG
CTTTCCCAGGGAGGGTCCCTGAATGTCCACTTCTTGTGACATCGGGTGAC
Contig 72 (550 bp)
AAGTCCATTAGGGAAGGGATTTGTGCAAACACAGAGACAGGTGCAGGGCT
GGGCCAGCTGCTGGGCTGGGGCTCCTCAAGGCGCCCGTAAACCCCTCCC
TGCCAGCCGCCTGCCGCCAAGGTCTGCTGTCCACCCCGGCCGGGCTGCTG
TGTTCCCGGCGTGTGTCCTGCGAACCCGACTCCCGTTCACCCCTGAGCAC
```

Fig. 6, contd.

```
TGCCTGGAGGCCGGCTGCCCAGGCGGGACGGGCCCTCAGGGCTGGGCTGG
CTCTTGGCCTGTGTTTCATTTCTGAGCAGGTCCTTCTCAGTGGGGGGGGC
CTTGGGTGAAGCAGGCATGTGCACCACTGGGGCCCTGTCCCCAGTGGGCA
TCCTGGGCGCTTGTCTGGCCCCCAAACCCCCAGGCCGTGTGCATCATACC
TTCACCCTGAGCCCCAGCCGAACCCCGGACATGTGCTGGGGGACCCTGGG
CACAGGGGTGAGGGAGCAGTGGCCTTGGTGGAAGCCCAGCCTTGGCACCT
GGGGAGGGGGTGCATCTGGCATGCTCTGCTGTAACCAAGCCCAGGGCAGG
```
Contig 73 (950 bp)
```
GACGTGCAGTAGCCATGACCTCTACGGCCCCCACTGACCAGCCCGTGTCC
TTGTCCCGAGACCGACCCCTAAGCAATAGGATGCAGCAGAAGTGACAGAA
CGGCCTCCGCGATGAGGTCGCAGAGGGCTCTGGCTCTGACTCAGGCCCCT
CATCCCTCGCTCTCCTGGAGCAGGGCCAGGTAGGGGCCCCCCAGAGACGC
CCTAGAGGAGGTGACGGGCAGCCAGCCCGCCCAGGGAAGGCCTGGGGAC
ACCAGGGAACAGAACGGCACAGGCTCCTGGCACAGTCTCCCAGGAGCCCC
CTGGTGGCACAGAAATCCTGACCGGCCCAGTGGAGGGGGCTGGGGCGGGG
CTCGGGGAGGAGGGACTGGGTGAGGCCGTCTGACTCCTGGCTGAGCGCCG
CATACTTGCTGCCTGCCCACGATGCCGGGCCAGGCCTTCCGCACGGACCC
AGGCTCACATTCGCCCTACATGCCACTGTGTGGGAGTTTGGGATGGTGTG
CCCGCTGGGCCCGGGGGTCAGGGCACGCTTCCCAGAGGAGCGGGTTCCAG
AAGGCCCAGGTGGAGAGGCGATAGGAGGGCTCCAGGGGGCTTCCCAGGCC
ACCTGCGAGGACCCTCCTGGGGGGAAGGGAGCGGAGGGGAGACAGCCGGGT
CCCTTAGGCCAAGGCTGAGTTGTGACCGCAGGGAGGAGGAGAGAAGGAGCA
CCCACAGCAGGGCAGGGGCTGCGGGAGGCTGTGCTGGGTGGCCGGGTGGT
GGGTCTGGGGGCCAGGACGTGGGAGGCCTCGAGGGGGGAGCAGGCACGG
GAGGGGCCCCTGGACGGCAGAGTCCCTGCTCCAGCTGCCGCCCCGACCCC
AGGTCCACCTTCATTTCACAGCCTGGCCCCCGGCCGCTCTGACCGGCCCT
GCCCATGCAGGTGTAGCGGGGCAGTGAGGGCCAGGCTCCGGCCGTCCCAA
```
Contig 74 (450 bp)
```
GCAGGCCTGGCAGCAGGGAAATGATCCAGAAAGTGCCACCTCAGCCCCCA
GCCATCTGCCACCCACCTGGAGGCCCTCAGGGGCCGGGCGCCGGGGGGCA
GGCGCTATAAAGCCGGCCGGGCCCAGCCGCCCCCAGCCCTCTGGGACCAG
CTGCGTTCCCAGGCCGCCGGCAAGCAGGTCTGTCCCCCTGGGCTCCCGTC
AGCTGGGTCTGGGCTGTCCTGCTGGGGCCAGGGCATCTCGGCAGGAGGAC
GTGGGCTCCTCTCTCGGAGCCCTTGGGGGGTGAGGCTGGTGGGGGCTGCA
GGTGCCCCTGGGCTGGCCTCAACGCCGCCCGGTCCCGCAGGTCCTCACCC
CCCGCCATGGGCCCTGTGGACGCGCCTCCTGCCCCAGGCTGGGCCCTTGC
TGGCCCCTCTGGAGCACCCCGCCCCCGGGCCCAAAGCCTTTCATGAACA
```
Contig 75 (1363 bp)
```
CCTCCAGCTGGGCCCGGCAGGGCACCGTGCCCCTCAGGGGACACCACGGG
GGGCCACAGTGGCCTCTCCTGCTCCAGGCTCTGCTCCCGCCTGGGGCCCC
CTGGGCCGCCCGCCCATGGCCAGGGCAAACTCCCAGTGCGGCTGCCCGTC
TGGGCAAAGAGGCCGCCAGGCCCCGCGTGGTCTTAGCAGGCACTGGCGGA
TGCCGNTAACTAACCATTTCTTCCGCAGGAGTCCGAATCTGCTCTGACCA
CGGGCCCTAAAAATCGCTCCTGGCCCGCAGAGGATCCCCGAACAGCGGGG
CTGCCTCCTGCTCCTCCTGCCGGGCCGGCACTCGGCAGGCACGTGCCCTC
GTCGTCCCCAGTCTGTCAACCGTCCCGTCGTTACGATCCCCAGAGTCCCA
CGCGCGGGCAGCTCTTTCCACACCCCGCACGGCCCCGGAGCTGCCTGGGC
ACCCAGATCGCCCCTGACGCCTTTGCTCCTAATTCTGCTGAAATACACAT
AACGTCTCCTTGAACGTTTGTCCATTTTCACGGGGACAATTCTGTGGCCG
TAGGTACACTCCCCTTGGGGCGCAGCCATCGCACCATCCGCTTCCAGGAG
GTCCCGTCGTCCCAGATGGACACTGTCCCCACTGATCCCTAATTCCCTGT
CCCCCCCAGCCCTGCCCTTCCTGTCTCTGTGGCCCTGGCGCCTCCAGGGA
GCCCCTGTGCGTGGGATCACAAAACGTGTGTCCCTTTGCGTCCGGTCGTGT
GTCTCTGAGCATCCGGAGCTTGGGGTGCTTCCACGCTGCGCCTGTGTCAG
GACGTCCTTCCCTTTTGCGGCTGCGCGATGCTCCCCGTGGGCTGCCCCA
CACTGCGCGTGTTCGCTCATCCATCCACTAAGGCTGAGTTACTTTTGGCG
GTTGTGAATACTGCTGTGTGAACACGGGCGTGCAAATACCTGCTGGAGGC
CATGCTCTTAGGCCTCTCGGGGGGCACACCCAGAGCGGATATGCTCAATA
AGGTAATTCTGTGTTTAGCTTTTTGGGGAACCATCAGGCTGGTCTCCAGA
GTGACGGAGCATGCGTCGCATTCACAGGAATGGTGCTCGAGGCTTTGAGG
TCTCCACCACTCGCTTCCTATTTTCTGTGCGTCACAGCCGTCGGAACGGC
TGGGTGGTGCCTCTGTGTGGCTTCAATGTGCTTTTTCTTTTCCTGGCTAT
GAGGTTGAGCGTTTTTTATGTACTTGCTGGCCATTCGCAGGGTTTTTGGG
GTTTCTTTTCTTTTTTGCCTTTGGGGACGGCGCCCAGAGCGTATAGAAGT
```

Fig. 6, contd.

TCCCTGGCTGGGGACTGAATCAGAGCTGCAGCTGCCAGCCTAGCCCACAG
CCGCAGCAACGCA

Contig 76 (500 bp)
TCATGCCATCGCCACCGCCCCCCACCCCGACGTTTCAAACACCAGAACCA
CCCCTCGGGCGGCAGAGAGAGGACCGGAAGGAGAGACAGCCTGGTCCCAA
GGCCTCGCCCGGTCCTGTGTCTCCGAGCGACATTTCTTTCTGTTTCCCTC
CTCCGCGGTCCAAGTTTCACCCATCAGAGGCGCATTGTTTTCATCATCTG
AAAAAAAAATCTCTGTCTCTTAATAAAACACAAGAAAAAGTAGCCTTCGA
AAGAAAGCACATGAATGATATGTGCTGGCGACAGTGCTGGCGGCCTCTGA
GCCGTGGTGGGAGGTGGGAGCCAGCGGAGCCCCTGACCGATCACGTGACC
CACGTCTCTCCTGCACAGCTGGCTGCACCTGCACGCGGTGACACAGGGAC
CCAGCCTCCTGCCAGCAGGTCACCCCACCCCGTCCGTCTCCTGTGGAAGG
GGCAGCGTTGCCTTCTGAGGGTGGGCTGCTCTGAGGGGCGTCCTTTGGCC

Contig 77 (626 bp)
GCCATGGGCTGCGGCGGTTCACGCGGCTTGCCGGCCTGCCTGGAAGTCCC
ACAGGACCAAGGGGAGGGCACGTCAGCACAGGGGCCCCGGGCACGGACGG
TGCCCCCAGCCGCCCCGGCCCCCGCCCTCCAGACAGGACGCCCGGTCACC
TTGCGGGGACAGCCAGCCTCGTGGCCTCGAGCAGAAGAAGTGAGAGTGGG
GTGCACAGGGGCCCCCGGGGAAGGAGAGGGGACAGCGGGGGTGAGCGGG
TGCGGGCGTGCTCGGGACCAGCCCCTGGCCTCTTGGCGCCTCCCTCCCCG
TCCTTAAACCGGGCCCAGCCTCTTGGGCCTCGACCCAAGGCTGTTTGGAA
AATAGGTGGACCGTGGCCCTGACCCGAAGGCCAGCGGGGACCCGAGTGCG
GTCCCCAATGGATCAGCAGGCGCCTGGGCAGCCTGCGGCCCCGGGACCCG
GAGACACAGGTGGGAATGGGAGGGAGGAGGGAGGAGACGGGAGGAGAGGAG
TGAGGACCAGCAGAAACCACGCCCTCCTCTCTTCCCGTCCTCGCCCTCGC
CTCCGACAGCTCCGACTCGGCTGCAAGGAAAAGGCCCCAGCCCAGCCCGC
CGCCACCGGGGGGGGGGGGGGGG

Contig 78 (500 bp)
TACTCGGGTTTGTTACCACTGAGCCACAAAGGGAGCTCCTAAAAATAATA
ATTTTCTTAAAGCCAATGACATGGAGAGCAGTTAGGGTGGAGGCTGGTGG
GTGGTGGGGCCGCGGCAGGCGCCCTGAAGGTCCTGAGTGGCACCCTTGGC
CGGGGGAGGTGGGTGGGCGAGGGGTGTTGAGAAGGGGCAGGGCCTCGTGG
GGGCAGGAAGGAAGAGCCAGTGGCTCCCAGTCCCCTGACCTTGCTGCCTT
GAGCCTGGTTCTCCCCAAAATTCTGTCTGTGTCCCTTCACTTCACGGAAG
CTTGGGGCCCGTTGCCAGGGAGACAGATGGGCTGGTGACACCCAAAATGA
GCCACCAGGAGGGGGCACTGACTTTAGCCAGCCGGTCACATCAAGAAGC
AAACAGGCCCCCCGCTGCTGTAAAGGCAGCTTGGGGCTGGGGTCCGGGAG
CACCCCCTGGGCTGGGGAAAGGGGGTCCTCTCAGGCCCCCGGGGAGGATG

Contig 79 (427 bp)
TCTATTCGCCGTGGCCGGAAGAGGCTAACCGTACATTGACCGGGCATCTG
GCGATGTATCACTTCTCTCCAACCGAAACTTCCCGGCAAAACTTGCTGCG
TGAAAACGTTGCGGATAGCCGAATCTTCATTACCGGTAATACAGTCATTG
ATGCACTGTTATGGGTGCGTGACCAGGTGATGAGCAGCGACAAGCTGCGT
TCAGAACTGGCGGCAAATTACCCGTTTATCGACCCCGATAAAAAGATGAT
TCTGGTGACCGGTCACAGGCGTGAGAGTTTCGGTCGTGGCTTTGAAGAAA
TCTGCCACGCGCTGGCAGACATCGCCACCACGCACCAGGACATCCAGATT
GTCTATCCGGTGCATCTCAACCCGAACGTCAGAGAACCGGTCAATCGCAT
TCTGGGGCATGTGAAAAATGTCATTCT

Contig 80 (650 bp)
GGCGTTGCCGTGAGCTGTGGTGCGGGTCACAGATGGGGCTCAGATCCCGC
GTGGCTGTGGCTCTGGCCTAGGCCGGTGGCTGCAGCTCCGATTCGACCCC
TGGCCTGGGAGCCTCCATATGCTGCGGGAGCAGCCCTAAAAAAAAAAAAA
AAAAAAAGGAAGAAAAGAGAAGAAAGAAAAGAAAAGACAAAAGTCAAAAG
GAGCTCCCCTGAGCGATGTCTGTCTACGAGCAGGTCCCTGGGAGCCTGAG
GCAGGGTGAGCCTGGACCCCTGAGGGCCACTCCAGACTCAGTGCTCTCAC
TGGCCAAGGTCTTTGGGGACCGGCTGGGGCGCGCGCAGGCTAAGGAGGA
GGTCAGAGGAGGGGCTTCAGGCTGCAGGGCCAGCGGCAGCTCTGGGCCCG
GGGCGGGGGGAGATGGCCTGAGGGCCTTGCGGGGGCTGGAGGGTGGGGG
GCTTCCTGGAGTGGGAAGACGGGAAGCCAGGTCAGAGGAGAGGAGCGAGG
GCTGAAGCTCCTGGAAGGCGCTGGCTACCCCAGCTGGCCCGCCCCGCTG
CCACATTCAACAGCCACCCGGCCTGTGGTCCTGGCAGGGTCCTGGCAGAA
AAGCCCCAAGGGCCCCAGCCTGGCCCTCTGGGCCTAAAGAGCCAAGCCCC

Contig 81 (550 bp)
TTAACCCACGGAGCAAGGCTGGGGATCGAACCTGTAACCTCGTGGCTCCT

Fig. 6, contd.

```
CGTCGGATTCGTTAACCACTGCGCCACGACGGGGACCCCCCAGGGCTGGC
GTTTCCCTCTGTGTGCACACAGTGGACCTGAGCCAACCAGCAGGGCCTTC
ACCACCACGGCGCAAGAGTCGGCAGCAAGAGAGCAGTGTCTCATGGCTCA
CTTTCTCCCCCTTCCCCGGAGTGGTGACAAAACCCCGCCGCCACCGGACT
CGGTTAGACAAGGCGGTGCCCAGTGCCCCCGTCTGTCACCCGCACGGCAC
GGCGCTCTCCTTTCTTTCTCGGGGCTCCACCACGTGTCCTCAGTTTCCGC
ATGAGAGTACCGCGGCTGGCGGGGTGGTGGCTCTGGGGTCGGGGGCCGTG
AGGGCAGGGCTGGGCTGGGGGAGGCAGGTCTTGGCCCATTACGCGGGGGG
CAGACTCCACATCACACGCTCTCTGTGCCTCTTGGCTGCCTGACACCATG
GACTTCAAACAGGAACAGCCGTGGAGGCATTGCAGCCCAGGGCCCGGGTT
Contig 82 (550 bp)
TGACACCTCCAGGCAGGAGGGTGCAGGCTGGGGTCCCAGGTAATGGTGTG
CTGGCCTGTGGGGCGTGGGCTCAGCTCTTAGGATGGTGGGCTGGGCGCCG
ACCCAGCAAGGACAGGGTGATGGCAGGTCGTGGGCTCAGCAAATGAGTGC
CCAGGTTGTGGGGGTGGGCACTTGGGGCTCAGGGGAAGCTCATCAGCTTG
GAGAGGGACGGGGGAGGGAGGGGGCCTTGGCCAGCTGGCCCAGATGCCTG
GATGTGAGCACTCACGTGCCCCGGGGTCCACCTCCCCTCCAGTGCCATCT
GGGCAGGAGGCTCCGATGCCTGTCCCTGGGACCCGCTGTCCTGAAATGAG
GTTCACTTGGTGCCTTCCCCAGAGATGCTCGGTCCGGAAGCTGACGAGGC
AGGAGTGCACAAGGGTCTGGGGAAATGGAGCAGAGTGCGGCTGGGGCACA
GAGGCTGCCCCCAGCCTGGGAAGATGGGGAGCTTTGCAGGGGTACCCCGC
CAGCTTGTGGGGCCCTGGATACCCAAGGGTGTGAAGAGGCTGAAGAGCGA
Contig 83 (984 bp)
CTGAGCCCAGCTATGTAGATTAGACCCCGGTCCGTCCCAAATTCTTCTCA
AAGCTGTCCCGAGATGAGAGATGAGGTTTTCGTGTCCTGTGCTCTCCTCG
CTTCCCCTGGGATGTGCCCTAGGGTGGGAGAGGGTGTGTCCCAGGGCTCA
GCAGGCGGTCCCATCTTCCCGAGACGGGAGAGATCCCCTCCTTCTCGGCG
CCTGTCCCCACGGCCCCCACAGACACCCCCCCCCGGCATGGCACCCAT
GCACCTGCCATCGTGCCCAGTAGGGGATGGGTTTGGCGAGACTGGAGATG
GCTGTAGCCAGTGAGACATGCCCTGCCACGTAGCCTGACCCCCTGGGTGT
GCTCTGTGAGATCTGGGGACCCCCAGCACACCTAGGGATCATCTTTGCCA
GCCTCCTGGGGAGCCTCTCAGAAATGGGGGCCCCCAGAAGGCTGGCAAAG
GTGATGGGGAGCGTGGGAAGTCTGGCGGTTGGCGGGGTGGGTGGGGGGCA
GTGCGGGCTGGGTGGGGGGTGCTCCGGGGTCGGAAGTGGTCCAGCAAGGT
TTTGGACACAAAGTCAGGAGGAAGGAGTGACGAGGAGACTTGCAGAATTA
CAGGTAGAATCAGGAACCCACATCGACGCCAATTGATCTATCCCCCCCTT
TGATTGTTTTCTCCTGGGGCTTTTTTCCNTTTTTTTTTTTTTTTTTTTT
TTAATCCCTCCTTAGCTTTTTACGCGCTCAACACCAAATTAAACGTACTC
CCCACCCCACGTAACAGGGGGGCGGTGACCCGAAGGACGAGGAGCACACG
AAGCCACCATCCGTCACCTTGGCGGCACCAGCCGCTGTCCTGCCCTCCGC
CCATTTATCGCCCTTGAATTGATTTTTGTTTTGCTCTGTCCCTGTCGCTT
GGGTAGAGTGGAAAAGGGAACCTCTGTGGGGGTGCCAGCCACTGGGCCCC
CCAAAGATTTCAGGGGAATGAAACGGCTGCCGCC
Contig 84 (550 bp)
TGCCCCTGACAACCCTGCCCTGTTAGCCACACTCGCGACTAATAAGGCGA
GAGGTCAGCGGGCAGCCCCACGGGGAGAAAGTGCCTCCGTGCCCCCCACC
CCTGGCTCTGATGGCCCAGCCTGGCACCCCAAGGTGGCCTCGGCCTTCCT
ACCTCCAAGGTCCAGGCGCATGTCCAAGCACCAGCAGAAGCTTCTCCAGG
GTTGGTGCCTGCTCAGGGCAGAAAGCAGGGGTGAGGCTCCCCAAAGGGCC
ACTGGCACCAATGCCCCCAGGCAGCCCCAGCGAAGGGGACAGCCCACCCC
CAGCCCGGGGACGCAGGCCTGAGGGGACATGGGGAACCCAGAGCAGGGCC
AAGGGGAGCAGAGCCCCTCCTCCGGGACTTGAAATCTTTCCCGGGGGGCC
CAGGGAGCTGGGGTCTGCAGAGGGCACTTTCAAAATACGGCCCACCCCCA
AATTGCCACGTGGGCCACAGAGCAAGGAGTCGCTGCCAAAGTGGCCTGGC
TTCAGCGCAGGAAGTTCCCCTCCTGGGGCCTCCCCTCCTATAGGCACAGG
Contig 85 (500 bp)
TGAGCCAGGGCCTGGCCCAGCTAAGCCCCTGGAGCCCTCCCGGCCTGTTT
CCTGCCTCCCATGCTGGCGGAGCTCGGCTTACTGAGCGGGGGCCAGGCCA
GTGTGCGTGTGGAGGTAGATTCCACTCAGCTGGAGGTTGAGGTGGGCAGG
GGGCCGCAGACCCTCAGGCCAGCTCTGGCCGGCCAGGTCCCTGAAGCTCC
CCCGGCTGGCCTCCCCGTCCCTGCCTCTGGCCTTGTCCTGGCCCTTGCCT
GACAAGCTTCTGTGGCTCTGCCTGCAGGAGAGACACTGGCTCCCCCGCTC
TCGGATGAGGACGGGGCTTTTCTGCACAAGTCCTGCCCCAGAATGTTTGG
GGCGCCAGCAGCTGAGCCCAGCACGTCTCCCCCTGCCCCTGGCTGGACAC
```

Fig. 6, contd.

GAATCCCGGCATCGAGGCGGGAAGGGGGATGGAGGGATGGGGCCTACCCA
CCCCTGCTCCCCACCCAGAATAGCTGGGCGGCCCCCATGGGAGGCCGCCC

Contig 86 (913 bp)
CTGTTTTCACGTCTTCTGAGGACACACCCAGAAGAGGGGCTGCAGGCGCC
CATGGTGACTCCATGTGTTCACTGCTGAGGCCTCTGCAGACCGTCTCCCG
CAGCAGCCGCACCCGTTTCCATGCCACCAACAGCGTGCGAGGCCGCACTG
TCCCCACGGCTGTGCAACTGTTTTGAATCTGAGTTATATAAGCAACAGAC
GCTCCTTCAAACACACTCACGTGCACACGTGCGCACAGGCGCACAGACAC
ACACACGGAGTAATAGGCCTCCCCCCCCCTCCCTGAGCCCAGAGGGGGCCT
GGGGCCCTGGAGCCTGTGCTTTAGGGCCTTTTAGGAAAGCTGGTGCCTCC
CAGAGGGGCCGCCCCGAGCGTTGGCTTCCCAAGTCCCCACCAACCCTCGA
CAGACTCAAACGTTGGTTTCTTTCGTGCTTTTGCCCAAGGGATGGGCCCG
AGGTGGCCCTGCCTGAGGTTTCAGCCCAGCGCCCCAGGCACCCTTTCTCT
CCCGGTCCCCGGCCACTTCATGGGACAGCGGGCCTTCCCCCACGTTGTCC
CCTGGGTTGTCGTGCTTTTCGTAATGAGACGGAGGCAGGTGCACCTGTCC
TGGGGTGAATTCTCTTCTGCAGGAACTCGCTTCCCCGGCGCCTGGTCTGT
CTGTTCCTCGGTTGTTGGAACCTCTCGTCACCAGAAAGGGTGGCTCTGAC
GTCGCCCTTTCCCTCCGTGGCTTTTGCAGTCTGGGTCTTGTCGGGGAACC
TGCCCCAAAGAGGGGAGTGACCCCCCACGAGGGAGACGTAGCTCCTGTGG
CGACAGCACCGGGGGCCCCCAGATTCATGGGGTTCACGCTCACAGTCGCA
TGACGCTGCCTTTGGACGAGGGCAGCTCAAGGGAAGCTTGTTTCCTGCCA
CGAGCCACAGGCA

Contig 87 (650 bp)
TCCACACCTGTGGAGCCGCTGCCTCGCTGATGCCCTCTGCCCAGCTGATG
GTCAGGTGCCCAGACTTGGGGCTCAGTCCAAACAGGGGCCCACAGGTGCT
GCACCTGGGCAAGGGAGCCTGTGCGCAGGGCCTCAGGTGTCCCAGGCTCG
CTGGGACCGAAGCGCACTGGGTCCTGGACTCCGGGCTTCCCCAGGGGCTG
CTCGGGGCCACCTGGAAATGAAGCCCCACCTGGCTCATAGGGTCCACGTG
AGGGCCCTGAGGCCACCAAGCCACCAAACAACTCAGTTAAGGGAGGGGAG
CTTGGGGCTGCTAAGCTCCAAGCGGGAAGCGGCCGCACTCAGCACTGCCT
CTCTGCCAGCCAGCCGCCCAGCTTGCTGACGTCCCAACCAGGCCAGGGAC
CCTGTCCCACAGATGCTGGGCCCTTCCAGTCTCTGCTCCCTGGAGGCGCT
GGGCACTGTGTGGGCACACAGCCCGCACCCGCCTGTAAGGAAGGGAAAGG
CCCCATCCTCAAAAAAGCCGTGGGCAGGTGGGCCATGATGGTCCTCCGAG
GCAGGTCCTCCTGGGACCCCTTGCTCCCTCGGGCTCGCCCAGGAGCCGCC
AGGTCTGCCCTGGATTAACTCTGCCCCGCATGTCATTTTCAAACTGGCTT

Contig 88 (700 bp)
TGGGGCCCTTTGGGGCCGGAGCGGCCAGTCTGCTGGGCCCGGGAGCAGGG
GGTCTCTGTCCGCAGGGAGGGGGCCTGGTCTCAGGGGAGGAGGAGGAGGCA
GGTCTCACCTGAAAGGATCTGCCTTCTCCTCAGGCCTCTGGGATGCCTGG
GCAGAGAAACCAGAAGGAAAGGCCCAACTTGCTGGCTGGTGGGGATGGGG
CCGGGGGTCGCTCCCGGCACACCCCCCCAAACCCCACCTTAGTGGCCAA
AGTGGGTGTCATGATGGCCACTGACCTCACGGGGGCGCAGGAGACAACAA
AATTTCAGCCACTCTTGGGGGAAGGACACTTGTGGCCTGAGTCTTAGGGG
CTGAGTTTCGGGGGGGACCCCCAGCTCTCCCCCCAGTATGAGACACCCTG
CCCACTCCTCCCAGCTGCTCCCCAAACCCAGTGCTTCTGGACGGGCATCT
CCCCGCTGCCCCTGCAGCCGCTGTCCTCTGACCATGTCCCCTCCCCACCT
CCCCTCTGCAGGGCCAGGCCTCCAGGGAGCAGAGCCGAGGCCCCACCCTA
GACTGAGCTGGGGACCGAGACCCCAAGTCGCCACCCGGTCTCTGCGTTAG
AGAGGGGGTTCCGGGGGGCACCCTGGGGCGGCACTGGGGGCGGGAAGGA
GAGCCCTGGGCCGTTCTGGGAAAGGTCTGGGAGGGAGGGAGGGGTTTTGC

Contig 89 (1400 bp)
GCACACCCGGAGAACAGAGGGAGGGGTCCTTACCAGTCTCAGGGTTTTTT
TGGGGATTTCTTTGAACTTGCCCTATTGGTTTCGAGGCTTCTGTTCTCTC
CAATCCCCCCTTCTGAACCCCCCCAAAAATGGGTTCAGCCCCCACCCCAG
CCAGAGGAAACCAATTGGGGGATTGGGGGGAGGCGGGGCCAGCAAAAGCC
TTGGGCCCCCAGCCCCCCTGGCTTTGGCCTCTGGCCTGCCAGGTAGGGGG
AGGGACGCGGTGACCTCCGGGGCCTGGCCACGGACTCTGCCCCCACCCC
CAGGGCAGACGTGCACAGGAGGGGAGAGGCTCCGAGGAATGAGGCCATCA
AAGGGACAGGTGAGGCCACGAGCCGTGGGACCTGGAAGTGTTTAGGGCCT
GGGGGACGAGGCTGCGGCCTGCGGGCTCCGTGGTCAGGAGGCCCTCTGCC
CACTGAGCAGCTCCCACCACTGGCACACGAGCCTCTCTGGGGTCCGGCTG

Fig. 6, contd.

GTCTCCGGCAGGGGTGGGCTCTGAACGTCCAGCTCCGCAGACAAATCAGA
TTCCCCCGAGCCCTGAGAAAGCCCCCTCCCCCAGCCCGTCTCCCCACCTG
TCGGTGGACAGAGTGACCCCTGCTGACCCCCTGCCCGGGCTCCCGCAGGA
GATGTGAGAGAGTAAGAGGCGGTACAGGACGGCCGGGGCGGCCCGGGCGA
GGTGCAGGTGTGTGGGTGTGAGGCTGGGCACAGGCTGGCACAGCCTCCCT
GGCCCAGTCCCTTGGGCACCTCTGGGCACCTCGGTGTGCCTGCCTCCTGA
AGGGATCCACCCTCCAGCCACCTCCTCTCGGGCCAGCCCCCACCCCACCC
CCGAGCTACAGATGCCTGCGCATTCGCCCCAAGTGTCCTGGACCCTGGAG
CCAGGCAGCCCACCCGCTCAGCCTGGCCAGACCCAGCGTTGCCCTTCACG
CCCTCCTCCCTCCCGCCGGGTCCTCGCGCTCGTCTCCTCAGGTTGGAAGC
CCCTTCCCACCTGCCATCTTGCCTGCGCCCAGGATACACGGCTCAACTCA
AGGCCTCACTCCTCGCCCTCTCCAAGGCTCTGTCCAGGCCCCTCTCTGAC
CTGGCACCACCTGCCGCCTCCTGGCAGCCCCAGCAAACCCCCTGCCACAG
TCCACGACAGTCCTCTTCTGGCTCTGCCCCCAGGATGCTTCTAGAACTGG
GGGGGGGGTCCTTCCAGCCCACGCAGCATCCACTGGGCCCTGGGCTCCCT
CCCCAGGTGCCCCTCAGAGCTTGCAGCTGGTGCAGACGGCTCTGCTCCGA
ACCCATGCTCCCTGCGCCCTTGGACCTGGTGAGATGTTGCAGGTCATTTG
GCTGCACCCAAAAGAGTGGCCCCTCAGGGTCCCCCCTGCGCCCCTCCATC

Contig 90 (350 bp)
GTACTGTAGGGCCTCATTCGAATAGCCTACTAGGTCACAGCTGATCCACA
CCTTAGGCCATCACAACTTCCCAGAGGTAGTGCCGCTCCTGTCGTTGAAC
AAGACGGTAGTGACTGCTGTGAGAGCTCAGATCTGGTGGGTCACTGACCG
AGTGTGGAACCCTGGGGGAAGGCTGTGGGGTGTCCCCGGCTGGGTGGCCA
TGTCATGTGCCCCTTTCTATCCCTTGGACGAGGCTGGTTCACTCGGCTCT
AGAGCCCCAAGCCCCAGCTGCTCTGCCAACCCCCCAAGCCTGAGCCTCAT
CAGACCCACCACCCCATCGCCATGGCTACGCAGGACACACCGCTCTCCAC
CCCCACCAGCCGCCCCACCTCCCCGAGGTTCCAAAGCTTGA
Contig 91 (1464 bp)
TCCAGGACCTGATGCAGCAGCCACGTCGCGAGGCCCCTCCCACGAGGCCC
CTTGTTGACCAGCGCTAGGGAAGGGGACCAGGGAGATGCTGAGAACGGGG
CCTTCCGAGGGGGCAGGTGGGACTGACTGTGACCCAACACTCCCCACCCC
CCTCTCCCGCTCCAGAGGGTGCCAGCCTGGAAGCTGGCAAAGTCCAATCC
ACAGGTGGGCTCACGTGGGGAGGCTGGTGGCCCCCACCTGGTGGGGCCCC
AAGCTGCCTCTGGGCGGGGTGGGGGCTGCTCCCAGCAGGGTCCCATCCAG
CTTCTCCCTGGGGAGACTCACAGTTCTGGGAGAAGGGTCCTGACTGCACC
GCAGCGCCCGCCCCCTCCCCAGACTCACCCAAGTTCTCTCTCTGCATCGG
TGACTGGTCTCCGCATTTGCCCAGGCTGGGCATCTGCCCAGAGGATACGT
CCAAAGGCAGGGCAAAGCCGGGCCCGTCCCCGGAGCTCCCCACAGGCGC
TGAGGGCTGGGCTGGATCTCGGGGGGGTGGAGGGGAGGACTCAGAAGGTG
CAGCGGGGTGGAGCGAGGCTGAGCCAAGGTGCACGCGAGGGCCAGAGAAG
GCCGAGGCGGGCAGGAGGAGAGAGCGCCAGCCTGGAGGGGGGTGGGTGCC
CTGGGCAGGTCTGGGGCTCAAGAAGAAGAGAGTGTGTGTGCAGGGGGCTG
TCCAAGCTGCCCGGGAGGCTGCCTGCCCACCTCCAGGGAGCAAAGCAGGG
AGGCTGCAGCTGGCCCGGCCGGCCGCTCTCCAGGACCACGCGTGGCCCAG
GCCTCAACGCTCCTCCCACAGCCCAGGAGACCCAGGGCACCGGGTCCATT
TACCGCGGGCTCCGGGTCCGTTTGCCTGCGCCCTGGGATGGACTGTGGGG
GCGGGGCGCTGTCTGGGGAGGAGGGAGGTGTCTGAGGCTGGACACCTTGA
AGGCAGGTGAGAGTGACAGGTCCGTGCGCAGGAGCCTTCGGCTCTGGATT
CTGGCCCTGAGCGAGGGGCTGGCTGGAAACTGGGCCGGGGCTGCCGCAGG
AGAGTGTGCAGGGAGAGGAGACGGGGTTTGGCCCCGGAGGTGCCGGGGTG
GTGCCCTGGAGTGCGGCTGAGCGGGAAGTGGGTGTTGGCGTCTGGAGACG
GGGGGTCGTGGGCTTGGGATGGTGACAAGACCCCCCAGGTGGAGGCGGCC
GCAGAGGAGGCAGAGAAGCCAGGCCCCAGCCCCACGGCGGGAGGCCTGGG
AGTCAGGAGGGACCAGCAGAGCCCTGGGCTCAGTGTCACCGGTCCTGGCA
CCTCGCCGACGGATGTCCTGGCCGTGCAGTGGTTGTCCCCTCACCCTGAG
CCCTGAGAACCATGCAGGATGCTGGTGTCACAGCAGGAGAGGGCCAGGGC
CTGGGGAGGAGTCTTACTGGAAGGCCTTCTCCTTCCGTTTGCAGCAGGCG
GGAATGACTGGGGG
Contig 92 (694 bp)
TGGAGCCAGGGCACGGCAGAGCGGTCCCGAGGCCGTGCGTGCTGACCCGG
GGGATGGGCGGACCTGGGGGTGGGCTGTGAGCCCAGGCATAGGGACCCCG

Fig. 6, contd.

```
ACTTGGGCACGGCCAGGTGGGGCCGGGCAAGGGGGAACAAGGACGCTGGC
CTCCAAGGGCCCCACGTGGGCACAGAGGAAGAGCCGACCCAGGTTGTGGG
CGCATGGAACCCCCCACTCTGGGGGCCAGGAGGCCGAACGTCCCAAGGGC
TGAGGCTGGGAGGGAAGAGTCCCTTTGGGGGTCAGTCAGTGTCCCTTGTG
GGTGCCCCCCTGCCACTGGCGGCACCTCTGACCCCAACTCCTTGCGGGTG
GACGGTGGATGGATTTCCTGCAGCCTTTCTTCTGGAATAGTCTCTGCCAT
CCTCGGGGAAGCAGTGATTGCTCTGCCCAAGTCCAGGCCCCGCCCTGCAA
GGTGCCTCCCACCCCAATGAGCCCCCGGACAGTTCGAGGGCTTCTCACGC
TACTGAGGGGTATGAACAGCTGTCCCCCTCGGAAAGTGGGGGACAGGCCC
CTGCCACTCCATCCTCGGGACGCCCGGTCTAGTCAGCACTTGTCTCCCTG
CCTTGTGCCCCCCTGACCTTTTTTGAGGACCATCAAAACCTCAGCCTCTG
CCCCAGGAGGTCAAGCCCCCCGTCCCCAGCCCCCAGACCAGCA
Contig 93 (900 bp)
CCAGCCCCATCCCCCGGCTGGTCCCCCACCACACAGAGCCCCCGTTTCCC
AGGGGACAGCACAGCCTGCCCCCAGGTCTTACATAAAGTCACCTTCTCAG
AGCTCCTGTCGCGGCTCAGGGGAATGAATCTGACCAGCATCCATGAGGAC
ACAGGTTTGATCCCAGGCCCCGCTCAGCAGGTTAAGGATCTGGCGTTGCC
GTGAGCTGTGGTGGAGGTCGCAAGACGTGGCTCAGATCTGGTGTGGCTGT
GACTGAGGTGGCGGCCAGCAGCTGCAGCTCTGATTGGACCCCTAGCCTGG
GAACCTCCATATGCCGCGGGTGCAGCCCTGAAAGGACAAAAATAAATAAA
TAAATAAAAGAAGTAAACACACCTTCTCTAGCCATAACCACCTGCCTAGG
GGCGGAGGGCCAGGAAGCGGCACCCCCCGCCCCAGGCTGCCCGTGCGCC
CGGGCAGGCGGCTCAGCCTGCTTTTTGTCTGTGATGTGAGCCGCCCCAGC
CCCACATGGAGGGGCTGGGCTGCGCAGTAACTGCTTTAACTGACGGGAGC
TTCGACCAGCAATTCACCAGCGGGCATGCAGCCGGGAAGGGAAGTTATTC
GTGTGTAGCTATTAGGCGCCGGAGTGAGGGTGTGCCTCGCCCTGGGCCCA
CCCCTGGGGGGAGGCATCACAGGGGTTTTGAACACCTGCCCATGAACACG
GGGCAAAAGCCAGCCAAGGGGGCAGGTGCCTGAGGCTGGGAACCAACCCG
TGTCTCTGAAATCCGGGGAATGCCCACTGCAGGCATGTTCAAAGGGTCAA
GACCGGGGCTCTGCCTGAGAAGGACTGGCGAAGGCCAACTACAAAAGCGC
ACCCCTCTGTGCAAACCCCCAACCAATGGAACAAAACTCCAGAGGGGCCA
Contig 94 (550 bp)
AGTCTGGGCTGTGTCCATGGGGTTGCCAAGGTGCCAGGCAGAGACCTTGG
GGACAAAGGTCCTGTGAGCAGAAGGACATGGCCACGTCCCCTGCTCAGCA
GGTGCCCAGGCTGGGGTCTGATGCCCTCGCTGGGGTGGGGCGGGTTGAG
GGGCCAGGCCCAGACACCCTTCGTCCCTGCCGGAGTTGTTTGCCCTTCTG
TTCCTGGAAGGCCCCCCTGCAGGTACAGGAGGCCCCTGGGGCTGACGCTG
CACCTTCTGACACCTGTGGTCTTGGGGATGGGACAGGACAGGGAGACCCC
GGGGCTGGACGGAGCGGGTAAGACAGAGAGTTGACTCTGTCCTCGAGTCT
GTGCAGGGCTGTCCCCGGCTTGGGCTTCGTCTGCAGGGCCTTTCGGGTCA
GGGTGGCCTCAAGGTGACGAAGACCTGGTCCTCGGGAGTCTGCAGGCGCA
AAAGTTGGAGCCCACCCCCCGGGAGGGGGCGCCAAGGACAGGAGGGCC
CAGGGAAGTCTGGGGCCTGCAAGGCCGTCCGGGCTGGGGAAGGCCAAGGT
Contig 95 (1200 bp)
GTTTGCTCTCAGCAGGCAAGGGCCTCCGAGGCCTTAATAGCCCATAATGA
CAGCGCCCGCTCCTGGCATGGGGCCCCGCCTGGCATGGGGCAGGGCAGGG
CAGAGCAAGCAGCATGCAGCTTCTACCTTCTTCCTGACCTCGTGGCCCCT
TCCGAGGCCTCAGGGGGTCCCCCGAGTGGGACCCCAGCCCTGGCTCTCCT
CTCCAGAGCCAGGCCCAAGGCTGGGAGTGGCCCAGAGATGAGGGTGCCCG
AGCAGGGCACTGCCTTGGCGTCCCCATCCCTGGCGCCTCAGGGCCGTACT
GTCCAAAACCAAAAGAAAGCAGTCAGCAAAACTTCTCCCAGCAAGCTGGG
GTCAAAGGTCGCTTCCGAGGCGTGATCAGGGTGGCCTTTGCTACTGTCAC
CGTGTGCCCTGGGAGAGGCACAGGGACACAGACACACACCTCCGAGAACC
TGGGGCTTCCAGGGCGTCAGGCTGCCTGGGCCATCCCGGGCCCCTGTGGT
CCCAGGATCTGCCGGGACCGTGAGGCCTGCGTCCCACCCTCTGCCTGGGA
CAGGCCCCACAGAGCTCACAGCCAGGGACCGGGACAGGGCCCCGCCTG
GGCCACCTGCCTCCAGCCTCACCCAGCCTGGGCCCCAGGCCTGTGCCTGC
GACACCCTGAGTCTCAGGACGGGCGCGGGACAAAGCCGCCCGGCCCCTCC
CCCGGCTGGGAGGAGACCCGCGTGGCCCTGACGTGTGGGCCTGTCAGAGC
TGAAATGTCACAGCAATTAGCCCTAACGAGGCCGAGGGAGGGAGCGGCGG
GGAGGCCGGCGGAGGGGATCACGAGCCGAGGGCCCGGAGCTGGCCACCC
CACCGGTCGATTCCAGGCACTCAGGGATAATTGGGTGTTTAGAAGTCAGG
CGGCAGCAGAGAGCGGGCCAGGCGGGCTGTGCCCCCCTCCCACCGCCCC
TTAACAGGTGCCCGAACACGCAGGTCTGGGGAGATGCTGAGGTCGCCAAG
```

Fig. 6, contd.

GGCACCCCTGGCCGTGCCGCGGGTGCTATGCTGGTTCGGCACCATGGGAG
CTGCACCTGCAGCTGTATTGGTCTGTGTGTGTGTGTGTGCACGCGTGT
GCGTGTGTACGTGTGTGTGTGTGTGTGTGTGTGTGTGTGTACGTGG
GGGGGGGGGGCAAGCCCGTGCGTGTGGTGCACAGTAGACATTTAGAAGGT
Contig 96 (600 bp)
GGGGACCAGGGCCCAGCCCTCCAGCTCCCACGCATACCTGCTAGGAGCTT
GCAACCTGCGAGAGCTTTGTGGACCCCTGCCGGGTGACCCCTGAAGCTG
GCAGCTCTCCTTGGCTCTGCAGCGGCTCTCTACACTACCCCCTCTCCAGC
GGCCTCGGGCCCAGACATCACCCACCCGCAAGGGAAGCAGCAAGCATCCA
CCAGCTGGGCCCTTTTCCCCCAGCCTGTGACCGGCCCCGCGCCCCTCAC
ACCTCTGCGGTCCAAGACCCCTCTCTGGCTGGGCCCTGGTGCTGCCCTTG
CCGTGCACATCTGGGGTCCATACCCCACCAACAGGCCCCACTTTTCTGTC
TCCCAGTGTCCCCCTCAGCTGCCCTGATGGGCCCACACCTGGCTTCTCTG
CTGCCCCCCTTGACCGCAAAAAGACTGGGGTCCAGGACCCCCTGCCCCAT
GACTGCCCTGGAAGACCTCAAGCCTCTCCTCTCAATCCTGACCCTTTAAG
GCTCTTGCCACGGAGAAAGCGGCTGGGGTTGGGGGAGGGTGTGGGTCCCA
AAGCAGCTTGCATACTTCTCCTGACTGGGAGCTCATTCCTCCACAGCGTG
Contig 97 (1350 bp)
CCCGCCTTATTTTTAAATTTCCGAAAACAAAAACCACACCTCTCCCGTCC
CCGAAATTATTTTGGTATAGTCTTATTCAAAGAAGTCCTGCCACTGAAGC
CCACTTGTCCTGTCCCGGGCTGCTTTGGCCAAGGGCCCTGACGGGCCCAG
GGTGGCTCATTCCCGCATCCCCGCAGAGGCCGCCTTCACATCCCATGCGG
GAGCCTGGCTTCCGGCACCCGGCTGTGCCCTCGCTGTGGCCATGGACTGC
TTTCGCAGAAGCATAGGGGCCACAACATGGGACAGCCTCGCTCTGCTCGC
TGTGGTTCCGCTGAACCTCTCAGCTGGACATCTGGGCAGCAAGCACCCCA
GCTTTGCTTCAGGCTCTGGTTCCAGGCTGGGCCCTCCTCGGCCCTGCCCG
CTGGGTGCCAAGCAGGGCTGGTCCGGCTGTGCCCCCGGGTCTATAGAAGC
CTCTGCAGGGCTTCCTACAGCCAGGCTGGGATTCGGCGGCTGCCCGGGAC
TGAGGCCCCCTCTGAGTCTGACCCCCCCATCCTTCCCTCCCACACAGCCC
CCCGCCCCCGCTTCTGCTTCAGTGAGGCCCCACCCTGCCTCACTCGCTGA
CATTTCCAGAACAGGGGGTTCCAGGAAGCCCTGAGCCTGCAGGGGACTCA
GTGACCAGCCGCATCTGAATTTTCCCTCCTTCTGATCTCTGGAGACACGT
CTGGCTCAGCCTGGCTCGAGTGCCCTGAGCTGGGGACCAGGACAGACCTG
CAGATGGAGGTCTGAGCCTGGGCAGGGCAGGGCCCAAGGCTCAGGGAGAA
ATTGCAGGTGTGAGATCAATGACCGGAGCCTGGATGGGGCCGCCCTGGCC
AGGGCAGCTTTCTCCCTGCAGCTCCCTGCCACTGTCCCCCCCAACTCTGG
GCTCCTGCTCTGGACCCAGTTGTGTGTTCCCCTCCTCCCAGCCGAGCCAC
CCTCCCCCATTCTGCCCCCCCCCAATCCAACACCCTATCGTGGGAACCAGT
GGAGCTGAAAGAAGGACCCCCCAAGGGCCCCCCAGCCGCTGTAATCCTTG
GGGGCCTCTGCCCAGGTGCCAGGTCTCGGGCAGGAGGGGCCGCGGGCACA
GCCGTGGCAGATGCGCCCCCCAAGCCTGGGCTCGGAGGAGCCCCGCCCCC
ACTGACATTTCCAGGCCGCCCGCTGCAGACCCGGCTGGCCGTGATATTTA
GACAGGGCTTATTTGCCGTGACTGGTTTTTGATGACTTTGGGGCCCAGGA
TGAGCTCAGCCGAGCCCGCGTTGGCCCACCTTGGTCTCAGCTTGGGTTTG
ATAATATAACGCGTTCAACTGAACCGCTGACGCCTGCGTGGGCCGAGGCC
Contig 98 (1354 bp)
GCTTGCAGTAGTTCATCAGATTGGACGACTCATAAATGTCAAGACATCTA
AAGATTGGTGCATCCAATCATTTCCCACCAGGTTGTTTTTTGTAGATGT
CAAGAAGCTGACCCAAAAACTCACGTGGAAATGCACGTCAACTGGGAGAG
TTGAAACAATTTCTAAAAAGAAGAAGGACGTCGTGGGAGGACTCTTCGCG
CTCTTTGGTTTCGCTTCACTTTATATTATTAGTTACTGATTTTCCTAAAA
GCTGCAGTAGTCCAGACAGTGGGCCTCTATGAAGGGAGGGGCTCAGAGAT
GGTTGGGACAGAATAGAAAGCCCAGAAACGGACCCCCGCAAATGTGGTCA
ATTGAGTTTGGGCAAGGATGTGAAAGCGGTTCAGTGGAGAAGAGTCTTTT
CAAGAAATCTCTGGTCCTGGATCCACTGCTCATCCAGGCCCAAGAGTGAA
CTTGGCGCACATTTCTCACAGTGTATACAAAAACTGACTCAAAATAATTC
ACATACCGTCGTGTAGCGTATGAAGCCATGAAACATCCAGAAGAAAATCT
CGGTAACCTCAGGGCATCTGGGGCCTCCACCCTCAGCACCACTGGCCTTG
GGGCCAGATACTTACGTGTTCTCCTGTGCACTGTGGGACGTGCAGCCAAA
CCCCAACAAGGTGACCATCAGAAATGTCTCCAGACGTCGCCAAATAACTG
CCAGAGAGCACAGGAGCCCCTCACTGAGAACCACAGGGTGGGCAGAGAG
ATCTCAGACATGACACGATTAGGGGAAAACAATCTGACACACTGGCTTTG
TTAAATTTAAAACTTTTCCCCTGTAAAAGGCAATGGTAAGACATTAAGAG
GCGAAGTGGCAGACTGGGAGAAAATATTTGCAAATCATGTATCAGATACG

Fig. 6, contd.

AAGAAGATGCAGGAAATCCTCAAAGTTCAGTCACAAGAAAACCCAATTCA
AAAACCAGCAGAGCAGACATACGATGGCAAATAACCACGAGAAAGTCAGC
ACCCGCTGTCCCTGGGGGGACGCGAGTCAAAGCCAGGAGGACACCAGGAT
ATGCCCACTGCCAAGGCTACGGATAACGGGAAGCAAGAGACACAGACAGA
AAGGATGCTTCGGTGCTGGGGAGGGTGGGGTGGGGCGGGGGGTCCCCCCC
TGGAGCAGGATGTGAAGGCACTTGGGGGGGGCTCTGCACTCCTGGGGGCC
TTTGGCACAGGCGGAGGGCCCGGGAAGGCTCTAGGGGCACGGAGAGGGGT
GCCAGGCTTCCTTACCCAGCCCAGGCAGACCAGGCCCTGTCATGAAGCCT
GACGTGCAGCAGCAAGAGCAACATGCTACAGACATGTGTCTGTGTGTGTG
TGTG

Contig 99 (1000 bp)
GGTTCTCAGGCGCACGGGGCAGAGGCTGAGGGTCCGAGGGGCTTTGGGTG
CTGGAAAGCCTGAGTTTGAATCCCAGCTCGGTTTCTTAAAGCTGTGTCTC
CACGGCCAAGGAATGGGGCCTCTCTGGGAAAGGTCTGGGGTGAGGCTGGC
GGGACCTGCCAGCCCCGGAGGGCATCTGACCAGACAGCTTCTCAAGCTCA
CAGGGCTTCATGGCAGGATGGGGAAGGCTGTGGTGGGGAGTGGGGAGCAC
TCGACACCCTGTCCAGGCCTCTTGAGTCACGGTGGCCTCTGAAAAGGGGT
TCTCTGTGTCCAATGAGCAAGTCTTTGTCCGGGGCAGGATTACTAAGTCC
AAGGGTGTCTGCCCCTCCGTGGGGCACAGAGCAGGGGCCCCAGATCACGT
GGCTGTAACTGCCAGGTTGCAAAGCCTGCCACCATGTCCCACTGGGTTCT
CCAGTTACCTTGGGAGGTGCAGGGTGGGGTGATGGGGAAACTGAGGCAGA
GAGCTGGCAAAAGAGTGCCGGCAGGGACTGCGGGCGCCAGACCCAGCTAA
CCGACCCTCACACGGAGCTGCTTCTACTTTGCAGCCTGGACGTGGGAAAA
GGTTACCCCACAGCAGCGTGTGCAGGCACGCTGGTATGTCTGTGTACTTA
TGCATATGTTCTACGTGCATGCACGTGAGTGTGCTGTGTGCATTGTGCCT
GTGTGTGTGTGCATGTGTGTGTGCACTCATGTGTCTATACGTGTGTGTAG
TGAATGCTTGTGCATGTGTATTTGCATGTGTATGTTTGTACGTGTGCAGT
GAATGCATGTGTGTGCAGTGGCGGCATGTGCGTGTGTGCGCATGTGTCTG
TTTATACCTGTGTGTAGTGAATGCATGTGCATGTGTGTGTTTACATGTGC
ACGTGAGAATGTGCACTCGTGCATGTTTGCATGTGAGTTTCATGTACACA
TGCTTTTAACGTGTGCACGTGTGCACATGTGTTTCTGTGTCCCTTGCACG
Contig 100 (1500 bp)
CGTATAAATATATTAATATAGAATAAAATAGATTGATAATATAGATAAAC
TAAACCCATTATCAATACCGGGTGGCCCCAGCAAAGGATACTAGCCAGTT
TATCAAGGTGCTAAGTCAGCACATAGAATGGCCACAAACGAAAACCTGTA
CTGCCTATGTCCACTCTAATGGAGTATGCCACTGACATCAGTGGTAGGTG
AGCTGAGTCCATCTGGGCTCCCAGTTCGGGCCCGGCTTGTCCCCCAACGG
AGGTTCCTTCCAGGGTTCCCCAAACCCAACCGGGCCCCCAGGTCTCCCTG
TCTTGACTCGTTTCTGGAGTCTTCTGGGGCTCTGCAGTCCTCCCTTGTTG
GGGCTTCTGTCCCCCTGCCCCTGGCCTTGCGGGCTCGGCCCTGCCCTGGG
TCCCGGGCCTGCGGGCTCACCCTCCTCTTTCCCTGGAAGAGAGGGAGCC
AGGCTGGGCCGGGCCAGGAGGGAATGCGCCTGACTCTGCTCCAGATGGAC
AGGTCGGGACATGCAGTGGCCTCGCCTTGGGCTGCTGAGCCAAGAGCAGG
ACGGGTTCTTTCTGGAATGTGGGGCCAGCCAGGTTCAGCGTGTGGGTGGG
CAGCCGCCAGCATCTGTCAGGGCCGCTGCAGGCGCGGGGAATGACCTCGA
CTTCTGCTTGGCACCCAGCTCTGGAACAGCCCCCTGCGGAGCCTCCGCCC
AGAGCTGGGCCAGAGGGTCCCCTGTGCCGGGGACCCCAGCAGGGCCCCTC
CCTGACTCTCCAACCCACCTGCCTGGGAGGAGTGGCCCCCTGGCCTCCGT
GGATCTCTGGGTCGGGGCTCAGCCGGCTTGACAGCCTGGGAACAGCCAAT
GCACATCCCCAGGCCTGGCCACACCCTTCCACCGGGAGCGGGCGGATCTG
CATTTCGCCAGGCTCTGCGGGCAGCTCTGAGAGCCCCGGGTCTCGGAGCC
CAGCCGTGGCCGTTGTACGCCCTGGGGGCTGTGGACAGCGTGTCCTCATT
GCCCCTCCGAGGTCCGGCCCAGGTCCCCTCCCACCTGCTCGCCCAGAGCC
CTCTCCCCACCAACCACACTTCCTGCTGTTCTGCAAGCGGGACACACACT
CCGGTTTCAGGACCTTTGCACGTGCCGCTTCCTCTGCAGAGAAATGCCTG
GAGCAGATGTTTGTCCGCACGGCTGCTCCGCGAGGCCTACCGAGAGCCCC
TCACCTAAACGGCCGGGCCTCAGCAGCCCGGGGCCCTGTCCCCACCGCCC
AGGTGGTGGGTTCTCCTGTGCCAGTGTGGGCATCTCTGTAAGATACCTGT
TTATCTGCTCATCGTCTGGTCTCCCCAGAAGGTAGAGCAGGGCCCGGCA
CAGCCGTCCTCGGGGTGGCCACTCGCCCTTGGGGCTCAGCCTCCATGCAG
GGAGGGACGCCTGGTGACACGAGAGCCCCGTGTGAGTGTGCCGGGCCGCC
AGCCTGCCTTAGGTCACAGCCAAAGCCGGCATTAACCACCAGGCCCTCGA

Fig. 6, contd.

Contig 101 (600 bp)
TCTAGAATACCTGGCCCTCCAGGGACGTGTCCTGTAGCTGCGGCTTTCAG
GGCAAAGTGTAATTAAACATCCCCAGGCTTCCCTTCCAGTTGGCACAGGG
CACCCACATGAGGAGCAGCCTCTGGGTGCCAAAGGGCCCACTGGTGCCAG
GCGCTGGGCTGAGTGCACCCCCGCATGCTTCCCGCCCACTCACCTGCTGG
CCCCACCCCTGACCACAGCACCTGTGGGAACACTAGGCCTGGCAGCCACA
CGCTGCTCTCACTGGAGGCCAGTGCCAGGCAGCCTGCTTGGCTACGCTAG
CAGATGCCCGCTCGCCTCTGCCCCTGCCCCTAGCCCATGCAGGAGCCCAG
GGTGGGGCACAGGAAGGACGATTGGGGCCCCAGGTCAGGCACATCCAGGC
CACAGCCGTGGCCACACGAAGGCGGCCCTGAGGGGGCGTTGGGGGGCAGA
CCCTGCCCCCCCGCTGCCGCCCCAGCTCCAGGCATTAATTCCCAGGGACC
TGTTGCACTGGGTGGCCGCCAGCCTGCCCCCTTGCCTTCCAAGGCCTCTA
AAATGCCCCTCTTTTCGTAAACTAGGACTTACCAAGCTCAGCGAGCCCTC

Contig 102 (1867 bp)
AGTATATCGGGTGAGACTGGGGACCGGTCTGCCGGGAAGCCCCACCATAA
AGGCCACGTTGGGCCACAGTCCGGGCCACGTGAGTGTGGGCGGGTCCGCG
GGTCTGCTCTTGGAACACCAGGATCTCTAAGAGGTACCAGCCGAGGCCAA
GTTCACGTGAGCAAGTGAGCAAATGACTGAATGAGAGCGTGAGCGAATGA
GTGAGGGGTGAGTCCGTCCACCACGCAGCCTAGGCTCAGCCAACCGCTGT
CCCCGCGTCTCCACTGGTGACCAGAACGGAAAGAGTGGGGAAAGAGTGGT
TGTCTCCCACAACCCAGTCCCCAACCCCCCTGGACGCCCCACCCCTCCAG
GGGTGCCGGGCCTGGCCTGTGGGCCCCAGTCTGGAGGCTCTGGCACCTTC
CTCATCCGTTCTCCCAGCACCCCAGGTTCGTGCTGAGCCCTCCTGGCCCA
CAGGCCTCGGGGACAAAGAGGGCCACCTGGAGGCTCAGGGAGCCTCACCT
GCCTCGTGGTCCTGGCGGAGGCGGGTCTGGACATGTGATAGACCGGCCTG
GGCTCAGCAGCTCCTGCTGGAAGATGTCAGGGACAGCCTGGGCCACTCTC
CCACCAGGAGAACTTATTCCTCGGTGGGGTCCCCCGGGGAAGGGATGGG
ATCCCAGCGGGGACCCCAGAGCGTCCAGCACACGGACCTGTCCCTCCAGC
CCCTGCCCCACACGGATGCTCACAGCTCAGCCTCGAACACGCACCTGTTG
GACTTTGCCTCCTGAGGCTGTCTTCTCAGCCGACGCGGGCCTCCGCTGCA
TGGTCTGGAAGCCCAGTGGGACTCGGTGGTGACAGGGAACAGGGGCTCTT
GGAGTGGGGTGCCGGGGGAGCCCCGAGGGAGCTGCTTGGGCCTTTGATGG
CTGAGTGGGCTGAAGTCAGGCAGGCTCCCCAGGGCTCCCTGACCCCCCC
CACCTCAAAAAATCCAGAGCATCCTTTGCTTTGGGTCTGGTGAGGCTCTC
TGAGGTCAGACCCTGCGTGGCTGGGCCAGTGGGGCTGGAGCAGGAAGAAA
GCAGGACAGCCCCCGCCCCTGGCCCAGACTCCCCAAACCCAGCAGGAGAC
ACCTGAAACGGGATGGAACCATCCTGAAAAGAGCCACCTCCTCCTCCTTA
TGCATCAGCTGCCGGGGTCTGGGGGCCCGCCCCAGGCCCCAGATGTCCGG
GCTGCTCCCGTCTCACATCCAGGGGTTTCTGGGCCCAGGACTCTGTCCCC
CCAAGCATGCAGAGGGTCCAGGCTGGGGTCTTCATGCCTGCCCGTGTGCA
TGGTGGGGAAGGAAGGGGACAGTCTGGAGACCCCCCGCCCTCCCCATGCG
TGGCGCCGGGGGACAAAGCCGGCTGGGGTCTCAGGTTTGGGTTCAGAGCA
AACGTTGATCTGACCTGGTTCTGAGATGCTCGGCCCGATGCTGCGTTGTC
CGCTCGCATTTTCCTGTTTTCTCTGGGAGGCGCTGCGTGCGCTGTGGCTT
CCGGCCAGCCCCACGGAGGGACGCAGGGTGGCTGGCGGGGTCTGGGGGCC
CCTGCCCGCACCAGAACGTCTGGCTCAGGTTTTTGTCCTCGTGACCCATC
ACTAAGGGCCACCCTCTGACCCGGAGCCCTGTCTCCGAGGTGGGAATTGG
GGGCTGTCCCTGGCGTCATAGGACCTGGTTGGGGGCATCCAGGGCTGTGT
CATGCCCCTCCCCAGAAGACTCTGGGGGCTGCGGGAGGGTTTCCCCAGCT
TCGGGCCAGCCTGGGGAGGGCGGAAGGCGCTGGAGGCCTTGCCTGTCCCA
GGGAGCATGGCTTCGCTGCAGACTGGGGCCCCGCACACCCAGCCACCACT
GGCCGTCTGGAAGCACT

Contig 103 (650 bp)
GTTGAGGATTCCTCGGCAATTTCCTCGTCACTGGCGCTCCAATCGCCTCG
ATGGGCTTCTCCTCCAGATACAGCTGCAGATCCTGGGCGGGCACACCGTT
GAGCGTCACCTCGTAGTGCAGATTGCACTCGTTGTCAATGGACATCCAGG
CCATGCCGACGGCATGTGGATTCTGTGCATCCGTGTGCTCCTGTCGCTTC
AGCAGAATGGGTTCCGCCGAGTCCCGAGCATCGGCCACTGGACGGGGCAC
TAGGCGGCCACGGATCAGGCTCGTCTCATGCTCGGTGGCCACATTAACGC
CCAGTTCGCCGGCATACAGCGACTCGAGGACCTTGGGACCCAACTTCTCC
ACACTACCAATGGCCTGGTTGAAGTTGAAGCTCGGCGTCAGATCCTCCAG
CTTGGCCTTCCGCTTGCCCTGCTCCTCAATCAAACTGATGTTGGGCCTAT
CCCGGGTGTTCACGTGCTCCGTTTCGATGTTGTAGGCCAGAGATCCATCG
GTGTTCAAGTAGACCCACGCCAAACCGCTGCTCTTGGTCGAGGATTCGGC

Fig. 6, contd.

ACTGTGCGGCGCCAGCAGGGTCTGGAAGATTTCGCAGCTGGCTCGGGTCA
CGATGTGTCCCTGGATGCGCAGATGTGGGTACTTCTTGGACTCCACGGTC

Contig 104 (1630 bp)
GGTGTTGTCACTGCTGTGGCTCAGACCCCTGCTGTGGCACAGGGTCCATC
CTTAGCCCAGAAACTTGCACATGCCACAGGTGCAGCCAAAAGAAAATTCT
TACTAATAAGTTGTTCATTTGCCTTTACGTAGAGTGGCATCAAACAGCAA
ATTTAAAACACCATCTATCAATACATAGACCGCGGTCAAAGGGAAAGAAC
TTTCTATTTCAGCACCTTTAACATGGCTTTGCCCGAATTTGGGACCAGGG
TGCTGTGTTTTCATCTCTCCCTGCAGGTGGTCCCCAGATGACCAGGCCGG
TCCTGGGCGGGAGGAGCCGGACTGTGGATCCAGTTGCTTCCCAAGACAGG
CTGACAGGAGAGCAGCAAGGGCCACCCCCAACCGAAACCAAAGCCAGAAC
GAGCAGAAAGATGCCGTCTTCCAAGTGGGGGCTGGGAGCTTCCTCCCATC
CTCCGGAGCCGTGAGGCTGCCCTGGAGCTGGCAGGAGCCACAGAGGACCC
GGCTTTGACCGCCCCTCTGGGACCCACAATCAGGACCCTGACTCAGATGC
TGAGGGGCCTGGACAACACCCCAGGACCCTGCTGCTTCCCCAGAACCGCT
GTGTCCATCAAGGTCCAGATGGCACCCGTGTCCCCACTGGAGCACGCACT
CCGTGGGGCAGGCTTTCCCTTGGGCACCGATGCACCTTGAGGGCAGAGAC
GGGGCCCAATAAACGTTTCCAAACCAGTGGGTGAGGGACCCGACCGGCCC
GACACGGCAGCCCGGATGCAGGGACTCCGTGCTTGGCCCAGCCTCCCTTG
GGGTGGTCCTGTGTCCTCAGGGGTGGATAGGCCATCATGTGGGTGGCCTC
TGGGGACATCCGTTCTCTGATTGGGTGAGTTTCAGCCACAGAGATATTCC
CAGGACTACAAAGCTGGGTCCCTTGGGGCACCTGCTGTCACAAAAAGACA
AGGCCCTGACCCCCAGTAGCCAAGTTCCCCAGGGGCTCCCCAGGGTCTG
GTCATCCAGACTGTGCCAGCCGTGCCTGCCCGCCCCAGTCCTGCCTGACCC
GAGTCTCTGTAAACATCCCCCGGCCCCACCCAGCTTTACCCCAAGGCCGA
AAGCACCAGCCCCCCTGCACCACAGATGAGGCCCCCATGGCTCCCCGACC
TAACTTCTGTCTGCAGTTGGCTTTCAGCCTCGGGTGGGGGCAAGGCCTGC
ATCTCAGGCTCCCGGGAGAAGTTGCTGCCTCCACAGCAGAGCCAGGGGCC
TGCTGACCACCTGGGCCGGGTCGGATCTGGTCTAGAATGCTGCTAAGGTG
TCCTTGCAGGCAGCCCCGGGCGGCCCCGCCCTCCAGGAAGGAAGGGGACA
TTGCCAGGACTCAGGAATGAAGCCATCCCAGGTTTTGAATCCCCGGTCCC
ACCACCTTCCACCTCTGACCTCAGGCACCTCGGCTTTCAGAGCTGCCCTT
TCTGACTCTGGGACACGGGGCTGTGAGGCGCTCTCGGTGTGTGACAGCTG
GGGGGGGGCACTCTCTAACGAGGGTGGGCGTGCCCAGGTGACTGACCACA
GCCCTTTCCTCTCTCAAAAACGCCCGCCCGAGTGACCTCACGGGAGGCAG
GGCCAGGAACCCCAAACCAAACCAGAATCA

Contig 105 (1820 bp)
AGTGAGCCCTGCAGGACAGTCTGCTGAGGGGTGTCTGGGCTCCTCAGAGG
CTCATGGCCACGGGCACTGGGAGGATAGCAGGTGGACCCCTGCATCCAGG
TCCCAGGTCCCAGGTCCCAGACCCCCGGACAGGCTTTCTATCTGCAGGAG
GGGGGCTCCTGGGGCAGCAGGGATGTGGCTGTGAGGCCTCGTCAGTCTCC
CTGTTTCTATCTCTCTCTGTATCACACACACACACACACACACACACACA
CACACACACACGCACGCACGCACACACACAGAGGCGTGACCAGGGCTGCA
GACAGGGCCATGGGAGGACTGCCCGGCAGTGCACCCAGATGGCCACACGG
TGGGGCCCTCGTCCCACTTTTGCTGCTGATGCTTCCGCCCAGGCTGCTGG
GAGCAAGCACTAGCTTCCCAGGGCTCTGACCAGAGAGGGATGGGAGGGGT
CATGGGTCAACAGGCGCCAGGGAATGGGGAATAGGATCTGAGGGGCGGGG
GCAAGGGGCCCAGGCGAGGCTGCAGTGCCCAGAGCTCCCTGCACCTGCAG
GACCAGCCACAGGCCAACAGCTGCAGGCAGAGCAGGGCTGCTCCTGTCCC
CAGAAGCTGGCACAGCACATGGGTCTGACAGCCCCACCCCGGGCCTCCC
ACAGAGGGGCGGGTCCCCAAACTCCTCCCCCGTCCCACCTCACAGCTCA
GCATCTCCACTGCCTGAGGACGAGCCCAACACACGGGCACACACACACAT
GCACGCACACACATGAATGCACCTGCAAGCACACACTCACACGTAAGCAG
GTACACACATGCATGCACACAATGAACACACATGCACGCACACACGCATG
CACACACGCACACACACTCAAACACGTACATGCAAGCACATGCTGGTCCT
TTGTCCCCGTGGAGGGGAGGATGGAGGCCCAGCCCGTGGGGAGGGCATGT
GGAGTGTTGGGGGGCTGGCTCCAACGCCCTCGCTCAACAGGCACCAACGC
TGGACTGAGATAAGCCGGGGCGCTGGCTCCCTTGGGGCCGCTCAGCAGGT
TTGACGCCCACCACAGGTGGCACTGCCTCTTTCAGAAGACGGATGTGGCC
ATGCCACCCTCACAGCCTCACCAGTCCCCCTCAGCTTTAGTGGTGTCCC
TGTCACTGTACCCGGGGCCTTCCTTCTTCCAGGGCCAAAAGCGAGTTCAG
GGGACAGTGGCGCCCCATAATTACTCACCCAGGGTGCTGTCCTCTGTGG
TGGCCTTGAGGCCAAGGTGCTCCCATGGGGCCCACAGGGCTGGCAGGGT
CACTTCCTGAGAGCACCCAGGGCCAGGGGGGTGGCCCAGGCCTGGCCGGT

Fig. 6, contd.

```
CCCCATCTGGAATGAGGGCCTTGCGCAGAGGCGGTGCACCCCTCTTTACA
GCAGCCCCGGGGGAGAGTGACTCCTGCGTCATGGACCTGGGGGCTGACCT
GTCACGTGTCTCGCCCAGTTGCACCCCATCCATTTCCGGGTGGAAGGGAC
AAAGCCATCCTGGTCGTCTCAGAGGACCTCTGGAGCCTCTTGGCCCCAGC
AGCCCAGCCCCTCCCGGGCCCGCATCCTCTGCCCACCCAAAATCACCTGT
GCCCACAGGGTCCCCTTCTGGGTGTCCAGGGCGACCCAGAACTGCCCCTG
CAGACACACCCAGCCCAGGACATGGCCGCCTTGCCGGGCCTGTCTGCCTG
GGGCAGCCTGACTGCCACAGACAGGCCGCTTGGAGGACCATCTGCCTGAG
CCCCCAAGGCACATCCCACGGGGCCCACACAGCCAGCGCCTGTAGACGAT
GCCACTTGGGGTGGGGGAG
```
Contig 106 (1500 bp)
```
TGCCGAATAGAGGTGGAAACCAAGACCCGAAAAAATGTCCACATTTTTCA
ATTATTAGAAATTTAGAAAAATATTTTACAGGAGTTAAAAGGTATTCCAT
TCTGGGGGCGGGTGGGCATGCCCACGGCATGCAGGCATTCCCCGACCAGC
GACTGAACTCGAGCCACGGCAGTCACCATGCTGGATCCTTAACCTGCTGA
GCCCCTGGGCAACTCCAGACACTCCATATTCATGTAAACTATTTTTTAAC
CAAAAAAATGACAAAGCTTTTCAAAACAAAACACATTTCATGGGAAGAGT
GGCATTGCTTCACGCCTGGATGGTCGCTGCGGCTTGCGGGACGACGAGGG
CCCCCGCGGGAGCGCCTCCGCACGGCGCATCAGGACGTGGTGTCCAGGGA
AGCGGGGTCACTTCACGGCCTCTCGGGTGCGCGTGGGTTTCCTTTTCGGC
ACCACACCCGGACTCAGCACTTGGGGGTTCTTAAACGTGAGAGGCACTGC
GGGGCTCGAAGCCACATCACTGACCTCCTCAGACTCTGTTATGTGAAAAC
CCATCCGTCCACGAGACCAAAGAGACAGACGAACAAACGCAAGGTGGCGC
CTAGGTTGGGCACAGCATGAGGGCAGAGCGGAAACCTTGGCGAAATCCCG
GCGAAGCCTGGACGTCGCCAGCTCTTACTTGACGCAAACATAGGGGGATT
CAGGAACTCTCTTTACCGCATTTGCAATTAATTTGCTGCAAATCTAAAAT
CGTTCCAAGCACAATGCTCACTGCATGGAAAAACCCAGGGGTAGGTCTCG
CCCGATCAGGATGTTTTCCCGTGCCCTCTGTGCGGGTGCTGCCCCCTGCG
CTGGTCAGTGAGAAGTGTCCCTCCACCGACGACATGAAACTTCCCAGGTC
CACGCTCTCTGCTGTCCTGGACGAAAACTCATCTCTGTGAATCTCCCGCC
AGCTCCGCGGGAGCCTTCCAGGGCTGGAAGGACGGCCGTCCCGTTCCAGG
GGGCAGGTGCACGCTTCCCAAAGCTCCGCGTCCTGCTAGGACGCTCAGAC
GGCATCACCCACAAACCCCACGAACTGTTTCCCTCGAGGCGACAGGCTCG
CCCTTCTCCGAGAAAGCAGCCCGCACACGTCAGCAAGGGGCCAGCTGCGT
TGTAACTCAAATGGCCACATAGAGTTTGTCCTGGAGGCACGGGGTCTGT
CTGGGCCGCACCACTGCACACGCAGAATATGCTGGGACACGCTCCGGGGT
CCAGCTTCATGGAATTAATAAAGTTTACTGCTTCACCAAGTACATTCTTA
AGTGTAGCTGGCCGCCAGCCTGGGCGTCCGCTCCGAGGCTGCCTCTCTGC
CTGGAACCCTTGTGCTGGGGGACCCTCTCTCCAGCCCCACCCCAGCCCCG
AGCCCAGGCAACATCCTTCTTGTAAGACACCCGCTACCCTGCCCTCCCGC
TTCTCCTTCTCTGGATCCAATCTCCTCCGCTTCTAAGCTCTCTTGAGGCT
```
Contig 107 (550 bp)
```
ATGGCACTCGCGGTTGTGACTGAGCTACCGGACGGCGCGAGCAGGGCCAC
GAGGGCGACAAGCGCGGGGCTGAGAACCTGTGCGAGGGCAGGTCCCTGCG
GCTGCAGACAAGCCTCTATCGCAGGCCCACAGACAGGAGCCCCCGTGTGA
CCCTCAGGCTGCGAGACCAAAGTCACGGCTCTGCTGGGAAAACCTCGAAC
CTGATGACTGGGTGGGTGACCCCAGGACCTTGAATTCCGGCCTCTGCAGA
ACGCTCTGAGCCTACGGGAGTGGCCACCCTCTCGGTTAGGGCCTGTGTCC
TTCCCTGGCTTCCAGCCTAGAGCAAAAGCATTAAATCACAGTGTGGCCCA
GCCCGGACCGTGCAGGACCTTAGACAAAAGAGGAGGGAGAGAGAGATGAG
GCAGAGAGGCAGAGAGACAGAGGTGGAGAGACAGATAGACAGAGACAGAG
GCAGAGAGAGAGACAGACAGACAGAGACAGAGGCGGAGAGACAGACAGAG
ACAGAGGTGGAGAGACAGGCAGACAGAGACAGAGGCCGAGAGAGAGACAG
```
Contig 108 (900 bp)
```
TTTCTAAACTCTCTTACTAGTTCTAGTTTTCTATTGTTTTCTGGGGGGGT
TCTATATAAACATTCGTGTCGTGATTGGAGATGGTTTTGTTTTTTCCTCT
CCAAACTGTATGCCATGTGTTTCTTTTTCTTGTCTTATCACACTGGCTAG
GACTTCCAGTAAAACACTAGATATGAACAATGAGAGGAGAGCCAGGCCTT
CTTCTCAGTCTTGGAGGAAACAGTCAGTCTTTCCTCATTTAGAATGAGAG
CTTTTCTTTTCTTTTCTTTCTTTCTTTCTTTTTTTTTTTTTAATAGGTT
AAGGAACTTCTCTTGTATTCTTATTTTTTAGAGTTGTTATTTTTTTTTT
CTCTCTTTTTAGGGCTGCACCCGAGGCATATGGAGGTTCTAAGGCTGGGG
TCGAATTGGAGCTACAGTCGATGGCCTACGCCACAGCAATGTGAGATCTG
AGCCACATCTGCGACCTATACCACAGCTCACAGCAATGTCAGATGGTTAA
```

Fig. 6, contd.

CCCACTGAACAAGGCCAGGGATTGAGCCCGCATCCTCATGGATGCCAGTC
AGTTTCGTGACCGCTGAGCCATGAAGGGAACTTCCAATAATGCACCAATT
TTAAATGAAAAAGACAAAGCATCCAGCCCACAGCCTGAGTAAGGAGTTTG
GAGGCCTGACCCCTGCGTGGTCCTGGGCCTGGGCCTGGGCTGGTCGGGGT
GGGGGGGGGTGGGGGGGACCCTGTGGACCCTCCCTCCTCAGCCAGGCCTG
CCCCTCCATCCCTAGCTGTCGGGGGCTCGGAGGAAGGCGGGTGGATGACG
GTCCCTGGGACCCCTCCTCATATGTATCTGGGTCCCTGGTCCCTCTGAGG
CCCAGGTCAGGTCATGGGAGTCAAAGGTCAGCCAAGGGGGTAGCCCAGAG
Contig 109 (950 bp)
TAACCCACTGACCGAGGCCAGGGATCAAACCTGCAACCTCATGCTTCCTA
GTCGGTTCGGTAACCACTGCGCCACAACGGGAACTCCTTTGCTTTTGTTT
TTAGGATTTCACATACACGTGATAACGTGCCGTATTTATCTTTCTCATCT
GAATTATTTCACTTAGCCTAAGCCCTTCAGGGTCCATCCATGGTGCTGGG
AGTGGCAGGATTTGCTTCTTTTTTTTTTTTTTTTGTGGCTGAAAATCAG
TCCAGGATTATCTTCTTTTTCTGTTCATCTGTGGAGGACACAGGCTGCGT
CCGTGTGACGCTCTGCCGGGAATACGGGGGCCGATCGCTTTCTGAGCCAG
TGTTCTCATTTTCTTGGGAGAAGTACCCGGAGTGGAACGGCTGGGTCGTC
CTGCAGTTCTGTGCTGCATTTTTTGAAGACGCTCGGAGCGCTTTCCACAG
TGGCTGCACCGACTGACATTCCCACCGAAGTGCACGGATTTCCCCATCCT
TTTTCCACGTTTTCCCCGCACTTGCTATTTTTGCCCTGTGGATGTCGGCC
TCTCCGTCAGGTGTGAGGGGAGTCTCCGTGCGGCCCAGGCGAGGAGCGAC
CGTGAGCGTCGTTTCACGTTCCTGTTGGGCCACCTGCGTGGCTTCTCCGG
AAAAAGGGCTGTTCAGGCTTCTTGCCCATTTCTCAGTCTGATTGTTTGGG
GGGTTTGCTGTTGAGTTGTGTGAGTTCCGCACGTATGGGGGGCATCAACC
CTTTATCAGCTATGCGATTGGCAAGTCCGTTCTCCCATGTTCCGCCGGCC
GCCTTGGCACGTGTGGGCGGTCTCCTTGGCTCTTCCTTGGTGCAGAAGGC
TTCGGTCTGATGTGGGCCCATTTGTTTATCTTCTTTTCTTTCCTCACCGT
TGTTTTGATGTCAGATGCAAAAATCCATTGCCAGGGTCTGTGCCGAGAAC
Contig 110 (306 bp)
CGCCACCTCAATCGCCGGTTTGTTCTGCAACACGGTCCAGATAACCAGCG
CACCTAACAGGTCGAACACTGCCAGAACTGCGAACAGCGGGCTGAAGCCG
ATGGTGTCAGCCAGTGCACCGACAACCAGCGCAAACAGCGTACTTGCCAG
CCATGCGGACATCCCGGTTAAACCGTTTGCCGTTGCCACTTCGTTACGAC
CAAACACATCGGAAGAGAGCGTAATCAGCGCGCCAGACAGTGCCTGGTGG
GCAAAACCACCGATACACAGCAGCATAATTGCGACATACGGGTTGGTGAA
CAGGCC
Contig 111 (800 bp)
GTTTTCCATGATGCACCAGGGGGGCCGGGACCGCAGCAGGGAAGGCTCCA
TCCTGGCTCTGTAAGACCTTGAAAACACCTCATTCCTCTGGTCTTGGCCT
GCTCTTCGGTACGCCAAGTTGCTGAGACTGATGTGGGGATCAGTGGGGAG
CAGGAATCTTTCTGATTCAGCCGTTTCAAAGTGTCCCAAGCAGAAGCTGT
GATGGCAATGCCAAGGCTATCCATGGAGGTGGCTGTGCCAGGGGCCCCAT
TTCCTGGGAGCCCATTCCAGGAAAGGAATCTTGTAGCCCCAGGCTCCAGC
AGCCAGTGCACGGCCCTGGGACTATCCGGGTAGATCAGAGGGAGGAACA
GAGCTGTGGATGGTAAGCAGGTGGCCCAAGTCCAATTTATGTCTGTGGTC
CCAGCAGGGTGCCCAGGAGGCCCCTCGTAACTCTTAAGAATCTTGGTCTG
GTCAGCTAAATTGTATGACCATTGTACTGAGCACACATCCCGTTTAAGTA
GAATTTTCAAGGATGACTAGGAGTTTGCCACCTGAAGGCAGGAAGGGCAT
TCCAGGCAGAGGGTACAGAGGTGAGAGGGAGGCTCTGACACTTTGGGCGT
GCAGGGGGTTTGATGTGACTGCAGCTGGCACACAGTGTATGCCCAGGCCT
GGCACGGCTGTGTTGGTGTTTGGAGAGGAAGGGAGAGGTGAGTTGAGCCC
AAGGTCTTCCAGGCCAAAAGACTGAAGGTGACCGCGGCTGTCCGGGGCTG
GCCCGCAGACCAGGAGGGAGCAGGTGGGAGCTGGCTCTTGTTCCGGGGAC
Contig 112 (3062 bp)
CACACCCCAGGAGAGGAAAGACCCACACAGTCCTGATGACAGCTTGGCTC
GGGGCTGGAGCCCCGAGTTATAAATGTCCATCACGAGCTGTGTTCTGTCA
GAGCCATCAGTGGGAAGGCCAGGCCAGCTCAGCAGCCCAAAAATGAAGAG
CTAGGTCTGGGATTGGGCCCAAGCAGAGGGCACAGGAAAGCCACATAAAC
AAGGCACCCAACCCCCTGTCATCCACCAATGTCACATTCAGGTCACACC
CCTGGTCTTCGGGGAGGTCCCCTAAGATCCGGTGGCAGGGGAGGAAAA
GTCTGACTGGATTCCTTGACAGGTGTATCAGCGGAAGGCCAGGAGGAGTG
CTCGGGCACTGCCACCTCCCAGGGGCATGATGGTCATGGACCAGATGGCA
GTTATGGGAGGAACCTCCCCGTGGTCAGAGCTCTGGGTGCTGTACCTGG
TCATGCATTTCGAGTGGAAGGAAAAGAAAACATACAACTCCACCCCCAGC

Fig. 6, contd.

```
AGCTTTAGGCTGTTGGTCTAAAGGTCCTGCCTCCTGGAAGAGACACGCCT
CTGTCAGCGGACACTGCTAAACCTAAAGGAAGAACTGCCACCTGGTCACG
GGACTTCCTAGGCCAACCAACCTACAGGTGACGGCCCGGAGCATCACGAG
GAGGTAGGGGACGGGAAGGGATGCATTTGCTGCTCAGCGGATCCACTGGG
GCGTTTCTGGAGCCCCCACGCCCACACTTTACTGCAAATGCACAAGCCCC
AGGCAGCAGGACAAGTCACAGTAGCTCTGGGTTATCCAAGGAGTCAGGGA
CCTACCTGGAAGAGTCTAGAACAGGTGACAGAGGAGGGAGAGGATGGTAC
CAGCAGTATAGGGAGAATCAGAAATCTGACCCACCCTGGGGCCTGACTG
ACTCCCAGACCAAATGCCACACTCAGGTTCCCCGTCTGCCTGCACTTCCA
GGGCTGGGCCACGGGAGTTATGGGCCCCAGGTAGCATCAGAGGCTCCCAG
GTACAGGCACAAGCAGCAACCACAGGAGGGATCCAGGCCAGGGAGCATCC
AAGAAGCAGCAGAAGCTCCACCTTAGGTACAGTTCTGGCACCTCCAAGTT
GAGAACATGTCCTAGACAGTGCCTGACCCCAACCCAATGGAGTGTCTGGG
ACTAGACTAGGCACGCCATTTTGGTCCCAGGTTGCCCCATCTGTACAAAG
GGTGTGCGGCCCCAGGGGGACACAATGAGCTCCCATGGGAAGGGTCTTG
CGAATCTCCTTAGAAGCAGATGTAAGAGGTGACGTCCAGCTTGTGCCTGG
GATGTAGAAGTGGAAAAAGCACCCCTCCCCCGACAAGGATGAAAGCAAGA
GGCACAAAACAACCTGAAATTCCCAACGCCCCTGGAGATCCTTGGAGAAC
TGGGATTCTCCACCTGTAGGGGCACCTGTGAGGAGAGGCTGTGTGAGCAC
CTGCTGACCTGGCACAGAGGATGCCCAATACTAAGAAGCATCAGCTAAAA
GTCTCCAGGAATTCCTGGAAGCTGAGGAAGGGCTCAGGAGAGGGTACAGA
AGCCCTGGGGCTATAGATATAAGGGACGTGCACACCCACTTGCAGGTCCC
CATGGACCCCAGGGACATTCACAGTGATGGGCAAGATTCCCAAAATGCAC
CCCTTGTGTGTGGGCCTGGTTCGGTGGGTCAGCAGACACCACACCAAAGG
CACAAAGCACACACCCTCAGGCTACTCCTCCCTCTCCCTTGTGGAACA
TGAGCCTTGAGATGCTGGGGCACGTGAAAAACACTGTCACACTTAGGTCC
TGGTGAAAACTGACTGCGGCCAGCGGAAAGAATCATAAAGACCCTACACC
CACACACAGCCTTAATTACAGCTGTGAGTGGGGCTGGAGCCCCAAGAATG
TCTACACCCATAAGACATAGCGTTAATCAGAAAAACAAGAACAGCCCCAA
CCCCACCACCAGGCTGACAACTAACAGGTCATGTTGGAATATCACTGGGA
ATGTTCTAGGAGTGTAGAAAGACACACCAACTAGGGCATGATGCAAAGAT
AATACTTCAGCCTGGGAGTGGATGTGACACAGGGAAAAGCATAAAGTGAT
GGCAGAGGACTTTGATGTCAGTGATGGAAGCCACAAAAACTTCTAGCTTA
GCTCCATTCCCAACAAGATTGACTGCAAACCCCATGCTAAAACAACAGCA
AAAAGAAAGAATCCTCATTTCCAGGCATAAAATTTTTCCCCAGTCTCTG
CTGTCCTCCATAAGATGTCTGATTTCAACAGGAATTACGAGGCTATAAGA
AAGGCAAGAAAAAACTACACACTGTCAAGAGAAAGCCATCAGAATAACCA
GACTCGTAGCACAGACACTGGAATTGTCAGGATATTTTAAATAACCGTGA
CAAATACATTAAAGATTCTAATGAGAAGGGGGTAGACATGTAAGATCACA
TAGATTTCAGCAAAGAGATGAAACTCGAAGGAAAATTAAATGGGAGCCCT
AGAGTGAAAAACACTGTAGCAGAGAAGATGGGTTCATCCGTAAACATGAC
ACAGCTTAGGAAAGAATCAGTGAACTTGAAGACAGGGCCACAGAAAATAT
CCAAACTGAAATGCAAGGAGGAAAAATAATGAAAGGGGGAGAGAGAAAAA
ATAAAAGAACAAAGCATCCAAGAGCTGGAGGGTGACACTGAAGAAGAGAG
CATAGGCATAGCTGGAATCTCAGAAAGAGAGAAAGAAATAACCCAAGATG
TAATGGATGAGAATTTCACAGAAGCGTTGTCAAGCAACAAACCATACATC
CAAGAAGCTCAGAGAACACCAAGCAAGGTAAGTACTGTAAAAAAATAGCC
CGAGGTATACCTCATTCAGGCTGCTGAAAATCCATGACAAAAGAAGTCTT
GAAAGTAGCCAGAAACAGAAGGCGTGTTCCATTCAGAGGGAAAAGACACC
ATTGTTGCCAGAAACCAAATAAACCAGGGCTGAAAGGGTAAAACTTTTTT
TTTTTTTTTTTTTTTTGGCCATGCCTGTGGCATGTGGAGGTTTCCCGA
TCAGGGATCAAC
Contig 113 (1300 bp)
AAACGGATAAATACAGGTGACCCACAGGCAGAAGCTGAAGTACAAACAGT
TCACAACGGCACCCAAAAAATACCGAAGGCTCAAGGGTAAATCTGACCCC
AGATGAAAGGCCTTCTCACGGAAAATGGCAAAGTGGCGCTGAGAGGCATG
AGAGGTTCGAATAGATGGAGGGCTCCGCCGTTTTCCCGGGTCCGAGGATT
CAGTGACGTCACGACGCCAATTCCTCTGAAACGCCTCTCTAGGTTCAGTG
CAGCCCAGACCCACTGGCAGCCGCCCTCGCTGCAGAGACAGCCCAGCTGG
GTCTTGAGGTTCCTACAGCGAAGCAAAGGGTCTAGAAAAAGCAGACGTCT
CTGGAAAGGGAGAAGCAGCCGATGGATTGGCATACGGCGACAGGAGATTC
CTCGGACAGTGGCACCAGGAGAGGGGTGGACAGAGACTGGTGCAACCGAG
CGGGCCCAGGAATAAGTCCACACCCACACGTACCATCTCGTTGTTTATTT
ATTTTTTCCTTTTCAGGGCCACTCCTGGGGCATGTGGAGGCTCCCCAGCC
```

Fig. 6, contd.

```
AGGAGTCGAATCGGAGCTGCAGCTACAAGCCTACCCCACAGCCACAGCGA
CACAGGATCTGAGCCATGTCTGCAGCCTACACCACAGCTCCCGGCAATAT
TGGATCCTTAACCCACTGAGCAAGGCCAGGGACTGAACCCACGTGCTCAT
GGATACTAGTTGGGTTTGTTACCACTGAGTCACAGTGGGAACTCCTTTAA
TTTTAATTTTTGAAGGTTCAGAACTCTTTAATTTTTTAGTGAGGTATAGA
TTATATTACGCACCATTTCTTTCTGACTTCGGTGCACGGCTTTTCAACAA
ATGGGTGCTGGACCTGCTGGGTGCCTTCTTCAAATGAACCACAAGCCCTC
CCTCGCGCCGTATGCAAAATTTAACTCGAGGGGCTCATAGACATAAACGT
AAACTCTAAAGCTATAAAATTTCCAGAAGAAAACGTAAGGAAAACCTTTG
GGGTCTTGGGCAAAGATTTCTTACCCATGACAGCAAAATTACAATCTACA
GAAGAACTGGTGGCCTTTATCGGCATTTAAAACACCTGCCCTTTGAATGA
TGCTGTCGCAAAACCGAACATGCAGCAAAACGGATGCAACTAGCAGGTCT
CACACTCAGTGACCCACGTCAGAAAGGGAAAGACACGCCACGTGACATCC
CTTAGATGCAGAATGTAAAACACGGCCCCCGTGAACCGACCTCAAGAGAG
AGACAGACCTACAGACGCAGCAAATTTGGGGTTGCCGAGGGGATGCCGG
Contig 114 (3000 bp)
TGTGAGACCCCTTGGCGGGCCAGGACCCCCCAAGGTGACCGAAGGCCTCA
GCGCCCCCAGCCGCCCCATCCCCCTCTTTCCCGACACAGGATTTTTTTCC
CACCAAGCTCTGTTCCCTTGGTCACGCTCTCACTTGAGCAGCCTCAGGGT
CTCCCGGTGCCTGTATCCACGACAGCGTGACCTTCTTGGTGTGTCAACCC
AGGACCCCACGCTGGCCAGCCACGCCTTCCCAGAGCACCCCCGCCCATCC
TCAGAGTCCAGAGGAAAGGCCCCCATTGACCCCAGAAACCAAAACGCAGA
GACTCTGGGACGCCAGCAAGAACGTACACTGACTCCCACCTGCTTCAGGC
ACGGAGGCAGGGGTGGGTTATGAGCGACCCCGTGGAAGGGCCTTCTTGTC
CATCGAGGGGCTTCCAGGGGCTCCTAGACGGGGATGAGTGTGGCAACATG
TCGCCGCATTACAAAAGACCCTGCAGTGCTGCTGGGATGGGTCCCCCGGC
TAGAAAAGCAAAGGATTCCAGCCCAGTCGAGTAGGAGGCGGCCTCGGAGG
CTGCAGAGGCGCGGGGGCGCTGACCACCACTCGGCAAGCCCCGTGTTGG
AGGGGACGCCCGGCCCGGCTGCAGCCGGTGCGCCTCCGGATAAGCTCCTA
AGAGGCCGCGTGCCCCATGCACGCGCGTGCACACACTCGCTGCCCGAGGG
TCCTTCAGCACAGACCTTGTGGGGACGGAGGACCTGGCAGGGGTGTGGCT
CTGGGGAAGGGGTCTGTCCCAGGAACCCTGTTCTGGATTTGGGGGTGGGC
GTGGATATCCCGTCCCAACCTACAGAAGGGAGGGGCTTAAAAAGAGCCCC
TTTGGTGTGAGGGGCCAGCAATCCTTTGGCTTTTTCTTGGCCCACTTGGA
GCTTGACGTCTGGTCAGTGACTGGGAGCCAGGGCCAGAGGGGGGCAGCCG
GGCTGAGGCAGGTTCAGGCCAACCATCTCTCGGCCACACTCCCGAGGTCG
GGCAGCTACGGGGCCCCCAGAGACACAAGCCCCAGGGGTCCTTCCCCCCC
GCCCCCTGCCCCAGATCACCAGGAGACCCAAGCAGCTCTGCCTCCCCGTG
CCTGAGAAATGCCCCATCTGGGTACCCAAATCACCCTCCCAGAAGGTAGA
GTGGGGGCCCAGGACAGGGGGACCCCAGTTACAGAGCCCCAGGCAGGCT
TCCCAGGGGCGAGGGGACTCCGTTTGGGGCACAGACGGAGGCAGAGCGGG
CTGATGGATTCTCCCCCGGTTCAGGGATGCTGGCTGCCTGGCCTCCAGGA
GCCGGCGGTGCCATCTGATCTGATTAAGGCCTGCAGTCCCAGCTGGGCGG
GCACAGCCTGGGGCTCGGCGGGCAGGGAAGAAGGCGCTGTCGCCCCAGC
CGGTCAGGCTCGCTTTCTCTTCATTTCCTCTCCATTAAAAGTGTCAGAAC
CATTTATTGATTTTTTAAATCAGGACGTGCTGTCCGTGACACAGCAAAGT
GAACAAAATCAGAGCAAAGAGAGGCCAGGGCTGAAGCCCCAGAGGGCGGC
GCCTCCAATCCGGGTTGTGCCCCGGGGCTCCAAGCCCCTTCTTCTTCTGG
GGTCCTGGGCGTAGTGGCCAGGGCAGAATGCACCTGCCGTCATCCTGGGA
GGCTTGGCCATCGCTGGCTTCTGTCTCATGACGCACCGTCGTTCCATATC
TACGGAAACAGCTTCGCATTAACAGGCAGGGAGGCGGTTGTTTCTCCTT
TATCTGCCCACCATCGGCGCTGGGGCCACGTGGAGCCCAGCCGGCTGACT
TCCCGCTCGCACGCAGGGCACTGATTGCAGGAACGAGGACATCCAGCCCC
CGCCTCTCAATGCCCCGGGTGCTGAGAGCATTTCGCCCAAACGGCTTGGG
TGGGACAAGGGATGGAGCTGTGCGCCAGGGGCCTGGCTGGGGCAGAAGGG
GGCCTGCCCGTGTCTGCCCGTGGCCTCCAGCACCCTCGGCTGCCAGGCTG
CTCTGGAGAGGTGCCCGGGGGCCGAGGGCCAGGGGCACCCTGTTCTGCCC
CACGTCTCTCTGTCCTGCTGAAAGTTCCACCAGACGCGTGCTATACCCTG
GGAGTCAGGAGGATGGGGGATAGTTGGGGCTTGACGTCTGTTTCTGAAAA
AACACCGTTTTCCCTGAAATATATATGTATTAATTTTTCGTCAAGATAAA
ACTGTGTATAGTTTTTCGTGATGAGAAAACGCATCCATCTTCCTTAGAAA
GCCTGAAGAGGTACAGGAGCCTATAAAGGACAAGATGACAGATGCCTCTA
ACGCACACCAAATGTGCGGTGGCCCCCAGGGGACCGCATAGACGGGGCGG
CTCCAGATGGCCACCGTGTGCGAGGGACACGGTTCAGGGTGGCAGAGTAT
```

Fig. 6, contd.

TCCTGGGGGGGGGGGCTCAGCGGTTCCCATTTCCCCCTCCCTTCCTTCC
TTCATTTCTTTCCTTCTTTCTTTCTTTTGTGGTTTTAGGGCCGCACCCG
CGGCGTGTGGAGGTTCCCAGCCTAGGGGTCTAATCAGAGCTACAGCTGCC
GGCCTCCACCACAGCTCACGGCAACGCCGGATCCTTAACCCACGGAGCGA
GACCAGGGATGGAACCTGGGACCTCATGGATCTTAGTTGGGTTTGTTCCC
GCTGAGCCACAACGGGAACTCCAGCCATTCCCATTTCTTGCTCCAGTTCC
AAGAATTCCAATTCTTATTCCTGTTCTTTAAGGCCAGAGGCGACAGCCAC
GCCGAGTCCCAGAAGCAGGGCTCAAGGATGCTGCTGTTGACTGTGTCCGT
GGGCGGGGGGAGTTGATAAGAACCCCCAACACAGGGTGGTGGCCAGCAAC
GGGGGAGGGAGGAGGGGGGCTGGTGGGGAAAAGTCCCCTGAACCCCATGG
GCTGCCCCCTCCAGGCTGGGGCACGACCCCGAGCCCCATGGCCCGAGGAG
AAACGGTCCCAGCCCCAGGCTGGGCTCCCGCACCCCTGCCCTGACCCCGC

Contig 115 (1895 bp)
TCATGGAAGCCCTTATCACAACCTCGGATCCAAAACCCACTGCGCGAGTC
CAGGGATAGAACTCGCATCCCCACAGACCCTATGTTGGGGTCTTAACCAG
CTGAGCCACATGGAAACTGGGTAATCTATTTTTAGATGTTCCTAGGGTTT
TTGGCCTTGCCTGTACGTGGGGACGCTGCTGGGCCAGGGATCAAACCCGC
GCCACAGCTGTGACCCAAGCAGAGCAGTGACAGCACCGGATCCTTAAGCA
CGAGGCCAGCAGGGAGCCCCTGTGTTTAGATTTTGGTGAGGATACTGCGT
GGGATTCAGGATATTCACTTTGGGGCTGTTGGAATTGCCCGTCGCTGTTT
AAGCAAAGAGAAATCCCTTCACTCTGTGTAACTGTGGGGAAATCCTTTAG
TCTCTTGAAACCATTGCGTGTGTTTAAGAGTGGTAACTCTGCCACCATAA
ATGCCCAGACCAGCGCCTTCCTGAGATCCGCTTTTGTTGCAAATATCTGG
TTTGAATGCTTTGATCGCCCGCACCAGACCAGGGTGGGCGGACGCCGCCG
GGGACCCGACGTGACCATCGTGCTTCTGTATCCGCCCTTTCTCCGGCACG
CGCCCCCTGGTTGCCTCTGGCTGCTTTTAGTGGAGGAACTGAAGCCTCGC
CACCCAGACCCCGAGACCGCAGGACCCACAATGCTTCAAACACCTGCCCT
CTGACTTTTACAGGTCAAGTTCGCCAACGCCGAATTTGCACCGATTGGCT
ACAGAGAGCACGGTGGCGCCAAGCCTCCACTTGGAGTTTTATAAGGTCTC
CCTCCAGCTCGCAATGAAAATGAGCTGTGATAAGGCAAAGACAAAATTAG
TATGAAATCCAGATGCTTCATCTACAATACAATGACCGCGGGATTTGGGT
CTGAGCGACTGAAATCAAGGTGGGCTTCCGGAGGGAGGCTGTTAGAGGAA
AGGCATTCACGGAGGCTCAGGTCCGAGAGGCTTCCACACCCCTAAGAGGG
CTGAGACGGCAAGTAGGGACCAAGCCCCGCAGTCGGGAGAGCTGGGCAGG
AAGGAAGTCTGAGGTCACCCCCACCTGGGGAGGAACTGCCTAGAGAAGCG
GGGGCGGGAAGCAGGGATGCCCAGTCCCAAGACAGGGACAGGGCGGAAA
GGGCTCTCTGCAGGCCCTCAATGCTGCCACAGTGTCCTCGTAAGAGGGAG
GCAGAGAGAATTGACACCGGGGAGACCACGGGACCACGGAGGTGGAGACC
GGGCTGCCCGCGCGTGCCAGTTGCTCCCGAAGCCGGCCCCTCCCCCAGAG
CCTTTGGGAAGAGGCGCCAACCTGCAGTTCTGCTACTCGGGGACAGGGAC
AGGGACAGCCCCCTGGAGCCGCCTCTTAGGGGCAGCATCCCCCAGAACCT
TCCTTAACAGACCATCTGGAGAGAGATGGGTCTGGGCTGCAGCTCCTGGA
ACTGTTTTGCCCACCCGGCGAGCACCAGTGGGTGCCAGCCTGGGCTGCCC
AGCCTCAGGGCCGGGGAGGGCTGAGGGCACTGGGGCCCGGCTCTGGGACT
CCCCTGCCTCCTGCCCGTGCAGGACAGCCACCTCCCAGCATCTGCTTCCT
GCCACCCACATCCCCAGGACCGTCAGCCCAGGCATGCCCTGGCGTCGGC
CACTCACACCACAGGCCAGGAACCCAAGGGGGCAACACAGAAGGGCAGTT
GCCATCTGCAGATGGAATGGACAAACTGGGGTCCGTGATGATGGCAGGCT
CTGGGCGCCCGGGCTGGCAGGGGAGCCAGGACTGTGCGGCCATCACAGGA
AGGGCATGACGGGGTGAAAGCAAGAGTGGAAACCTCTGCCACCCGCCTGG
GCGCACATACCGGCCACCCTGCAGCCCCACCCCCATTTGTTTGCT

Fig. 8

Contig 1 (1040 bp)

GCGCGCCGGATCCTTAATTAAGTCTGAGAGATCTGCGGCCGCGGCCAGGGTCTGCTTCTG
GCCAAGTGTGGGGCTCTGCTCCATCCTGGCTCGGAGGTCCACCCATGGCAAAGCCTGGGG
TCCTCCCACTGAATATTTGGGGGTCCACTCGTGCCAAAGGCTGGGTGTCCAGTGTGCCAA
CGGTACATGGAAGCAATGTCTTCCCAAGGACCGTCCAAGGTGTGGTCAGGCCTGGACAGC
TGTGAGTCCCTTCGGGACTAGACTTGGTGGCCGAACCCTAGGGACCGTGCCCGAGGGCCC
CCACGAGGCCAGGTGTTTGCCCCAGGGACAGAACGGCCAAGGGTGGCCGAGGGTTCTTTT
TGTTTGTTTTTTCTTCTTTCTCTTTTTCTTTGGCCGAGGGTTCTTAAAGCGCTCTCTCTG
CTCTTTGTCCCGATCCTGAGCGGGCAGTGTCCTGGTCGGTGGGGTGCTGGGCAGCCGCAG
CAGGGCTGAGAGAGCCCGGCTTGTCACTAGGGCGCGCCGGTGAGCCCAGCGGGCATGCCG
TGTCCAGACGTTGGATGGGGCAGCGAGGGGACTGGGGTGCCCCAGCCCCCGTGGGAAGCC
CGCCCTGTGGAAGCCGCTGTGCTCGCCACAACAAGCACCGTCGACTAGCTGGTGAATCAG
CGCCCGTCGCCCGCGTAATCCCAGGCGCTTTCTGCCCAACCTGAGCCCTGACCCCACACC
CCTTGCGACCGCTCCGTGGACCCTGGGGCGATGAGGTGAACCGTGGGCTTGGCCATCGTG
GTGGCAGACGGTGGCACACCCGTGCGCCTGTCGGCCCCCTCCATCCAGGAGCAGAGTGC
GCACCCAGTGGGGCTGGGCAGGGAGCCGCCTCCACCTCCGCCCTGAGGGGACGGGACTC
TTTCGACCCGGAGTGGGAAGGGACATATGCGGACGATGCCAGACCCTGTCTGTGGGGGA
GGGGGAGAAGGCCCTCTTTGGAGAATTCCAGGACGGGTGAGGAACGTGTGCTGGACCGGC
CGGGTCGGAGGTGGGCCTTG

Contig 2 (9234 bp)

GGCAACCAGGGGAAGATGGGGAAGCGGGGTGCAGGGGCGTTTGCGCGGGCCAAGGACCAC
CTTGGAAATCTGGAGCCTGGCAGGAGCGGCGCAGGGTTGAGGGGCTGGCTTGGGCAGGGC
TGGCTGGCACCTGGGAGCCTGGCGGGGTTGAGGTCCGGGCTCCCAGGTGCCCTATAGGCA
GGGCAACATCGGCATGGGGGGTGACAGGCCCGAGCTGGGGTGCGGAGGGAAGAGGGGGGA
GCCAGGCATTCATCCCGGTCAATTTTGGTTTCAGGTCGTGGCGGCTGGTGGTCAGGGGGA
GTTGGAGAGAGGTTCGCCCCGGGGCCTGGGCAGCGGAGGTGTAGCTGGCAGCTGTGGGC
AGGTGAGGACAGCCGTCTGCCGGGCCAGGTGAGTCCCCTTCCCTCCCCAGGCCTTGTTTC
TCTGGCCTCCTGCTCATCCGGAGGTTCTGGGGAGCGAGGGCCGGCGAGGCGAAGCGGCTGAC
CCCCCGGCAGAGTGGCGGCGGACGACAGGCAAGGCGGGCAGAACAGGTGACACGTCTCAG
GGGGAGCTGGGACCGGGCGGGGCTGGGGGGCCGGGGCCGTCCCAGGTGGAAAGAGCATCT
CAAGCGAGTCTGGTGGGAGACGAGGCAGGGCTGCCAGCAGGGAGGAGACGCAACAGGCGG
GGGGCATTCCAGGCCCGGGTCGGACAGGACCCGTCGGGGGTGTCAGGACAGTGGGGTCCC
CAGCCGCCACTTCACCCACTGCAATTCATTTAGTAGCAGGTACAGGAGCGGCTCTGGCCG
GGCCTCTTGAGGCCTGAGCTGGAGCCTCGAGGGCCGGAGAATGGGAAAGAAGGTGCAGTG
TGCCAGACAGACGTCACCTGGAGGGAGCACGGCCGTGGGACGGGCCCCAGAGAGATTTC
GGCAGCAGGGAGGCTGCGCGGGCCCAGCCTGCGGACGTGCGTTCCCACGCAGCACTGCGG
CCCAGGGGCTGGCGCGGCAGGGCCCCCGGTGTCCTTGGTGGCACTGTGCGCCCTCGCCGC
TCGCCCCTGGGACTGGCACGGCAGACAGGACAGCACCCAGGGGAGTCAAGGGCACTGACG
AGACCAGACTAGGCGAGGCGGGTGGGGTGGAATGGATGTGACCTCTGGGGGGAGGGAGGT
GGGGACGCAGGCAGGGCGAGGCGCCGGAGCCTGGCGGCGAGCGAGGCCAAGGCGGGCCT
CTGCGGGTGACAACTGAGCACATATGGGTACCTTTGCGCTCGCACCGGAGACAGGTGAGT
GTCTGGCCCCGGCCTGCCGCCCTCCCGGCCCCGCCACTGCCTCTGCCCTCCCCCTCGACC
AGGGCCCTCTGCTTCCCCACAGCCTCGTCTCCAGTGGGGGTGGACACACTGCCAGCACCA
CAGGCCGGACGCCAGGATGTGCTTGGAG**GGACATGACACAGTCCGGTGTGACGGAGAGGG
ACAGACGTGACGCCGTCCGGCCTTCCTGGTGAGCGCAGGTCCAGGCCTTGGCCCCCAGGC
CAGCCGCCCCACCCCCCACCCCTCATGGCCGTCTT**CTGTCCCGCAGAACACTCTCGGCTG
GCCCCGCGGGGGAGCTGCCACACCCAGCGTCTGTTCCTTTGCCTTCCTGAAGGAGCACGT
GCATGACTGCTGCTCTCTGGACCCCAGAACCCTCAAACGACAAGGTGAGGCAGGTCCCGC
CTCGCCCCACACGTGGAAGGGCGTGGGCGAGAGCCGGGCGCTCACGGTGCCCCCCTCCC
CCTGCAGAGATGGTGCTACCCAGCTCATGCCTGGGCCTTGGACCCGGACTTCTTCAAGTC
CTCCTAGCTCTGACTCAA**GAATATGCTGCATTCTGGAGCCACTACACTACTTGACTCAGG

Fig. 8, contd.

AATCAGCTCTGGAAGGTGGGCGCGCGCTCCTCCCGCTCCCGGAGCCCCGCCCGCTGCCCG
CTCCCCGCTCACGTCCTGTCTCTGTCCTCGTCCGCAGGTTGAGCCAAAGGAACAGACGTC
CCACACCACCGGACCAACGGCACCCGCGGGGTTCCCCACCCCCCGCCCGGCCACTCCACC
TCGGCGGCCACCCCCTGCTGCGCCCTGGAGACACCACCAGCCTCCCTCTCTCCCCTTCCT
CCTTTTTTTCCTCTGTCTTTTCTCTTCTCTTCTTTCCTCTCCTTTGCTCAGAAGACTCGG
GGCA**TCCAGGACTCTGTGTCCCCGTCCTTCCTGAATTAATTTGCACTAAGTCGTTTGCAC
TGGTTT**GGAGTCCTGGAACCAGCCCCGGGTCTCGGAGCGGGTGTGTGAGCTGCCGAGTGG
CCTGGCCTCCTCGGCCCGCGCCCCCTCAGCACCTGCCATTGTCCATCTCTGTCTGGGGGT
GACTGGGTGGGGGCCTGAGTGTGTGGGG**CCCCGCCCTCCCCTCTCCTAGTCTGGAAGCTC
CGACCA**CCGAGCAGACCTCAAACGCTGCACTGAGTGTCCATCTCGTCATGTGCCCCTCCT
CGCCAGGGCCACCCCAGAGCCCTGGACTCATCAATAAACTCAGTTACCGGAATCTGTCTC
AGGGGCTTTGCAATTGGGCTGGGGGTGCGCCGGGGAAGGGGGGATGAGATGGGGAACAT
GCAAGGAAGGGCCTGTGGGCTGGGGGACACAGAATGGGTGGGGAGGGGGCTCACAGGACT
CGGGGGGTAATGAACGTGGGGCTGGGCGCAAAGGGGAGTGGGACGTGGGGATCAGGGCGG
GGGGCCTGGAGGATGCAGGGTCCCTGCAGGGAAAGGGGGCCGAGGGCGTGAGGCATGTCC
TCAGCCCTGAGAGGCCCTACCCCACAAAGCACAGCCTGCGCGCGACCTCCAGGCCCCCAA
ACCCCCGCCCCAGACCCTGAAGCCCTGGTCCAGGGCAGTGGGTCTGACTGGCGGAAGGAA
CATGCCACCCAGGCTGGCCACACCACTGGGACGCCCATGGGCGGCCACTTTCATCAAGAG
CCTGGCAGGCCCTGAGTGCTGGGCTGGAGGGCACAGAGGGTCCCCCTCCCCTCACGCTTT
GCGGTGCTGGGGCACCGCAGGAGTGCCCAACAGGAGACCCCAGGAAGTCTGCTGGGCTGC
AGCGAAGGGCAGGGTAGGGGGGCGGCCCACAGGGGCCCAGCTCAGTAGGCAGGTGGCAGT
GGGAGGCGGCAGAAAGTTGGAAAGGGTGGACTGGGCACGTCAGGATCTCGTGGCGGCAGC
CCCGGAGCCACGGCCTTGGGTGCACTGCAGCCCCCACGGTTGGTGTCCCGGTCCCAGGCA
GCAGCTGGGCTGGTGACGCCCCTCTGCCTCTGCCCACCCCCCCCACCGCCCCCCCGCCAG
CCTCCCAGCCCCTGGGCGCCTGGCGTGACGCTGGGAACGCGAGGGAGCAGGCCTCGGAAA
CAGGGCTGGGTCCTTGACCCCTTCCTCTGCTCAGGGCAGTCAGGAAATGCCTAGCGGGCC
GACTGACCGAGAGGAGATAGCGGAGGCCTGGGAGACCCCGCGCTCGTGCCGTTCCCAGCG
TCCGGCCGCGTGGCCCTTGGCTGGCCTGGTTTGGGCCCATGAGCTCACCCCCCGCCCCC
CACAGCCTCCCCGCGTCTGGTCTCCTCTCTGGGCCCTGCTGTCCCTCCTGACGGGGGACA
GAGCCCTCCAGGGCCCCGGGGGGACGGTCCCGGGTCAGCAGGGCGGGTGGGCAGCACAGC
TGCGTTTGGTGAAGCCCCTGCCCAAAGCACCCTCAGCGTTTCCTCTGCGCGTCCGGCCGC
CCCCGGAGGCTTTCCCAAGTCCACGGGCAACTCGCAGGCGAGCCCACTCCACCTCCATCA
CGCGGGTTTGGCCAGCGGCAGAAGCACTCGCCCCTTCAGGCGTCAGGAGTTAAGCCCCTCC
AAGGCCCGGTGCTAATCAGCTGCCTCTCCTGGAGCTTCGCAAAGCGGGCTCTCAGAGCCC
AGCTTCCCGGGGGCTCACCGTGGTGGCATGGGCACCACAGGTGGCCGGAGGGGCACCGAG
CACGACGGGGCTGTGGGGGGTGGAGGAGGGAGGTTGGTGACTCCGAACCTCTACTGAGGC
ACACAGAGGACACGGCCGCTTCCAGGGGAGTCAGCCTGCGAAGGGCAGAGGGGCTGTAGC
CTCCCGGTCACGCCCTCGCCTCTGCCCTGGATTCCTCCTGGGGGCCCGCGGCTCGTCGGG
GAGGTGAGTGCCCCTGGATGGGCGTAGGCTGGGGGGGCAGGGAGTGGGGGAGCCCCGAGG
CCCTGGGCCCACAGCCCTGTCTTGCCCCACACACAGGGCTGTCTACACTGGGTGCCCACT
TGCTCTGCTTCTAGGCTGTTCCCTGGGCAGCTGCCTGGAGGGCCGTGGGCACAGTGCGGG
CAGCCAGTGGGGAGGCCGGGGATGGGGCCGGGATAGGGACCCCTGCCCCTGGGTGAGCC
CCACCTGGGCTGGGAAGACAGCAGCAGCGCCCCTTCAGGTCCATGGACCAGGGGACCCAG
GGTGGACTGTGTTTACCTTCAGCCCAGGCCAGTTTCCTGCTTGAGAAAGCCCGGGAGGGG
GTGCGGGACAGGCCCGGGCCCCCCACGCAAAGGCAGTTTCGCAATGTCCCTGCGCTGACT
GAAATGTCACCAGGCACACGGCTTGAATTTCTCCCCCAGACCTGGCAGGGCGGGGGTGG
GGGCACCGGGCTGCTGGGATCTTGGCCCCTGAACCTCCCCGGCCCTGCGGCCAGGGAGG
GTTTAGGCTGAGTGACAGCCCACGGAAACCTGGACCCGACATGTCTGTGTGTCCATGTGT
GTCTGTGTGTGCGTCCACCTATGCGTCTGCGTGTGTGTCCATGTGTGTCCACATATCTGT
GTCCACGTGTCTGTGTCCACGTGTCTGTGTCCACGTGTGTGTCCACGTGTGTCCATGTGT
CTATGAGTCCTTGTGTGCATCTGTGTGCCCGTGTGTCTGTGTCTGTCCCCTGCAGTCC
CCGTGGACCTGTCTCTTATACACATCTCAACCTG
GCAGCGCCCCTTCAGGTCCATGGACCAGGGGACCCAGGGTGGACTGTGTTTACCTTCAGC
CCAGGCCAGTTTCCTGCTTGAGAAAGCCCGGGAGGGGGTGCGGGACAGGCCCGGGCCCCC
CACGCAAAGGCAGTTTCGCAATGTCCCTGCGCTGACTGAAATGTCACCAGGCACACGGCT
TGAATTTCTCCCCCAGACCTGGCAGGGCGGGGTGGGGGCACCGGGCTGCTGGGATCTT
GGCCCCTGAACCTCCCCGGCCCTGCGGCCAGGGAGGGTTTAGGCTGAGTGACAGCCCAC
GGAAACCTGGACCCGACATGTCTGTGTGTCCATGTGTGTCTGTGTGCGTCCACCTATG
CGTCTGCGTGTGTGTCCATGTGTGTCCACATATCTGTGTCCACGTGTCTGTGTCCACGTG
TCTGTGTCCACGTGTGTGTCCACGTGTGTCCATGTGTCTATGAGTCCTTGTGTGCATCTG
TGTGCCCGTGTGTCTGTGTCTGTCCCCTGCAGTCCCCGTGGACCTGTGTGGTCTCTGG
TGTGCAGCCCTAGCCGCGGCCCGTCCCAGGCTGAGTGTCCCCAGGGTGCAGCACAGCTGT
GACGAGGGTGTGGGTCCCGCTGGCCGTGTCGCTGGGCTGTGGGCCCTATCCTCTTTGTGG
CTGCTCTGCAAGGCCTGATGGCTTTTGTGTGGCCTGGCCGTTCGGGTCCATGCCCCCTGG

Fig. 8, contd.

```
AAGAGCAACGTCTGAGCTAGCTCCACGCGTGGGTCCATCTCGGCCCAGGTTTAATGAGCC
ACTTTCAGGCAGGGATTGCACAGGAGGCAGGGTGGGAAGTGGCTCTGCTCAGACCCCTGA
ACAGGGTCTGGAGATTCTCCAAGGGCACAAAAGAACGGACGATGCCCCTGGGGTCAGCGA
CAATGCTCCCTGAGAAATCTTGGCACACAGGGCTGGGCCTGCGAGGTGGCCCCTCGCCCC
ACCCCAGCCTCCTGGAGGACAACCGTCGCCCTGCTCCCAGAGCTGGGGGGCGCCACACGT
GGGGCACAGGGAGCATGGGCCCGATTCCAGGCCTGGGCTCCCTCTCGTGTCCAGGATCTC
CCCGTGTCTTGTCTCAACAAGCCCCTGACTTGGAGGCCCCAGGGTGACCCCTTAAAGGGG
GAACAGAAGGTTCTAGAAGGAGCGTGGCCAGCTTTGGCTTCCCTAGGGCTGTGGTGACCA
CACTGGGCCACGGCCCAGGCCACCCCACCCGCCTCCTTCCCCCTGGCCCCCTCCCTTCCC
CGCACCTCTCCCTGGCCTGCACCTGGTGACACGGCTGGCTCCCAGCCAGGGCTGAGGGGG
ACCAGCGGGGCCCCTTCCTGGAAGCCCACCTGCAGGCCGGCTTGCTGGGAAGGGGCCTGC
TCCTCGCCGGCCCCACCCGCCCGGGGCCGTTTCCTGGAAGCGGTCACTGGATATTTTGTT
CCTTGTCAGCGCCGAGCTTGCATAAAGCAGACACTGAGCTCCTTGTCCTCCGGGAGCACG
CGCTCCATCACCGAACACCTGGCCGGACACAGGCGGGCAGCCGGGCCTGGGGGAGCAGCG
CGGGCCTGGGGCCGGACCAGCAAACGATCACGGCGCCGAGCGCAGGGCCCGCGCCGCTTC
TGCAGGCCGCCCCCACGTGCCCAGGCCCAGCGGTGCCCATCCTGCAGGCTGGGAGGAGGC
TGTGGGCGCAGAGCTGAGAAGGGGGCAGAGGCACTGGGGGGGGACAGCCGTGTTCCCACA
CTTTGCAGAAACCTTGGCCGGCCTGGATGTCTTGCTGGGAGAGCTGGGGGAGGGGACAGG
GCAGGAAGCCGGTCCCCCCGAGCGGGGTAGGAAGAGGCCTCGGCCCTGGGAGGAGGAGGA
GGGGAGGGCAGTGAGATGGAAAGAGCACCAGGGGCTCGAGGCTTCTTTCTGGAACAAGGA
CTAGAAGGAGGAGGCCGGGCAGCTGCTTGGGATGCTTGGAACAGGCCGGCCCCAGTGCTG
ACAGGGACGTGACCTGGGGCCGGTCCCGGGCCCAGGCGGGCTGGGAGGGCGCCTGGTGG
GTCAGCGCCACTCAGAGCCCTGGCAGCAGGGGGCCTGGGCACGGCTGCAGGACAGAGCTC
AGGACACAGATGGGGCGAGGACTGAGTGGGCACCACAGATGCTCCCAGGAGGTGGCCA
AGGAGTGGCCTTGGGATCCCAGGATGGCCCTGGTCCCAGAAGATGCGGCAGCCCAAGGGA
CCAGGCCAGGGCCGCAGGGGGCCACAATCTGAGCAGGGCTCAGGCCCAGGGCAGAGGCCC
CCTCCCACCCAGCCCTCCCTGGGCCCGCCTCTCC
GTGCAGGCAGTGGGCTCAGATGGGGCAGACATGAGACCAGGTCCAGGGAGAAGCGGGGCC
CCTTGGCTTCATTCAGGTGGCTTTCAGACCGCGCCCCGTGCGTGGCAAGGCCCACAGCGC
TCAGGAGCACACAGACCCCCACCACGGGCTCCCCAGGTTGGGCGGTGACATCAGCCCTG
TGTCAACAGCAGGAGCTGGCAGCTCCCCACCGGGGCTTAGGGAGCGGGGACCCTGAGCCA
CCCTGCCACCGCCCCACCCCACCGTGGCCCACACGAGGGCCCGCTGCTCTGGGTCTGGGG
CCAAGGCCCCCCAGGCGCCTGGCACTGTCTGCCCCTCCCGCTGGCTCTCCGTCTCCAGTG
TCCCCGCCAGAGAGCATGGGGCCACAGGCCTGAATGCCACCCTCTTCCTCCCTCTGGAGG
GGGCCTGAGGTTTTGGGGGTTCACAGAGTGGCCTCCGGGGTGGGTCCAGGCCCAGCGAGG
CAAAGCGACCCCAGGGAGTCCCGCGGAATGTGGCAGCCCCCCCCGTAGATCTCGGGGG
GGCCAAGCTCTGGTTGACCTCCATCCTGGGGCTGTGGGCCTTTGGTCAGTGGGGAGGGTC
ATGACACCCAGCCCACCAGCTGGTGACAGCCCTGGACGTGCCGGCTCAGGGCTGGCCTGC
CCCTGCAGCCTTGAACCCCTGTTCTCTGGGAGTGGGGGCGCAGGGGCGCCGGGGCAGGG
TGAGAGACGAGAGCCTCTCTTCCCAGAACTTCTGCCTGCGATGAGGACCCAGCAGGGGCC
TCTCCTCACCAGAGGGCCTCTGCCGGCTGCAGGGCCCCAGAGAGGCCCAGAGGCTGGAGG
CCGGGCCTTGGGAAGAGGCCGGACTTCCAGAAACCAGCTGCCCGCTCCGCAGCACCCAGC
GCCCACTTGGGAGGGGGCGCGCCCCCGTGCCCCGCCCGGGTCCACTGCTGGGGCCGCCA
CAATAAAGTTTGTCCCTGCTGGTTACTGTCCGTGTCTGAGAGGTTTCTGGAGCCTGGCCA
CAATGGGCGTCAGGATGCGGCTGGGAGGGAGCCTCGCGAGTCAGAGTGTGCTGGTCTCGG
ACAGGCCCCGGCGCCCCAGCCCGTGCTCTGTGGACAGATGGGTGGGTGGGTGGGTGTCG
GAGGGGGTTGGAGAGGGTGGGCGGGACGAGGGGCTTCCTGCACTCTGTCCCAGGGAAGCG
GGGACCAAGGAGGGGACAGCCCCGGTCACCAGGAGGGTCCTGTCCCTCTCACCCCCCGG
GACAGGTGAGCTCCCCGGAGCCGCCCTTCTGGGACAGGACCCCACGGCCAGGCCACGGCC
CCCCCCACCCCGTGGTCCCTCCGTCCCACGGCCGGCCTGGGGGGCCACGGGCCCAGGGCC
CCCGCTCCCCGTTGGCCCTCCGAGGGTGAACGACCTCGCCTGGGACGTGGGGCAGAGGGC
AGGCGCCAAGAGTGACCCCTGGGACACGTGGCTGTTTGCAGTTCTGGAGGCAGCCGAGA
TAAAGCGGCTGTTTTCCCAGTGGGCTCAGGGCCAGAGGGGGGCGAGGGGCAGCCCCAGTC
AAGGCCGGCCGCTGCCTCGGGCTCCCCTCTGTGCGGAGGGAGGGGGCCGGTTGCACAGC
AGCCCCTGCCCGCCGCCCGCCGCCGGCGCAGGCACCGTGGGACCCGGCCTGGTGCCCCT
CCCCCGCCCCTGCTCAGGGCCAGCCCTCTCTGGTTCCCAGGACGCCCCGCCCCGCAGG
CGGCCAGAGAGTCCCAGAGTGTTAGCCTCCCACGTGTGGGATCCTGTCATATGCGACAGC
TTAACTCAGGCCGAATTTCATGGGTCCTGGATTTGGGTGGGCACGGCCCCTGCACAGCGG
GGCTGGAAGCCTAAGGCGGTGGGCGTGGGGGTGAGAGGCCCGCAGACAACAGGAGGGAGG
CTGGGACACTTCAAGGGTTGACATGCTATGCCTGTCACGGATAAATGC
```

Contig 3 (5347 bp)

```
AGATGTGTATAAGAGACAGGGGCTGGGTGGGAAGGACAGAGGGTGGGGCCGGAGGAAATG
```

Fig. 8, contd.

```
GGATGCAGAGCCCACCGTGCACGCTCTGCTGGCCTTTGAGCCTCGCTGAGTCGCAAGAAG
CCCTCGGGCCTGGAAACAGACCCCCGGCCCCCACCCCCACCCCGGCCCCCGGATTACCCC
GGCATGGCTGGAGGGCCCGAGAAGCCACCCAGGCTTCCCGTGCCGAGCTGGGTGCTGGGC
CCAGCCGAGCGGGCTTGACGCCACGCTTAGCCCTCCCCAGGGAGCCCAGGGTCGGAAGGA
AGAGGCCGGCCGGAGGGCCGTGGCCGCTCAGGCTGGAGGGGGCCCCCGGGTCAGGATGGG
CCCCAGACGTCCCCGCTCCCCGGCCATCCGTCACGGAGCTGTCACCCAGGAACGTGCTCC
AGACGTGCTTTCCTGCCGCCGAGGCCCCGAGCAGGCTCCAGGCGCCCCCACCCCCGAACG
CCCACGCACACCCTCGGTCTGCGAACACCCTGCCGTCATCCGGTGGCCCCGGTTCCCGCC
GCCCGCGCCATCCGGGTGCCCCTTCCTCCCTGGGTCGGGGGCCATGCCCTCAGCGGGCAC
GCAGGCCTGTGCAGGTCTGTTCTGACTCTTCCCCAAAGACGCAGGCCGGCTGCGGGCGCC
CCGACCTCGTCTGAGGCCCGTTTGTGCTCACTGGCTGTCTCAGAAAGGGGTGCCCACGGG
AAGCGCGTGTTCCTTGGGCCGCAAGGCAAGGGAGCCCACCCCAAGGTGGCTGAGGGCAAA
TGGCCCAGGGCTCTAAGGAGTCCCTGGGGGCCGGGCCGGCCTGCAGCTTGAGGAGGAGA
GCCCTGGCTCTGCTCCCCGGGCAGGTGAGCCCACGGCAGGGGCTCCCCAGCAGCCTTG
GCAGGAAGCAGTGAGGAAGGGGTGAGGATGAAGGCAAGGGGGCCTGCGGGGACTTGGGCA
AAGCCCCTGAAGAACTGAGTTCCTCGGAAAGGCCGGAGCCCTCAGCCGAGCCTCGGCCTC
CGAGCGATGGAGGCGGCCCACCTGCGGCCCCAGGGTGCAGCTGTGCATCCGTCCCCCTCG
GGCCTCCCCCTGCCCCCCGGCCACCACACTCTCCCCCTTTTGCCTTTGATCACTTGAGT
GCGACAGCTTGTGCGGCCTGAGCCCCAGAGACCGCTGCCCCCCTGCCGCCAGCCCCACGG
GAGCGTCCACCTGGGCCTGGCCTGGGCACTCATCCCTCCCGGATGAGGCCTTTCTAGCCT
GGGCCGCCCCGGGAGCGGCAGACCCAGCCCCTCGCCCCCCTCCCCCAGTGAAGGTGCTGC
CTGGTGGTCTGGGGAAGCCCCTGGAACAGGGGCGCAGGTCCCACACGGGTGCTCTGGCC
TCCAGCTGCCAGGGAGGGCCGCGCTCAGGCCAGGGTCCCCTCCACCAGAACCGCCAGGGC
CCTGGGGAAAACCTGTCTGTGCTAACAGGGCCGCTCCCCGGGACTCCACGGAGAGGTGCG
AGGGACCCCTGAGCACCCACCGCCACTAAGGGGCCCAGCCAGCTCGCGGGTGCAGGCAGC
CGGCTGGGCGCTCACATGCATACTGCTCTCTGGCTTTGTGTGTGCGCCTGGGTTGGGGTG
AGCGGAGGTGCCCGAAGGCGGAAGAGCCCACCCTCCACTCGGGGACCTATTTCAGCAAGA
AGACGGATGGGACTGCCGGGCATGGACAAAGGAACAGGATGAACCTTCTGGAACGCACAA
GGCTTCCACGGCTGACCGGTCATAGGAAGGCGCGTCTCTAGGCCAATCCACCGTCCACCG
TCCATTCCCCAGCCCTCGAGAGGGGGCAGGATGGACCGCTGCAGCGTGAGAGAGCTCTGG
GGCGCTCCCACAGGGCAAAGTCCCAGGGCACTGACCTCAGAGCCCAACCAGGCCACCGGG
GCTGGGCCCACCAGGGAGCCGGGGCCAGGGTCAGGGTCAGGGCCCAGAGTGCGGGAAAGG
GTGGCGTGTTGCTTGGGCGGCGGGCGCGCAGACGGCCCCTCGCACCCCCCGACAGCCCT
GGAGCTGAGTGAAGCCCGCGGGTCACCTTGGCTGGGGTTGGGGTCTCCTGCGACCGGCAC
CCCAGCTCAGGTCATCCTTGCTGTACCGCAGAGGGGCAGGGGTTCTGAGCAGGGACAGGG
TGGGCCGCGCAGGAAGCCCCCTTCTCTCTGAGGCTGCCCCCGGCCCTGGAGCCTCTCTGGG
GCATGCCACCCCCTCTCACAGACGCCTCCCAGGAGCCCCCACTTTCCTGCTGCGTGGTGAG
GGTGTCTCTCACCCGATTCCTGGCCCCTGCAGGTCGAGTGAGTCCCTGCTAAGCCTGGGG
TTGGAGCAGGTGCAGGGCATCACCACACAGCAGCAGAGGCTGTGGGGGCCCCTGAGAGGC
GCTCCCAGGTACCCTCCTCAGGGGGCTGAGCCCGGGGTTGACCCGGGACCTCGCCTGCCC
CAAAGCCGGCGCCCTCCTCCCGCCCGCCCGACCAGGGCCAGAGAAGCAGGTGTGGGCGG
CACAAACCCAAGTCAGCTTCCAGATCCTGCTGGGGCCGCGTTGAAACTCGAAGCCCCCAG
GCTGGGAGGTCTAGACACCCCTGCCCAGACCGACAGCCTGGGCCTGGCTCACAGCTGCCT
GGGGGCCCAGGGGTGCACCTGCCCTGTGGGTGGGGGTCAGAGGGCAGGGAACCCTCGGGA
AGGTCCCCCAGGGTCAAGGTTGGGCCTAAGCTCCGGTGACCTCTGGGAAGTCTGGGGCTG
GGTTTTGTTCCCAGAGGAGAGAGGGCCAGTAGCCTCAGAGGGGCTGTGGCACGGTGGGAA
GGCCCCAGGTGACCCCAGAGCGTGCGAAGCAAGCCCCCTTGACTGCAAAGC
GCAAAGGGCAGAGGTGGGGTGGGAGCCTCGACCCCCCGAGCCCAGGTACACAGGGGGAAG
GGCGAGGGATCCGGCAGGGGCCCACACCCGCCACCCCAGGCAGCCCACAAAGCCTTTGGGC
CCGGAGCCCCAGATGGGCCCAGCCCAGCTCTGGGAACAGTCTTCCCAGAATTCCCCAGCT
CTGGGTACCAACAGGGCTGCCCGGCCCCAGAGCCCTCGGGCGGGAGACCCTTCCCCAGG
GGGATCTCCTAAGTGGCAAGGCCTGTTGGGAGGGGCTGGTGAGAGGCCACTCTGGCGGGA
AGACCCCCAGCCACCTGGAGCCCCTAGCCACTGCCTGCTGCGGCTCCCTAGGGATCCAGG
GCCATCAGAGAAGCTCCAGCGACACTGTTTATTTTCAAATGACACTTTTTAAGAAAAACA
GCCTCACCCAAATGCTTGGCCCTGAGTCTGGAATGTGCAGACAGACAGCTGCCCCTCCCC
AGAGCCTGCACGGCCCTCCGGGTGGGGGAGGAGCAGGGGGCACCCCTGGGACCGGGCCGC
AGGCTGTCAGGGCACGGAACGTGTCTCTGGGCCCTGTCCTCAATTCCCGGTGCCCAGTGG
CCCCAACTTCCCAGCAGACCCAGCAGGGCCCCAGCTTGTCTTGGCCTGGCCGCTGGTCCT
GTCACCCCAGGCCTGGAGTTCTGGAAGATTCTGCTCCTGCTCCCGTGTGCACATACCACT
CCCCGGGGCAGCCCTGCACTTCTGTTCCTGCTGGGCTCCCTGCCTGCATCCGTGAGGCCT
GCAGCCCGCCTGATCTTCCAGGTCCTCCTCCGAGCCCCCGCCTCCAGGAAGCCCTCCAGG
AGAGCTCAGGAGGGTCGGCTCCCTGCGCGCAGCTGTCAGACCCCTGGGCCCACCCCGCCG
GCTGCTAGGGTCCAGGTTCCCCACAAGCCCTCGGGCAGAGGCTGGGCGCTGGGTCCCTC
GGAGACAACTGGCTCCGAGGCCTTGCCCTAGACGGGTTTCCGGGAGCCCGTCCCCAGCGG
```

Fig. 8, contd.

CACCCACTGAGTTTTGAACACTTGGCGCCACCCCCACACCCCAGGCGGTGGCCAGGAGGC
CTCCTGGGCAGCAGACAGTCCGTGAGGTGGCCCTGGGGTGGCTCCTGACCTGGGCGCTGG
CCCAGCCCTGGGCACAGCTTTCCAGATCTTGCCTGCCGCTTCCTCCAGGCTGCCTCGGCC
CCTCCCGCCTGGGGGTGCCCAGCTTTTCCTGGAGGATGCCCACCCTTGCCCATGGTCAGG
GAGGGGCTGAGAAACCCCACCTCGTGCCTCTGCCCGGCCTATGCCAGGGGAACCAGGTTC
CCTCCCGCAGGAGGGGACCGAGTCCCTGACAGCCCACTGCAGAGGGGAGGAGGTGCCTGG
CTCTGCCCCCAGCCCCACCAACCCCGTGGCTTCCTGTTTCGCAGCCCACAAAGCACTAAA
GGCCGCAGGTCCTGGAACATCAAAGACCCGGGAAGTCCATTGTATTGAATTGAGTGTAAA
TGAGCCTGAGGCCTGTGGCTTGCGTTTCCCACAATTACCGCTGCCCGGGAAGGGCTCCGG
AACCGACACAGCCCCCAGGGCCCCTTGCCCATGTGGGGAGCCCAGGCTGGCCTGAAGAAG
CCCCATAAGGTGGACCCCACTTTGAGCCCCCACGAGAGTGGGCCAAGGACCAGGTCAGGG
GCTGCCCAGGCTCTGGGCCTCCTCTGCCTGCCAGGTGGGCTCCCTCGGGGCCCAGCCTGG
CCTGCAGGACCTTCCCACGCTGAGTTCCCCAGCCTGGTATGAGCGTAGTGGACGGCAGCC
ATGCCCAGCACTCAGGGGCCTGAGGGACAGAGCGGGAACTCCAGCCCCCGGGTCCTCGGC
CCCTAGGATCCTTCTAGGTGGGGAAGCCCAAGGGAGCAGAGGGGTGAACGCAGCTGTGTG
GGGCCCCAGGCTGCCGAGCAGACCCCTCCTGCTCCACTCCTCGGCCGAGTGGGCGCCGAG
ATGCCGGGGCAGTGCCATTTCCCAGGCGCCACCGGAGGCTCCCAGAGGGAGTGAGGCACG
AGCTGGGAGGGAGGGCGGGGGGGCTGGGGAGGCAGAGAGCGGAGGCCGGAGGCCGGTGAG
GAGGCCCGAGGGGGCCTGGAGTCAATGACCCAGGGATTATCGTGCTGGGTCTTTGCAAA
GTTGGCTGAGCAAACGCCGGAGCCAAGGGTCAGGGAGACGGGACTGGCGGGGCCCCGCGG
CCCCCTTTCCCCTTTCTGGAAAAAGCCTGTTTCCCAGGTCAAAATCCAGCTCATGATCCG
CCCCCTTTGGGACTGATGTTCAGAGGCCCAGTGGTCCCAGCACCTCTGTCCACCGCCCCC
CCCACGCTCCCGGGGCCGCCAACCCCTGTGGGCTGCGAGGTGCGGGCACCTCTCCCTTCG
AAGCAAAGCCCTGCCCTGCGTGGGCAGCGTGATTTCCTGCTTCTCTGGGGCTGCACTTTG
ACTGGGGTGGGGGGGTGG

Contig 4 (1592 bp)

AGCCCCTCAGCCCCTCCGAGCAGCTGCTGGGCTCAGCGGGCTCGCCCCCCGATGTGCGGC
CCTCCATAATCAATCATGGAGGGCCGGGCCCGGGGGGGCGGGCCGACCTGTCAGCCAGC
TCCAAGGGCAGGGACAGCTGCTGTTCCGGAGGGTTCCCAGGGGCCAGCCCCACCAGACAG
CGGCCTCGGCCCCCCTTCCCCGAGGGGCACCCCCACGGAGGGGCCCAGACCGGAGGGACTC
GGGGCCCAGAGGCCAGGGCAAGAGTGAAGGCAGCGCCGGTGGGAGCGGCGGTCAGCGGGG
TCCAGGCTTCAGTTCCCAAGGAGCCCCATGCCCTGAGCCCGCACTGAGCCCTGTGCAGCC
TGTGGGTGCCGCCGAGGCCCGCCACCCCGCCCCCACCAGCCTGGGGTCGAAGGAGGGAG
GGGGTGGCCTGACGGATGGTAACAGCTGCTCCCCCCACCTCGCCGGCGTGGACAGGGCTC
GCTTCTCCTGCCCGAGCCCCGGCTGCCCCATCCGTCACGGCCCACCCAGGACTGTGCGT
CCAGCCTCCCTCCCTCCTAATCCCCCCGCATTTTCCGAATTCTCGGGCCACTGCTGCTTC
CTCCTCAAATTCCTGGCCCCCCTCGCCCCATCCCCGCCATGGGAAAGGGCCGCGATGCCA
GGACACTTGCTGTCTCGGCCGGGCGGGGGAGGACAGCTGGCTGGGCCGCGCAGCTGT
GAGGTGCGGGGTGCCAGGGAGAAGGGCCCAGATTAGGGGGCGTCATGGGAAAGCTGGA
GGGAACGCTACCCAGAGCCCCTCCTGCCGCAGCCTGTGCTGCTCCCTCTCCGCATTTCTG
GCCTCTGAGTGCTCCCTGGAGGGAAGGGACCACTGTGTCCTGCCGGCCTCTGGCTCTGCC
AGGAATGTCCATCTGTCCGGGCCGGGTTACCTGGCTCAGAGCGTGGGTACCAGCTCATCC
AGCCCTGACGCCTGCTCTCGGGAACAGTGGATGGGCCAGGCGCCCCCGTCACACCCCGCA
GCTGGGCTCCACAGACGGGCCCGGGATGGCCACGGAGGTGGGGGGCGGCCCCAGGGCGAG
GCTCCCTCCTGGAAGGGCTAGAGTGTGGGCTGCGCGGAGAGGGAGGCCGGACGGCCAGGC
CAGGTGCAGCCCGGGGCAGGTGCTGGTGGGGGCTGTGACCCACGTGTGCAGCTCAAGGGT
CCAGGAGCCCAGGGACAGAGCCTCAGGGACAGCCTCAGAGCCACAGCAGGAAGCCTG
GTGGCAGTAGCTGGCGGGGCCGTGGGGTGCTCGGCCCTGCAGACAGAGGCAGAGGCAGGC
TCCCTGCTGATGACAGGGGCTTTCTCTGTCCCCTGGGGGCGGAGGGGGCCCGACCATGG
ACCCCGGGCCTCCTCTCGCACGATTCCCAGGCCAGCCTGGTCTCAGGCAGTCCAAGGTTG
CACAATGGTCTCCATCGTCCAGAGTTGCAGAGCCAGCACTCTCCCACTGGACGGCGGCCC
GGGGTGGGCTGCACCGCCGCTCAGGGCTCAGGGCCGCGGCCGGCCAGCCCNCCGCAGGCC
TTGACCCTGTCTCTTATACACATCTCAACCCTG

Contig 5 (831 bp)

TGAGATGTGTATAAGAGACAGGCCTTGACCCTGGGCCTGGCTCAGCTGCGCGCCCTCCTC
CTTGCAGCTCCGCCTCGACCCCATCCATCAGCCATTTTCCTACCCTTCCTGTAATAAAAA
ACCCGAAGCGGCGTGGCCCCGTGTCCGCTGGGGTGACTGCGGCCTGCCTGCTGGTGGCTC
CCACCTGGGCCCGGCCCCCTGAAAACACACACCCGGCGATGGCTTGCCCGGGGCCCTGGT
GGAGGGGCGGGGGGCCTCGCCTGCCTCTTGTCTGAAATTTTCGGTCCCACATGCCCCGAC
TCCTCTCCCGGCCCACCCTGCAGGCCCGGCCGGTGCCCCGGCCACTTTCCCGAAGGACGG

Fig. 8, contd.

ACTCAGCATTTCCCAGGGCACCTGCTGATGGTGCCCAGACCCCGGGGGCCTTCCCGCCGG
GCGCGGCCCCACGTCGCCCCTCCAGTGGCCACAGCGGGCCTGGGCCAAGGCTGGGAGTTC
TGCACGGGCCTGGGGGAGGAAGGCGGGGGAGAGGGGACAGTCTCCTGGCGGGGACGAGGG
TGGGGGCAGCAGGTGGGGAGTTCCCACAGCCGGGGCAGCGGGACGCCGCTTGGCTGCCCT
GGGTCTCAGCCGGGGACAGTGCCCACCAGGAGAGAGACGGCAGACAGTACAGCCCACCCG
TTTTATATCCTCTCAGGCGGTCTGTGCTTTATTGGGGTAAATATGCAGGACATAGAAACT
CTGCCACTGGACCCCTTGGCCGGGGGACACAGCAGCGGCATTGCATGCTTTCTGGGTGCA
GCGCAGCCAGCACCACCGGCCAGAGCACCCCATCTTCCCGATCAACCGGAC

Contig 6 (4634 bp)

CTCTGGGCTAGCACCGTGGGGGCTTTGCCAGAGTGGAACTGAACTGGGTCCACCCCGGAG
CCCAGAGGGCGGTGAATGGGAGGCAGAGCCCATCCTGGGAATGGACCAGAAGAAAGGGAG
CGGGGGTGGGGGAAGGGGCATCAGATCCTGGTCCTTCCTTGTCGCCTGCGGTCCCTCTGC
CACCACTCCCCGAAGCTGATCTGGAGCACACGCGTCGTTAAAGCCGCCATCGAGGCCCCA
CTTCTGACAGACGGAAGGGGGCAGAGTGCCTTCCTCACCGGCCTCGCCCTGGGAAGGCCC
CTCCCTGCAGCCCAGGAAGCCAGCAGCAGGTGACAGAGCCAGGGGCCCAGGGCCCCAGGG
ACGGGCTCGCGCGCCCGAGCCGGGGGTCCCTTGGCGTCCCCATCCTCTCGTCCTGGAGCC
CTCCTGGGTGACCACAGGAATGTGCAAGGCGGCAGCCGGGTGGCGGCCGGGAGGCGGGTG
GGAGGCGGGCGGGGTGGCCTCTTCACGGGCGGGCCTGAGAGATGGGCGCCCGTCCGGCCC
TGGCGTCATCGTCTCCGCGTCTCTACCCACTGAGCAAAGACACACGAAATGAAGCTCGAA
CGAGCACAGCCAAAGAACGGCCGTTTCTGTCCTTTCTTCTTAATCCCTTTGGCTTAGGGT
TTCCCGGCCTGGACAGCCTGCCCAAGGGCACATGGGCATCCGTCCGGGACATTCAGGCA
GTGACCAATCCCAGGCCACCCAGGCTGTGCCCTGCGTCGTGGGCCATTTCCCAGCCGGCC
AGAGATGGAGCAGCCACTGCGGGTCCCCGAGTCTCGGTGAGACAGTCAAGGATGGACCTT
GGATGGAGACCGGCGTGCGGCCATGTCCGTGGGTGAAGGAGGCGTGCAGGCCGTGCTGGG
GGACATGGTTGCTGTCCCCTCGGCCAAACCATGAAAAGCAGCCCTCTCCCCCAACCCCCA
GCACCAACCCGGAGACCACCCTCGGCCGGAGCCCAGCACGGCCACCGTCACGTCTCGGTC
GTCCAGCTTGGGACAGGTCAGTTCCCAGATGTCCAGGCTGGAGCTGGTCCTTGAAGATCC
TAGGGGTCCAGCCCAGCACAGGAGGGCCAGGTGAGAGCCCCCTGTGGTTCTAAGGATGCA
ACCAGGGGCCGGCGGGGTGCCTGCCCTAGAGGGGGTAACTCGGCCCCCTGGGGACCAGTC
ACCCCAGGAGGTCCCCAGAGCCCAGCTCGGAGGGCCACAGGTGCCCAGAGTCCCACCTGG
GGAAGGCTGCCCCTCCTGCCAGCCCCGAGCCGGGCCCCTGGCGCCCGCGTCCAGCCGCG
ACCCCGGGGAGATATTCACCCCCTGCCCCCGTGAATCAGGAGGCCCCGAGCCCATGTTTT
CAGTCCTTTTCCTCCCATCCCAGCCCCCAGGAGAAGAGGTGCTGAACTGGGTCCCCTGG
AGGCTCCTGAGCCCCAGAACAGTGCCCTCTGAGCAGACGGGCACTCTCAGACCAGCTCAC
GCTGGACAAGTCAGCTCCTGCCTGCCGCCTGATGGGCCCTTGGGAGAAGCAGACATGGTG
AGGAAAAGGCCCCTGTGCCCTTCACCCTAATTCCCCAGCCCCAAGTCCCACTGGGTTGCC
AGCTTCAACCTAAGCAAATAATTCGTGCCCTCTAAACAAACGCGCGGGAATCCCACCTGC
CCTTCCCCCGCCCGCCCCCC
ACCCCTGGCCTTGACCTCCAAAAGCACTTGAGGGGGCTTTCTCCAGACACCCTCCAACCC
CGACCCCATGAAGAAGGGGTGATGGGGCTGTTACCCCAACAAGCAAGAGAACGAAGCCCA
GAGAGGAGTTGGCGTGGACAGCAGGGGTCAGGCCCCTTTGCCCCGAGGGCAGGGCTGGTG
CCACCTGGGTCAGGCGGCAGGCCCTGGAAAAGCACCGGAAATGAGCACACCTGGGTCTCT
AGAAGGTTCTTCCAGACCTCTGGGGGCTGAGTCATTTCAACACTCCTGGGCCGGGCAGGG
CTTCTTCTTGGCCCCGAGGGACAAGGTCCCCTTCGTCCGGGGGTACGGCCCCTGGACCC
CTGTCCCCCGCACCCCACCCTCCGCCTGGTGAGGGCCGCGGCCAGCTCTGGACACAGATC
CCTCAGAGCCCCTTCTCCCTCCCTGCTCCCTCGTCTTCCCAAGATGCCCCGGCCTCCAGG
TGGGGCAGCCAGGCGGCAGAATGTGGTCCAGGCCTCTCGGCCCCACCCACACCCCCTGC
TCTGCCCTGACAGCCTCCAAGACGCAGGCACGTCGCTGCGTTCTGCGTCCTGTCTCCTCA
TGGCACAAAACGGTGCCCGCCTAGCTTCCCCCAGAGAAGGGAGATCGTGCTCCCCGGACG
GACCCTGCTCTGCCTGTCCTCCCGCCCGGCCTTCAGGGCCTCTCCCCAAGGGTGGCCGCG
AGGAGGCCCTCGCCTCCGGCCACGGGGGCTCCATCCTCCCGAGCCCGACAGGCCTCCGCC
TGGTGGTCCGACCTCTTCCCCAAGGCCCCGCCCATCCTCCTCGCGCTCCCCCAAACCCTG
CCTCTTTCCCCAGCGCCCTTGTCCCCACGGAAGACCCTCCACCCGTGCCATTACACGCTC
TCGCCCCACCCTCCCAGCCACCCCCCCTTCCCCATCCTCCTGGAAGCTCCCACTTCCTTC
CCGTCTCCCACGGCAGCAGAGGGTCAGCAGCTCAGGGGTCCTGGGGCCGTGGAGATGGCC
TGCCCGGGGGTCTCGCTGACCGCCTCCTACGGAAGCTGTGCCGGGGGGTGGGGTGTCTC
TGCCCGAACGGCTGGAGGACGAGCCACATCCCAGGGCAGCCGGAACCTGCGTCCTGGTCT
GAGACGGAGAGGCTGGGTGCAGGTGGCTGAGGGGCCTGCACACAGCTTGGCCTGGGGTCC
CCTAGGTGACAACACTGGCTGAACACTCATTGCTGCTCCCCTTCCAGGGTGACCCTGGGG
TCCCCGTGTGGCCCTCAGGGCACACGGGGGCCCCACCAGGCCTCACAGAACCCCAGTGGG
ACTGCACCCAGGGCCCACAGAAGTGCGGGGGCACTGGGGGTCCAGAAACAACCCCACAAC

Fig. 8, contd.

CAGGCCAAGGTGGCCAAGGCCTTACTCGAGCGGGGCTGCCCGTCCCAAGAGACTCTGGCC
AGTCGTCCGGATCCAGCTTCCCGGGGCCGGGCCGCCCGCTGGGCTCCAGGCGGTTCTGGG
GGGCCCTCCCCCGGGGGTTCGCCCTCCGCTCTCAGCAGCAGGAAGAGGAGCGCGGCCAGC
GGATGGGGAGAAGAGGGCGCCCTGGCCATCTTGCTCCCCCTGGGACTTGAGGAGGGTCTC
GGGCCGGGCAGGCGGGACCGGGAGCCACAGAGACCCTGGAGGAGGCAGCATGGCGGGGAG
GTGACCGGGAAGAGGGCCGTGTCCCAGGCTCACAGCCCGGCCTGGCCGCCCGGCCCTCG
GGAGGCGTGCCGCTGACCGCCTGGCCGGGAGGTTTGCTGCGTGTGGGGTTTGCAGAAAGT
GCTGAGCTGCTGAGCCCACAGGCCAGGCTCAGAGGGGACAGGAAGGAGGTTGCTGCCCAG
CCTCGGGCACTGCTGACCCATCTCCCGTTTCCAGGGCACCAGAGCCACCTAATCTGCCGG
CTCTGTGCCCAGGGACAGGCTTGCCTGATCTCTCAAGGCCGGGCGCTCCGCCTTCCCTGG
GAGAGGGTTAAACATCCAGCCCCAGCCAGCATCTCGGGCAGGTTCCTGGCTCCCCCCGCT
CGTGCCTCCTCTGAGACCCTGGTCGGCACACCTTTCCCTTGAGAGGAGGAGGAGGAGGAA
AGCGGATGGAACCAGTGACCCTGCAGCCCCTGAGGGCACCTTCCCACGTGCCCCCGCCCG
CCCCGCGTCCTCCGCCCCCAGTTCTCACGGCCCCAGTCCTGATGGAGGGAGGGCGACCTC
CGGGCTCCCTGGCTCCCGCCGGCTCCGGAAGACAGGGCCGCTCGGCTGGGGCTGCAGGGA
GGGGCCCGAGACGCAGGAGAGCAGCCCGGAGGCAAACCCGCGGGTCTTCCAGAAGGAGG
CCTGGCAGGGGAGGGGGGTGCCACCACTGCTGTCCCTCTCGTGCCACAGTGGAGGGTGT
GGGTGGGCAGTGCCGGGGTGGGAAGTGCAGAAAGACCCTGGACCGTGGGGCTGGGCCGCC
ACGGGGGAGCGGGGTCTGTCAGGGACCCTGGGGGAGGGAGGCGAAGGGCTGGGGCAGAGG
CCGGATCACTTCCAGATTTGCTGTGGGACCAAGGGCCGGACCTCGGGGTGACTTCTTTTG
TGTGCTGGCCACAGGGGGGCCCCGGCGAGGTCACACGGAAGGGGCTTCGGACCTGGCCT
AACAAGCCCACTCCCGAGGAAGATGCAAGGGGAGGCAGACGGAAGGGCCGAAGGGGCGA
TCGGGGGACACCGCGGCAGGGCCGGGGCAGAGAAGGGAGGCAGAGGGCAGAGAAGGGAGG
CAGAGGGCAGAGAAGGGAGGCAGAGGGGCCACATGCTTGGAGGGCCAGGGAGGAGCGGGA
ACGGCGTCCGGCGTCCAGCGCCGAATCAGGCCCGTCAGGCGGAGGGTGCGTGGACCTGCC
TGGCCTTCACGAGCACAGTCAGCAGGCTGTCTCTTATACACATCTCAACCATCAT

Contig 7 (482 bp)

AGCAATGGGGCCGTGACCTAAGGAGGCAGGCCCAGGTCAGTGGGGTGACCTCTCGTGGCC
CCGATGTTTGGAAATCCCCAAATCAAAATGACCCATCCGACAAGCTTGCATGCCTGCAGG
TCGACTCTAGAGGATCCCCGGGTACCGAGCTCGAATTCGCCCTATAGTGAGTCGTATTAC
AATTCACTGGCCGTCGTTTTACAACGTCGTGACTGGGAAAACCCTGGCGTTACCCAACTT
AATCGCCTTGCAGCACATCCCCCTTTCGCCAGCTGGCGTAATAGCGAAGAGGCCCGCACC
GATCGCCCTTCCCAACAGTTGCGCAGCCTGAATGGCGAATGGCGCCTGATGCGGTATTTT
CTCCTTACGCATCTGTGCGGTATTTCACACCGCATATGGTGCACTCTCAGTACAATCTGC
TCTGATGCCGCATAGTTAAGCCAGCCCCGACACCCGCCAACACCCGCTGACGCGAACCCC
TT

DOTPLOT of: meq24kb.pnt  Penalty: 34094.32  December 6, 1999 12:40
COMPARE Window: 21  Stringency: 17  Points: 3,497

Fig. 10

IDENTIFIED POLYMORPHISMS:

POLYMORPHISMS TYROSINE HYDROXYLASE GENE - CONTIG C3 (figure 6)

| | | |
|---|---|---|
| 1 | GGATCCAGCC (A:T) GCAGCC | 1081 bp |
| 2 | ACAACCCCC (-:C) TCCCACAG | 1149 bp |
| 3 | TGCGGAGGGG (A:G) GACCTG | 1186 bp |
| 4 | AGGT (CAAGGCCAGGT:-) CGAGG | 1210 bp |

POLYMORPHISMS INSULIN-IGF2 - CONTIG C4 (figure 6)

| | | |
|---|---|---|
| 5 | CCC (C:A) CCCC (A:C) CGCCGC | 438 bp |
| 6 | CCC (C:A) CCCC (A:C) CGCCGC | 443 bp |
| 7 | CGCCGCAGCA (G:A) GCCG | 455 bp |
| 8 | GCTTATGG (G:A) GCCGGG | 503 bp |
| 9 | CACGGC (T:C) TC (G:A) GAGCA | 525 bp |
| 10 | CACGGC (T:C) TC (G:A) GAGCA | 528 bp |
| 11 | GTCTGC (A:G) GGCAGGTG | 571 bp |
| 12 | CAAGCCCGG (G:T) CGGTT | 636 bp |
| 13 | ACCTC (A:G) AGGCCCCA | 710 bp |
| 14 | GC (C:T) GGGCCCAGCCGC | 867 bp |
| 15 | ACCAGCTG (C:T) GTTCCC | 903 bp |
| 16 | GGC (C:G) CTCTGGGCGCC | 1148 bp |
| 17 | GGGGG (C:T) GTCCCGGGA | 1305 bp |

Fig. 10, contd.

| | | |
|---|---|---|
| 18 | GCGGT(C:T)GGGGGAGTT | 1320 bp |
| 19 | CGCCC(C:T)GGTCCCGCT | 1400 bp |
| 20 | TCCC(G:A)TCTGCCGGCC | 1519 bp |
| 21 | GA(T:A)GCCCCATCCCCC | 1547 bp |
| 22 | GG(C:T)GGCTGCTGCGGC | 1607 bp |
| 23 | TGGCTGC(G:A)GTCTGGG | 2222 bp |

POLYMORPHISMS IN CODING REGION - CONTIG C10 (figure 6)

| | | |
|---|---|---|
| 24 | GCGCA(G:T)TGATTGGCA | 341 bp |
| 25 | CGCCCCCCCC(-:C)(G:C)GG | 2247 bp |
| 26 | CGCCCCCCCC(-:C)(G:C)GG | 2248 bp |
| 27 | GCAGCCGGCTC(C:T)TGG | 2257 bp |
| 28 | GTTGTTG(C:T)TCTGGGA | 2413 bp |

MICROSATELLITES

| | | | |
|---|---|---|---|
| 29 | *PIGQTL1*: | (AT)$^{11}$ | 112 to 133 bp Contig 57 |
| 30 | *PIGQTL2*: | (GT)$^8$<sub>GCACGCGTGTGCGTGTGTAC</sub>(GT)$^{17}$ | 1074 to 1144 bp Contig 95 |
| 31 | *PIGQTL3*: | (CA)$^{19}$ | 223 to 260 bp Contig 105 |

MARKER ASSISTED SELECTION FOR IGF2

Sire line *(IGF2+/IGF2+)*      Dam line boar *(igf2-/igf2-)*
Terminal sire *(IGF2+/IGF2+)*   x   Parent sow *(igf2-* paternal = fatter)
              ↓      (Prolificacy + longevity ↑)

Slaughter pig *(IGF2+* paternal = lean / *igf2-* maternal = silent)
(Carcass quality and uniformity ↑)

Fig. 11

SELECTING ANIMALS FOR PARENTALLY IMPRINTED TRAITS

CROSS-REFERENCE TO RELATED APPLICATION

This application is a continuation in part of U.S. Ser. No. 09/868,732, filed on Nov. 1, 2001 now U.S. Pat. No. 7,255,987, which is a national stage entry under 35 U.S.C. §371 of International Application No. PCT/EP99/10209, filed on Dec. 16, 1999, and published as International Publication No. WO 00/36143, in English, on Jun. 22, 2000, which claims the benefit of European Patent Application EP 98204291.3, filed on Dec. 16, 1998, the contents of the entirety of each of which are incorporated herein by this reference.

STATEMENT ACCORDING TO 37 C.F.R. §1.52(e)(5)—SEQUENCE LISTING SUBMITTED ON COMPACT DISC

Pursuant to 37 C.F.R. §1.52(e)(1)(iii), a compact disc containing an electronic version of the Sequence Listing has been submitted concomitant with this application, the contents of which are hereby incorporated by reference. A second compact disc is submitted and is an identical copy of the first compact disc. The discs are labeled "copy 1" and "copy 2," respectively, and each disc contains one file entitled "2183-7695US sequence listing.ST25.txt" which is 170 KB and created on Jul. 17, 2006.

TECHNICAL FIELD

The invention relates generally to biotechnology and, more particularly, to methods for selecting breeding animals or animals destined for slaughter having desired genotypic or potential phenotypic properties, in particular, related to muscle mass and/or fat deposition.

BACKGROUND

Breeding schemes for domestic animals have so far focused on farm performance traits and carcass quality. This has resulted in substantial improvements in traits like reproductive success, milk production, lean/fat ratio, prolificacy, growth rate and feed efficiency. Relatively simple performance test data have been the basis for these improvements, and selected traits were assumed to be influenced by a large number of genes, each of small effect (the infinitesimal gene model). There are now some important changes occurring in this area. First, the breeding goal of some breeding organizations has begun to include meat quality attributes in addition to the "traditional" production traits. Secondly, evidence is accumulating that current and new breeding goal traits may involve relatively large effects (known as major genes), as opposed to the infinitesimal model that has been relied on so far.

Modern DNA-technologies provide the opportunity to exploit these major genes, and this approach is a very promising route for the improvement of meat quality, especially since direct meat quality assessment is not viable for potential breeding animals. Also for other traits such as lean/fat ratio, growth rate and feed efficiency, modern DNA technology can be very effective. Also these traits are not always easy to measure in the living animal.

The evidence for several of the major genes was originally obtained using segregation analysis, i.e., without any DNA marker information. Afterwards, molecular studies were performed to detect the location of these genes on the genetic map. In practice, and except for alleles of very large effect, DNA studies are required to dissect the genetic nature of most traits of economic importance. DNA markers can be used to localize genes or alleles responsible for qualitative traits like coat color, and they can also be used to detect genes or alleles with substantial effects on quantitative traits like growth rate, IMF etc. In this case, the approach is referred to as QTL (quantitative trait locus) mapping, wherein a QTL comprises at least a part of the nucleic acid genome of an animal where genetic information capable of influencing the quantitative trait (in the animal or in its offspring) is located. Information at DNA level can not only help to fix a specific major gene in a population, but also assist in the selection of a quantitative trait which is already selected for. Molecular information in addition to phenotypic data can increase the accuracy of selection and therefore the selection response.

Improving meat quality or carcass quality is not just about changing levels of traits like tenderness or marbling, but it is also about increasing uniformity. The existence of major genes provides excellent opportunities for improving meat quality because it allows large steps to be made in the desired direction. Secondly, it will help to reduce variation, since we can fix relevant genes in our products. Another aspect is that selecting for major genes allows differentiation for specific markets. Studies are underway in several species, particularly, pigs, sheep, deer and beef cattle.

In particular, intense selection for meat production has resulted in animals with extreme muscularity and leanness in several livestock species. In recent years, it has become feasible to map and clone several of the genes causing these phenotypes, paving the way towards more efficient marker-assisted selection, targeted drug development (performance enhancing products) and transgenesis. Mutations in the ryanodine receptor (Fuji et al., 1991; MacLennan and Phillips, 1993) and myostatin (Grobet et al., 1997; Kambadur et al., 1997; McPherron and Lee, 1997) have been shown to cause muscular hypertrophies in pigs and cattle respectively, while genes with major effects on muscularity and/or fat deposition have, for instance, been mapped to pig chromosome 4 (Andersson et al., 1994) and sheep chromosome 18 (Cocket et al., 1996).

However, although there have been successes in identifying QTLs, the information is currently of limited use within commercial breeding programs. Many workers in this field conclude that it is necessary to identify the particular genes underlying the QTL. This is a substantial task, as the QTL region is usually relatively large and may contain many genes. Identification of the relevant genes from the many that may be involved thus remains a significant hurdle in farm animals.

SUMMARY OF THE INVENTION

In one aspect, the invention provides a method for selecting a domestic animal for having desired genotypic or potential phenotypic properties comprising testing the animal for the presence of a parentally imprinted qualitative or quantitative trait locus (QTL). Herein, a domestic animal is defined as an animal being selected or having been derived from an animal having been selected for having desired genotypic or potential phenotypic properties.

Domestic animals provide a rich resource of genetic and phenotypic variation; traditionally, domestication involves selecting an animal or its offspring for having desired genotypic or potential phenotypic properties. This selection process has in the past century been facilitated by a growing understanding and utilization of the laws of Mendelian inheritance. One of the major problems in breeding programs of domestic animals is the negative genetic correlation between reproductive capacity and production traits. This is, for example, the case in cattle (a high milk production generally results in slim cows and bulls) poultry, broiler lines have a low level of egg production and layers have generally very low muscle growth), pigs (very prolific sows are, in general, fat and have comparatively less meat) or sheep (high prolific breeds have low carcass quality and vice versa). The invention now provides that knowledge of the parental imprinting character of various traits allows selection of, for example, sire lines, homozygous for a paternally imprinted QTL, for example, linked with muscle production or growth; the selection for such traits can thus be less stringent in dam lines in favor of the reproductive quality. The phenomenon of genetic or parental imprinting has never been utilized in selecting domestic animals, it was never considered feasible to employ this elusive genetic characteristic in practical breeding programs. The invention provides a breeding program, wherein knowledge of the parental imprinting character of a desired trait, as demonstrated herein, results in a breeding program, for example in a BLUP program, with a modified animal model. This increases the accuracy of the breeding value estimation and speeds up selection compared to conventional breeding programs. Until now, the effect of a parentally imprinted trait in the estimation of a conventional BLUP program was neglected; using and understanding the parental character of the desired trait, as provided by the invention, allows selecting on parental imprinting, even without DNA testing. For example, selecting genes characterized by paternal imprinting is provided to help increase uniformity; a (terminal) parent homozygous for the "good or wanted" alleles will pass them to all offspring, regardless of the other parent's alleles, and the offspring will all express the desired parent's alleles. This results in more uniform offspring. Alleles that are interesting or favorable from the maternal side are often the ones that have opposite effects to alleles from the paternal side. For example, in meat animals, such as pigs, alleles linked with meat quality traits, such as intra-muscular fat or muscle mass, could be fixed in the dam lines while alleles linked with reduced back fat could be fixed in the sire lines. Other desirable combinations are, for example, fertility and/or milk yield in the female line with growth rates and/or muscle mass in the male lines.

BRIEF DESCRIPTION OF THE SEVERAL VIEWS OF THE DRAWINGS

FIG. 3: Lodscore curves obtained in a Piétrain×Large White intercross for six phenotypes measuring muscle mass and fat deposition on pig chromosome 2. The most likely positions of the Igf2 and MyoD genes determined by linkage analysis with respect to the microsatellite marker map are shown. $H_0$ was defined as the null-hypothesis of no QTL, $H_1$ as testing for the presence of a Mendelian QTL, $H_2$ as testing for the presence of a paternally expressed QTL, and $H_3$ as testing for the presence of a maternally expressed QTL.

FIG. 6: Nucleic acid sequences of contig 1 to contig 115 derived from BAC-PIGF2-1, which was shotgun sequenced using standard procedures and automatic sequencers (SEQ ID NOS:10-117).

FIG. 8: Nucleic acid sequences of contig 1 to contig 7 derived from BAC-PIGF2-2, (the 24 Kb NotI fragment not present in BAC-PIGF2-1) which was subcloned and sequenced using the EZ::TN transposon approach and ABI automatic sequencers (SEQ ID NOS:118-124).

FIG. 10: DNA sequence polymorphisms in the IGF2 and flanking loci from genomic DNA isolated from Piétrain, Large White and Wild Boar individuals. (Polymorphisms Tyrosine Hydroxylase Gene C3 (1-4) (SEQ ID NOS:128-132), Polymorphism Insulin-IGF2 C4 (5-23) (SEQ ID NOS: 133-170), Polymorphismes in Coding Region C10 (24-28) (SEQ ID NOS: 171-180), Microsatellites (29-31) (SEQ ID NOS: 181-183).

FIG. 11: Representation of a suitable marker-assisted selection program for the IGF2 mutation.

DETAILED DESCRIPTION OF THE INVENTION

Figure 1:
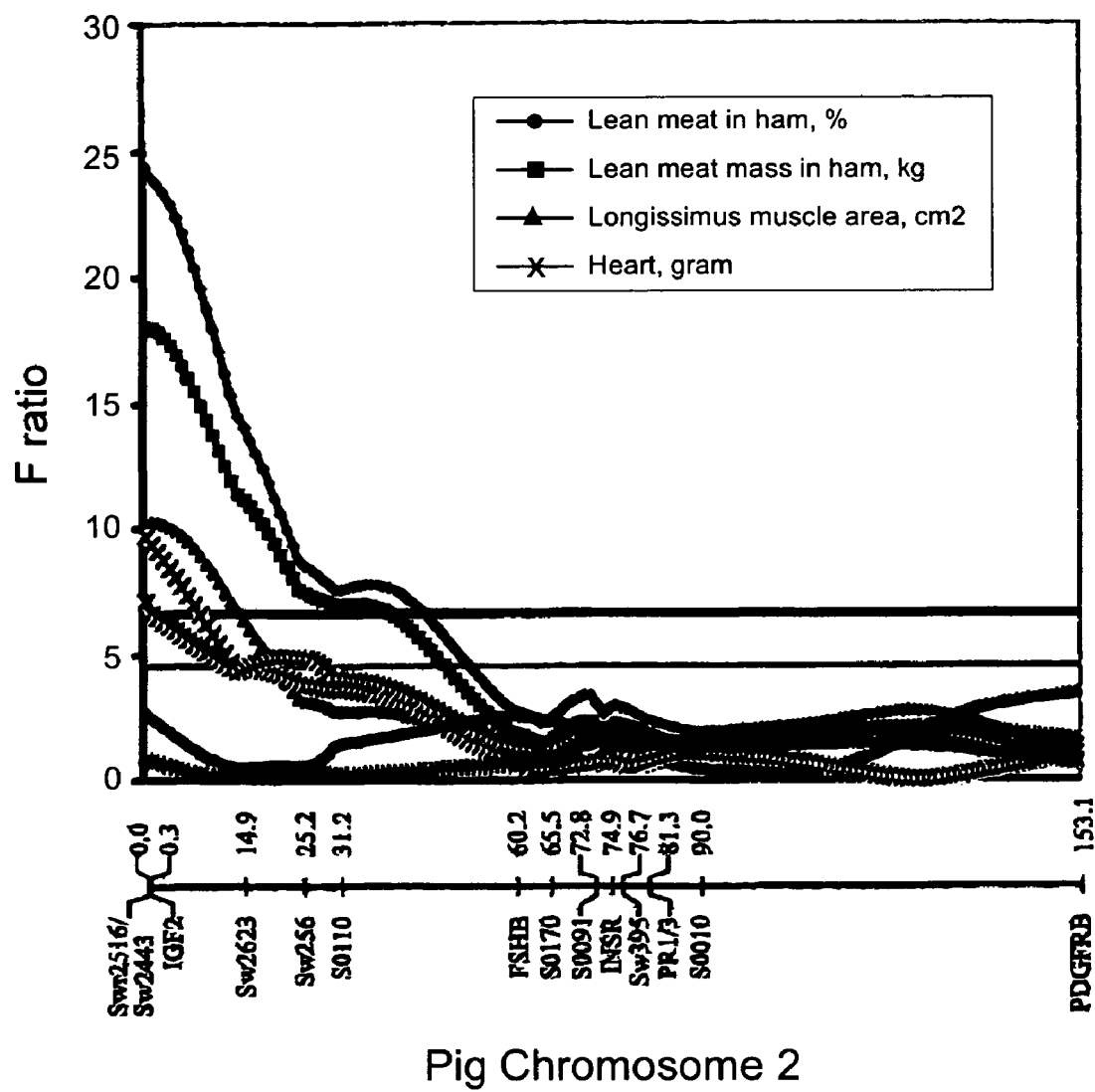
FIG. 1: Test statistic curves obtained in QTL analyses of chromosome 2 in a Wild Boar/Large White intercross. The graph plots the F ratio testing the hypothesis of a single QTL at a given position along the chromosome for the traits indicated. The marker map with the distances between markers in Kosambi centiMorgan is given on the X-axis. The horizontal lines represent genome-wise significant (P<0.05) and suggestive levels for the trait lean meat in ham; similar significance thresholds were obtained for the other traits.

In a preferred embodiment, the invention provides a method for selecting a domestic animal for having desired genotypic or potential phenotypic properties comprising testing a nucleic acid sample from the animal for the presence of a parentally imprinted quantitative trait locus (QTL). A nucleic acid sample can, in general, be obtained from various parts of the animal's body by methods known in the art. Traditional samples for the purpose of nucleic acid testing are blood samples or skin or mucosal surface samples, but samples from other tissues can be used as well, particularly, sperm samples, oocyte or embryo samples can be used. In such a sample, the presence and/or sequence of a specific nucleic acid, be it DNA or RNA, can be determined with methods known in the art, such as hybridization or nucleic acid amplification or sequencing techniques known in the art. The invention provides testing such a sample for the presence of nucleic acid wherein a QTL or allele associated therewith is associated with the phenomenon of parental imprinting, for example where it is determined whether a paternal or maternal allele of the QTL is capable of being predominantly expressed in the animal.

The purpose of breeding programs in livestock is to enhance the performances of animals by improving their genetic composition. In essence, this improvement accrues by increasing the frequency of the most favorable alleles for the genes influencing the performance characteristics of interest. These genes are referred to as QTL. Until the beginning of the nineties, genetic improvement was achieved via the use of biometrical methods, but without molecular knowledge of the underlying QTL.

Since the beginning of the Nineties, and due to recent developments in genomics, it is conceivable to identify the QTL underlying a trait of interest. The invention now provides identifying and using parentally imprinted QTLs which are useful for selecting animals by mapping quantitative trait loci. Again, the phenomenon of genetic or paternal imprinting has never been utilized in selecting domestic animals, it was never considered feasible to employ this elusive genetic characteristic in practical breeding programs. For example, Kovacs and Kloting (*Biochem. Mol. Biol. Int.* 44:399-405, 1998), where parental imprinting is not mentioned, and not suggested, found linkage of a trait in female rats, but not in males, suggesting a possible sex specificity associated with a chromosomal region, which of course excludes parental imprinting, a phenomenon wherein the imprinted trait of one parent is preferably but gender-aspecifically expressed in his or her offspring.

The invention provides the initial localization of a parentally imprinted QTL on the genome by linkage analysis with genetic markers, and the actual identification of the parentally imprinted gene(s) and causal mutations therein. Molecular knowledge of such a parentally imprinted QTL allows for more efficient breeding designs herewith provided. Applications of molecular knowledge of parentally imprinted QTLs in breeding programs include: marker-assisted segregation analysis to identify the segregation of functionally distinct parentally imprinted QTL alleles in the populations of interest, marker-assisted selection (MAS) performed within lines to enhance genetic response by increasing selection accuracy, selection intensity or by reducing the generation interval using the understanding of the phenomenon of parental imprinting, marker-assisted introgression (MAI) to efficiently transfer favorable parentally imprinted QTL alleles from a donor to a recipient population, genetic engineering of the identified parentally QTL and genetic modification of the breeding stock using transgenic technology, development of performance enhancing products using targeted drug development exploiting molecular knowledge of the QTL.

The inventors undertook two independent experiments to determine the practical use of parental imprinting of a QTL.

In a first experiment, performed in a previously described Piétrain×Large White intercross, the likelihood of the data was computed under a model of paternal (paternal allele only expressed) and maternal imprinting (maternal allele only expressed) and compared with the likelihood of the data under a model of a conventional "Mendelian" QTL. The results strikingly demonstrated that the QTL was indeed paternally expressed, the QTL allele (Piétrain or Large White) inherited from the F1 sow having no affect whatsoever on the carcass quality and quantity of the $F_2$ offspring. It was seen that very significant lodscores were obtained when testing for the presence of a paternally expressed QTL, while there was no evidence at all for the segregation of a QTL when studying the chromosomes transmitted by the sows. The same tendency was observed for all traits showing that the same imprinted gene is responsible for the effects observed on the different traits. Table 1 reports the maximum likelihood (ML) phenotypic means for the $F_2$ offspring sorted by inherited paternal QTL allele.

In a second experiment performed in the Wild Boar X Large White intercross, QTL analyses of body composition, fatness, meat quality, and growth traits was carried out with the chromosome 2 map using a statistical model testing for the presence of an imprinting effect. Clear evidence for a paternally expressed QTL located at the very distal tip of 2p was obtained (FIG. 2; Table 1). The clear paternal expression of a QTL is illustrated by the least squares means which fall into two classes following the population origin of the paternally inherited allele (Table 1). For a given paternally imprinted QTL, implementation of marker-assisted segregation analysis, selection (MAS) and introgression (MAI), can be performed using genetic markers that are linked to the QTL, genetic markers that are in linkage disequilibrium with the QTL, or using the actual causal mutations within the QTL.

Understanding the parent-of-origin effect characterizing a QTL allows for its optimal use in breeding programs. Indeed, marker-assisted segregation analysis under a model of parental imprinting will yield better estimates of QTL allele effects. Moreover, it allows for the application of specific breeding schemes to optimally exploit a QTL. In one embodiment of the invention, the most favorable QTL alleles would be fixed in breeding animal lines and, for example, used to generate commercial, crossbred males by marker-assisted selection (MAS, within lines) and marker-assisted introgression (MAI, between lines). In another embodiment, the worst QTL alleles would be fixed in the animal lines used to generate commercial crossbred females by MAS (within lines) and MAI (between lines).

In a preferred embodiment of the invention, the animal is a pig. Note, for example, that the invention provides the insight that today half of the offspring from commercially popular Piétrain$_X$ Large White crossbred boars inherit an unfavorable Large White muscle mass QTL as provided by the invention causing considerable loss, and the invention now, for example, provides the possibility to select the better half of the population in that respect. However, it is also possible to select commercial sow lines enriched with the boar's unfavorable alleles, allowing to equip the sows with other alleles that are more desirable, for example, for reproductive purposes.

In a preferred embodiment of a method provided by the invention, the QTL is located at a position corresponding to a QTL located at chromosome 2 in the pig. For example, it is known from comparative mapping data between pig and human, including bidirectional chromosome painting, that SSC2p is homologous to HSA11pter-q13.[11,12] HSA11pter-q13 is known to harbor a cluster of imprinted genes: IGF2, INS2, H19, MAH2, p57$^{KIP2}$, K,LQTL1, Tapa1, /CD81, Orctl2, Impt1 and Ip1. The cluster of imprinted genes located in HSA11pter-q13 is characterized by eight maternally expressed genes H19, MASH2, p57$^{KIP2}$, KVLQTL1, TAPA1/CD81, ORCTL2, IMPT1 and IP1, and two paternally expressed genes: IGF2 and INS. However, Johanson et al. (*Genomics* 25:682-690, 1995) and Reik et al. (*Trends in Genetics* 13:330-334, 1997) show that the whereabouts of these loci in various animals are not clear. For example, the HSA11 and MMU7 loci do not correspond among each other, the MMU7 and the SSC2 loci do not correspond, whereas the HSA11 and SSC2 loci seem to correspond, and no guidance is given where one or more of, for example, the above-identified parentally expressed individual genes are localized on the three species' chromosomes.

Other domestic animals, such as cattle, sheep, poultry and fish, having similar regions in their genome harboring such a cluster of imprinted genes or QTLs, the invention herewith provides use of these orthologous regions of other domestic animals in applying the phenomenon of parental imprinting in breeding programs. In pigs, the cluster is mapped at around position 2p1.7 of chromosome 2, however, a method as provided by the invention employing (fragments of) the maternally or paternally expressed orthologous or homologous genes or QTLs are advantageously used in other animals as well for breeding and selecting purposes. For example, a method is provided wherein the QTL is related to the potential muscle mass and/or fat deposition, preferably with limited effects on other traits, such as meat quality and daily gain of the animal, or wherein the QTL comprises at least a part of an insulin-like growth factor-2 (IGF2) allele. Reik et al. (*Trends in Genetics* 13:330-334, 1997) explain that this gene in humans is related to Beckwith-Wiedemann syndrome, an apparently parentally imprinted disease syndrome most commonly seen with human fetuses, where the gene has an important role in prenatal development. No relationship is shown or suggested with postnatal development relating to muscle development or fatness in (domestic) animals.

In a preferred embodiment, the invention provides a method for selecting a pig for having desired genotypic or potential phenotypic properties comprising testing a sample from the pig for the presence of a quantitative trait locus (QTL) located at a *Sus scrofa* chromosome 2 mapping at position 2p1.7. In particular, the invention relates to the use of genetic markers for the telomeric end of pig chromosome 2p in marker selection (MAS) of a parentally imprinted Quantitative Trait Locus (QTL) affecting carcass yield and quality in pigs. Furthermore, the invention relates to the use of genetic markers associated with the IGF2 locus in MAS in pigs, such as polymorphisms and microsatellites and other characterizing nucleic acid sequences shown herein, such as shown in FIGS. 4 to 10. In a preferred embodiment, the invention provides a QTL located at the distal tip of *Sus scrofa* chromosomes 2 with effects on varies measurements of carcass quality and quantity, particularly muscle mass and fat deposition.

In a first experiment, a QTL mapping analysis was performed in a Wild Boar×Large White intercross counting 200 $F_2$ individuals. The $F_2$ animals were sacrificed at a live eight of at least 80 kg or at a maximum age of 190 days. Phenotypic data on birth weight, growth, fat deposition, body composition, weight of internal organs, and meat quality were collected; a detailed description of the phenotypic traits are provided by Andersson et al.[1] and Andersson-Eklund et al.[4]

A QTL (without any significant effect on back-fat thickness) at an unspecified locus on the proximal end of chromosome 2 with moderate effect on muscle mass, and located about 30 cm away from the parentally imprinted QTL reported here, was previously reported by the inventors; whereas the QTL as now provided has a very large effect, explaining at least 20-30% of variance, making the QTL of the present invention commercially very attractive, which is even more so because the present QTL is parentally imprinted. The marker map of chromosome 2p was improved as part of this invention by adding microsatellite markers in order to cover the entire chromosome arm. The following microsatellite markers were used: Swc9, Sw2443, Sw2623, and Swr2516, all from the distal end of 2p.[7] QTL analyses of body composition, fatness, meat quality, and growth traits were carried out with the new chromosome 2 map. Clear evidence for a QTL located at the very distal tip of 2p was obtained (FIG. 1; Table 1). The QTL had very large effects on lean meat content in ham and explained an astonishing 30% of the residual phenotypic variance in the $F_2$ population. Large effects on the area of the longissumus dorsi muscle, on the weight of the heart, and on back-fat thickness (subcutaneous fat) were also noted. A moderate effect on one meat quality trait, reflectance value, was indicated. The QTL had no significant effect on abdominal fat, birth weight, growth, weight of liver, kidney, or spleen (data not shown). The Large White allele at this QTL was associated with larger muscle mass and reduced back-fat thickness consistent with the difference between this breed and the Wild Boar population.

In a second experiment, QTL mapping was performed in a Piétrain X Large White intercross comprising 1125 $F_2$ offspring. The Large White and Piétrain parental breeds differ for a number of economically important phenotypes. Piétrains are famous for their exceptional muscularity and leanness[10] (FIG. 2, while Large Whites show superior growth performance. Twenty-one distinct phenotypes measuring growth performance (5), muscularity (6), fat deposition (6), and meat quality (4), were recorded on all $F_2$ offspring. In order to map QTL underlying the genetic differences between these breeds, the inventors undertook a whole genome scan using microsatellite markers on an initial sample of 677 $F_2$ individuals. The following microsatellite marker map was used to analyze chromosome 2;:SW2443, SWC9 and SW2623, SWR2516-(0,20)-SWR783-(0,29)-SW240-(0,20)-SW776-(0,08)-S0010-(0,04)-SW1695-(0,36)-SW R308. Analysis of pig chromosome 2 using a Maximum Likelihood multipoint algorithm, revealed highly significant lodscores (up to 20) for three of the six phenotypes measuring muscularity (% lean cuts, % ham, % loin) and three of the six phenotypes measuring fat deposition (back-fat thickness (BFT), % back fat, % fat cuts) at the distal end of the short arm of chromosome 2 (FIG. 1). Positive lodscores were obtained in the corresponding chromosome region for the remaining six muscularity and fatness phenotypes, however, not reaching the experiment-wise significance threshold)(a=5%. There was no evidence for an effect of the corresponding QTL on growth performance (including birth weight) or recorded meat quality measurements (data not shown). To confirm this finding, the remaining sample of 355 $F_2$ offspring was genotyped for the four most distal 2p markers and QTL analysis performed for the traits yielding the highest lodscores in the first analysis. Lodscores ranged from 2.1 to 7.7, clearly confirming the presence of a major QTL in this region. Table 2 reports the corresponding ML estimates for the three genotypic means as well as the residual variance. Evidence based on marker-assisted segregation analysis points towards residual segregation at this locus within the Piétrain population.

These experiments therefore clearly indicated the existence of a QTL with major effect on carcass quality and quantity on the telomeric end of pig chromosome arm 2p; the likely existence of an allelic series at this QTL with at least three alleles: Wild-Boar<Large White<Piétrain, and possibly more given the observed segregation within the Piétrain breed.

The effects of the identified QTL on muscle mass and fat deposition are truly major, being of the same magnitude of those reported for the CRC locus though apparently without the associated deleterious effects on meat quality. We estimate that both loci jointly explain close to 50% of the Piétrain versus Large White breed difference for muscularity and leanness. The QTL had very large effects on lean meat content in ham and explained an astonishing 30% of the residual phenotypic variance in the $F_2$ population. Large effects on the area of the longissumus dorsi muscle, on the weight of the heart, and on back-fat thickness (subcutaneous fat) were also noted. A moderate effect on one meat quality trait, reflectance value, was indicated. The QTL had no significant effect on abdominal fat, birth weight, growth, weight of liver, kidney, or spleen (data not shown). The Large White allele at this QTL, when compared to the Wild Boar allele, was associated with larger muscle mass and reduced back-fat thickness consistent with the difference between this breed and the Wild Boar population. The strong imprinting effect observed for all affected traits shows that a single causative locus is involved. The pleiotropic effects on skeletal muscle mass and the size of the heart appear adaptive from a physiological point of view as a larger muscle mass requires a larger cardiac output.

In a further embodiment, the invention provides a method for selecting a pig for having desired genotypic or potential phenotypic properties comprising testing a sample from the pig for the presence of a quantitative trait locus (QTL) located at a Sus scrofa chromosome 2 mapping at position 2p1.7., wherein the QTL comprises at least a part of a Sus scrofa insulin-like growth factor-2 (IGF2) allele or a genomic area closely related thereto, such as polymorphisms and microsatellites and other characterizing nucleic acid sequences shown herein, such as shown in FIGS. 4 to 10. The important role of IGF2 for prenatal development is well-documented from knock-out mice as well as from its causative role in the human Beckwith-Wiedemann syndrome. This invention demonstrates an important role for the IGF2-region also for postnatal development.

To show the role of Igf2, the inventors performed the following three experiments:

A genomic IGF2 clone was isolated by screening a porcine BAC library. FISH analysis with this BAC clone gave a strong consistent signal on the terminal part of chromosome 2p.

A polymorphic microsatellite is located in the 3'UTR of IGF2 in mice (GenBank U71085), humans (GenBank S62623), and horse (GenBank AF020598). The possible presence of a corresponding porcine microsatellite was investigated by direct sequencing of the IFG2 3'UTR using the BAC clone. A complex microsatellite was identified about 800 bp downstream of the stop codon; a sequence comparison revealed that this microsatellite was identical to a previously described anonymous microsatellite, Swc9.[6] This marker was used in the initial QTL mapping experiments and its location on the genetic map correspond with the most likely position of the QTL both in the Piétrain X Large White and in the Large White×Wild Boar pedigree.

Analysis of skeletal muscle and liver cDNA from tenweek-old fetuses heterozygous for a nt241 (G-A) transversion in the second exon of the porcine IGFII gene and SWC9, shows that the IGFII gene is imprinted in these tissues in the pig as well and only expressed from the paternal allele.

Based on a published porcine adult liver cDNA sequence,[16] the inventors designed primer pairs allowing amplification of the entire IgfII coding sequence with 222 bp of leader and 280 bp of trailer sequence from adult skeletal muscle cDNA. Piétrain and Large White RT-PCR products were sequenced indication that the coding sequences are identical in both breeds and with the published sequence. However, a G⊗A transition was found in the leader sequence corresponding to exon 2 in man. Following conventional nomenclature, this polymorphism will be referred to as nt241(G-A). We developed a screening test for this single nucleotide polymorphism 9(SNP) based on the ligation amplification reaction (LAR), allowing us to genotype our pedigree material. Based on these data, IgfII was shown to colocalize with the SWC9 microsatellite marker (θ=0%), therefore virtually coinciding with the most likely position of the QTL, and well within the 95% support interval for the QTL. Subsequent sequence analysis demonstrated that the microsatellite marker SWC9 is actually located within the 3'UTR of the IgfII gene.

As previously mentioned, the knowledge of this QTL provides a method for the selection of animals such as pigs with improved carcass merit. Different embodiments of the invention are envisaged, including: marker-assisted segregation analysis to identify the segregation of functionally distinct QTL alleles in the populations of interest; marker-assisted selection (MAS) performed within lines to enhance genetic response by increasing selection accuracy, selection intensity or by reducing the generation interval; marker-assisted introgression (MAI) to efficiently transfer favorable QTL alleles from a donor to a recipient population, thereby enhancing genetic response in the recipient population. Implementation of embodiments marker-assisted segregation analysis, selection (MAS) and introgression (MAI), can be performed using genetic markers that are linked to the QTL; genetic markers that are in linkage disequilibrium with the QTL, the actual causal mutations within the QTL.

As indicated above, the insulin-like growth factor 2 (IGF2) gene was mapped to the distal tip of the short arm on chromosome 2 in swine. Gene mapping studies indicated that this paternally expressed QTL at the IGF2 gene region has a large effect on back fat thickness and carcass leanness (e.g., Jeon et al. (1999), *Nature Genetics* 21, 157-158; Nezer et al. (1999), *Nature Genetics* 21, 155-156). Recently, a mutation in the regulatory region of the IGF2 gene has been identified to be the cause underlying the QTL effect on muscle growth and fat deposition (Van Laere et al. (2003) *Nature* 425:832-836). This single nucleotide substitution (G-A), located at position 3072 in the intron 3 of IGF2 gene, increases gene expression of IGF2 in muscle threefold, stimulates muscle growth at the expense of back fat and results in leaner swine carcass and lower back fat.

The large effect of the QTL on lean meat and back fat without influence on growth or meat quality, makes this an attractive QTL to use in the breeding program. Terminal sires have been selected to be homozygous for the lean allele (AA) in order to pass the full effect to their offspring. Field results have been reported by several authors (Scheller et al. (2002) *Proceedings of the 27th Annual National Swine Improvement Federation*, Des Moines, Iowa, USA; Buys, N. (2003) *Proceedings of the 28th Annual National Swine Improvement Federation*, Des Moines, Iowa, USA, pp 146-149).

It is generally believed that prolificacy and sow longevity is reducing as a result of the genetic selection for increased leanness and lowering fat deposition (See, e.g., P. Mathur and Y. Liu (2003), *Proceedings of the 28th Annual National Swine Improvement Federation*, Des Moines, Iowa, USA, pp 155-163). Body fat deposition is necessary to sustain sow reproduction performance, for example, to support adequate milk production and to limit body weight loss. The selection for leaner carcasses, demanded by the packing industry and consumers, may conflict with the prolificacy and longevity of the sow and lead to increased replacement costs of sows in pig production. The QTN (quantitative trait nucleotide) in the IGF2 gene might provide a possibility to overcome this conflict. The imprinting character of the gene might be used to produce lean slaughter pigs from fatter dams, that inherited the wild type allele from their father (genotype of Grand parent boar=GG), crossed with terminal sires being homozygous for the lean allele (AA). The objective of this experiment was to investigate a possible effect of the QTN at the IGF2 gene on prolificacy and longevity.

The details of the experiment are described in Example 5. It was found that sows that inherited the wild type allele from their father had significantly more piglets born alive, total born and weaned, while there was no effect on stillborn piglets (See, Example 5, Table 4). No effect on any of these prolificacy data could be observed when data were analyzed according to the allele inherited from the mother (maternal allele). Also, if sows from heterozygous dams were taken into account and grouped according to the maternal allele, again no significant effect on prolificacy could be observed, which was expected since the maternal allele is not expressed.

The parity or average number of cycles per sow was also found to be higher in sows that inherited G from their father as compared to those that received the A allele, which points to a beneficial effect on longevity. This is related to higher litter size, since that is a major criterion for elimination in the selection program.

Thus, the IGF2-intron3 G3072A mutation (herein also referred to as IGF2+ or A-allele; the wild type being the igf2- or G-allele) has an influence on prolificacy and longevity in sows, which allows for the possibility to use the same imprinted QTN for different selection in sire and dam lines. Terminal sires should be homozygous for the lean allele to give uniform and lean slaughter pigs, while dam lines can benefit from a selection for the wild type allele since this has a beneficial effect on prolificacy and longevity. Because of the imprinted character of the gene, selection for the fatter allele in sow lines will not influence the carcass quality of the offspring.

Thus, the invention provides a method for selecting a domestic animal for having desired genotypic properties comprising testing the animal for the presence of a parentally imprinted quantitative trait locus (QTL) or a mutation therein and to the use of an isolated and/or recombinant nucleic acid comprising a parentally imprinted quantitative trait locus (QTL) or a mutation therein or functional fragment derived thereof to select a breeding animal or animal destined for slaughter having desired genotypic or potential phenotypic properties. The test may, for instance, comprise testing a sample from the pig for the presence of a quantitative trait locus (QTL) located at a *Sus scrofa* chromosome 2 mapping at position 2p1.7., wherein the QTL is paternally expressed, i.e., is expressed from the paternal allele.

In particular, the genotypic or potential phenotypic properties are selected from the group consisting of muscle mass, fat deposition, lean meat, lean back fat, sow prolificacy and sow longevity. In particular, improved sow prolificacy may include such phenotypic expressions as higher teat number, more piglets born alive, higher litter size, higher number of total born and weaned piglets with no effect on stillborn piglets. Improved sow longevity may in particular include such phenotypic expressions as parity or average number of cycles per sow.

Thus, the above-described IGF2 mutation influencing lean meat also influences a number of other positive traits and allows for marker-assisted selection in opposite directions in sire and dam lines due to the parentally imprinting character of the mutation. The mutation increases muscle mass at the expense of back fat with on average 2-4% more lean meat. This effect on leanness is of the same magnitude as reported for the Halothane gene but without any of the well-known deleterious effects on meat quality and animal health. Homozygous positive terminal sires (IGF2+/IGF2+) will pass the full effect to the slaughter pigs, regardless of the genotype of the mother. Furthermore, such selection principle allows for the possibility to push a far higher proportion of lower grading pigs into the higher payment categories. The experiment described in Example 5 shows that parent sows benefit from inheriting the negative gene (igf2-) from their father: they are more prolific and have an increased longevity. Parent sows are fatter but this will have no effect on the carcass quality of the slaughter pig (see illustration in Example 5).

In a further embodiment, the invention provides a method for selecting a pig for having desired genotypic or potential phenotypic properties comprising testing a sample from the pig for the presence of a quantitative trait locus (QTL) located at a *Sus scrofa* chromosome 2 mapping at position 2p1.7., wherein the QTL is paternally expressed, i.e., is expressed from the paternal allele. In man and mouse, Igf2 is known to be imprinted and to be expressed exclusively from the paternal allele in several tissues. Analysis of skeletal muscle cDNA from pigs heterozygous for the SNP and/or SWC9, shows that the same imprinting holds in the pig as well. Understanding the parent-of-origin effect characterizing the QTL as provided by the invention now allows for its optimal use in breeding programs. Indeed, today half of the offspring from commercially popular Piétrain×Large White crossbred boars inherit the unfavorable Large White allele causing considerable loss. Using a method as provided by the invention avoids this problem.

The invention furthermore provides an isolated and/or recombinant nucleic acid or functional fragment derived thereof comprising a parentally imprinted quantitative trait locus (QTL) or fragment thereof capable of being predominantly expressed by one parental allele. Having such a nucleic acid as provided by the invention available allows constructing transgenic animals wherein favorable genes are capable of being exclusively or predominantly expressed by one parental allele, thereby equipping the offspring of the animal homozygous for a desired trait with desired properties related to that parental allele that is expressed.

In a preferred embodiment, the invention provides an isolated and/or recombinant nucleic acid or fragment derived thereof comprising a synthetic parentally imprinted quantitative trait locus (QTL) or functional fragment thereof derived from at least one chromosome. "Synthetic" herein describes a parentally expressed QTL wherein various elements are combined that originate from distinct locations from the genome of one or more animals. The invention provides recombinant nucleic acid wherein sequences related to parental imprinting of one QTL are combined with sequences relating to genes or favorable alleles of a second QTL. Such a gene construct is favorably used to obtain transgenic animals wherein the second QTL has been equipped with paternal imprinting, as opposed to the inheritance pattern in the native animal from which the second QTL is derived. Such a second QTL can, for example, be derived from the same chromosome where the parental imprinting region is located, but can also be derived from a different chromosome from the same or even a different species. In the pig, such a second QTL can, for example, be related to an estrogen receptor (ESR)-gene (Rothschild et al., *PNAS* 93, 201-201, 1996) or a FAT-QTL (Andersson, *Science* 263, 1771-1774, 1994) for example derived from another pig chromosome, such as chromosome 4. A second or further QTL can also be derived from another (domestic) animal or a human.

The invention furthermore provides an isolated and/or recombinant nucleic acid or functional fragment derived thereof at least partly corresponding to a QTL of a pig located at a *Sus scrofa* chromosome 2 mapping at position 2p1.7 wherein the QTL is related to the potential muscle mass and/or fat deposition of the pig and/or wherein the QTL comprises at least a part of a *Sus scrofa* insulin-like growth factor-2 (IGF2) allele, preferably at least spanning a region between INS and H19, or preferably derived from a domestic pig, such as a Piétrain, Meishan, Duroc, Landrace or Large White, or from a Wild Boar. For example, a genomic IGF2 clone was isolated by screening a porcine BAC library. FISH analysis with this BAC clone gave a strong consistent signal on the terminal part of chromosome 2p. A polymorphic microsatellite is located in the 3'UTR of IGF2 in mice (GenBank U71085), humans (GenBank S62623), and horse (GenBank AF020598). The possible presence of a corresponding porcine microsatellite was investigated by direct sequencing of the IGF2 3'UTR using the BAC clone. A complex microsatellite was identified about 800 bp downstream of the stop codon; a sequence comparison revealed that this microsatellite is identical to a previously described anonymous microsatellite, Swc9. PCR primers were designed and the microsatellite (IGF2ms) was found to be highly polymorphic with three different alleles among the two Wild Boar founders and another two among the eight Large White founders. IGF2ms was fully informative in the intercross as the breed of origin as well as the parent of origin could be determined with confidence for each allele in each $F_2$ animal.

A linkage analysis using the intercross pedigree was carried out with IGF2ms and the microsatellites Sw2443, Sw2623, and Swr2516, all from the distal end of 2p.[7] IGF2 was firmly assigned to 2p by highly significant lod scores (e.g., Z=89.0, θ=0.003 against Swr2516). Multipoint analyses, including previously typed chromosome 2 markers, revealed the following order of loci (sex-average map distances in Kosambi cM): Sw2443/Swr2516-0.3-IGF2-14.9-Sw2623-10.3-Sw256. No recombinant was observed between Sw2443 and Swr2516, and the suggested proximal location of IGF2 in relation to these loci is based on a single recombinant giving a lod score support of 0.8 for the reported order. The most distal marker in our previous QTL study, Sw256, is located about 25 cM from the distal end of the linkage group.

The invention furthermore provides use of a nucleic acid or functional fragment derived thereof according to the invention in a method according to the invention. In a preferred embodiment, use of a method according to the invention is provided to select a breeding animal or animal destined for slaughter, or embryos or semen derived from these animals for having desired genotypic or potential phenotypic properties. In particular, the invention provides such use wherein the properties are related to muscle mass and/or fat deposition. The QTL as provided by the invention may be exploited or used to improve, for example, lean meat content or back-fat thickness by marker-assisted selection within populations or by marker-assisted introgression of favorable alleles from one population to another. Examples of marker-assisted selection using the QTL as provided by the invention are use of marker-assisted segregation analysis with linked markers or with markers in disequilibrium to identify functionally distinct QTL alleles. Furthermore, identification of a causative mutation in the QTL is now possible, again leading to identifying functionally distinct QTL alleles. Such functionally distinct QTL alleles located at the distal tip of chromosome 2p with large effects on skeletal muscle mass, the size of the heart, and on back-fat thickness are also provided by the invention. The observation of a similar QTL effect in a Large White×Wild Boar as well as in a Piétrain×Large White intercross provides proof of the existence of a series of at least three distinct functional alleles. Moreover, preliminary evidence based on marker-assisted segregation analysis points towards residual segregation at this locus within the Piétrain population (data not shown). The occurrence of an allelic series as provided by the invention allows identifying causal polymorphisms which—based on the quantitative nature of the observed effect—are unlikely to be gross gene alterations but rather subtle regulatory mutations. The effects on muscle mass of the three alleles rank in the same order as the breeds in which they are found, e.g., Piétrain pigs are more muscular than Large White pigs that in turn have higher lean meat content than Wild Boars. The invention furthermore provides use of the alleles as provided by the invention for within line selection or for marker-assisted introgression using linked markers, markers in disequilibrium or alleles comprising causative mutations.

The invention furthermore provides an animal selected by using a method according to the invention. For example, a pig characterized in being homozygous for an allele in a QTL located at a *Sus scrofa* chromosome 2 mapping at position 2p1.7 can now be selected and is thus provided by the invention. Since the QTL is related to the potential muscle mass and/or fat deposition of the pig and/or the QTL comprises at least a part of a *Sus scrofa* insulin-like growth factor-2 (IGF2) allele, it is possible to select promising pigs to be used for breeding or to be slaughtered. In particular, an animal according to the invention which is a male is provided. Such a male, or its sperm or an embryo derived thereof, can advantageously be used in breeding animals for creating breeding lines or for finally breeding animals destined for slaughter. In a preferred embodiment of such use as provided by the invention, a male, or its sperm, deliberately selected for being homozygous for an allele causing the extreme muscular hypertrophy and leanness, is used to produce offspring heterozygous for such an allele. Due to the allele's paternal expression, the offspring will also show the favorable traits for example related to muscle mass, even if the parent female has a different genetic background. Moreover, it is now possible to positively select the female(s) for having different traits, for example related to fertility, without having a negative effect on the muscle mass trait that is inherited from the allele from the selected male. For example, earlier such males could occasionally be seen with Piétrain pigs but, genetically, it was not understood how to most profitably use these traits in breeding programs.

Furthermore, the invention provides a transgenic animal, sperm and an embryo derived thereof, comprising a synthetic parentally imprinted QTL or functional fragment thereof as provided by the invention, i.e., it is provided by the invention to introduce a favorable recombinant allele; for example, to introduce the estrogen receptor locus related to increased litter size of an animal homozygously in a parentally imprinted region of a grandparent animal (for example, the father of a hybrid sow if the region was paternally imprinted and the grandparent was a boar); to introduce a favorable fat-related allele or muscle mass-related recombinant allele in a paternally imprinted region, and so on. Recombinant alleles that are interesting or favorable from the maternal side are often the ones that have opposite effects to alleles from the paternal side. For example, in meat animals, such as pigs, recombinant alleles linked with meat quality traits such as intramuscular fat or muscle mass could be fixed in the dam lines while recombinant alleles linked with reduced back fat could be fixed in the sire lines. Other desirable combinations are, for example, fertility and/or milk yield in the female line with growth rates and/or muscle mass in the male lines.

The invention is further explained in the detailed description without limiting the invention.

Example 1

Wild Boar×Large White Intercrosses

Methods

Isolation of an IGF2 BAC clone and fluorescent in situ hybridization (FISH). IGF2 primers (F:5'-GGCAAGTTCT-TCCGCTAATGA-3' (SEQ ID NO:1) and R:5'-GCACCG-CAGAATTACGACAA-3' (SEQ ID NO:2)) for PCR amplification of a part of the last exon and 3 UTR were designed on the basis of a porcine IGF2 cDNA sequence (GenBank X56094). The primers were used to screen a porcine BAC library and the clone 253G10 was isolated. Crude BAC DNA was prepared as described.[24] The BAC DNA was linearized with EcoRV and purified with QIAEXII (QIAGEN GmbH, Germany). The clone was labeled with biotin-14-dATP using the GIBCO-BRL Bionick labeling system (BRL18246-015). Porcine metaphase chromosomes were obtained from pokeweed (Seromed) stimulated lymphocytes using standard techniques. The slides were aged for two days at room temperature and then kept at −20° C. until use. FISH analysis was carried out as previously described.[25] The final concentration of the probe in the hybridization mix was 10 ng/μl. Repetitive sequences were suppressed with standard concentrations of porcine genomic DNA. After post-hybridization washing, the biotinylated probe was detected with two layers of avidin-FITC (Vector A-2011). The chromosomes were counterstained with 0.3 mg/ml DAPI (4,6-Diamino-2-phenylindole; Sigma D9542), which produced a G-banding like pattern. No post hybridization banding was needed, since chromosome 2 is easily recognized without banding. A total of 20 metaphase spreads were examined under an Olympus BX-60 fluorescence microscope connected to an IMAC-CCD S30 video camera and equipped with an ISIS 1.65 (Metasystems) software.

Sequence, Microsatellite, and Linkage Analysis.

About two μg of linearized and purified BAC DNA was used for direct sequencing with 20 pmoles of primers and BigDye Terminator chemistry (Perkin Elmer, USA). DNA sequencing was done from the 3' end of the last exon towards the 3' end of the UTR until a microsatellite was detected. A primer set (F:5'-GTTTCTCCTGTACCCACACGCATCCC-3' (SEQ ID NO:3) and R:5'-Fluorescein-CTA-CAAGCTGGGCTCAGGG-3' (SEQ ID NO:4)) was designed for the amplification of the IGF2 microsatellite, which is about 250 bp long and located approximately 800 bp downstream from the stop codon. The microsatellite was PCR amplified using fluorescently labeled primers and the genotyping was carried out using an ABI377 sequencer and the GeneScan/Genotyper software (Perkin Elmer, USA). Two-point and multipoint linkage analysis were done with the Cri-Map software.[26]

Animals and Phenotypic Data.

The intercross pedigree comprised two European Wild Boar males and eight Large White females, 4 F$_1$ males and 22 F$_1$ females, and 200 F$_2$ progeny.[1] The F$_2$ animals were sacrificed at a live weight of at least 80 kg or at a maximum age of 190 days. Phenotypic data on birth weight, growth, fat deposition, body composition, weight of internal organs, and meat quality were collected; a detailed description of the phenotypic traits are provided by Andersson et al.[1] and Andersson-Eklund et al.[4]

Statistical Analysis.

Interval mapping for the presence of QTL were carried out with a least squares method developed for the analysis of crosses between outbred lines.[27] The method is based on the assumption that the two divergent lines are fixed for alternative QTL alleles. There are four possible genotypes in the F$_2$ generation as regards the grandparental origin of the alleles at each locus. This makes it possible to fit three effects: additive, dominance, and imprinting.[2] The latter is estimated as the difference between the two types of heterozygotes, the one receiving the Wild Boar allele through an F$_1$ sire and the one receiving it from an F$_1$ dam. An F-ratio was calculated using this model (with 3 d.f.) versus a reduced model without a QTL effect for each cM of chromosome 2. The most likely position of a QTL was obtained as the location giving the highest F-ratio. Genome-wise significance thresholds were obtained empirically by a permutation test[28] as described.[2] The QTL model including an imprinting effect was compared with a model without imprinting (with 1 d.f.) to test whether the imprinting effect was significant.

The statistical models also included the fixed effects and covariates that were relevant for the respective traits; see Andersson-Eklund et al.[4] for a more detailed description of the statistical models used. Family was included to account for background genetic effects and maternal effects. Carcass weight was included as a covariate to discern QTL effects on correlated traits, which means that all results concerning body composition were compared at equal weights. Least-squares means for each genotype class at the IGF2 locus were estimated with a single point analysis using Procedure GLM of SAS;[29] the model included the same fixed effects and covariates as used in the interval mapping analyses.

The QTL shows a clear parent of origin-specific expression and the map position coincides with that of the insulin-like growth factor II gene (IGF2), indicating IGF2 as the causative gene. A highly significant segregation distortion (excess of Wild Boar-derived alleles) was also observed at this locus. The results demonstrate an important effect of the IGF2 region on postnatal development and it is possible that the presence of a paternally expressed IGF2-linked QTL in humans and in rodent model organisms has so far been overlooked due to experimental design or statistical treatment of data. The study also has important implications for quantitative genetics theory and practical pig breeding.

IGF2 was identified as a positional candidate gene for this QTL due to the observed similarity between pig chromosome 2p and human chromosome 11p. A genomic IGF2 clone was isolated by screening a porcine BAC library. FISH analysis with this BAC clone gave a strong consistent signal on the terminal part of chromosome 2p (FIG. 1). A polymorphic microsatellite is located in the 3'UTR of IGF2 in mice (GenBank U71085), humans (GenBank S62623), and horse (GenBank AF020598). The possible presence of a corresponding porcine microsatellite was investigated by direct sequencing of the IGF2 3'UTR using the BAC clone. A complex microsatellite was identified about 800 bp downstream of the stop codon; a sequence comparison revealed that this microsatellite is identical to a previously described anonymous microsatellite, Swc9.[6] PCR primers were designed and the microsatellite (IGF2ms) was found to be highly polymorphic with three different alleles among the two Wild Boar founders and another two among the eight Large White founders. IGF2ms was fully informative in the intercross as the breed of origin as well as the parent of origin could be determined with confidence for each allele in each F$_2$ animal.

A linkage analysis using the intercross pedigree was carried out with IGF2ms and the microsatellites Sw2443, Sw2623, and Swr2516, all from the distal end of 2p.[7] IGF2 was firmly assigned to 2p by highly significant lod scores (e.g., Z=89.0, θ=0.003 against Swr2516). Multipoint analyses, including previously typed chromosome 2 markers,[8] revealed the following order of loci (sex-average map distances in Kosambi cM): Sw2443/Swr2516-0.3-IGF2-14.9-Sw2623-10.3-Sw256. No recombinant was observed between Sw2443 and Swr2516, and the suggested proximal location of IGF2 in relation to these loci is based on a single recombinant giving a lod score support of 0.8 for the reported order. The most distal marker in our previous QTL study, Sw256, is located about 25 cM from the distal end of the linkage group.

QTL analyses of body composition, fatness, meat quality, and growth traits were carried out with the new chromosome 2 map using a statistical model testing for the possible presence of an imprinting effect as expected for IGF2. Clear evidence for a paternally expressed QTL located at the very distal tip of 2p was obtained (FIG. 2; Table 1). The QTL had very large effects on lean meat content in ham and explained an astonishing 30% of the residual phenotypic variance in the $F_2$ population. Large effects on the area of the longissumus dorsi muscle, on the weight of the heart, and on back-fat thickness (subcutaneous fat) were also noted. A moderate effect on one meat quality trait, reflectance value, was indicated. The QTL had no significant effect on abdominal fat, birth weight, growth, weight of liver, kidney, or spleen (data not shown). The Large White allele at this QTL was associated with larger muscle mass and reduced back-fat thickness consistent with the difference between this breed and the Wild Boar population. The strong imprinting effect observed for all affected traits strongly suggests a single causative locus. The pleiotropic effects on skeletal muscle mass and the size of the heart appear adaptive from a physiological point of view as a larger muscle mass requires a larger cardiac output. The clear paternal expression of this QTL is illustrated by the least squares means which fall into two classes following the population origin of the paternally inherited allele (Table 1). It is worth noticing though that there was a non-significant trend towards less extreme values for the two heterozygous classes, in particular for the estimated effect on the area of longissimus dorsi. This may be due to chance, but could have a biological explanation, e.g., that there is some expression of the maternally inherited allele or that there is a linked, non-imprinted QTL with minor effects on the traits in question.

Figure 2:
FIG. 2: Piétrain pig with characteristic muscular hypertrophy.

The IGF2-linked QTL and the FAT1 QTL on chromosome 4.[1,9] are by far the two loci with the largest effect on body composition and fatness segregating in this Wild Boar intercross. The IGF2 QTL controls primarily muscle mass whereas FAT1 has major effects on fat deposition including abdominal fat, a trait that was not affected by the IGF2 QTL (FIG. 2). No significant interaction between the two loci was indicated and they control a very large proportion of the residual phenotypic variance in the $F_2$ generation. A model including both QTLs explains 33.1% of the variance for percentage lean meat in ham, 31.3% for the percentage of lean meat plus bone in back, and 26.2% for average back fat depth (compare with a model including only chromosome 2 effects, Table 1). The two QTLs must have played a major role in the response during selection for lean growth and muscle mass in the Large White domestic pig.

A highly significant segregation distortion was observed in the IGF2 region (excess of Wild Boar-derived alleles) as shown in Table 1 ($\chi^2$=11.7, d.f.=2; P=0.003). The frequency of Wild Boar-derived IGF2 alleles was 59% in contrast to the expected 50% and there was twice as many "Wild Boar" as "Large White" homozygotes. This deviation was observed with all three loci at the distal tip and is thus not due to typing errors. The effect was also observed with other loci but the degree of distortion decreased as a function of the distance to the distal tip of the chromosome. Blood samples for DNA preparation were collected at 12 weeks of age and we are convinced that the deviation from expected Mendelian ratios was present at birth as the number of animals lost prior to blood sampling was not sufficient to cause a deviation of this magnitude. No other of the more than 250 loci analyzed in this pedigree show such a marked segregation distortion (L. Andersson, unpublished). The segregation distortion did not show an imprinting effect, as the frequencies of the two reciprocal types of heterozygotes were identical (Table 1). This does not exclude the possibility that the QTL effects and the segregation distortion are controlled by the same locus. The segregation distortion may be due to meiotic drive favoring the paternally expressed allele during gametogenesis, as the $F_1$ parents were all sired by Wild Boar males. Another possibility is that the segregation distortion may be due to codominant expression of the maternal and paternal allele in some tissues and/or during a critical period of embryo development. Biallelic IGF2 expression has been reported to occur to some extent during human developments[10,11] and interestingly a strong influence of the parental species background on IGF2 expression was recently found in a cross between *Mus musculus* and *Mus spretus*.[12] It is also interesting that a VNTR polymorphism at the insulin gene, which is very closely linked to IGF2, is associated with size at birth in humans.[13] It is possible that the IGF2-linked QTL in pigs has a minor effect on birth weight but in our data it was far from significant (FIG. 2) and there was no indication of an imprinting effect.

This study is an advance in the general knowledge concerning the biological importance of the IGF2 locus. The important role of IGF2 for prenatal development is well-documented from knock-out mice,[14] as well as from its causative role in the human Beckwith-Wiedemann syndrome.[15] This study demonstrates an important role for the IGF2-region also for postnatal development. It should be stressed that our intercross between outbred populations is particularly powerful to detect QTL with a parent of origin-specific effect on a multifactorial trait. This is because multiple alleles (or haplotypes) are segregating and we could deduce whether a heterozygous $F_2$ animal received the Wild Boar allele from the $F_1$ male or female. It is quite possible that the segregation of a paternally expressed IGF2-linked QTL affecting a trait like obesity has been overlooked in human studies or in intercrosses between inbred rodent populations because of experimental design or statistical treatment of data. An imprinting effect cannot be detected in an intercross between two inbred lines as only two alleles are segregating at each locus. Our result has therefore significant bearings on the future analysis of the association between genetic polymorphism in the insulin-IGF2 region and Type I diabetes,[16] obesity,[17] and variation in birth weight[13] in humans, as well as for the genetic dissection of complex traits using inbred rodent models. A major impetus for generating an intercross between the domestic pig and its wild ancestor was to explore the possibilities to map and identify major loci that have responded to selection. We have now showed that two single QTLs on chromosome 2 (this study) and 4[1,2] explain as much as one third of the phenotypic variance for lean meat content in the $F_2$ generation. This is a gross deviation from the underlying assumption in the classical infinitesimal model in quantitative genetics theory namely that quantitative traits are controlled by an infinite number of loci each with an infinitesimal effect. If a large proportion of the genetic difference between two divergent populations (e.g., Wild Boar and Large White) is controlled by a few loci, one would assume that selection would quickly fix QTL alleles with large effects leading to a selection plateau. However, this is not the experience in animal breeding programs or selection experiments where good persistent long-term selection responses are generally obtained, provided that the effective population size is reasonably large.[18] A possible explanation for this paradox is that QTL alleles controlling a large proportion of genetic differences between two populations may be due to several consecutive mutations; this may be mutations in the same gene or at several closely linked genes affecting the same trait. It has been argued that new mutations contribute substantially to long-term selection responses,[19] but the genomic distribution of such mutations is unknown.

The search for a single causative mutation is the paradigm with regard to the analysis of genetic defects in mice and monogenic disorders in humans. We propose that this may not be the case for loci that have been under selection for a large number of generations in domestic animals, crops, or natural populations. This hypothesis predicts the presence of multiple alleles at major QTL. It gains some support from our recent characterization of porcine coat color variation. We have found that both the alleles for dominant white color and for black-spotting differ from the corresponding wild type alleles by at least two consecutive mutations with phenotypic effects at the KIT and MC1R loci, respectively.[20, 21] In this context it is highly interesting that in the accompanying example we have identified a third allele at the IGF2-linked QTL. The effects on muscle mass of the three alleles rank in the same order as the breeds in which they are found i.e., Piétrain pigs are more muscular than Large White pigs that in turn have higher lean meat content than Wild Boars.

There are good reasons to decide that IGF2 is the causative gene for the now reported QTL. Firstly, there is a perfect agreement in map localization (FIG. 2). Secondly, it has been shown that IGF2 is paternally expressed in mice, humans, and now in pigs, like the QTL. There are several other imprinted genes in the near vicinity of IGF2 in mice and humans (Mash2, INS2, H19, KVLQT1, TAPA1/CD81, and CDKN1C/p57$^{KIP2}$) but only IGF2 is paternally expressed in adult tissues.[22] We believe that this locus provides a unique opportunity for molecular characterization of a QTL. The clear paternal expression can be used to exclude genes that do not show this mode of inheritance. Moreover, the presence of an allelic series should facilitate the difficult distinction between causative mutations and linked neutral polymorphism. We have already shown that there is no difference in coding sequence between IGF2 alleles from Piétrain and Large White pigs suggesting that the causative mutations occur in regulatory sequences. An obvious step is to sequence the entire IGF2 gene and its multiple promoters from the three populations. The recent report that a VNTR polymorphism in the promoter region of the insulin (INS) gene affects IGF2 expression[23] suggests that the causative mutations may be at a considerable distance from the IGF2 coding sequence.

The results have several important implications for the pig breeding industry. They show that genetic imprinting is not an esoteric academic question but need to be considered in practical breeding programs. The detection of three different alleles in Wild Boar, Large White, and Piétrain populations indicates that further alleles at the IGF2-linked QTL segregate within commercial populations. The paternal expression of the QTL facilitates its detection using large paternal half-sib families as the female contribution can be ignored. The QTL is exploited to improve lean meat content by marker-assisted selection within populations or by marker-assisted introgression of favorable alleles from one population to another.

Example 2

Piétrain×Large White Intercrosses

Methods

Pedigree material: The pedigree material utilized to map QTL was selected from a previously described Piétrain× Large White F2 pedigree comprising>1,800 individuals.[6, 7] To assemble this F2 material, 27 Piétrain boars were mated to 20 Large White sows to generate an F1 generation comprising 456 individuals. 31 F1 boars were mated to unrelated 82 F1 sows from 1984 to 1989, yielding a total of 1862 F2 offspring. F1 boars were mated on average to 7 females, and F1 sows to an average of 2.7 males. Average offspring per boar were 60 and per sow 23.

Phenotypic information: (i) Data collection: A total of 21 distinct phenotypes were recorded in the F2 generation.[6, 7] These included:

five growth traits: birth weight (g), weaning weight (Kg), grower weight (Kg), finisher weight (Kg) and average daily gain (ADG; Kg/day; grower to finisher period);

two body proportion measurements: carcass length (cm); and a conformation score (0 to 10 scale; reference 6);

ten measurements of carcass composition obtained by dissection of the chilled carcasses 24 hours after slaughter. These include measurements of muscularity: % ham (weight hams/carcass weight), % loin (weight loin/carcass weight), % shoulder (weight shoulder/carcass weight), % lean cuts (% ham+% loin+% shoulder); and measurements of fatness: average back-fat thickness (BFT; cm), % back fat (weight back fat/carcass weight), % belly (weight belly/carcass weight), % leaf fat (weight leaf fat/carcass weight), % jowl (weight jowl/carcass weight), and "% fat cuts" (% back fat+% belly+% leaf fat+% jowl).

four meat quality measurements: pH$_{LDi}$ (Longissimus dorsi 1 hour after slaughter), pH$_{LD24}$ (Longissimus dorsi 24 hours after slaughter), pH$_{GI}$ (Gracilis 1 hour after slaughter) and pH$_{G24}$ (Gracilis 24 hours after slaughter). (ii) Data processing: Individual phenotypes were preadjusted for fixed effects (sire, dam, CRC genotype, sex, year-season, parity) and covariates (litter size, birth weight, weaning weight, grower weight, finisher weight) that proved to significantly affect the corresponding trait. Variables included in the model were selected by stepwise regression.

Marker genotyping: Primer pairs utilized for PCR amplification of microsatellite markers are as described.[19] Marker genotyping was performed as previously described.[20] Genotypes at the CRC and MyoD loci were determined using conventional methods as described.[1, 12] The LAR test for the Igf2 SNP was developed according to Baron et al.[21] using a primer pair for PCR amplification (5'-CCCCTGAACT-TGAGGACGAGCAGCC-3' (SEQ ID NO:5); 5'-ATCGCT-GTGGGCTGGGTGGGCTGCC-3' (SEQ ID NO:6)) and a set of three primers for the LAR step (5'-FAM-CGC-CCCAGCTGCCCCCCAG-3' (SEQ ID NO:7); 5'-HEX-CGCCCCA GCTGCCCCCCAA-3' (SEQ ID NO:8); 5'-CCTGAGCTGCAGCAGGCCAG-3' (SEQ ID NO:9)).

Map construction: Marker maps were constructed using the TWOPOINT, BUILD and CHROMPIC options of the CRIMAP package.[22] To allow utilization of this package, full-sib families related via the boar or sow were disconnected and treated independently. By doing so, some potentially usable information was neglected, yielding, however, unbiased estimates of recombination rates.

QTL mapping: (i) Mapping Mendelian QTL: Conventional QTL mapping was performed using a multipoint maximum likelihood method. The applied model assumed one segregating QTL per chromosome, and fixation of alternate QTL alleles in the respective parental lines, Piétrain (P) and Large White (LW). A specific analysis program had to be developed to account for the missing genotypes of the parental generation, resulting in the fact that the parental origin of the F1 chromosomes could not be determined. Using a typical "interval mapping" strategy, a hypothetical QTL was moved along the marker map using user-defined steps. At each position, the likelihood (L) of the pedigree data was computed as:

$$L = \sum_{\varphi=1}^{2^r} \prod_{i=1}^{n} \sum_{G=1}^{4} (P(G \mid M_i, \theta, \varphi) P(y_i \mid G))$$

where $$\sum_{\varphi=1}^{2^r}:$$

is the sum over all possible marker-QTL phase combinations of the F1 generation. As there are two possible phases for each parent (left chromosome P or right chromosome P), there is a total of $2^r$ combinations for r F1 parents.

$$\prod_{i=1}^{n}$$

is the product over the n F2

$$\sum_{G=1}^{4}$$

is the sum, for the ith F2 offspring, over the four possible QTL genotypes: P/P, P/LW, LW/P and LW/LW $P(G|M_i,\theta,\varphi)$ is the probability of the considered QTL genotype, given (i) $M_i$: the marker genotype of the ith F2 offspring and its F1 parents, (ii): the vector of recombination rates between adjacent markers and between the hypothetical QTL and its flanking markers, and (iii) $\theta$ the considered marker-QTL phase combination of the F1 parents.

Recombination rates and marker linkage phase of F1 parents are assumed to be known when computing this probability. Both were determined using CRIMAP in the map construction phase (see above).

$P(y_i|G)$ is the probability of the phenotypic value of $(y_i)$ of offspring i, given the QTL genotype under consideration. This probability is computed from the normal density function:

$$P(y_i \mid G) = \frac{1}{\sqrt{2\pi}\,\sigma} e^{\frac{-(y_i - \mu_G)^2}{2\sigma^2}}$$

where $\mu_G$ is the phenotypic mean of the considered QTL genotype (PP, PL, LP or LL) and $\sigma^2$ the residual variance $\sigma^2$ was considered to be the same for the four QTL genotypic classes.

The values of $\mu_{PP}, \mu_{PP}, \mu_{PL}=\mu_{LP}, \mu_{LL}$ and $\sigma^2$ maximizing L were determined using the GEMINI optimization routine.[23]

The likelihood obtained under this alternative $H_1$ hypothesis was compared with the likelihood obtained under the null hypothesis $H_0$ of no QTL, in which the phenotypic means of the four QTL genotypic classes were forced to be identical. The difference between the logarithms of the corresponding likelihoods yields a lodscore measuring the evidence in favor of a QTL at the corresponding map position.

(ii) Significance thresholds: Following Lander & Botstein,[24] lodscore thresholds (T) associated with a chosen genome-wise significance level, were computed such that:

$$\alpha = (C + 9.21 GT)\chi_2^2(4.6T)$$

where C corresponds to the number of chromosomes (=19), G corresponds to the length of the genome in Morgans (=29), and $\chi_2^2(4.6\,T)$ denotes one minus the cumulative distribution function of the chi-squared distribution with 2 d.f. Single point 2 ln(LR) were assumed to be distributed as a chi-squared distribution with two degrees of freedom, as we were fitting both an additive and dominance component. To account for the fact that we were analyzing multiple traits, significance levels were adjusted by applying a Bonferoni correction corresponding to the effective number of independent traits that were analyzed. This effective number was estimated at 16 following the approach described by Spelman et al.[25] Altogether, this allowed us to set the lodscore threshold associated with an experiment-wise significance level of 5% at 5.8. When attempting to confirm the identified QTL in an independent sample, the same approach was used, however, setting C at 1, G at 25 cM and correcting for the analysis of 4.5 independent traits (as only six traits were analyzed in this sample). This yielded a lodscore threshold associated with a Type I error of 5% of 2.

(iii). Testing for an imprinted QTL: To test for an imprinted QTL, we assumed that only the QTL alleles transmitted by the parent of a given sex would have an effect on phenotype, the QTL alleles transmitted by the other parent being "neutral." The likelihood of the pedigree data under this hypothesis was computed using equation 1. To compute $P(y_i|G)$, however, the phenotypic means of the four QTL genotypes were set at $\mu_{PP}=\mu_{PL}=\mu_P$ and $\mu_{LP}=\mu_{LL}=\mu_L$ to test for a QTL for which the paternal allele only is expressed, and $\mu_{PP}=\mu_{LP}=\mu_P$ and $\mu_{PL}=\mu_{LL}=\mu_L$ to test for a QTL for which the maternal allele only is expressed. It is assumed in this notation that the first subscript refers to the paternal allele, the second subscript to the maternal allele. $H_0$ was defined as the null-hypothesis of no QTL, $H_1$ testing the presence of a Mendelian QTL; $H_2$ testing the presence of a paternally expressed QTL, and $H_3$ testing the presence of a maternally expressed QTL.

RT-PCR: Total RNA was extracted from skeletal muscle according to Chirgwin et al.[26] RT-PCR was performed using the Gene-Amp RNA PCR Kit (Perkin-Elmer) The PCR products were purified using QiaQuick PCR Purification kit (Qiagen) and sequenced using Dye terminator Cycle Sequencing Ready Reaction (Perkin Elmer) and an ABI373 automatic sequencer.

In Example 2, we report the identification of a QTL with major effect on muscle mass and fat deposition mapping to porcine 2p1.7 The QTL shows clear evidence for parental imprinting strongly suggesting the involvement of the Igf2 locus.

A Piétrain X Large White intercross comprising 1125 $F_2$ offspring was generated as described.[6,7] The Large White and Piétrain parental breeds differ for a number of economically important phenotypes. Piétrains are famed for their exceptional muscularity and leanness[8] (FIG. 2), while Large Whites show superior growth performance. Twenty-one distinct phenotypes measuring (i) growth performance (5), (ii) muscularity (6), (iii) fat deposition (6), and (iv) meat quality (4), were recorded on all $F_2$ offspring.

Figure 3A:
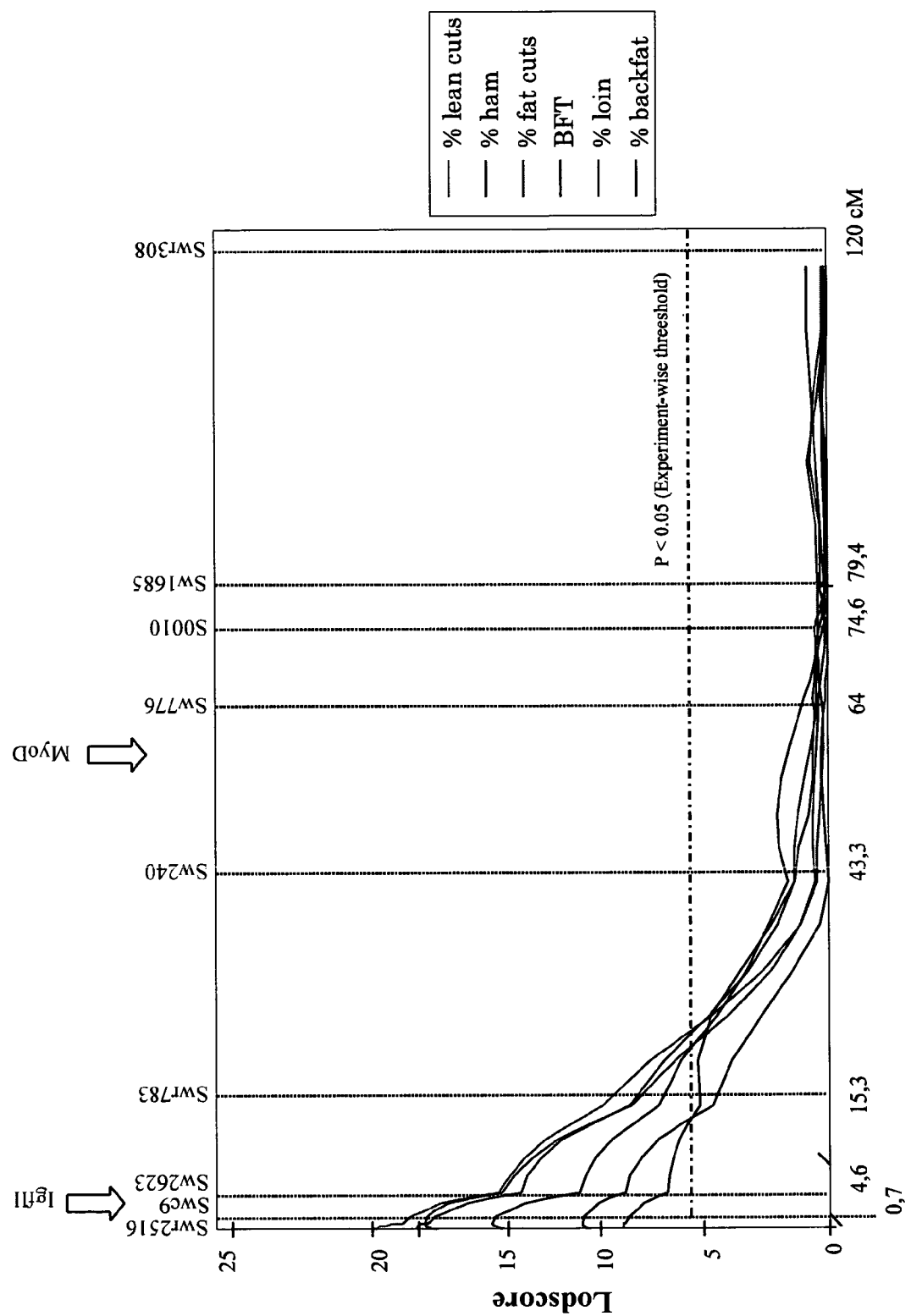
FIG. 3A: $\log_{10}(H_1/H_0)$.

In order to map QTL underlying the genetic differences between these breeds, we undertook a whole genome scan using microsatellite markers on an initial sample of 677 $F_2$ individuals. Analysis of pig chromosome 2 using a ML multipoint algorithm, revealed highly significant lodscores (up to 20) for six of the 12 phenotypes measuring muscularity and fat deposition at the distal end of the short arm of chromosome 2 (FIG. 3A). Positive lodscores were obtained for the remaining six phenotypes, however, not reaching the genome-wise significance threshold (=5%). To confirm this finding, the remaining sample of 355 $F_2$ offspring was genotyped for the five most distal 2p markers and QTL analysis performed for the traits yielding the highest lodscores in the first analysis. Lodscores ranged from 2.1 to 7.7, clearly confirming the presence of a major QTL in this region. Table 2 reports the corresponding ML estimates for the three genotypic means as well as the corresponding residual variance.

Figure 4:
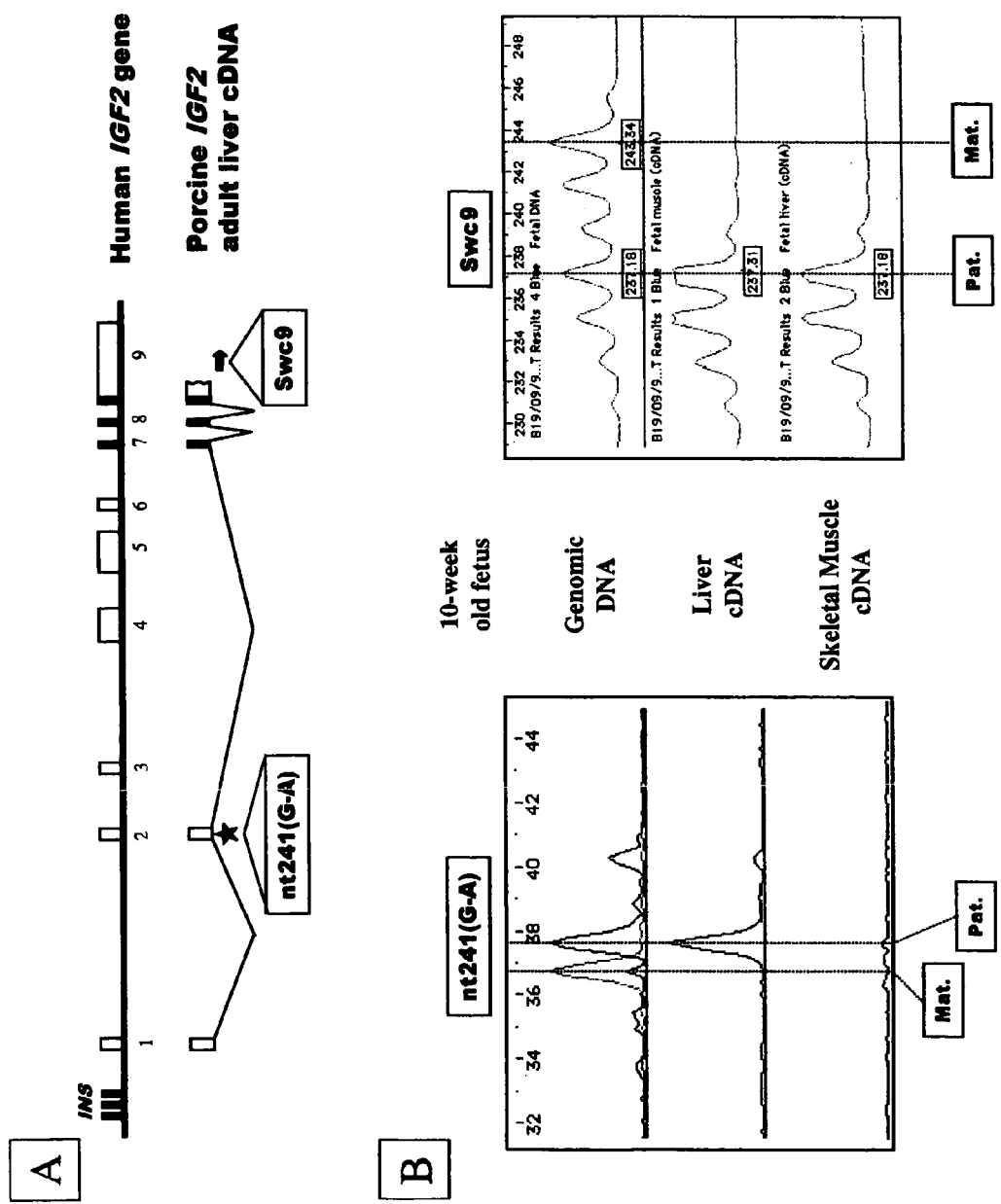
FIG. 4: Panel A. Structure of the human Igf2 gene according to reference 17, with aligned porcine adult liver cDNA sequence as reported in reference 16. The position of the nt241(G-A) transition and Swc9 microsatellite are shown. Panel B. The corresponding markers were used to demonstrate the monoallelic (paternal) expression of Igf2 in skeletal muscle and liver of ten-week-old fetuses. PCR amplification of the nt421(G-A) polymorphism and Swc9 microsatellite from genomic DNA clearly shows the heterozygosity of the fetus, while only the paternal allele is detected in liver cDNA (nt421(G-A) and Swc9) and muscle cDNA (Swc9). The absence of RT-PCR product for nt421(G-A) from in-fetal muscle points towards the absence of mRNA including exon 2 in this tissue. Parental origin of the fetal alleles was determined from the genotypes of sire and dam (data not shown).

Bidirectional chromosome painting establishes a correspondence between SSC2p and HSA11pter-q13.[9, 10] At least two serious candidate genes map to this region in man: the myogenic basic helix-loop-helix factor, MyoD, maps to HSA11p15.4, while Igf2 maps to HSA11p15.5 MyoD is a well known key regulator of myogenesis and is one of the first myogenic markers to be switched on during development.[11] A previously described amplified sequence polymorphism in the porcine MyoD gene[12] proved to segregate in our $F_2$ material, which was entirely genotyped for this marker. Linkage analysis positioned the MyoD gene in the SW240-SW776 (odds>1000) interval, therefore well outside the lod-2 drop off support interval for the QTL (FIG. 1). Igf2 is known to enhance both proliferation and differentiation of myoblasts in vitro[13] and to cause a muscular hypertrophy when overexpressed in vivo. Based on a published porcine adult liver cDNA sequence,[14] we designed primer pairs allowing us to amplify the entire Igf2 coding sequence with 222 bp of leader and 280 bp of trailer sequence from adult skeletal muscle cDNA. Piétrain and Large White RT-PCR products were sequenced indicating that the coding sequences were identical in both breeds and with the published sequence. However, a G A transition was found in the leader sequence corresponding to exon 2 in man (FIG. 4). We developed a screening test for this single nucleotide polymorphism (SNP) based on the ligation amplification reaction (LAR), allowing us to genotype our pedigree material. Based on these data, Igf2 was shown to colocalize with the SWC9 microsatellite marker (=0%), therefore located at approximately 2 centimorgan from the most likely position of the QTL and well within the 95% support interval for the QTL (FIG. 1). Subsequent sequence analysis demonstrated that the microsatellite marker SWC9 is actually located within the 3'UTR of the Igf2 gene. Combined with available comparative mapping data for the PGA and FSH loci, these results suggest the occurrence of an interstitial inversion of a chromosome segment containing MyoD, but not Igf2 which has remained telomeric in both species.

Igf2 therefore appeared as a strong positional allele having the observed QTL effect. In man and mouse, IgO is known to be imprinted and to be expressed exclusively from the paternal allele in several tissues.[15] Analysis of skeletal muscle cDNA from pigs heterozygous for the SNP and/or SWC9, shows that the same imprinting holds in this tissue in the pig as well (FIG. 4). Therefore if Igf2 were responsible for the observed effect, and knowing that only the paternal IgC allele is expressed, one can predict that (i) the paternal allele transmitted by F1 boars (P or LW) would have an effect on phenotype of F2 offspring, (ii) the maternal allele transmitted by F1 sows (P or LW) would have no effect on phenotype of F2 offspring, and (iii) the likelihood of the data would be superior under a model of a bimodal (1:1) F2 population sorted by inherited paternal allele when compared to a conventional "Mendelian" model of a trimodal (1:2:1) F2 population. The QTL mapping programs were adapted in order to allow testing of the corresponding hypotheses. $H_0$ was defined as the null-hypothesis of no QTL, $H_1$ as testing for the presence of a Mendelian QTL, $H_2$ as testing for the presence of a paternally expressed QTL, and $H_3$ as testing for the presence of a maternally expressed QTL.

Figure 3B:
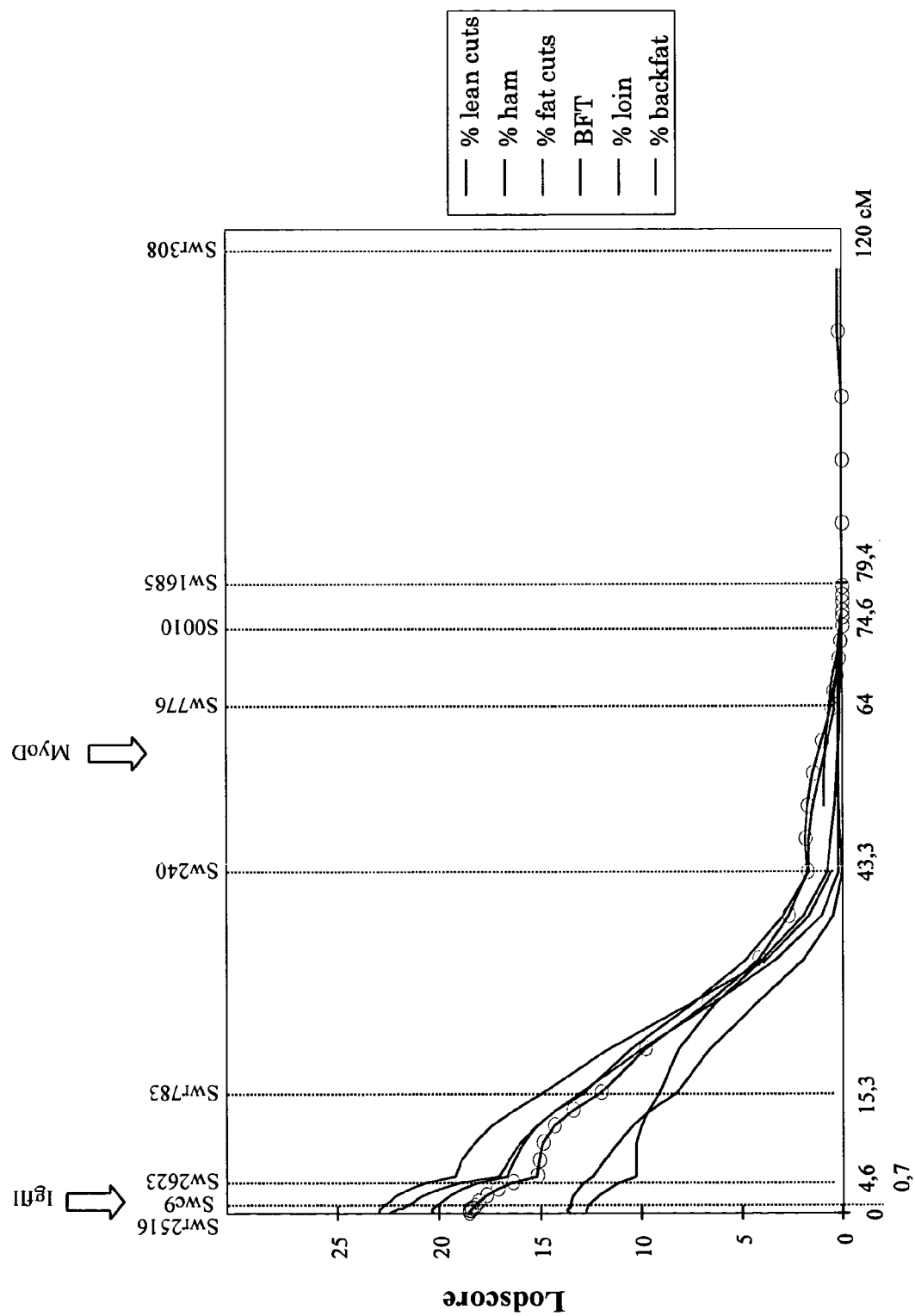
FIG. 3B: $\log_{10}(H_2/H_0)$.
Figure 3C:
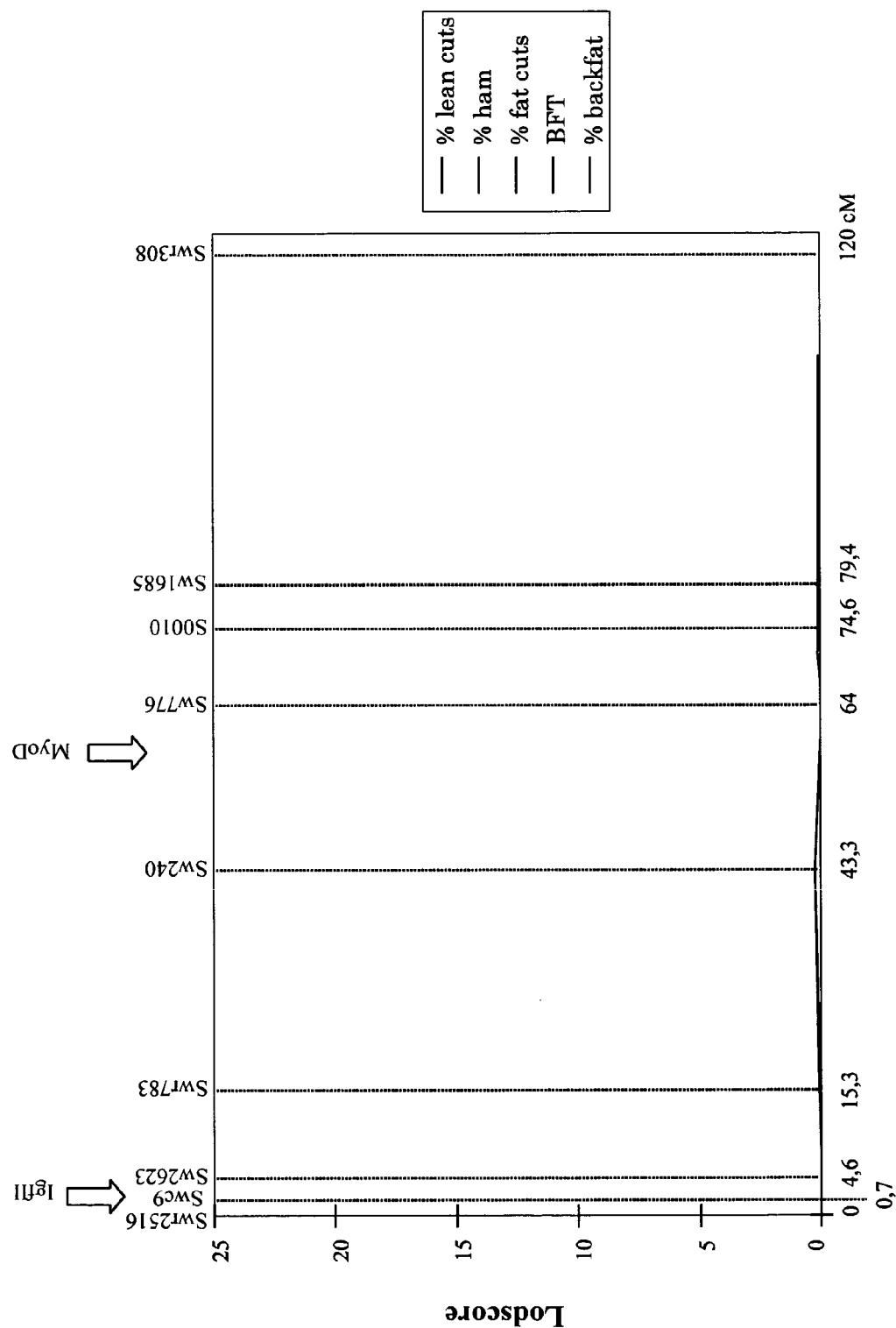
FIG. 3C: $\log_{10}(H_3/H_0)$.

FIG. 3 summarizes the obtained results. FIGS. 3A, 3B and 3C, respectively, show the lodscore curves corresponding to $\log_{10}(H_2/H_0)$, $\log_{10}(H_3/H_0)$ and $\log_{10}(H_2/H_1)$. It can be seen that very significant lodscores are obtained when testing for the presence of a paternally expressed QTL, while there is no evidence at all for the segregation of a QTL when studying the chromosomes transmitted by the sows. Also, the hypothesis of a paternally expressed QTL is significantly more likely ($\log_{10}(H_2/H_1)>3$) than the hypothesis of a "Mendelian" QTL for all examined traits. The fact that the same tendency is observed for all traits indicates that it is likely the same imprinted gene that is responsible for the effects observed on the different traits. Table 2 reports the ML phenotypic means for the F2 offspring sorted by inherited paternal QTL allele. Note that when performing the analysis under a model of a Mendelian QTL, the Piétrain and Large White QTL alleles appeared to behave in an additive fashion, the heterozygous genotype exhibiting a phenotypic mean corresponding exactly to the midpoint between the two homzygous genotypes. This is exactly what one would predict when dealing with an imprinted QTL as half of the heterozygous offspring are expected to have inherited the P allele from their sire, the other half inheriting the LW allele.

These data therefore confirmed our hypothesis of the involvement of an imprinted gene expressed exclusively from the paternal allele. The fact that the identified chromosomal segment coincides precisely with an imprinted domain documented in man and mice strongly implicates the orthologous region in pigs. At least seven imprinted genes mapping to this domain have been documented (Igf2, Ins2, H19, Mash2, p57$^{KIP2}$, K$_v$LQTL1 and TDAGS1) (reference 15 an Andrew Feinberg, personal communication). Amongst these, only Igf2 and Ins2 are paternally expressed. While we cannot exclude that the observed QTL effect is due to an as of yet unidentified imprinted gene in this region, its reported effects on myogenesis in vitro and in vivo[13] strongly implicate Igf2. Particularly the muscular hypertrophy observed in transgenic mice overexpressing Igf2 from a muscle specific promoter is in support of this hypothesis (Nadia Rosenthal, personal communication. Note that allelic variants of the INS VNTR have recently been shown to be associated with size at birth in man,[16] and that the same VNTR has been shown to affect the level of Igf2 expression.[17]

The observation of the same QTL effect in a Large White× Wild Boar intercross indicates the existence of a series of at least three distinct functional alleles. Moreover, preliminary evidence based on marker-assisted segregation analysis points towards residual segregation at this locus within the Piétrain population (data not shown). The occurrence of an allelic series might be invaluable in identifying the causal polymorphisms which—based on the quantitative nature of the observed effect—are unlikely to be gross gene alterations but rather subtle regulatory mutations.

The effects of the identified QTL on muscle mass and fat deposition are truly major, being of the same magnitude of those reported for the CRC locus[6, 7] though apparently without the associated deleterious effects on meat quality. We estimate that both loci jointly explain close to 50% of the Piétrain versus Large White breed difference for muscularity and leanness. Understanding the parent-of-origin effect characterizing this locus will allow for its optimal use in breeding programs. Indeed, today half of the offspring from commercially popular Piétrain×Large White crossbred boars inherit the unfavorable Large White allele causing considerable loss.

The QTL described in this work is the second example of a gene affecting muscle development in livestock species that exhibits a non-Mendelian inheritance pattern. Indeed, we have previously shown that the callipyge locus (related to the qualitative trait wherein muscles are doubled) is characterized by polar overdominance in which only the heterozygous individuals that inherit the CLPG mutation from their sire express the double-muscling phenotype.[5] This demonstrates that parent-of-origin effects affecting genes underlying production traits in livestock might be relatively common.

Example 3

Generating a Reference Sequence of IGF2 and Flanking Loci in the Pig

The invention provides an imprinted QTL with major effect on muscle mass mapping to the IGF2 locus in the pig, and use of the QTL as tool in marker-assisted selection. To fine tune this tool for marker-assisted selection, as well as to further identify a causal mutation, we have further generated a reference sequence encompassing the entire porcine IGF2 sequence as well as that from flanking genes.

Figure 5:
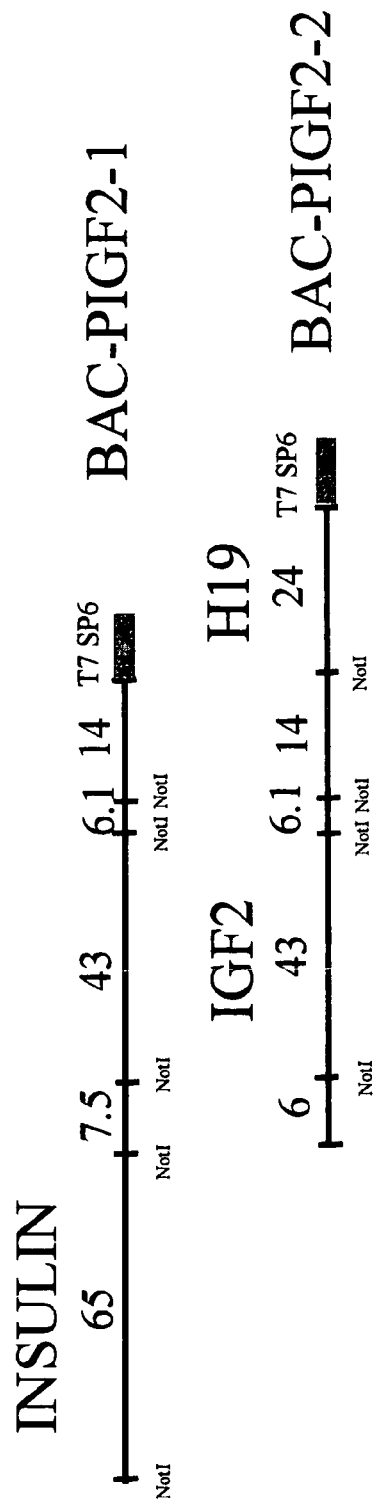
FIG. 5: A NotI restriction map showing the relative position of BAC-PIGF2-1 (comprising INS and IGF2 genes), and BAC-PIGF2-2 (comprising IGF2 and H19 genes).
Figure 7:
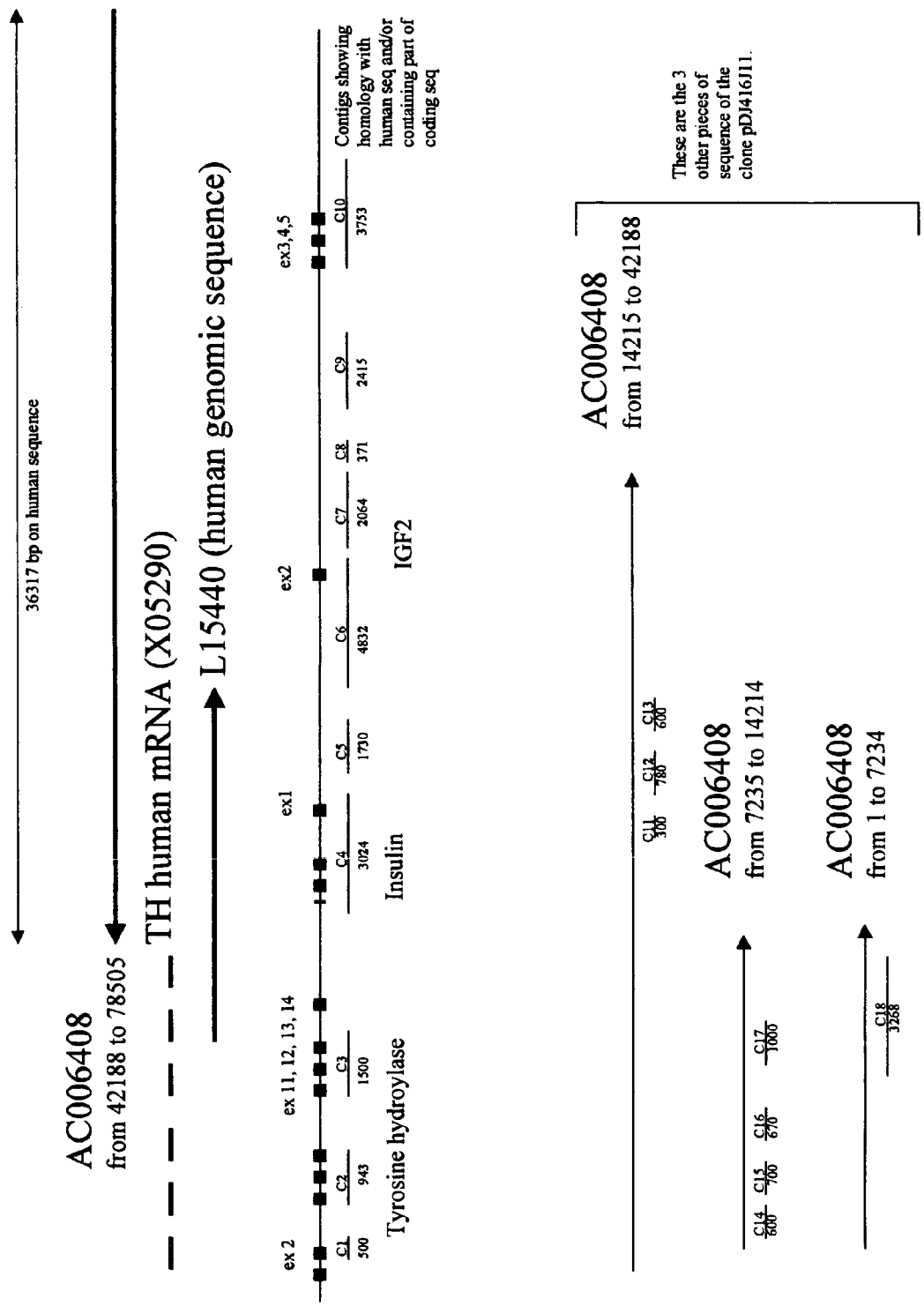
FIG. 7: Similarity between porcine contigs of FIG. 6 and orthologous sequences in human.

To achieve this, we screened a porcine BAC library with IGF2 probes and identified two BACs. BAC-PIGF2-1 proved to contain the INS and IGF2 genes, while BAC-PIGF2-2 proved to contain the IGF2 and H19 genes. The NotI map as well as the relative position of the two BACs is shown in FIG. 5. BAC-PIGF2-1 was shotgun sequenced using standard procedures and automatic sequencers. The resulting sequences were assembled using standard software yielding a total of 115 contigs. The corresponding sequences are reported in FIG. 6. Similarity searches were performed between the porcine contigs and the orthologous sequences in human. Significant homologies were detected for 18 contigs and are reported in FIG. 7.

Figure 9:
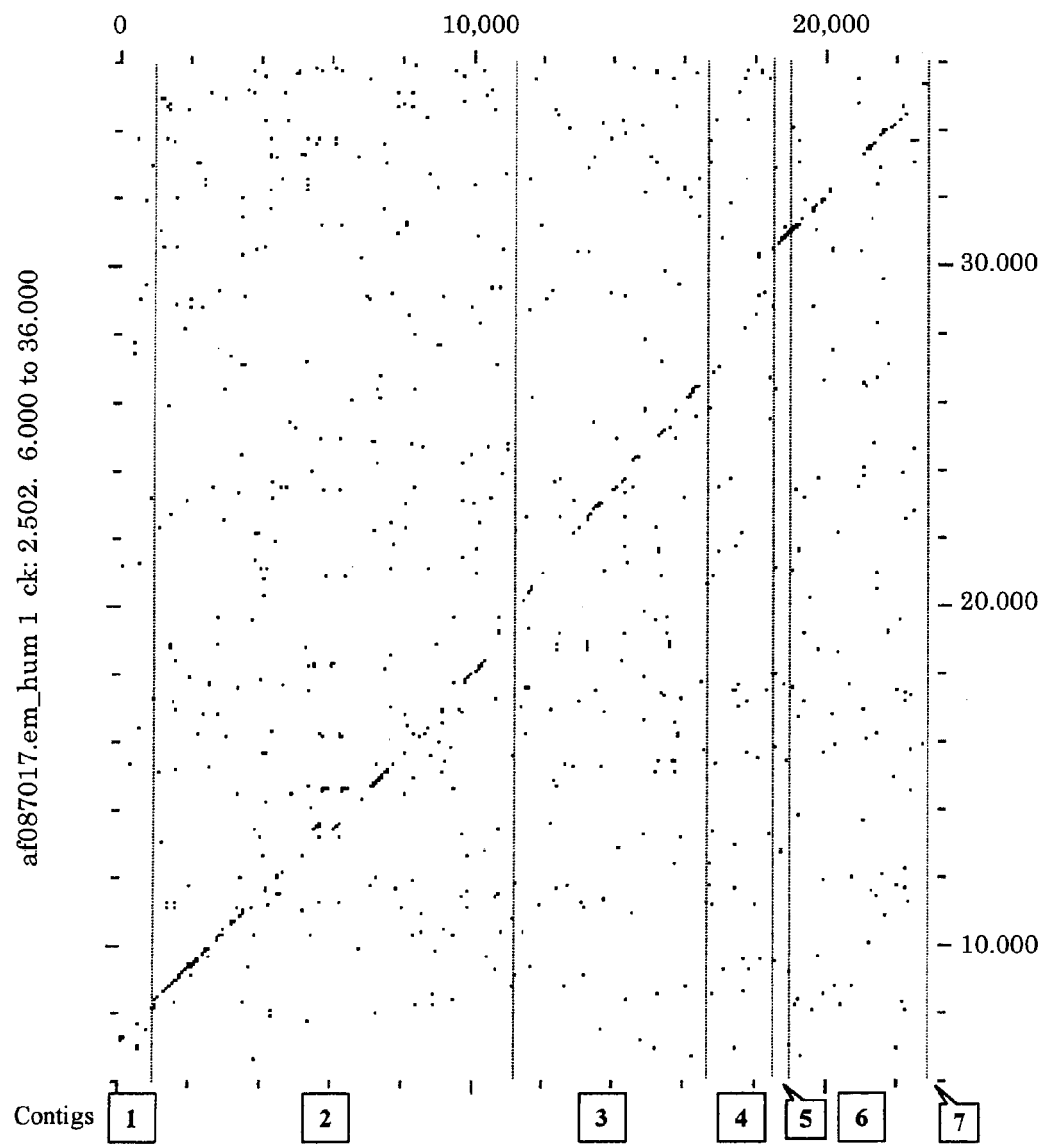
FIG. 9: Similarity between porcine contigs of FIG. 8 and orthologous sequences in human.

For BAC-PIGF2-2, the 24 Kb NotI fragment not present in BAC-PIGF2-1 was subcloned and sequenced using the EZ:: TN transposon approach and ABI automatic sequencers. Resulting sequences were assembled using the Phred-Phrap-Consed program suit, yielding seven distinct contigs (FIG. 8). The contig sequences were aligned with the corresponding orthologous human sequences using the compare and dotplot programs of the GCG suite. FIG. 9 summarizes the corresponding results.

Example 4

Identification of DNA Sequence Polymorphisms in the IGF2 and Flanking Loci

Based on the reference sequence obtained as described in Example 1, we resequenced part of the IGF2 and flanking loci from genomic DNA isolated from Piétrain, Large White and Wild Boar individuals, allowing identification of DNA sequence polymorphisms such as reported in FIG. 10.

Example 5

Effect of the IGF2-intron3-G3072A Mutation on Prolificacy in Sows

This example shows presently described unique inheritance method of paternal imprinting, wherein only the gene inherited from the father is expressed, and wherein the gene inherited from the mother is a silent gene and has no effect on the carcass quality of the offspring.

Material and Methods

Animals. The animals used in this experiment are purebred animals belonging to three different closed dam lines based on Large White and Landrace breeds. From 1999 until 2005 blood samples were collected from all nucleus sows and boars. Genotypic frequencies per line were calculated on 555 sows in total.

Measurements. Individual blood samples are linked to individual phenotypes. For all sows the following parameters were recorded: total born, live born, stillborn and weaned piglets per litter. At test weight of 110 kg carcass measures were performed on live animals using Piglog 105 (including back fat 1, back fat 2 (3rd-4th rib), loin eye depth and lean meat percentage).

Genotyping. DNA was extracted from the pig blood samples using the Wizard Genomic DNA purification kit according to procedures provided by the manufacturer (Promega, Madison Wis., US). An allelic discrimination assay was performed using the ABI Prism 7700 sequence detection system (Applied Biosystems). The final concentrations used in the 5 μl master mix were: 2.5 μl Taqman Universal PCR Master Mix, NoAmpErase Ung (Applied Biosystems, Foster City, Calif.), 1× Assay Mix, 10 ng DNA and 2,375 μl $H_2O$ (Foster City, Calif.).

Statistical analyses. The statistical analysis was performed using the statistical software SAS. The gene frequencies were calculated from PROC FREQ. IGF2 effects were analyzed using SAS PROC GLM with paternal or maternal allele as class variables and taking into account parity and sire. For the calculation of the effect of the IGF2 mutation on the traits measured, a subset of data was made in which only sows that originate from sires that are heterozygous for the IGF2 mutation were used. Sows that inherited the G allele were compared with those that inherited the A allele. Another subset of data was made in which only sows from heterozygous dams were retained. In this dataset the effect of the maternal allele was analyzed.

Results and Discussion. Allelic frequencies are presented in Table 3. All three dam lines segregate for the IGF2 mutation, although frequencies differ according to the line.

A subset of data was made in which only sows derived from heterozygous sires that segregate in the population were retained. A comparison was made between sows that inherited the A or the G allele from their father.

Sows that inherited the wild type allele from their father had significantly more piglets born alive, total born and weaned, while there was no effect on stillborn piglets (Table 4). If the same dataset was analyzed according to the allele inherited from the mother (maternal allele) no effect on any of these prolificacy data could be observed. A second subset of data was created in which only sows from heterozygous dams were taken into account and grouped according to the maternal allele. Again, no significant effect on prolificacy could be observed, which was expected since the maternal allele is not expressed.

The parity or average number of cycles per sow was also higher in sows that inherited G from their father as compared to those that received the A allele, which points to a beneficial effect on longevity. This is related to higher litter size, since that is a major criterion for elimination in the selection program.

The effect of the paternal allele for IGF2 was also analyzed on conformation measures at ca. 110 kg live weight. These data are presented in Table 5.

Although no significant effects of IGF2 paternal allele on Piglog results could be observed, there is a tendency towards higher muscularity and lower back fat in the sows that inherited the A allele form their father. The fact that this difference is not significant could be due to the low number of animals on the one hand, and the use of a threshold value on back fat in the selection program on the other.

These results show an influence of the IGF2-intron3 G3072A mutation on prolificacy and longevity in sows. This opens the possibilities to use the same imprinted QTN for different selection in sire and dam lines. Terminal sires should be homozygous for the lean allele to give uniform and lean slaughter pigs, while dam lines can benefit from a selection for the wild type allele since this has a beneficial effect on prolificacy and longevity. Because of the imprinted character of the gene, selection for the fatter allele in sow lines will not influence the carcass quality of the offspring.

A suitable marker-assisted selection program for the IGF2 mutation may now be represented as depicted in FIG. 11.

REFERENCES

Literature Cited in Example 1

1. Andersson L. et al. Genetic mapping of quantitative trait loci for growth and fatness in pigs. *Science* 263, 1771-1774 (1994).
2. Knott S. A. et al. Multiple marker mapping of quantitative trait loci in a cross between outbred wild boar and Large White pigs. *Genetics* 149, 1069-1080 (1998).
3. Edfors-Lilja I. et al. Mapping quantitative trait loci for immune capacity in the pig. *Journal of Immunology* 161, 829-835 (1998).
4. Andersson-Eklund L. et al. Mapping quantitative trait loci for carcass and meat quality traits in a wild boar×Large White intercross. *Journal of Animal Science* 76, 694-700 (1998).
5. Fronicke L., B. P. Chowdhary, H. Scherthan and I. Gustavsson. A comparative map of the porcine and human genomes demonstrates ZOO-FISH and gene mapping-based chromosomal homologies. *Mamm. Genome* 7, 285-90 (1996).
6. Alexander L. J. et al. Physical assignments of 68 porcine cosmids and lambda clones containing microsatellites. *Mammalian Genome* 7, 368-372 (1996).
7. Rohrer G. A. et al. A comprehensive map of the porcine genome. *Genome Research* 6, 371-391 (1996).
8. Marklund L. et al. A comprehensive linkage map of the pig based on a wild pig-Large White intercross. *Anim. Genet.* 27, 255-69 (1996).
9. Marklund L., P. E. Nyström, S. Stem, L. Andersson-Eklund and L. Andersson. Quantitative trait loci for fatness and growth on pig chromosome 4. *Heredity* In press (1998).
10. Ohlsson R., F. Hedborg, L. Holmgren, C. Walsh and T. J. Ekstrom. Overlapping patterns of IGF2 and H19 expression during human development: biallelic IGF2 expression correlates with a lack of H19 expression. *Development* 120, 361-368 (1994).
11. Ekström T. J., H. Cui, X. Li and R. Ohlsson. Promoter-specific IGF2 imprinting status and its plasticity during human liver development. *Development* 121, 309-316 (1995).
12. Hemberger M. et al. H19 and Igf2 are expressed and differentially imprinted in neuroectoderm-derived cells in the mouse brain. *Dev. Genes Evol.* 208, 393-402 (1998).
13. Dunger D. B. et al. Association of the INS VNTR with size at birth. *Nature Genetics* 19, 98-100 (1998).
14. DeChiara T. M., E. J. Robertson and A. Efstratiadis. Parental imprinting of the mouse insulin-like growth factor II gene. *Cell* 64, 849-859 (1991).
15. Sun F. L., W. L. Dean, G. Kelsey, N. D. Allen and W. Reik. Transactivation of Igf2 in a mouse model of Beckwith-Wiedemann syndrome. *Nature* 389, 809-815 (1997).
16. Davies J. L. et al. A genome-wide search for human type 1 diabetes susceptibility genes. *Nature* 371, 130-136 (1994).
17. O'Dell S. D. et al. ApaI polymorphism in insulin-like growth factor II (IGF2) gene and weight in middle-aged males. *International Journal of Obesity* 21, 822-825 (1997).
18. Falconer D. S. and T. F. C. Mackay. *Introduction to Quantitative Genetics*, (Longman, England, 1996).
19. Hill W. G. Rates of change in quantitative traits from fixation of new mutations. *Proc. Natl. Acad. Sci. USA* 79, 142-145 (1982).
20. Marklund S. et al. Molecular basis for the dominant white phenotype in the domestic pig. *Genome Research* 8, 826-833 (1998).
21. Kijas J. M. H. et al. Melanocortin receptor 1 (MC1R) mutations and coat color in the pig. *Genetics* In press (1998).
22. Beechey C. V. personal communication (1998).
23. Paquette J., N. Giannoukakis, C. Polychronakos, P. Vafiadis and C. Deal. The INS 5' variable number of tandem repeats is associated with IGF2 expression in humans. *Journal of Biological Chemistry* 273, 14158-14164 (1998).
24. Sambrook J., E. F. Fritsch and T. Maniatis. *Molecular cloning: A laboratory manual.*, (Cold Spring Harbor Laboratory Press, Cold Spring Harbor, 1989).
25. Chowdhary B. P., C. de la Sena, I. Harbitz, L. Eriksson and I. Gustavsson. FISH on metaphase and interphase chromosomes demonstrates the physical order of the genes for GPI, CRC, and LIPE in pigs. *Cytogenetics Cell Genetics* 71, 175-178 (1995).
26. Green P., K. Falls, and S. Crook. *Documentation for CRI-MAP, version 2.4.*, (Washington University School of Medicine, St. Louis, Mo., 1990).
27. Haley C. S., S. A. Knott, and J. M. Elsen. Mapping quantitative trait loci in crosses between outbred lines using least squares. *Genetics* 136, 1195-1207 (1994).
28. Churchill G. A. and R. W. Doerge. Empirical threshold values for quantitative trait mapping. *Genetics* 138, 963-971 (1994).
29. Anonymous. *SAS version 6.10*, (SAS Institute Inc., Cary, N.C., 1990).

References Used in Example 2

1. Fuji J., K. Otsu, F. Zorzato, S. Deleon, V. K. Khanna, J. E. Weiler, P. J. O'Brien and D. H. MacLennan (1991). Identification of a mutation in the porcine ryanodine receptor associated with malignant hyperthermia. *Science* 253: 448-451.

2. MacLennan D. H. and M. S. Phillips (1993). Malignant hyperthermia. *Science* 256:789-794.
3. Grobet L., L. J. Royo Martin, D. Poncelet, D. Pirottin, B. Brouwers, J. Riquet, A. Schoeberlein, S. Dunner, F. Menissier, J. Massabanda, R. Fries, R. Hanset, M. Georges (1997) A deletion in the myostatin gene causes double-muscling in cattle. *Nature Genetics* 17:71-74.
4. Andersson L., C. S. Haley, H. Ellegren, S. A. Knott, M. Johansson, K. Andersson, L. Andersson-Eklund, I. Edfors-Lilja, M. Fredholm, I. Hansson, J. Håkansson and K. Lundström (1994). Genetic mapping of quantitative trait loci for growth and fatness in pigs. *Science* 263:1771-1774.
5. Cockett N., S. Jackson, T. Shaw, F. Famir, S. Berghmans, G. Snowder, D. Nielsen and M. Georges (1996). Polar overdominance at the ovine callipyge locus. *Science* 273:236-238.
6. Hanset R., C. Dasnois, S. Scalais, C. Michaux and L. Grobet (1995). Genetypes at the locus for halothane sensitivity and performance in a Piétrain×Large White F2. *Genet. Sel. Evol.* 27: 63-76.
7. Hanset R., C. Dasnois, S. Scalais, C. Michaux and L. Grobet (1995). Introgression into the Piétrain genome of the normal allele at the locus for halothane sensitivity. *Genet. Sel. Evol.* 27: 77-88.
8. Olivier L. and J. J. Lauvergne (1967). A study of the inheritance of the muscular hypertrophy of the Piétrain pig: preliminary results. *Annales de Médecine Vétérinaire* 111: 104-109.
9. Rettenberger G., C. Klett, U. Zechner, J. Kunz, W. Vogel and H. Hameister (1995). Visualisation of the conservation of synteny between humans and pigs by heterologous chromosome painting. *Genomics* 26: 372-378.
10. Goureau A., M. Yerle, A. Schmitz, J. Riquet, D. Milan, P. Pinton, G. Frelat and J. Gellin (1996). Human and porcine correspondence of chromosome segments using bidirectional chromosome painting. *Genomics* 36:252-262.
11. Yun K. and B. Wold (1996). Skeletal muscle determination and differentiation: story of a core regulatory network and its context. *Current Opinion in Cell Biology* 8:877-889.
12. Knoll A., M. Nebola, J. Dvorak and S. Cepica (1997). Detection of a DdeI PCR RFLP within intron 1 of the porcine MYOD1(MYF3) locus. *Animal Genetics* 28, 308-322.
13. Florini J. R., D. Z. Ewton and F. J. McWade (1995). IGFs, muscle growth, and myogenesis. *Diabetes Review* 3:73-92.
14. Catchpole I. R. and W. Engstrom (1990). Nucleotide sequence of a porcine insulin-like growth factor II cDNA. *Nucleic Acids Research* 18(21):6430.
15. Feil R., T. F. Moore, J. Oswald, J. Walter, F. Sun and W. Reik (1997). The imprinted insulin like growth factor 2 gene. Pp70 In *Genomic Imprinting*. Eds. Reik & Surani. IRL Press at Oxford University Press.
16. Dunger D. B., K. K. L. Ong, S. J. Huxtable, A. Sherriff, K. A. Woods, M. L. Ahmed, J. Golding, M. E. Pembrey, R. Ring, the ALSPAC study team, S. T. Bennett and J. A. Todd (1998). Association of the INS VNTR with size at birth. *Nature Genetics* 19: 98-100.
17. Paquette J., N. Giannoukakis, C. Polychronakos, P. Vafiadis and C. Deal (1998) The INS 5' variable number of tandem repeats is associated with IGF2 expression in humans. *J. Biol. Chem.* 273(23):14158-14164.
18. Andersson-Eklund L., L. Marklund, K. Lundström, C. S. Haley, K. Andersson, I. Hansson, M. Moller and L. Andersson (1998). Mapping Quantitative Trait Loci for carcass and meat quality traits in a Wild Boar×Large White intercross. *J. Anim. Sci.* 76:694-700.
19. Rohrer G. A., L. J. Alexander, Z. Hu, J. W. Keele, T. P. Smith, C. W. Beattie (1996). A comprehensive map of the porcine genome. *Genome Research*, in the press.
20. Georges M., D. Nielsen, M. Mackinnon, A. Mishra, R. Okimoto, A. T. Pasquino, L. S. Sargeant, A. Sorensen, M. R. Steele, X. Zhao, J. E. Womack and I. Hoeschele (1995). Mapping quantitative trait loci controlling milk production by exploiting progeny testing. *Genetics* 139: 907-920.
21. Baron H., S. Fung, A. Aydin, S. Bahring, F. C. Luft and H. Schuster (1996). Oligonucleotide ligation assay (OLA) for the diagnosis of familial hypercholesterolemia. *Nat. Biotechnol.* 14(10):1279-1282.
22. Lander E. and P. Green (1987) Construction of multilocus genetic linkage maps in humans. *Proceedings of National Academy of Science (USA)* 84: 2363-2367.
23. Lalouel J. M. (1983). Optimization of functions. *Contrib. Epidemiol. Biostat.* 4:235-259.
24. Lander E. S. and D. Botstein (1989). Mapping Mendelian factors underlying quantitative traits using RFLP linkage maps. *Genetics* 121:185-199.
25. Spelman R. L., W. Coppieters, L. Karim, J. A. M. van Arendonk and H. Bovenhuis (1996). Quantitative trait loci analysis for five milk production traits on chromosome six in the Dutch Holstein-Friesian population. *Genetics* 144: 1799-1808.
26. Chirgwin J. M., A. E. Przybyla, R. J. MacDonald and W. J. Rutter (1979) Isolation of biologically active ribonucleic acid from sources enriched in ribonuclease. *Biochemistry* 18:5294-5299.

TABLE 1

Summary of QTL analysis for pig chromosome 2 in a Wild Boar/Large White intercross[1]

| Trait | F ratio[2] QTL | Imprinting | Map position[3] | Percent of $F_2$ variance[4] | Least squares means[5] | | | |
|---|---|---|---|---|---|---|---|---|
| | | | | | $W^P/W^M$ n = 62 | $W^P/L^M$ n = 43 | $L^P/W^M$ n = 43 | $L^P/L^M$ n = 30 |
| Body composition traits | | | | | | | | |
| Lean meat in ham, % | 24.4*** | 19.1*** | 0 | 30.6 | $63.6^a$ | $64.2^a$ | $66.4^b$ | $67.3^b$ |
| Lean meat mass in ham, kg | 18.1*** | 16.8*** | 1 | 24.3 | $4.69^a$ | $4.72^a$ | $4.94^b$ | $5.02^b$ |
| Lean meat + bone in back, % | 12.2** | 9.6** | 0 | 17.4 | $66.3^a$ | $66.7^a$ | $69.3^b$ | $70.8^b$ |
| Longissimus muscle area, $cm^2$ | 10.3** | 4.8* | 1 | 15.4 | $31.9^a$ | $33.0^a$ | $34.5^b$ | $35.2^b$ |
| Fatness traits | | | | | | | | |
| Average back fat depth, mm | 7.1* | 8.7** | 0 | 10.4 | $27.2^a$ | $27.7^a$ | $25.5^b$ | $24.7^b$ |

TABLE 1-continued

Summary of QTL analysis for pig chromosome 2 in a Wild Boar/Large White intercross[1]

| Trait | F ratio[2] QTL | Imprinting | Map position[3] | Percent of $F_2$ variance[4] | Least squares means[5] | | | |
|---|---|---|---|---|---|---|---|---|
| | | | | | $W^P/W^M$ n = 62 | $W^P/L^M$ n = 43 | $L^P/W^M$ n = 43 | $L^P/L^M$ n = 30 |
| Weight of internal organs | | | | | | | | |
| Heart, gram | 97** | 11.4*** | 0 | 14.4 | 226$^a$ | 225$^a$ | 238$^b$ | 244$^b$ |
| Meat quality traits. | | | | | | | | |
| Reflectance value, EEL | 5.7 | 6.1* | 1 | 8.1 | 18.6$^a$ | 18.4$^a$ | 21.8$^b$ | 19.7$^a$ |

*P < 0.05;
**P < 0.01;
***P < 0.001

[1] Only the traits for which the QTL peak was in the IGF2 region (0-10 cM) and the test statistic reached the nominal significance threshold of F = 3.9 are included.
[2] "QTL" is the test statistic for the presence of a QTL under a genetic model with additive, dominance, and imprinting effects (3 d.f.) while "Imprinting" is the test statistic for the presence of an imprinting effect (1 d.f.), both obtained at the position of the QTL peak. Genome-wise, significance thresholds, estimated by permutation, were used for the QTL test while nominal significance thresholds were used for the Imprinting test.
[3] In cM from the distal end of 2p; IGF2 is located at 0.3 cM.
[4] The reduction in the residual variance of the $F_2$ population effected by inclusion of an imprinted QTL at the given position.
[5] Means and standard errors estimated at the IGF2 locus by classifying the genotypes according to the population and parent of origin of each allele. W and L represent alleles derived from the Wild Boar and Large White founders, respectively; superscript P and M represent a paternal and maternaloriigin, respectively. Figures with different letters (superscript a or b) are significantly different at least at the 5% level, most of them are different at the 1% or 0.1% level.

TABLE 2

Maximum likelihood phenotypic means for the different F2 genotypes estimated under (i) a model of a Mendelian QTL, and (ii) a model assuming an imprinted QTL.

| | Mendelian QTL | | | | Imprinted QTL | | |
|---|---|---|---|---|---|---|---|
| Traits | $\mu_{LW/LW}$ | $\mu_{LW/P}$ | $\mu_{P/P}$ | R | $\mu_{PAT/LW}$ | $\mu_{PAT/P}$ | R |
| BFT (cm) | 2.98 | 2.84 | 2.64 | 0.27 | 2.94 | 2.70 | 0.27 |
| % ham | 21.10 | 21.56 | 22.15 | 0.83 | 21.23 | 21.95 | 0.83 |
| % loin | 24.96 | 25.53 | 26.46 | 0.91 | 25.12 | 26.14 | 0.93 |
| % lean cuts | 65.02 | 65.96 | 67.60 | 1.65 | 65.23 | 67.05 | 1.67 |
| % back fat | 6.56 | 6.02 | 5.33 | 0.85 | 6.43 | 5.56 | 0.85 |
| % fat cuts | 28.92 | 27.68 | 26.66 | 1.46 | 28.54 | 26.99 | 1.49 |

TABLE 3

Allele frequencies for the IGF2-intron3 G3072A mutation in sows of dam lines (Number of sows within genotypes is presented in parenthesis)

| Line | AA | GA | GG |
|---|---|---|---|
| A | 0.04 (4) | 0.28 (25) | 0.68 (61) |
| B | 0.30 (42) | 0.37 (52) | 0.33 (46) |
| C | 0.80 (259) | 0.19 (62) | 0.01 (4) |

TABLE 4

Effect of paternal allele inherited from heterozygous sires on prolificacy

| Trait | A | G | Significance* |
|---|---|---|---|
| Number of cycles analyzed* | 240 | 276 | |
| Born alive/litter | 10.37 ± 0.18 | 10.90 ± 0.16 | 0.0075 |
| Total born/litter | 11.04 ± 0.19 | 11.48 ± 0.17 | 0.0371 |
| Stillborn/litter | 0.63 ± 0.07 | 0.59 ± 0.06 | NS |
| Weaned/litter | 9.11 ± 0.21 | 9.92 ± 0.16 | 0.0134 |
| Parity | 2.95 ± 0.12 | 3.54 ± 0.12 | 0.0035 |

*Model taking parity and sire into account, NS = not significant P > 0.05

TABLE 5

Effect of paternal allele inherited from heterozygous sires on carcass measures at 110 kg live weight (Piglog 105)

| Trait | A | G | Significance* |
|---|---|---|---|
| Number of sows analyzed* | 70 | 64 | |
| Back fat 1 (mm) | 14.90 ± 0.27 | 15.08 ± 0.27 | NS |
| Back fat 2 (mm) | 13.20 ± 0.29 | 14.14 ± 0.30 | NS |
| Loin eye (mm) | 56.28 ± 0.45 | 55.72 ± 0.41 | NS |
| % lean meat | 57.31 ± 0.26 | 56.69 ± 0.28 | NS |

*Model taking sire into account. NS = not significant P > 0.05

What is claimed is:

1. A method for selecting a porcine for having a paternally imprinted quantitative trait locus (QTL), said method comprising:
   identifying in the porcine the presence of an IGF-2 gene having a paternally imprinted QTL comprising a genetic marker characterized as nt241(G-A) or as Swc9 on chromosome 2 of the porcine;
   wherein the paternally imprinted QTL is associated with fat deposit, muscle mass, lean meat, lean back fat, sow prolificacy, and/or sow longevity; and
   selecting a porcine based on the presence of the paternally imprinted QTL.

2. The method according to claim 1, further comprising:
   testing a nucleic acid sample from said domestic animal for the presence of the paternally imprinted QTL.

3. The method according to claim 1, wherein a paternal allele of said paternally imprinted QTL is predominantly expressed in said porcine.

4. The method according to claim 1, wherein a maternal allele of said paternally imprinted QTL is predominantly expressed in said porcine.

5. The method according to claim 1, wherein the paternally imprinted QTL is associated with sow prolificacy comprising a phenotypic expression selected from the group consisting of teat number, number of piglets born alive, litter size, number of total born, number of weaned piglets, and combinations of any thereof.

6. The method according to claim 1, wherein the paternally imprinted QTL is associated with sow longevity comprising a phenotypic expression selected from the group consisting of parity, average number of cycles per sow, and combinations thereof.

7. A method for selecting a pig for breeding by identifying a pig having a paternally imprinted quantitative trait locus (QTL) associated with lean meat, lean back fat, sow prolificacy, and/or sow longevity such that when the pig is utilized in a breeding program, the offspring of the pig that inherit said QTL from the male parent has lean meat, lean back fat, sow prolificacy, and/or sow longevity compared to a control thereof, wherein the method for selecting a pig comprises:
   identifying a paternally imprinted QTL associated with lean meat, lean back fat, sow prolificacy, and/or sow longevity by detecting one or more genetic markers selected from the group consisting of genetic markers linked to the QTL on chromosome 2 of the pig, genetic markers in linkage disequilibrium with the paternally imprinted QTL on chromosome 2 of the pig, and combinations of any thereof;
   wherein the paternally imprinted QTL comprises the insulin-like growth factor-2 gene (IGF-2) as well as the genetic markers Swr2516, Swc9, Sw2623, and Swr783 on chromosome 2 of the pig;
   wherein the QTL is present on chromosome 2 of the pig at position 2p1.7; and
   wherein the identification of the pig having the paternally imprinted QTL associated with lean meat, lean back fat, sow prolificacy and/or sow longevity selects the pig for utilization in a breeding program.

8. The method according to claim 7, wherein said sow prolificacy comprises a phenotypic expression selected from the group consisting of teat number, number of piglets born alive, litter size, number of total born, number of weaned piglets, and combinations thereof.

9. The method according to claim 7, wherein sow longevity comprises a phenotypic expression selected from the group consisting of parity, average number of cycles per sow, and combinations thereof.

* * * * *

SEQUENCE LISTING

<160> NUMBER OF SEQ ID NOS: 183

<210> SEQ ID NO 1
<211> LENGTH: 21
<212> TYPE: DNA
<213> ORGANISM: Artificial
<220> FEATURE:
<223> OTHER INFORMATION: Primer

```
<400> SEQUENCE: 1
ggcaagttct tccgctaatg a                                              21

<210> SEQ ID NO 2
<211> LENGTH: 20
<212> TYPE: DNA
<213> ORGANISM: Artificial
<220> FEATURE:
<223> OTHER INFORMATION: Primer

<400> SEQUENCE: 2
gcaccgcaga attacgacaa                                                20

<210> SEQ ID NO 3
<211> LENGTH: 26
<212> TYPE: DNA
<213> ORGANISM: Artificial
<220> FEATURE:
<223> OTHER INFORMATION: Primer

<400> SEQUENCE: 3
gtttctcctg tacccacacg catccc                                         26

<210> SEQ ID NO 4
<211> LENGTH: 19
<212> TYPE: DNA
<213> ORGANISM: Artificial
<220> FEATURE:
<223> OTHER INFORMATION: Primer

<400> SEQUENCE: 4
ctacaagctg ggctcaggg                                                 19

<210> SEQ ID NO 5
<211> LENGTH: 25
<212> TYPE: DNA
<213> ORGANISM: Artificial
<220> FEATURE:
<223> OTHER INFORMATION: Primer

<400> SEQUENCE: 5
cccctgaact tgaggacgag cagcc                                          25

<210> SEQ ID NO 6
<211> LENGTH: 25
<212> TYPE: DNA
<213> ORGANISM: Artificial
<220> FEATURE:
<223> OTHER INFORMATION: Primer

<400> SEQUENCE: 6
atcgctgtgg gctgggtggg ctgcc                                          25

<210> SEQ ID NO 7
<211> LENGTH: 19
<212> TYPE: DNA
<213> ORGANISM: Artificial
<220> FEATURE:
<223> OTHER INFORMATION: Primer

<400> SEQUENCE: 7
cgccccagct gccccccag                                                 19

<210> SEQ ID NO 8
<211> LENGTH: 19
```

```
<212> TYPE: DNA
<213> ORGANISM: Artificial
<220> FEATURE:
<223> OTHER INFORMATION: Primer

<400> SEQUENCE: 8
cgccccagct gcccccccaa                                              19

<210> SEQ ID NO 9
<211> LENGTH: 20
<212> TYPE: DNA
<213> ORGANISM: Artificial
<220> FEATURE:
<223> OTHER INFORMATION: Primer

<400> SEQUENCE: 9
cctgagctgc agcaggccag                                              20

<210> SEQ ID NO 10
<211> LENGTH: 500
<212> TYPE: DNA
<213> ORGANISM: Sus scrofa

<400> SEQUENCE: 10
gggtgggcag cttcctccca gaccgcagga ggcccaagtt ccctggccct gcccacccag    60
ggccagctga agcaggtcag agacacccgc tcctgtccct cctgtcacct aacccaacag   120
gccgggcccc agggacacag gccacatggc atctccccccc atgccccctgc cccaaggcgc  180 ccagcaggtg aggctggagc agagtctggg tcctgcgggc cagaccgagg gcaggacagc   240
tgggcatctg tcctcacagt ccccgcgctt tgtcgggagg cggcagagcc tcatccaaga   300
cgcccgcaag gaacgggaga aggcggaggc gcggctgcc gcgtccgagc ccggggaggc   360
cctggaagtg ggggcccttg ccgagcggga cgggaaggcc ctgctgaacc tgctcttcac   420
cctgagggcc accaagcccc cctcgctgtt ccggtccctg aaaaaattct aggtgagggg   480
gcgggccagg gctccccggg                                             500

<210> SEQ ID NO 11
<211> LENGTH: 943
<212> TYPE: DNA
<213> ORGANISM: Sus scrofa

<400> SEQUENCE: 11
tgctcctcac acccgggcg gggctgctct tggggccatc ctccccatgg gcccagcacc     60
cactctggcc ttcacacctg ccgtcttctg ggaagtcctc tggttcccaa ggaaagtttc   120
tgagctggac aagtgccacc acctggtcac caagttcgat cctgagctgg acctggacca   180
cccggtgagc cggtgcctcc cctccccggc cgccatgtct cccatcccca ggggtgtccc   240
cacactcagg gccgggactg ggcgtgaacc ccggggttggg acggatgttg gcctgctgtg   300
tggctcctgg cggaacagag aggcctggct gggtgccacc ccagggcccc gccgatga    360 cacgggccgc gtctgggctg ggcgggcagg gcggccaggc agggcagcct ccgatggcgt   420
ccccggctgt caccagggct tctcggacca gttgtaccgc cagcgcagga agctgattgc   480
ccagatcgcc ttccagtaca ggcagtaagt ccctccaggg cctcagcctg ggggcccaga   540
cctcagcctg ggcctcacgc cagacctggg ggtggaggga agggaggttg tctttgtcac   600
caacgccacc accttcactg tcaccatggt caccgactct gggtccccaa atcacagctg   660
aggaaactgg ggcacagagt ggttaagcat cttgctgaag ccacacagct ggcggagcat   720
```

-continued

| | |
|---|---|
| ttggccccgg cccctcctgc ggctcccaca cgtgctccct gaggggcccg ggactgacag | 780 |
| ctgtcccctc ctcagaggtg accctattcc ccgcgtggag tacacagccg aggagattgc | 840 |
| cacctggtga ggccctgtga cagcggctgg gaggggcggg agtgggggaa gggacaggaa | 900 |
| gacctcagaa ttcccgcgtg gaacgtggtg gcctctatca tga | 943 |

<210> SEQ ID NO 12
<211> LENGTH: 1500
<212> TYPE: DNA
<213> ORGANISM: Sus scrofa

<400> SEQUENCE: 12

| | |
|---|---|
| ggggagggga tgctcagacc cgctctggga agaagagagc ctcagaagaa atcccttccc | 60 |
| aagggtcacg cggtggagcc caggggcccg ctaggggccg attcccacag ctcgtgctgc | 120 |
| cacctgctgg cgctcccagg aactgcggag gcggtggggg ccctggatgg gtccggcagt | 180 |
| gggctcgcag gagacccctg gagggctgc ggacacccca gctgccactc acaaggtgcc | 240 |
| caagcggcgg tggcaatggg ctgagcctct ccccccctcc tcctccgcag gacattggcc | 300 |
| tcgcatccct gggggtctcg gacgaggaaa ttgagaagct gtccacggtg gtttctcccc | 360 |
| cctgcagggc cctgggttcc agccaggccc tcctgtccaa ggggtgtcgt cctcacgctg | 420 |
| tgaccgcccg ggagcctgga tcggttctgc ctggtgggc ggtgcccggg ccacgggcag | 480 |
| caggggcagc ggtgcgggcc ccagccgtgt ctgagccccc ttgccgcctg tccccaccag | 540 |
| ctgtactggt tcacggtgga gtttgggctc tgcaaacaga acggcgaggt gaaggcctac | 600 |
| ggggctgggc tgctgtcctc ctacggggag ctcctggtga ggcctccccc acgcgctggg | 660 |
| gcctgggtcc ccggggagg tgaccccgtc ggtgccttgt ggattccagc tctcgggagg | 720 |
| ctggagcgag gggctgccct cctggggggca ccaagaaagc tggtctgcgc ccctctccac | 780 |
| acacctgtgc ctgggccctg ggggganccc tgctggggga tgtgggtgca cagccagggc | 840 |
| caccagggag tcaggacacg gggctcccct ccctcgggtc cctgagaccc ctggcctccc | 900 |
| gccagcactc cctgtccgag gagcccgaga tccgggcctt cgaccccgac gcggcggccg | 960 |
| tgcagcccta ccaggaccag acctaccagc ccgtctactt cgtgtctgag agtttcagtg | 1020 |
| acgccaagga caagctcagg tgggccgggg cccggggccc ccaaactgga ggatccagcc | 1080 |
| tgcagccccg cctatgagcc catttcccag cagagggagc tgctgcggac cccaccgtca | 1140 |
| caaccccct cccacagctg gaaccccaga aagcctgcgg aggggggacc tgcagggctg | 1200 |
| tggccaggtc aaggccaggt cgaggccagg cttttagggg tgaagtctga ctttgtaaga | 1260 |
| gggggtgcag ggtccttccc agcctcctcc cctccgagca gctgggggcg ggcgggggt | 1320 |
| gcgatgaagg cagagatgac gcagccaccc gttcaccctc aggaggcgcc tcctgtccag | 1380 |
| ccaggctcct gttgtcacag gggaaactga ggcccaggt gtgtgtgtgg ggggtgatt | 1440 |
| ctcacacaca agcttaggga cagggacata acggcctctc cagggcacac agtctggagg | 1500 |

<210> SEQ ID NO 13
<211> LENGTH: 3024
<212> TYPE: DNA
<213> ORGANISM: Sus scrofa
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t

```
<220> FEATURE:
<221> NAME/KEY: misc_feature
<222> LOCATION: (62)..(62)
<223> OTHER INFORMATION: n is a, c, g, or t
<220> FEATURE:
<221> NAME/KEY: misc_feature
<222> LOCATION: (103)..(103)
<223> OTHER INFORMATION: n is a, c, g, or t
<220> FEATURE:
<221> NAME/KEY: misc_feature
<222> LOCATION: (110)..(110)
<223> OTHER INFORMATION: n is a, c, g, or t
<220> FEATURE:
<221> NAME/KEY: misc_feature
<222> LOCATION: (168)..(168)
<223> OTHER INFORMATION: n is a, c, g, or t

<400> SEQUENCE: 13
ttaantccan gttggcccga caagttttcc ccatttgaaa aggggccagt taagccccaa      60
cncaattaat tggaagttag ctcccctcat taggctcccc agnctttacn ctttatgttc     120
cggttcgtat ttttgtggga attgtagcgg atacaatttc tctcaagnaa ccagctatgc     180
ccatgattac gcggtacagt agttcatcag tccccccgc ccatgggaca gcgaagggaa      240
ccagtatgtc gtggggccgg gtctaaaggg gtcaccacca gggaggggca ggggctccag     300
gaggcagggc cactgagcgg tacctggtgg ggggaggtgg tggggccaca cccaggagtc     360
ctgtgccccc cccactcccg ccgttggaca tgagaagcag gggccagcct gcgggtccct     420
gagttcagcg cccccccccc ccaccgccgc agcagcccgg ggtctcagca ggctgctgtg     480
ctgggggcgg gggcgcttat ggrgccggga gcagccccc cccacggctt cagagcatct      540
ctggggcctc agggatggac cggggtctgc rggcaggtgt cctctcgcgc ccccactccc     600
tgggctataa cgtggaagat gcggcccaag cccggkcggt ttggcctttg tccccagcca    660
gtggggacag cctggccctc aggccgctcg ttaagactct aatgacctca aggcccccag     720
aggcgctgat gacccacgga gatgatcccg caggcctggc agcagggaaa tgatccagaa     780
agtgccacct cagcccccag ccatctgcca cccacctgga ggccctcagg ggccgggcgc     840
cggggggcag gcgctataaa gccggccggg cccagccgcc cccagccctc tgggaccagc     900
tgtgttccca ggccaccggc aagcaggtct gtcccctgg gctccgtca gctgggtctg      960 ggctgtcctg ctggggccag ggcatctcgg caggaggacg tgggctcctc tctcggagcc    1020
cttggggggt gaggctggtg ggggctgcag gtgcccctgg ctggcctcaa cgccgcccgt    1080
cccccaggtc ctcacccccc gccatggccc tgtggacgcg cctcctgccc ctgctggccc    1140
tgctggcsct ctgggcgccc gccccggccc aggccttcgt gaaccagcac ctgtgcggct    1200
cccacctggt ggaggcgctg tacctggtgt gcggggagcg cggcttcttc tacacgccca    1260
aggcccgtcg ggaggcggag aaccctcagg gtgagccgag ggggygtccc gggagcggty    1320
gggggagttt ttaaggagga aattggtaaa agtgaccaac tccctgggag ctgagcccag    1380
agacacccct cccacgcccy ggtcccgctc gagaagcccc ccttccctcc cctcctcccg    1440
aggcggctcc agggaggaat cttacggagt caaggcccgg gtgccgctgg tctccgagtg    1500
acatggccgt ggtgtcccrt ctgccggccc acatgcccgt gagagawgcc ccatcccct    1560 gggagggggc cccgtgccgg gcaggcgcg ggaggcccag gaccggtggc tgctgcggct     1620
tccactccag ggtgggcggg gtgggggtg gctgtctctg tgtgaccggc tctccccgca     1680
gcaggtgccg tggagctggg cggaggcctg ggcggcctgc aggccctggc gctgagggg     1740 cccccgcaga agcgtggcat cgtggagcag tgctgcacca gcatctgttc cctctaccag    1800
```

```
ctggagaact actgcaacta ggccgcccct gagggcgcct gctgctcccc gcacccaaa     1860 acccaataaa gtcctgaatg agcccggccg agtcctgtgg tctgtgtggc ctggggcggg     1920
ggccctggtg ggggagggc cagaaggctg tgggggcct gcctgcgacc cctctctgct     1980
ctcgccacat cggctgctct aagcttcctc cacatgcatc gggtgccac aggcacatgg     2040 gcaccggggg accagggccc agggcagggc ccttcaatgt ggcgagctct ggttttcagg     2100
gctccagaca ccccctcctg ggtgcccact gctgcacagg gtcactctga gggtcacagg     2160
gcacccaccc agactgctct tgggcacaca aaatagccca ggggcttctt gggctggctg     2220
crgtctggga ggtcagagag tgaccccgcg ggaccaagac ctggccagcc tgccagtcgc     2280
ccaggccaaa ccaatctgca cctttgctga aggttccacc cgggccagca ctggggggcgg     2340 ccgggcctag agctgggcgc ccgggcccca gggactgcac accgccaga ggtgggcctg     2400 agggggtggca gcaggctctc cgcctgggac ccagccagct gggcagctca cctctcaaca     2460
cgaggctctc acctgtgtcg tccctcccc acgccacac agacacccct ggggagaagt     2520
cacaggcccc cagcaggccc cgcccctgga gaggaggcca gggctgggca ggcgggtggc     2580
cggccggaca ctggacccgg aagggggta ggcggctggg atgagtggcg agctgtccat     2640
gggagcaccc agcggcccca ttggcaccag tacaggcagg ggcacctgca gcagctgagg     2700
tacgtggggt ccccggactg gttggtgtcc ggctgccctc tgggaggcag cgggctgagc     2760
ttgtggtcct gccaaccagg gagacccgtg accaccctgc tgcttcccct ccccccagg     2820 gccagcagac tcctttggga ctcggggccc ctgagccgcc cccactcgca ggactcacgg     2880
ggtgtgcggt cctgggtgag tgggggcttg ggagagggtc actcttgtcc gtcgggtggg     2940
gaaggctgag agtcatggtg tgacagcgcc ctcggcctgc cgggtggggg gtctcccttc     3000
tcccgagccc agatccccgg gtac                                           3024
```

<210> SEQ ID NO 14
<211> LENGTH: 1730
<212> TYPE: DNA
<213> ORGANISM: Sus scrofa
<220> FEATURE:
<221> NAME/KEY: misc_feature
<222> LOCATION: (530)..(530)
<223> OTHER INFORMATION: n is a, c, g, or t

<400> SEQUENCE: 14

```
cgtcacccgc agaagccagg cccacaggcc ttggctcagc ccctccaccc aggcccacgt      60 tccgccccctt ctgggaactg aggacagcc cgccctcgcc ctcggacctg gcttcgtttg     120
ccctggcatc tggcagtggc cggcagctgc gttcagccct ggatgacacc ctggcgtgag     180
cggtgggtcc ccgtgctgag ggcagccccc acacacgtcc tgctcacttg ccttgtgtct     240
gctccgcatc ccgtcatcac acatgccatg ctggggcacc gtagcgcctt gccctgtgtg     300
gcactgtggc actgtgttcc tgatgggaag actgaggctg gggtcaggcc cgctgctgcc     360
caccctctaa ggacattctg ccggtgcagc tgcctccagg ctggcccccc ggattgcatc     420
tgcttctggc acgatgaac tggcacctct gcctgaccat tagggctgta tttgccttct     480
cctgttggca gtaaatattt actgtccctc cctgttcctc caggcccgan ccagttcctg     540
aggggcatgg gaggtggaca caaaggtgcc caagcagccc cctgctcttg agggcccagt     600
gtctggtggg ggccagcctg ggaaggagga gcgagactag gaaccagagg cctgtgttcc     660
tggaaaaggc ccctggcag agttccggct ggtgtgtgtc cagctaggct gtgagtcttc     720
aaactgggga gcccggcccc tggacccagg cagggctgca cccctggtgc cagtgcttca     780
```

-continued

```
ctgggtgggc acctgtcccc accaggcaag gtggtccgag cggtcattca cagacagaac      840
cagcagaggg cgccaaagcc ccacttttga caaactcccc ttcgccctga gccgaaagtc      900
caggcggcag gtggacctct ctgcagggct ctgccacccc tgctgccgct tgccagcact      960 cacagggct gcgggggtg cccaacaggc cggctaccct gagctctgga ggcgatggag       1020
tttaggaggg aacgagggga ctcctggggg tgactttctt cagcgcccac attgcggccc     1080
agcaaaccga ggctggagga ggccgggcac ctgtgcccag ctggagcctt tgctgagggt     1140
ctccaaggcc tggggaaatt gaggctgggg gctggggggt gtcactgtcg gccaggagg      1200 cccctcgctc tgattggagc cgcctcggcc acttgagcca ggaggctcac atgaggcggg     1260
ggctgcaggg acaggaccct cggggcccgg gaggccttgg aggggtcca gctgggccag     1320 ggttcgttct ttcccgggtc catgtccacc gccctcccgc tgctgggagg agaggaggtc     1380
cagggcagaa agaatgcgtg gggatggggg ggtggtcagg ggtctgggag ctgtggaaac    1440
aacaaacaga cagcgaggtc ctggggcgcc cggcccccccg ccccctccgg cactgttgtt   1500
tctggccggg gtgcagggac agcgaggcag attccttcga aagtggagac tggcgggggg    1560
cccctcgggt cctcagctca ccccctgagc tagcccgccc actcggctcc aacctcccgc    1620
aggcccctgg cacggtctcc aggagtccac tgaggggtcc ccaaagctgc caccaggagc    1680
tgggcctggg tctgtcacca ccccaccccca ccctccaagt ctgagatatg                1730
```

<210> SEQ ID NO 15
<211> LENGTH: 4833
<212> TYPE: DNA
<213> ORGANISM: Sus scrofa
<220> FEATURE:
<221> NAME/KEY: misc_feature
<222> LOCATION: (127)..(127)
<223> OTHER INFORMATION: n is a, c, g, or t
<220> FEATURE:
<221> NAME/KEY: misc_feature
<222> LOCATION: (519)..(520)
<223> OTHER INFORMATION: n is a, c, g, or t
<220> FEATURE:
<221> NAME/KEY: misc_feature
<222> LOCATION: (545)..(545)
<223> OTHER INFORMATION: n is a, c, g, or t

<400> SEQUENCE: 15

```
atgtgagctg cacagcatga gccctcggcc ccactgctgt ggccttgcgg acattgaggt       60
gtgtgccgcc cagggcgacc acaccctggc ctctcaggat gcccgtacag aggcggctgg      120
gtcgtangag gtgcggggct ctggggaccg ctggtgagtt caggacgggg gtcatgccac      180
ctcctctctg aaggtttggt gaggtggccc ttctcttatc gtgatgacaa tactgatttc      240
tggaagagcc aggtgttttc tgaggctgtg gttgcacttc tccacgtggc cacaaggtgc      300
cgggctcggg tcagatttga aagcccctgc gggagcgggt gtcatgcgcc agattcagct      360
tgcctcctgc gggtctgggg tcaggacgtg gtccccagca gtctgctcca gagcctgtca      420
gtgatgtgtg ggatttacc gctagaacac agtttcctct gattctcaga accagcaga     480 tgctttagga ggggcgtgca ggtttcacct gtgctgcann gccccctgcc acctggtcgg      540
agccncaaga cggcatctaa agatcagttc ctcatcatca gttccgcagt gctggggtgg     600
gggcagatga gaacctcagg gctgggcgca gaggtgggga gccgcctgg accccgacac      660 tgcaggggg cctccccctt gtaggaagaa caatgtcgct ttgccaccca gccctctccc      720
cagggtgccc cgaactgttg ctcctaagac ctctgggctg tgtgctgtaa ttctataagt     780
```

```
ggccaccagg tgtcagcagg aggccactta agcatccatg tggcggaaac ctggagctgg    840
gggttcctaa gggtccctcg agtgtctcct gaataaatag gcgctgacct gatcccagg     900
aagggataac cctctcccag gcctaagagg cagtggggca atgaggttta tgtgtccact    960
gtaccccaa attgtctctt ccttccctct accctgtgtc cccaccgtgg acgatacacg    1020
gagtgcgagg ctgcgggtca cagccctcac agccccaaag ctgcaggtcc tgcctcaggg   1080
gcaccgcagc ttggctggtc ccccttgggt cctccccacc ctgacccgtc ctctgctccc   1140
ctcccttgc ttaaatgctc tgcgtttcaa ggttctgatg gaataaaata gccctgcact    1200
ggtgtgttcc tctttgggc tgtgccagaa gtgggaattc agaccagggc agagctcaga    1260
ttccacatac tgtgttaggg atggcaggtg ccacatttcc aggagtttca ttggtggttt   1320
gtaaatgcta cttccgtttc agcccctcag ctgcccacct cctcaattta ggacccccc    1380
cctttggcgg gttgcccatg aaccacatc atctggcgtg gggtgagccc tttatcctcc    1440
ctggccccac tgggagggtt tggggaagtc ccagctaaat ttctccgtag ggacctggaa    1500
ggagcccttg tgacatctgg gcacagataa gaggtagggg gcacaggccg tgaacacttg    1560
aagctgcaga gccagagca gagccagcag gagcaagtga ctgctcccca ccccaagaac    1620
tgtgggctgc gtcacacact ccccactgtg tgccctggac ctgacagggc ctttagcctc    1680
cctgcatccc tccccaccca agaacccagt gaggcacccc acttgccct ccttagtgtt    1740
gttatggctc tggggcatct gcattttgtt taggacaccc ccagctagat ttaagtcccc    1800
ccaagtgtga ctctttcctc cactgaaaac cctgtcctcc caccaaaggg ccctatccct    1860
ttagctgagc caaggaaatt caggaggggc cttgaatgac aaaggaagag ggggagagtt    1920
aaacccaac actggctggc aagctgggtg gggtggacac cccagggtgc aggggtgcag    1980
tgaaggtagc ggctggtggc cttctggaaa ctacatgtga ctttgccatt aggtgagtct    2040
ttgctttgcc cctgctctat ctgcaggctt atggaagaag tttaaattcc cagggacact    2100
tggtctaacc aggcagcgct tgtatctggg cccttcccca gctgctgacc actctgagtc    2160
tgcgccttag ttggagtttt ggccaagctc aagaggctgt ggaccccagt catcccaccc    2220
aggggtgcct gtgggcagga cgctgctgcc tgccatttgc tgcagtattg tcactgtccg    2280
gcaccacaca catggtgcag ggggtggtat caggtgccac tggggaaggg agaaaactcc    2340
caggtgagtc ccctgcctct ggaagcaaga tggacatgac cgcactgtgt tgcagctgca    2400
ttgggaggcc ccgaagaaag atttttctga tctttctcga accctgcttt tccccatcat    2460
gccccgcccc cattttaccc gtgccacgcc cactggtgtg ccggggtgtc aagtgactga    2520
caagtgtcaa tctactgagg ccctgcccac tctccacccc ccacatagt cccacctccc     2580
agctggcagg gagaacttcc agctaatgcc catgcccaca aatgtctttc tgtcagccta    2640
gagctggacc aaatctccac cctgtaacat gctgtgccct ggcgtgggaa ggtgccagag    2700
ccagttgccc cagcagcccc agaaccacta agttggcaca aagctaccca aatttggagg    2760
ggcttgggga agggcatgga ggggatgagg aggtgagggg caaaactaat ttcagttagc    2820
atttgagcag gtgccacgct cagcgtggag aggctctctt gcttctaggg acccattatg    2880
atgcacacgc taaaagcgcc cttcaccatc tctccagcct cagctttgtc ccctcctcc    2940
tcctcagcgc caacccggct ggagggtctg gccactacag ccagagcgcc cctactttg    3000
gtggcgactg ctactattgg cccaaccagc ggatcaccgg ccaggcagtt tcggcagaga    3060
gtctggggca ccagtgactc cccgtcctc tttatccacc acccaggagc ttcagggact    3120
acacagcgac tagagggcag gtaactggtc tgccctccct agggctgccc cctcagagtg    3180
```

-continued

```
tgtgagaaaa gctgcattga gtgtttgggt gcaggtgggc tggggcttg gggcagccaa      3240 caggaacggc gggacctctg cttccagagg accccagatc ctggcaagct tcgactttgg      3300
aggggacagg aaagacaggt ggagagggga cacttccctc ttctgtacag acgcccaccc      3360
ggagccacag aggcttttgc aaggaaaata ggttttccct cactaatgca gcaggcaaaa      3420
tgggaggggc aggggtggag ggtagtgccc ccgcccccag caggagggca cagctgtttc      3480
tgcaaatgta aaaagcagg gttttctgt gtgagaagtt ccctcttgct gcatgtcccc      3540
acccccgcca ccaaagacaa acaggacact gtgcagaggg gccagagccc cgagattttg      3600
gagttgtttt tatatgcata tataccattt tgaaagcaaa gcttccctct cccctactcc      3660
ctacatgtcc cccttcacca aaaatccca ccacgtaact ggaaaggga gtgagaagga      3720 cgacgaaggg gcactgtccc ctcccgtccc acagcgggac ttaaaacgta cagcttttcg      3780
cctccggaca gtgtgccgcc ccctggcccc cgtcacgctc ccctgcccgg ggggctgagt      3840
gtggggccag ggcctgtctc caggcatgca ttattttgtg catgaaggtt ttgtcccgcc      3900
cacccaggct ggtgttgggg ggaagggggtt cattgctcca aagaagccca tctccccct      3960 cagccacctt cagccgcctt cgcaaggcag agctgtgtcc tctgctgtgt gcctggcccc      4020
ctccttgctt ctattcaagg tggaagtgtt ggggggagga gaagagtttt tatattgtgt      4080
ctgtgatccc ccgaggcagg gcatttgtgt gcggcccccc agccccagg cccaggcaga      4140 tgggccagcc tgcccgacag aagggtctcc tgctgcttgg ctgcagggaa acccagctct      4200
gggtgaaccg tgggcacctt ccttcctcca tgccctgtat ttaaagaagg agagctgggg      4260
ggccagaggc acaggaggg gagccacggc cccaggtctg acaagatgac ctgcgggcct      4320
ctccacccaa gagtcgggt gggggggcgg atttggtttg aaaagagaac aaataggaac      4380 acactctta ttttccccag gggccgaaga gtcacccctg aacttgagga cgagcagccg      4440
gattccagcc cccagcccca gggccccaca tctcctcggg ctcagccgcg cgccccagct      4500
gccccccagc ctgagctgca gcaggccagg gctgcccgag accccagccc caggtgagc      4560 tgctgcagcc tgtggcccag gagatctccg ccggctcaga actgaggcgg gcagcccacc      4620
cagcccacag cggtgagtgt ctccagaccc cagggcaggg cccggtgtcc cccggcacag      4680
agagctgtgc tgcaggccca gacctcccag gccgttttag ttcccatctc cccttggggg      4740
aggggtgggg ctcagagggg ctggggtgca tccgcagagc tggggtgcag ggctccaggt      4800
gcctctctcc caggcggctg gcccggaggg ggg                                 4833
```

<210> SEQ ID NO 16
<211> LENGTH: 2064
<212> TYPE: DNA
<213> ORGANISM: Sus scrofa
<220> FEATURE:
<221> NAME/KEY: misc_feature
<222> LOCATION: (46)..(46)
<223> OTHER INFORMATION: n is a, c, g, or t

<400> SEQUENCE: 16

```
ctggtttcgc actcctccgg ggactgttga agtacccgag agcgcncgcg gagcgccggg       60
gcgagcgggg gtggccgccg ggggtgctcc cgggcccccg gaccgagcca gggacgagcc      120
tgcccgcggc ggcagccggg ccgcggcttc gcctaggctc acagcgcggg agcgcgtggg      180
gcgcggccgc tgccgggagt ccgcctgcct cctcggaggc ggccgaccgg ggagcctggg      240
ggaccccgag cgcccgggga gcagcgcccc gacacgcccc gggccgctct cggcttcctc      300
```

-continued

```
cottccagcc ggcgcccgcg cggccgggct tcggcaccgg ggcgctctca gtggcaggag      360
aagcgtgcgc tcccgcgggg tgggggaccc gcaggaaacc cgcaccgcct ggagccgccg      420
ccgcgcggcc agcgctcgcg tcccccgggg agggcgccac tgctccgcgc gcgcgtcccc      480
cgacgccccg cgcgcttccc cggccggccc gggatcctaa cctctctctc ggtcgcagcc      540
ccgcatcccc agggctccag gccccggcg acttgcccgc tcctcccaat tgcagacacg       600
acttttctg ggacctccca aaggacagcc tggctccagg gtcccccaga tacattcacc       660
atttctccag atcacaagtg ggttttcgg gcactaactt ccagagacct caaagcacat      720
gagcccctac tggctttccc aggtttccac tagtggcctc ggtccccacc tcactgggga      780
ttgtctccca ggctcttcgc ggtgtgatcc cacccattcg cgcccaggtc ccgcagtgcc      840
aatccctcct ctagaaaact taaacactga ctcctggtct cggggtgagg ctgcccaatg      900
tgcctgactc cccagaaggt ataccagtgt ttttctggca tttgggcacc gttcccccaa      960
aacacgtgaa gctcttttcc cgcgtcccca taatttggga cgccaggggc acccaagctt     1020
agcgcccctg tttggctccc ccacaccgcg aagccctgct ccctggggtt cacgacagtt     1080
tgggacttta tctgccaagt tccacaaact gattggcccc aagctggggt ccctaaattg     1140
tacacaaaga accccagccc cccccccaa ctccagtaca ggaagcgatg gccccaggga      1200
cctcggagt tggaacgtgg cttcctaagc cttcaccaaa attgaggctt ccgcgcatg       1260
gcgcgctgat gcccttgctg aatcagaagc actctgccct ctgattcctg ctttccacaa     1320
ccctgagagc atgatttctg gtcccccaaa ctcactgagc aaaaatcttt ttgtgggggc     1380
tgcaaagata ggaggcattt ctctccggag ctctccaaac tccctttgcct ataatcaagt    1440
tccctaaaac ttagacagag cttcccaggc cccagaggca cacagagcca ttattggagc     1500
tgcgtttaat gatgacaggg accatgggtc atgcagctcc cccaagtcac aaatgcccca    1560
ggtatccttg ctccagcca agcccaaagc aaactcttgc acagatccca tatcttgtta     1620
tgtcaagcgc tttgcgtgtc ccagtaaaca aatagtctga gtgttttctc cacctcataa     1680
cattcggaat attaaaaaaat tccctgggcc cccggagctg acagacaaga atccgggctt    1740
cctaaaattc agaactgatt cccaaatccc aggccaacgc cagaccctct cccaatctgg    1800
agccctccg actggacaca ctggactcct aagtattacg cgctgtcctc caggcacccc     1860
aaatgcattc aaagtgacgc tttggtcaca gaaaggcact gatttcttgg gctccaaagc    1920
agccatgca cccccgagtc accccaaact tagtcagcat ttcccgggtc tccctccgca    1980
ctgcaaactc ccaactgcgg acaccggttc ttcaggaccc accgcctaga cggtcttaat    2040
cccttttccc ccagacctag attc                                            2064
```

<210> SEQ ID NO 17
<211> LENGTH: 371
<212> TYPE: DNA
<213> ORGANISM: Sus scrofa

<400> SEQUENCE: 17

```
agattcaaaa actattttc tggggcctcc aaattgaggt gctgcctgcc agtcctccaa       60
aataaactga ggggttttt gtttgtttgt tttttgttt gtttgttttt ttttaccttt       120
ccacgaaaca atccaacttt tttgaccat tgatttatgg gtcccctgac tttatgaccc      180
ttgcccaag tccccctaaa tgtaggccat tttccacggg cctcccaaaa tgaaattgcc       240
cagatcccgc cgaaaaaat atcccgggt cctggaaatc ccaggtatta caggcctgcg       300
gctgacaccc ctccttgcta ctaaccaggt tccctgaagt ttagagatca ctacctaatg     360
```
aacaaatcca c                                                           371

<210> SEQ ID NO 18
<211> LENGTH: 2415
<212> TYPE: DNA
<213> ORGANISM: Sus scrofa

<400> SEQUENCE: 18

| | | | | | | |
|---|---|---|---|---|---|---|
| ccaaaactgg | ggccctatct | tactagggtt | ccctaaatgc | agacagcgcc | cgggaaaata | 60 |
| ggggcgtttt | ttttcctgtt | tgccaaaaat | aaactaattg | aaaccaattt | ttagaattaa | 120 |
| aatctaaaat | gaccttgatt | ttctgcgttc | tccaaatgta | cttttcacag | cccaggttgc | 180 |
| ccccagttta | gacggtgttg | cttgaatctc | taaagcaccc | tgaggatttt | tcccgaggaa | 240 |
| gccaccacaa | ctacggaatt | tactgtcctt | cggggccaca | agcctccagg | ccaccaactt | 300 |
| ggatttctaa | accgtggaaa | tcagcctcca | cttccctccg | ccaccccgag | ggtctgctca | 360 |
| gaccccccaa | acgtgcccgc | tgttcttctc | ccccaaatt | ttatttagag | aatatgcctc | 420 |
| tctcggttc | tgccaagttt | cccgctgaga | cttcctcggt | catccccaaa | tcctcttccc | 480 |
| cacagtccgg | gagccccac | aagcttaccg | acccacatgc | tggggtcccc | caacttaaac | 540 |
| gcgatcccct | gtccccaga | ttcaccgagt | gatttccctg | gtcctcagac | tgggactctt | 600 |
| ttactggagt | ctcgaattta | gccattaatc | acagttctcc | actccgacgc | aggctccctt | 660 |
| gggtccccac | gtcggggaca | tgggttctct | tgcctgcaaa | tcaggctgct | ctgacttgca | 720 |
| ttcaggcctt | tgggcattgt | tccccgcccg | ccgcggtctc | ggttctcccc | ccatcccgcg | 780 |
| cacgacgggc | actgggtctg | ggcctcttgg | tgtctcctac | aagtccccgg | agctcctcgg | 840 |
| acttgggaac | tgtctcttgc | gttccccaaa | tacactcggc | ccggcagtgt | gtccgccagg | 900 |
| acgtaggcag | agcttctccc | gcgtccagga | aaacgactgg | gcattgcccc | cagtttcccc | 960 |
| caaatttggg | cattgtccct | gggtcttcca | acggactggg | cgttgccccc | ggacactgcg | 1020 |
| gactgccccc | ggggtctcgc | tcaccttcag | cgcgtccacc | gcccgctgca | gagcgctcgc | 1080 |
| tctccgtctc | tcggctccca | gcgcgcttgg | ggacgcagcc | tccgggcctc | cagccttgcg | 1140 |
| gtgagctccc | cgtcgcctcg | cgtgtcccgg | cccggctccc | aaacccactc | gccgccgtcc | 1200 |
| cgctggggct | ggcactggcc | tccggcgact | gccgggaca | cgggagcgga | gcgcgggagc | 1260 |
| ctgctgcagg | ccagcccgtc | ggccgggccg | cgcgccctga | aacgcgcgcg | ctttcgtttt | 1320 |
| gctcttttgca | aaggtcacaa | ccgtggggaa | aacgcctcgg | cggcccccaa | gcggggcagg | 1380 |
| cagggcgttg | ggaaggaggg | acacgcggga | gaggagcacc | ccgctggggc | ggcgcagcgc | 1440 |
| ggcgcctcca | gccgccgggc | ggaggatccc | gggaggcgcg | cgcggagcgc | gggcgaagtg | 1500 |
| attgatggcg | gagcgagggg | gccagcggat | cgcgggcttc | cgccggcggc | ggccccttcc | 1560 |
| cctcggaggg | actcgggcgg | cccgggtttc | tggggcgcgg | cggggcgcgg | gggcttgtgc | 1620 |
| gtggtctcca | cttggtaaaa | atcacaacga | ctttttacgt | cgccccgact | ctccaggaga | 1680 |
| tggtttcccc | agacccccaa | attatcgtgg | tggcccccgg | ggctgaaccc | gcgtctacgc | 1740 |
| aaggccaacg | cgctgaggac | gggggaacca | ttatccggat | attttgggtg | ggccccccaaa | 1800 |
| gcgagctgct | tagacgcgcc | ccggtgagct | cggtcctgca | ggtaggcttg | gagcgaggtt | 1860 |
| ccccgccctg | ctcctctctc | ttcgggcagg | cgcggccagg | ccggccggcc | ctccccacgt | 1920 |
| acggcacctg | gcggccgccg | agacgactcc | ccggttcccg | cgcggcaccg | ggggcgctc | 1980 |
| gggctctggc | tgcggctcga | ggcgctgcgc | ctgctcgggc | aggtggaggc | ttcacgccgg | 2040 |

-continued

| | | | | |
|---|---|---|---|---|
| gcccgcgccc | agggacgacc | ccttaccccg | caggtcccag | cgggactcgg | ggcccccgga | 2100 |
| tccagcgtct | agccacctgt | gcccgcaccg | ccgcgagggc | ttgtgacacc | taccaccctg | 2160 |
| gccgccccgc | gtccccccgc | gcacgaatgt | agggatcctg | acaccccgga | acctaagacg | 2220 |
| gggcccccat | acactttcgt | acagcgattc | gggatttctc | tcgaactctg | cagatctgta | 2280 |
| tggcaaagtt | gatggcctgc | attattttc | tgataattca | gcgaaagatg | gcgaccagag | 2340 |
| ctatgcgcgt | ctgggtttta | aaggcgaaac | ccaaattaac | gatctggtca | acgaacagat | 2400 |
| acagcatacg | ttttt | | | | | 2415 |

<210> SEQ ID NO 19
<211> LENGTH: 3122
<212> TYPE: DNA
<213> ORGANISM: Sus scrofa

<400> SEQUENCE: 19

| | | | | | | |
|---|---|---|---|---|---|---|
| agattccaat | gggatcccg | atgaggaagc | cgctgctcgt | gctgctcgtc | ttcttggcct | 60 |
| tggcctcgtg | ctgctatgct | gcttaccgcc | ccagtgagac | tctgtgcggc | ggggagctgg | 120 |
| tggacaccct | ccagtttgtc | tgcggggacc | gcggcttcta | cttcagtaag | tagctcagcg | 180 |
| ggcacgggg | gcgggcgga | cacagcaggt | gctccatcgg | tgctgccccg | gtacctgtgc | 240 |
| gggtccttcg | ggatggatgg | tgtggggac | ggggggcggg | gggcggccaa | gggaggacct | 300 |
| ctcctccgag | ggtctgagac | ttcagagcgg | gggcgccctg | gccctgcgca | gtgattggca | 360 |
| cctgccatgt | gcctggctgg | ggctcacacc | ccctgacgtt | cctgcagcgt | gactcgaaac | 420 |
| gggaaaccga | agggacgggt | ggcacgggt | ggggaggcag | accgtgagtg | gcaggcgtgc | 480 |
| gagggggttct | ttcgggcggg | gtggcccagg | caggccccac | aggatgacag | cctgtcccct | 540 |
| cctgctcctc | cttgacctgc | ccacagccag | ggctgcaggc | actgacattc | acccatggta | 600 |
| ttgtggtgcc | tgacgtcttg | gcagtgggca | tgggttcatg | gactgttgga | ttgaaagtgg | 660 |
| aataagatgg | gttgaaaacc | aataagaata | aaggcgcgtg | tggctggcgg | catctgcgag | 720 |
| aggtgaccgc | tgccctccct | ggggttgggc | tttgggtggg | ttcccatggg | tggggcgggc | 780 |
| cgccatgcag | ggtgcccgcc | tgctggcctc | agagtgcttt | gccgtcctca | tctttctctc | 840 |
| tggcccccgt | cccgctcctg | aggctggctg | gctgggcccg | cggagacctc | cgctcccgcc | 900 |
| tcgtctgtgc | ccagggagca | gggtggaccc | tcccttgggc | tcttgcctgc | acctcccagc | 960 |
| aggctgggcc | tcagtgtcct | tacctgtagg | atgggtcagg | ggcgtcctgg | agagagtcct | 1020 |
| cgggacaatg | gggaggctgg | gggcaggccc | agcctgaccc | tgaaggtggg | agtgtgtgct | 1080 |
| cccctgggc | tcagccagcc | gcgcttgggg | ccgggagggg | gtgggggacg | tggctggggc | 1140 |
| aagttgtcaa | gggccgcgag | gctcaccccc | gcccatcgct | ccccatgtgg | cagcctcttc | 1200 |
| tgcagcctct | acttacccac | cctctgaaat | gggctgaaaa | cacccatctt | ggcatgccaa | 1260 |
| agcttctctg | taaaaagcgt | tgctgcttct | tgatgcttct | gaggccctg | cctgccctgg | 1320 |
| cctctgagcc | ctctctctcc | tgcctcgttt | ggggcaggg | agtggcacca | tagaatctgg | 1380 |
| cgctgggcct | gggagcggc | cccctcgtgc | caggcttccc | cgaaaggagg | gctgggctga | 1440 |
| gctcccgacc | ctctggaccc | cttaccagga | ccccttacca | ggggcttccc | ccccccccc | 1500 |
| ccccggtggc | ggcgggctgg | gctggggcct | tttccttgca | gccgagtcgg | agctgtcgga | 1560 |
| ggcgagggcg | aggacgggaa | gagaggaggg | cgtggtttct | gctggtcctc | actcctctcc | 1620 |
| tcccgtcttc | ctcctcctcc | tcccattccc | acctgtgtct | ccgggtcccg | gggccgcagg | 1680 |
| ctgcccaggc | gcctgctgat | ccattgggga | ccgcactcgg | gtccccgctg | gccttcgggt | 1740 |

```
caggggccacg gcccacctat tttccaaaca gccttgggtc gaggcccaag aggctgggcc      1800
cggtttaagg acggggaggg aggcgccaag aggccagggg ctggtcccga gcacgcccgc      1860
acccgctcac ccccgctgtc ccctctcctt ccccgggggg ccctgtgcca ccccactctc      1920
acttcttctg ctcgaggcca cgaggctggc tgtccccgca aggtgaccgg cgtcctgtc       1980 tggagggcgg gggccggggc ggctgggggc accgtccgtg cccggggccc ctgtgctgac      2040
gtgccctccc cttggtcctg tgggacttcc aggcaggccg gcaagccgcg tgaaccgccg      2100
cagccgtggc atcgtggaag agtgctgctt ccgtagctgc gacctggccc tgctggagac      2160
ctactgcgcc accccgcca agtccgagag ggacgtgtcg accctccga ccgtgcttcc        2220 ggtaaggcag cccctctctc ggcagcgccc cccccggggg gggggctgtc tcctctgagc      2280
cgggggaccg gggcgcagcc ggctcttggg cttcaagtgc tgccagaggg gccttccccg      2340
ctggggaccc tggccagaag ccagggcagt cttcgctctg tcgcagggca ggcaggcagg      2400 aggacccccgc agaggttgtt gttctgggac aggggctggg gggccaggcc ccccctgac     2460 gggccttcc cctctcagga caacttcccc agatacccg tgggcaagtt cttccgctat        2520
gacacctgga agcagtccgc ccaacgcctg cgcaggggcc tgccggccct cctgcgcgcc      2580
cgccggggtc gcacgctcgc caaggagctg gaggcggtca gagaggccaa gcgtcaccga      2640
cccctgaccg cccgtcccac ccgagacccc gccgcccacg ggggcgcctc tcccgaggcg      2700
tccggccatc ggaagtgagc caaattgtcg taattctgcg gtgccaccat ccacctcgtg      2760
acctcctctc gaccgggacc gcttccatca ggtccccctt ctgagatctc tgtacccttc     2820
tgtctgcggg catctccgcc ccgggccccg tgccccaacc tccccatgtc aggctagtct     2880
ctcctcggcc ccttccatcg ggccgagggc atccaaacca caaacccaat tggcttggtc     2940
tgtatctccc cccaaattat gccccccaatt atccccaagt tacataccaa aaattgaacc    3000
cctcaaccac acccacatac aatcagcccc cgtaaaacga attggcatct ttaaaacacc    3060
agaaaagcga attagcttta aaaaaaaaat aaacccaaaa tatcaattag ctgaaaaaaa    3120
aa                                                                    3122

<210> SEQ ID NO 20
<211> LENGTH: 630
<212> TYPE: DNA
<213> ORGANISM: Sus scrofa

<400> SEQUENCE: 20
tactaaaaat aaattggctt aaaaacaatt ggcaaaataa aagaatttgg ccccccccctt     60 ccttctcttt cttttcggac cttgagttaa attggctgtg acccatcatc caagagaaag     120
gaagggacca aaatttgcag gtaggcttgt cgccgctcac agccatctcc ctcctcctgc     180
cacaccctcg ccggccactg gcggtgtggc accaaggacc cagtcccgtc ctctctctag     240
tcccatgacc gagaccgcgg tggagttggc tgggagaccc cgtgagatca gaggagggga     300
gcacggaacc agaaacccaa acctgcacag gtacaacatg actggccccc cgcacagccc     360
aagacctctc atctcagtct ccacttaaaa agcacctgta cccacacgca tccctgcaga     420
aacacacaca cacacacaca cacacacgca cgcacgcaca cacgcgcgca cgcacgcgca     480
cacacacact catgcgtata cacacacaca cacgcacgca cgcgcaccca cacacacaca     540
tgcattcaca cacacacaca ctcgtgcata cacgcgtgcg cgcgcacaca cacacacaca     600
cacactctct ctctctgtgg gatccctgag                                      630
```

```
<210> SEQ ID NO 21
<211> LENGTH: 500
<212> TYPE: DNA
<213> ORGANISM: Sus scrofa

<400> SEQUENCE: 21
tggctctggc ataggctggc agctgcagct ctgactggac cccttgcctg ggaacctcca      60
tatgccgtgg aagcggccct agaaaaggcg aaaaaaaaaa aaaaaaaaaa acaaccaaac     120
aaacaacaaa agccaaaaca cacagaactc acagacacaa gaagagactg gtggttgcca     180
aaggtggggt cgagggtggg aaaaatgagg agaggggggca aaacacacaa acgtgcagcc     240
ataaaatggt aaagtcccgg ggacctccgg tagcgcgtgt ggggactcgg gttgagaaca     300
caccgtgatg tgtattcgcg agttgctaag agtccctgtt ggagaaacaa atgcgtatcg     360
acgtgtggaa atgaaagtta acccgacctg ctgtcgtgat cactttgcaa cacatacaga     420
catagaatca ttatgtttta cccctggagc tgacagcgtt atacgtcccc cagcctcaat     480
ttaaaaacag cgttgccgtg                                                  500

<210> SEQ ID NO 22
<211> LENGTH: 400
<212> TYPE: DNA
<213> ORGANISM: Sus scrofa

<400> SEQUENCE: 22
ttcatactgt gcaatgccag ccttaaatgc acagaggaga gcattaactt ctttgcagaa      60
tcactgaaat gataccactc atgttttgca acttgcactt gggcgttatt ttattggtgc     120
cggaacagcg cgatgtggc accaaactag cgccgctgtt tttatttccc ctcggtatcc     180
gcgctctcgc tgtcttcccc cccttccgct tgcagctgag gaaagggctg agaggaggaa     240
agtctgcatt cacccatctc cccctgcctc tgttgtcatc cttcacagaa gtggtggcct     300
gtgcggggaa gtcactaaac ctaggcaggt gtcccgtggg gtcatgcttg ttacaccttt     360
gtgcacctgg cccaagttct gggtggagcg agaacgtggc                           400

<210> SEQ ID NO 23
<211> LENGTH: 559
<212> TYPE: DNA
<213> ORGANISM: Sus scrofa
<220> FEATURE:
<221> NAME/KEY: misc_feature
<222> LOCATION: (549)..(549)
<223> OTHER INFORMATION: n is a, c, g, or t

<400> SEQUENCE: 23
agctagcccc cccagccagg gccaggcctc tcctgccacc cgcccagcca gcatgtctca      60
agaggagggg gcctctaagg gatgaggacc tgctccagtc ggagacacga agccccgccg     120
gctcctcccc gaaagtccag ctgcggcttt cgagcacggc tgcgcccttc gtcaatcatt     180
tcagccacag aagtgaaagg cgctttcgtg gccgaggcag gcgggacaca gaatggaatc     240
ccaccccaga gcgaagagcc gccgtgggtg aagcgcgtct ctggtgggga ccgggccggg     300
aacttcacat gggggtcgct gtccccatct cccatcgtc attactgcag gggctcggcc     360
acacccggag ctgcggggc cagtgctgga cactggacct ggcctccgtc ctatgatgtc     420 atggggcgg ggccagcaca gggcagtggc cacacctcgg gcctccagc accagccagg     480 atggcagagg gccccacccc accacggggc atgtacatcc cagaggacca gctgagcaag     540
gcttgatang ggcttcaac                                                  559
```

<210> SEQ ID NO 24
<211> LENGTH: 450
<212> TYPE: DNA
<213> ORGANISM: Sus scrofa

<400> SEQUENCE: 24

| | | | | | |
|---|---|---|---|---|---|
| cgtgcaggga | cccgtgcggg | ccttcctgtg | gccacagaga | acaaacacac | cattatcttc | 60 |
| agccccaccg | cgcggcctgt | taatgggtaa | actggggcaa | ggggggcccct | gcctgaggcc | 120 |
| ggggtgggga | gcgcaaggca | tggcctgtgt | gccccagccc | agtccttcag | ggcgctgctg | 180 |
| tcctgcaccg | ggggccccag | gaagcagagc | acccagcttc | tccccctattc | tagaaccagc | 240 |
| ccccagaacc | ctggacccag | acccaggccc | aggggatact | gacagagcca | cggcaaggcg | 300 |
| gccactccac | accccacaga | ggggccagca | aaccccagtc | actgcgcagc | ccatgcccag | 360 |
| ggggcagatg | ggacacgaga | gcagccctca | tccacagcag | gcaggggagt | gaactggtgc | 420 |
| aaaacggggc | ggttccacga | aagttaagca | | | | 450 |

<210> SEQ ID NO 25
<211> LENGTH: 535
<212> TYPE: DNA
<213> ORGANISM: Sus scrofa

<400> SEQUENCE: 25

| | | | | | |
|---|---|---|---|---|---|
| tgccagagac | ctcagagctg | ggctctgcct | tcccgggctg | acacggaggg | ctgtggcttc | 60 |
| caccacccca | ggccacagcc | agcctgccca | agtccctgaa | gtgtcccccag | aggtggccct | 120 |
| gcctccacgc | ccaacatcag | gcctgctgca | gccctggacg | gcccccctgtc | ccccggaagc | 180 |
| cctcggggct | ctctcgcgtc | gcctctgggg | aaccctcggt | aatgtggccc | agccgtgcag | 240 |
| tggccggatc | atttgctcag | gggggcccaa | ggcaggggggg | tgacacatcc | gcaagtaccg | 300 |
| catatgcaca | ggatatggat | tgggtgtgga | tttaaccttt | tcgcaaatgt | ctctgccggt | 360 |
| acaaatattg | tttctaatcc | tctgcctccc | tgagccggtg | agtctgcccg | ggagctgcgg | 420 |
| ggagctggct | tgctgaacct | gccctggccc | ccaccccccaa | gggagccccc | ggccagtgct | 480 |
| gagggcagga | agcttgggca | caggctgcag | aggccagcgc | tggcctcagt | cacct | 535 |

<210> SEQ ID NO 26
<211> LENGTH: 868
<212> TYPE: DNA
<213> ORGANISM: Sus scrofa
<220> FEATURE:
<221> NAME/KEY: misc_feature
<222> LOCATION: (310)..(310)
<223> OTHER INFORMATION: n is a, c, g, or t
<220> FEATURE:
<221> NAME/KEY: misc_feature
<222> LOCATION: (857)..(858)
<223> OTHER INFORMATION: n is a, c, g, or t

<400> SEQUENCE: 26

| | | | | | |
|---|---|---|---|---|---|
| tattgaagac | cctatcatga | gttcccagag | cggaggggtg | gaagcagggg | cctacagccc | 60 |
| actccccatc | actccagacc | cgtccggggc | tggtgtcccc | tgccccctac | tcctgtctct | 120 |
| ggtgggcgga | cgctcgaagg | aggcactctg | gctggagcc | tggagggtcc | ctgaactccc | 180 |
| gctgccacct | gggccctcgg | gctcctcctg | cgctgggacc | cgcggtggtg | ggaagcagcc | 240 |
| ctgctcagtg | ggaggaggca | gggctgtggc | cgccccgcac | ggccctgggg | gggacgcacg | 300 |
| caggacgcan | gtgggcgtgt | gtgagtccgt | ctacacgtcc | agccaagggc | ggccgcgacc | 360 |

```
ggccagggtg ggcagcccca gcctcagcag ggcgctctct ggggctcagg ctgcgccgac    420
gggagatgag gggtgaggcg cagtctgggg ctgctgccgc agaacctcgc ccagctggca    480
gctgggcaca gggagacctg tactcccaga acctgaggct ggacgtccga acccgcgtg     540 ccggcctctt gggtgcctgg tcagggtcct ctttctggtt tgtgggcaga acctcctcag    600
cgcgtccttg catggggtgc taatcacgga gtaaggagcc agagaatgag cacggagta    660 tccagtgtta accctggagt atggagacgg gagtactaat tgtggagcat ggctctaagg    720
aatggagtat tcgtcacgga gaacgcgggg ccgggtgaaa tacggagagc ggcgtacgga    780
caacggggac ggggtatccg aaggggagga tggagtatcg gccggagggt ggagaatgga    840
cactagagga tgtatanngg gcgtcaat                                       868

<210> SEQ ID NO 27
<211> LENGTH: 500
<212> TYPE: DNA
<213> ORGANISM: Sus scrofa

<400> SEQUENCE: 27
accagtttcg atgagcaatc ccagcggcgt aacattatgg ctgcagcctg gtcaatgccg     60
gtggagtttg aacctccacg cgtggcgatt gtggtagata atcgacatg gaccagggag     120 ttgattgaac ataacggtaa atttggcatc gttatcccgg cgttgcagc aactaactgg     180 acgtgggcgg tgggaagtgt gtcggggcgt gatgaagata atttaattg ctatggcatt     240 ccggttgtga gaggcccggt atttggtttg cctctggtcg aggaaaaatg tctggcgtgg     300
atggagtgtc gattgctacc tgcgacttct gcgcaagaag aatacgacac gctgtttggc     360
gaagtagtat cagcagcggc agacgcacgg gtatttgtcg aaggccgctg gcagtttgat     420
gatgataagc tcaatacgtt gcatcattta ggtgctggga cgtttgttac cagcggcaag    480
cgtgttacgg cgggttaagc                                                500

<210> SEQ ID NO 28
<211> LENGTH: 900
<212> TYPE: DNA
<213> ORGANISM: Sus scrofa

<400> SEQUENCE: 28
atgtttgatg tccgcgcgtg ctgtaaaaat ttacgctgct cgcgttcttt ggcttcgtcc     60
accaccggaa aacggacaaa aatttccgtc ataccttttt ctttcaggcg gaagccaatg    120
tcgtaatctt cagtaagact ctgcacgtcg aaagcaatac cgtcaccgtc agctaacagt    180
gcggtcacgg cgcggcggct gaaacaggtg ccgacgcctg cgctgggcac ttgtccggcg    240
agggcttcac gcaccggaac atctttgcca tgcagctctg aaaactcatc aatgtaagtc    300
atgctggtga agtgcgtcca ttcgcgttcg aacggataca ccgggatctg aatcagatct    360
ttacgctcga ccagatagtt gaacagacgc aattccatcg gtgaaatcac atcttcggcg    420
tcatgcagaa taaaaccagc aaaagcgaaa ttggcgctac gctcaaattg ggtgatggcg    480
tccagcacgt tgttcagaca gtcggctttg ctggtgggc caggacgcgc gcagactacc    540
ttatgcacat tcgggaagcg agcgcacact tcgtcaacat cacgctgagt atcggggtcg    600
ttggggtagg tgccaacaaa gatatgatag ttttcgtagt cgagcgtggt cgccgccagc    660
tcggccatat tgccgatgac gcccgtttca ttccacgccg gaaccataat cgctaacggt    720 tttttcatctg gttatacag ttcgcggtaa ctcattcgcg ggtagcggcg ataaacactc     780
aacttgcgtt taatgcggcg tacccagtat acgacatcta taaaaaaatc gtccagcccg    840
```

```
ctgatgaaca tgatgaccgc taacgttatc gcgattactt ttaagccgta tagccaggta    900

<210> SEQ ID NO 29
<211> LENGTH: 500
<212> TYPE: DNA
<213> ORGANISM: Sus scrofa

<400> SEQUENCE: 29
agctggatgc cccagctgt ggtcccttcc cttccctcag ggcaggttct gtccctcttg     60
cagccaccgt cactgctgtg gacaggtctg cacacccgcc gtccaccaag agcgtggcag   120
gtccctgggc acgggccggc tcctgacgca ccatgtgttc aaggcaagag cactggacag   180
agggtccaga cgtccccttg tcctgctcag gcctgggcgg gggcagccct ggcgggagag   240
gccctgggca tcagagcctc tgtggcctgg agcttggcgc cctgccctcc ccacctccgt   300
cctgctcctc gccgcgctgc acggacctct cccggccccc caggctcatt actcttaagg   360
accctagccc cctatgctga aatgctgtac ctcgtgcttg ttttcatctg tttattacct   420
tatcttcatt cctgcttgat gatatctggt tattctttat tgattatata tatcttgttc   480
gtgtttttat aggacactgt                                              500

<210> SEQ ID NO 30
<211> LENGTH: 450
<212> TYPE: DNA
<213> ORGANISM: Sus scrofa

<400> SEQUENCE: 30
agtgcggtcg ggccgtcctg acgctcaaca ccgtatttcc acgcgaccgc ggattcaacc    60
tggtcacacg gacgccatgt agacatgttc ggggttacgc gcagagaagc gacctgctca   120
accggctggt gagtcgggcc gtcttcgccc agaccgatgg agtcgtgggt gtaaaccatc   180
acctgacgct gtttcatcag cgcagccata cgtacgcgt tacgtgcgta ttccacgaac    240
atcaggaagg tggaggtgta cggcaggaag ccaccgtgca gggagatacc gttagcaatc   300
gcggtcatac cgaactcgcg aacaccgtag tggatgtagt tacccgcagc atcttcgttg   360
attgctttag aaccagacca cagggtcagg ttagacggcg ccgggtcagc agaaccgccg   420
aggaattccg gcaacagccg gacgaacgct                                    450

<210> SEQ ID NO 31
<211> LENGTH: 450
<212> TYPE: DNA
<213> ORGANISM: Sus scrofa

<400> SEQUENCE: 31
tcaggccaat ctgtctggtc tccaatgggg acaatttggt tctttaggct tctgtccaat    60
ggtccgaatg gcccactccc cgggcgccgg ccaagggtcc tctgtgcctc gggtgggctg   120
gcacggaccg ccccagggt cgtgccagcc ccgtcaccgg ggcccagaag cttcgggcct    180
ctagctggct agtcgggctg ctgtgcaggg gggctgcgct gggggcagag gcggggtga    240 ggtaaacctc ccagccgccc ggggtccctg ccgcagccct aggcgccgag acggtggctg   300
ggtcggtacc gccagacccg agggcctcgg ggcccgggtg accccagctg tcgcacacgc   360
tcgcagctct cttgctcatc agggctcatc cctctggacc tctcctactg ccccacctca   420
ccccgcctgg accccatgaa gccccgcgga                                   450

<210> SEQ ID NO 32
```

<211> LENGTH: 600
<212> TYPE: DNA
<213> ORGANISM: Sus scrofa

<400> SEQUENCE: 32

```
taaaactagc tctagtagaa acattttatt taaaaataaa aaacctgact acgtcgggag    60
ttcccgttgt ggctcagtgg ttgacgaatc cgatgaggaa ccatgaggtt gcgagttcga   120
tccctggcct cgctccgtgg gttgaggatc cggcgttgcc gtgcgctgtg gtgtaggttg   180
cagatgaggc tcggatcctg cgtggctgtg gctcgggtgt aggccggcgg ctacagctct   240
gatgagaccc ctagcctggg aacctccaca tgccctggga gtggccctag aaaaagggca   300
aaagacaaaa aaacaaaaga aaaggaaaa taaaataaaa aagactatgt aaatgaaatt    360
aacgactgcc tagggtggga tttacagcat gggaagtaca gcatggccgt gacagtgcaa   420
gggtgaggcg ggaaaatgga aataggttag gtgagtttct cctgctattt gtgatgtggt   480
ctgctatcgc ttgaagacgg actgcagtga gataaatatg tacagtaagc atccgaaaaa   540
ccgccagaac ggcaaaacga atgactccaa gtaagaaccc aaaagagaaa aggaaataat   600
```

<210> SEQ ID NO 33
<211> LENGTH: 450
<212> TYPE: DNA
<213> ORGANISM: Sus scrofa

<400> SEQUENCE: 33

```
gcgcgggcgt tccggctggg gtatttaacg tggtcaccgg ttcggcgggc gcggtcggta    60
acgaactgac cagtaacccg ctggtgcgca aactgtcgtt taccggttcg accgaaattg   120
gccgccagtt aatggaacag tgcgcgaaag acatcaagaa agtgtcgctg agctgggcg    180
gtaacgcgcc gtttatcgtc tttgacgatg ccgacctcga caaagccgtg gaaggcgcgc   240
tggcctcgaa attccgcaac gccgggcaaa cctgcgtctg cgccaaccgc ctgtatgtgc   300
aggacggcgt gtatgaccgt tttgccgaaa aattgcagca ggcaatgagc aaactgcaca   360
tcggcgacgg gctggataac ggcgtcacca tcgggccgct gatcgatgaa aaatcggtat   420
caaaagtgga agagcatatt gccgatgcgc                                    450
```

<210> SEQ ID NO 34
<211> LENGTH: 450
<212> TYPE: DNA
<213> ORGANISM: Sus scrofa

<400> SEQUENCE: 34

```
ggtggatgct ggcgatagcg tcatcctcgc ttatgccgtg cagcgggcaa ggataaagcg    60
cgcgataaac atgacccggc atcagcccca tgcccgcaga gtacggattc accttgccgg   120
tcagcgccag cgtgtaatgc gtgcgcccgt gatacgcgcc gctaaaagcg atggtgccgc   180
tacgttggt ggcggcgcgg gcgatttta ccgcgttttc caccgcttcg gaaccggtcg    240
taaccagcag cgtttttcttg gcgaaatcgc ccggcaccttt ctgattcata atctcgcaca   300
gctccagata cggctcgtaa gccagcacct ggaagcaggt gtgcgacagt tttttcaact   360
gcgcttccac cgcggccacc accttcggat gcaagtgccc ggtattgagc accgtaatcc   420
cgcccgcgaa atcaagatac tcacggcctt                                    450
```

<210> SEQ ID NO 35
<211> LENGTH: 500
<212> TYPE: DNA
<213> ORGANISM: Sus scrofa

<400> SEQUENCE: 35

```
acgtgaggtt tgggggagga aagcgggga cgagcagccc gagaggagtg ggggctggcc    60
tgtggctgat gaaactctga gaaggttaag agcccccatt tttgtcttcc tcttttttat   120
tatggaaaat tccaaatgga tgcaaaagtc ccaaacctaa ctggacatct tcttggtacc   180
aggaacggtc aggcacttat gatgcaccga gccccgaggg aaaaaccctg ccgtcctgga   240
gcccacggtc cagcagggca cacaggcccc agcccgcaag cggcacggct gagtcagtga   300
atggcgtgcc ctctggtcaa ggacgggcac tctggacccc agggaagcct ctgaggagcc   360
cccttcacag cgtcaaaaac tgttaacagg ccatgttcg cacccccca cacgtggt      420
tcagaagcag accccaggca tcgtaatatg tcatccgtga gttccctgtg tgccaccaac   480
agaaagccca tcgtcacgtt                                              500
```

<210> SEQ ID NO 36
<211> LENGTH: 400
<212> TYPE: DNA
<213> ORGANISM: Sus scrofa

<400> SEQUENCE: 36

```
cggcatcgat gtacatggta cgcaaggcac tcgtaaggcc ccgagcctct aggccttgtc    60
attgtcacgt gctgctcgcg gggatcagca gccaggcttg tgaccccggc cactttgaca   120
gataaggaca cagagaggcc acagcactgg tgtgaggccc cacagccagc agcccagggc   180
agggaggact gggtctcacc tgcctcagct gggcccagcc tccctgggag tcccggagtc   240
tccccagctt aggagtgtcc ctggaaccct cttctctccc cttccgccc tcacccggac   300
cccctgcctc ccccccacca accccctccc cctccttctt tcaccttgag ctcccctctg   360
aggacctcta ctgttcctgc ttatcctccc ctttgagcca                        400
```

<210> SEQ ID NO 37
<211> LENGTH: 500
<212> TYPE: DNA
<213> ORGANISM: Sus scrofa

<400> SEQUENCE: 37

```
tggcggtgaa ctatgtcgtg cgtgaagagc atttgtggtc ggtagcgcgt tatatgcggg    60
aagtttaggc gaactggaca gcctgggttt atccggtagc gaaatccgct tcacggtaa    120
aacgctgcta cgctggtgg aaaaagcgca gacattgccg gaagatgcct taccgcagcc   180
gatgcttaac ctgatggaca tgccgggtta tcgtaaagcg tttaaagcga ttaagtcgct   240
gattactgac gtgagcgaaa cgcataagat cagcgccgaa ttgctggcat cgcgtcggca   300
aatcaaccaa ctgctgaact ggcactggaa actgaaaccg cagaacaatt tgccggagct   360
gatttccgag ctggcgtggt gagctgatgg cggaagcatt acacaattta ttgcaggaat   420
atccgcagta aaatcttccg aagccggact gggcgcgctc agcgccacat ccggcttcgg   480
caaactacaa atccaacacc                                              500
```

<210> SEQ ID NO 38
<211> LENGTH: 500
<212> TYPE: DNA
<213> ORGANISM: Sus scrofa

<400> SEQUENCE: 38

```
gatttcacaa gcctgaccca cgcggaaatg cgctaacagc gtaaagtcgt gcggccagaa    60
```

```
tttttttcgtc tcttcgcttt gcgtcaattc aaaagtcagc gctacgccat cagcatcttc      120
atgatgtgat ttcagcgtcc acggcaggtt gcgggcaaaa ccgtgcgcag gcagaccttg      180
ttgtgccgcc ggaccaaacc acggccagca aaccggtacg ccaccgcgaa tagcgacgcc      240 attttttgaac ggtgtgttgt tgctcaacca cagaacttct tcttcacccg caggtttcca    300
cgagagaagg tgtgcgccct gtaatgcaaa agaggctttt acctgggat gatcgaccac       360 aatgaggtcc agttcatcca gtttacgacg ggagaggaca ggggagatttt gttcgatgac    420 cggaagggca aaatttttct taatcatgac gcagtccttt aacttcattt tatcaggtaa     480
aaaaaagagc gaccgaagtc                                                  500

<210> SEQ ID NO 39
<211> LENGTH: 300
<212> TYPE: DNA
<213> ORGANISM: Sus scrofa

<400> SEQUENCE: 39
acctgatcag gctctgcact gtgttcatca gcggagccga gatatttgac cgccccatgc      60
ataacggaaa ggcgtgggta aaccccccggg cgcgttcctt tatcaagatg acgttcgaat   120
attccggcag gtgcagtttg tttattccag aaaggcgttg agcgcgtatg aatataattc    180
tgtgggattt gaagcatcct tttccctcct tcggtgaatg cgctgaaaac ggcttattcc    240
agccggttca gggtacgcct gataatttgc atttaaaata ccatttattg ggtactttttt  300

<210> SEQ ID NO 40
<211> LENGTH: 450
<212> TYPE: DNA
<213> ORGANISM: Sus scrofa

<400> SEQUENCE: 40
atccttttgg ggtctggcaa ttacgcaata aagaaggccc ccatgcgatt aaagtcaccg      60
gcccactgtc gtctaatcat ggagaaattg tccatcagtg gggtctcgat gggcagggga    120
ttgctctgcg ttcctggtgg gatgttagcg aaaacattgc cagtggtcat ttagtgcaag    180
tgctaccgga atattaccag ccagcgaacg tctggtccgt ttatgtttca aggctggcga    240
cgtcagcgaa agtgcggata acggtagagt ttttacgcca gtattttgcc gagcactacc    300
ggaatgtttc actgttgcat gcctgattta tgattcaatt atcgggttga tatcagttta    360
aaacctgatt ttctcctttc taagccgcta cagatttggt agcatattca cctttaatcg    420
cgcatgatct aaagataatt gaagaggtta                                      450

<210> SEQ ID NO 41
<211> LENGTH: 450
<212> TYPE: DNA
<213> ORGANISM: Sus scrofa

<400> SEQUENCE: 41
aatgtactgg caaaaagcca atggcgaagc gtggggaacg ttacatgctc tgctggcgga      60
tattaatagt cagggtcagg tgcagatggc gatgaacggc ggcatctatg atgaaagcta    120
tgcgccgctc ggtttgtaca tcgaaaacgg tcagcagaag gtggcgttaa atctcgcttc    180
aggtgaaggg aatttctttta tccgtcctgg cggcgtgttt tatgtcgcgg gagataaagt   240
cggcatcgtt cgtctggatg ccttcaaaac cagtaaagag attcagtttg cggtgcagtc    300
agggccaatg ttgatggaaa acggtgtaat taatccgcgt attcatccca acgtcgcctc    360
aagcaaaatt cgtaacggtg gttgggatta ataaacatgg gaacgccgtg tttttgttga    420
```

```
gccagcaggc aacaaatttt tatgattttg                                      450

<210> SEQ ID NO 42
<211> LENGTH: 400
<212> TYPE: DNA
<213> ORGANISM: Sus scrofa

<400> SEQUENCE: 42
gacattaatc atttcaaaat caaagccccg gttttccatc gcccgtttgg tggcgtggca      60
ctgaacgcaa tcgttacgag tgtaaatagt aatgcgcatg attcgtattt ccgtttaaaa     120
tgaagatacg gcgcgatgat acgcgtcggg ttgtctctct gttgatacag agatactaga     180
tgtagttgaa aaaagattca accacacaat atatagccca gtaggggtcg aaattaccct     240
ggatatgagc gtgacggggt aggggatttt tgtgattca ccaggcaaaa agaaaccccg      300
aagacaggct tcggggtcaa agacgcgtat ttattatcat ttttgcacta cgatttgcgc     360
atgcttaaca gtgcgccgat taaaatatct accgcagctg                           400

<210> SEQ ID NO 43
<211> LENGTH: 500
<212> TYPE: DNA
<213> ORGANISM: Sus scrofa

<400> SEQUENCE: 43
gcaaaatcac gtccgcgacc tggcgttgtc gctgggccat attggcaaag gagctggatt      60
gcggtgcctg caaagtgccc tgaataatgc cattgtcctg taccgggaag aaacctttcg     120
gaatgaacac ccacagcagc acgctaagca gcagcgtgct gagtgccacg cttaaggtca     180
gccacggatg attcagcact ttcgccagtc acgaccata ggcggcgatt atcctgtcga      240 acatttttc cgaggcacgg gagaagcggt tctgtttacg caacgactcc tggctgagca     300
tccgcgcgca catcatcggt gtcagggtca gcgacaccac cgctgagatc aaaatcgcta     360
ccgccagggt aatagcaaat tcgcggaaca gtcgcccgac gatatcgccc ataaacagca     420
gtgggatcaa caccgcaatc agtgagaagg tcagcgagat aatggtaaag ccgatttcac     480
ctgcgccctt gagcgccgcc                                                 500

<210> SEQ ID NO 44
<211> LENGTH: 400
<212> TYPE: DNA
<213> ORGANISM: Sus scrofa

<400> SEQUENCE: 44
agctatctac ggcaaaaggc acggtagtca atttcgttgt taaatacatc aagcgtttgg      60
cgccgaaata ccatctgcca gatgccattt catttcgtag cgcactgcat aacggctacc     120
ggatgcagta cgtcaaaccc gaactggggc cggaaggatt tagcttttct gcaatacacc     180
ggcggcacca ctggtgtggc gaaaggcgcg atgctgactc accgcaatat gctggcgaac     240
ctggaacagg ttaacgcgac ctatggtccg cgtgttcatc cggcaaaga gctggtggtg      300 acggcgctgc cgctgtatca cattttttgcc ctgaccatta actgcctgct gtttatcgaa     360
ctgggtgggc agaacctgct tatcactaac ccgcgcgata                           400

<210> SEQ ID NO 45
<211> LENGTH: 450
<212> TYPE: DNA
<213> ORGANISM: Sus scrofa
```

<400> SEQUENCE: 45

```
gattagcgcc agatgctcgc catcgaaaag ttgaatcaac cccagctgcg ggtaataagt      60
gcgcgtacga acaaattcag tatccagggc tatcgccgga aaggcacgga cggcttcaca     120
caaagaagcc agcgcatcgt ccgtggtaat catttggtaa ttcaaattgt tttctcttta     180
gtgggcgtca aaaaaaacgc cggattaacc ggcgtctgac gactgactta acgtcaggc     240
tttattgtcc actttgccgc cgcgcttcgtc acgtaattct cgtcgcaaaa ttttttccgac   300
gttagatttc ggtaactcat cacgaaactc caccagcttc ggtactttgt atcccgtgag    360
ctgacggcgg caaaaagtca ccagtgactc ttcggtaagc gatggatctt ttttcactac    420
gaagattttc accgcttcac cactggagcc                                     450
```

<210> SEQ ID NO 46
<211> LENGTH: 750
<212> TYPE: DNA
<213> ORGANISM: Sus scrofa

<400> SEQUENCE: 46

```
gagcagcccg cgtgatgaca ggcatgcgcc cgcgtcggct ctctctctct ggtgcactga     60
gtcacaggat ggcggcggtg ggcgcggtgg tggaagcggt cctggagggc tcgggaggga    120
ggatgcgctc aagctggctc cccgtggggc tggcccggag tagcctccgt gagggcaccg    180
tgtctgctcc cagagcccgc tccccggcct gccctgcctc ccttccctgc cccagttccc    240
ccggagcccc tggatcccga tgggaggcgc ccctggggag aggggaccag ggaggggccc    300
agagctctga ggccaccaga cctggccagg acccttcgtg ggaagaagag gtgggcccca    360
aaggcaccta gagagaggga ggctctgctg gctgggggc cttccaggcg gggcttccag     420
gcagggccag tgtcctgggg gctggaggga gtccctggct gctgggggc ggcaggagca     480
cctgggggcgt ctgggaagag agcgggagga gactggagcc aactgggggg acagaggagg   540
ggtccaaccc cagcggtggt gttggggggtg ctggtggtgg aggccctgag aggctgtgct   600
gggggggcaga gcgggtgctg ggaggggaga aggggtcccc agggctcatg ggcccttcgc   660
agcagtggca gttggggtgg gtggctgtct ctagggctgt accacggtgg gtgcctggag   720
aaagaggtcc taccccctagt ctttgctgca                                    750
```

<210> SEQ ID NO 47
<211> LENGTH: 300
<212> TYPE: DNA
<213> ORGANISM: Sus scrofa
<220> FEATURE:
<221> NAME/KEY: misc_feature
<222> LOCATION: (299)..(299)
<223> OTHER INFORMATION: n is a, c, g, or t

<400> SEQUENCE: 47

```
tggggacccc actccagccc cactgagtga cgcgcccccc tgtggtccca ccgccaaccc     60
tgcctcacac cagaggggct gtggccacac cttgtccaca gcctgtccct gagaccacga    120
gcccccgggc tcagccccct cctcacccct ggaccgagga gaagccccca cctgggctca    180
gctcttggag ctaaacttcc aggaaggttc tggtgccctc gggtcttaga gcatggtggg    240
gaggggggatg ctggtggggg cgcaagccct ccccacattt cgcactcgac ccggtgggng   300
```

<210> SEQ ID NO 48
<211> LENGTH: 300
<212> TYPE: DNA
<213> ORGANISM: Sus scrofa

<400> SEQUENCE: 48

```
ccggctagaa gccacgagag cccccaggcc ccgcccgacg tctctcctgc agggattcgg      60
cagccctggg gccacagggc ctgagcagac cttggggttc cggtgtgact ccagccaggg     120
tccctactgt gtaggcacca gggcagagtc agccctggga ccatggccac agctgctccc    180
gcctgagccg ggccccccgc ccaggctggg cccctcagt gcactgtccc aagccagctg      240
ctctccccac ctccaccttc tccatccagg tcctgcccca cggcctttgc tcaggcccag    300
```

<210> SEQ ID NO 49
<211> LENGTH: 500
<212> TYPE: DNA
<213> ORGANISM: Sus scrofa

<400> SEQUENCE: 49

```
ttgactggca ctagcacgag ctctgtaccc ggggatctgg gctcgggaga agggagaccc      60
cccacccggc aggccgaggg cgctgtcaca ccatgactct cagccttccc cacccgacgg    120
acaagagtga ccctctccca agccccacct cacccaggac cgcacacccc gtgagtcctg    180
cgagtggggg cggctcaggg gccccgagtc ccaaaggagt ctgctggccc tgggggggag    240
gggaagcagc agggtggtca cgggtctccc tggttggcag gaccacaagc tcagcccgct    300
gcctcccaga gggcagccgg acaccaacca gtccgggac cccacgtacc tcagctgctg      360
caggtgcccc tgcctgtact ggtgccaatg gggccgctgg gtgctcccat ggacagctcg    420
ccactcatcc cagccgccta ccccccttcc gggtccagtg tccggccggc cacccgcctg    480
cccagccctg gcctcctctc                                                 500
```

<210> SEQ ID NO 50
<211> LENGTH: 500
<212> TYPE: DNA
<213> ORGANISM: Sus scrofa
<220> FEATURE:
<221> NAME/KEY: misc_feature
<222> LOCATION: (500)..(500)
<223> OTHER INFORMATION: n is a, c, g, or t

<400> SEQUENCE: 50

```
ggggttgccg caggctgctg tgtaggtcgc agacgcagct tggatctggc gtggctgtgg      60
ctgtggctgt ggctgtggca taggtcagcc actgcgactc cgatttgacc cccagcccgg    120
caactcccac atggcacagg tgcagcaggg aaaataaata aatgaaataa aataggtga      180
agacagtgga tttcatctct tggggttgcg gtaagctcta cacaataggg agtttaccat    240
tttacctgtt tcaagtggca ctgagtcagc tcacagtcct gagggcccac agatgccgtc    300
tgcctgggag attgttcctc tcaccacact gcccctctgt ccccactaaa tactcactgc    360
cctccccgtc ccaagggccc ctgccccacc ctctgcttcc tgtctctgaa cttgctggcc    420
accagcgacc gtctggtgac ctcactcttc ggccccattt gtcgcacacc ccacctggcc    480
tctccccggc atgggcagan                                                500
```

<210> SEQ ID NO 51
<211> LENGTH: 600
<212> TYPE: DNA
<213> ORGANISM: Sus scrofa

<400> SEQUENCE: 51

```
gggatatttg ggggcatatt tgggggggag atccccacaa ggcatttggg gtttgtggtt      60
```

```
tggaatgccc ccgggcccga tggaggggc cggggaagaa tctaagcctt acttggggag      120
ggttgggccc cggggccccg ggccggaaat gcccccaaga cagaaggtgt acaaaatttc      180
tcaaaagggt gacccttaat gaaacgggtc ccggttggaa agaggtcacc agggtggatt      240
ggtggcaccg cagaatttac gacattttgg ctctcttcca atggccggac gcctggggat      300
aggcgccccc gtggacggcg gggtctcggg tgggacgggc ggtcaggggt cggtgacgct      360
tggcctctct gaccgcctcc agctccttgg cgagcgtgcg agcgcggcgg gcgcgcagga      420
gggccgcgca ggcccctgcg caggcgttgg gcggactgct tccaggtgtc atagcggaag      480
aacttgccca cggggtatct ggggaagttg tcctgagagg ggaagggccc gtcagggggg      540
ggcctggccc cccagcccct gtcccagaac aacaaccttt gcgggtcct cctgcctgcc      600

<210> SEQ ID NO 52
<211> LENGTH: 179
<212> TYPE: DNA
<213> ORGANISM: Sus scrofa

<400> SEQUENCE: 52
atcttcatat tcatgcagaa gacactctcc tgcctttcta tcttggggaa aaggacgatg       60
tcacttatgc aataaagccc acttgctggc cggggcttga cattattcct tcctgtctgg      120
ctctgcaccg tattgaaact gagttaatgg gcaaatttga tgaaggtaaa ctgcccacc       179

<210> SEQ ID NO 53
<211> LENGTH: 500
<212> TYPE: DNA
<213> ORGANISM: Sus scrofa

<400> SEQUENCE: 53
ctcgggctgc ttccaggggg ccttggggag ccatagaatg ctatggagca agagagtgct       60
atggtcagac gactttgggg gaaggtctgg gagaagaggg gtgactggcc actgtgataa      120
agagtgggcg cttccttgag ataacacggt gggcagccga ggtggacctg tgcaggtgga      180
gaaggcctcc tgccgcggcc agtacgtggc tctgggctgc cggacacgag aaagcccacc      240
tccacggctg cctccaggcg gcccttcctc tcttcacacc gccgggccat gcccaggtgc      300
aggtgccatc agagggtgct caagagaagc tctgggctgg ggttgtccca ggtcccggaa      360
gccccgtgtc ccaggggcca cctgaggaag cgtgggcgca cagagactgt ccctcggtgc      420
tcagagaggg tcccgtcccc acggcaacga cgcccaaggc ggaggtggtc agaggtcttg      480
ggagggagga tggccgcgca                                                  500

<210> SEQ ID NO 54
<211> LENGTH: 900
<212> TYPE: DNA
<213> ORGANISM: Sus scrofa

<400> SEQUENCE: 54
tgtgttgcac ctgttgctgc ctgtcgactc taggatca atactcctta cataattaag        60
gagaacaaaa tggaacttaa aaaattgatg ggacatattt ctattatccc cgattacaga      120
caagcctgga aaatggaaca taagttatcg gatattctac tgttgactat ttgtgccgtt      180
atttctggtg cagaaggctg ggaagatata gaggattttg ggaaacaca tcccgatttt      240 ttgaagcaat atggtgattt tgaaaatggt attcctgttc acgacaccat tgccagagtt      300
gtatcctgta tcagtcctgc aaaatttcac gagtgctttt ttaactggat gcgtgactgc      360
cattcttcag atgataaaga cgtcattgca attgatggaa aaacgctccg gcattcttat      420
```

```
gataagagtc gccgcagggg agcgattcat gtcattagtg cgttctcaac aatgcacagt      480
ctggtcatcg gacagatcaa gacggatgag aaatctaatg agattacagc tatcccagaa      540
cttcttaaca tgctggatat taaaggaaaa atcatcacaa ctgatgcgat gggttgccag      600
aaagatattg cagagaagat acaaaaacag ggaggtgatt atttattcgc tgtaaaagga      660
aaccaggggc ggctaaataa agcctttgag gaaaaatttc cgctgaaaga attaaataat      720
ccagcgcatg acagttacgc aatgagtgaa aagagtcacg gcagagaaga aatccgtctt      780
catattgttt gcgatgtccc tgatgaactt attgatttca cgtttgaata gaaagggctg      840
aagaaattat gcgtggcagt ctcctttcgg tccataatag cagaacaaaa gaaagagctc      900

<210> SEQ ID NO 55
<211> LENGTH: 450
<212> TYPE: DNA
<213> ORGANISM: Sus scrofa

<400> SEQUENCE: 55
ccagccacca gctggaccct cccggagagg ggctgcctcc tctttcccgc ccagacgccc       60
cccagcaatc tgtggccaag agggagtgat accgaagatg ccacatggg ggcgccagcc      120 cacagggaac cccaggaagg cgctggaccg tcaggagtca gggctgctgt gcacccatgt      180
ggcctgggga ctttccacag cctggtggag atggccgggc acaccgctgc ctcggggaa      240 cgtgcacacg ggtggtacat gtggccggag cccagggcac agggtgaggg gagaagggag      300
catgcgggtg cagactcgga gcccgcgcgt gaggtgctgg gtcctcagga cacgctctgg      360
gagtggagga cccccatcca cgccctcacc cagtgtgtgc ccgcctgctc ccccggaaac      420
cctcacagac acgagggcac acccagcccc                                      450

<210> SEQ ID NO 56
<211> LENGTH: 1133
<212> TYPE: DNA
<213> ORGANISM: Sus scrofa

<400> SEQUENCE: 56
atggcgctca ttagaattcg acctcggtac cttgggatct tttgaccccct acctcacgcc       60 atctacaaca tttacctccg aatgaatgag agacaccaaa agcaaattca tagaagagaa      120
aaaaaggtaa cctggacttt aaaaatgtaa acttctgctc tttaaaaggc agtgctaatg      180
aagttcaaat acaaaccaca gaccataaga aaatacttgc aaatcttgtt ctgacaaaga      240
ctagtgttca gaacatacga cgatcaggga gaggaaaacc agcaatccta taaaactgga      300
caaagaattg gggggaaaaa aaacccactt ggccaagaag ttggtaaata aggccatgaa      360 acatgctca acatcatgag tcattagaaa aatgcaaatt aaaattataa tgagatacta      420
ctacacagct atttgaatgg ataaaaaatg ttttaaaaac tgattatacc caggtttggc      480
aagaacatga gaaacgagat tttcacacac gattggtgga aaacagaaaa tggtccaccc      540
actttggaaa agagctgggc acttccctca aaagttaaac atacatccag gacctcacac      600
aggctttcca ccacaggtgt ttattccaga gacatgaaag cgctcatcca cacaaagact      660
cgtaaatgaa ggtttatagc accgtttgtg gcccgaactg agaaacccca aatgaccttt      720
aaccagagaa tatctaaaca aaatatccat tcacattaat cacccataag aaggaacggg      780
ctatggggac gggaaccgta ttgaagaggg tcaaaataca tacgcagcat caaagaagcc      840
tgcccaaagg acacacactg cagggttcca tggactgaaa ctcgagaagg tgaaaactcg      900
```

-continued

| | |
|---|---|
| ccagcagtga cagagagcag gtccgagatc aacctgatgt ggaggaaagt gaaccctcgt | 960 |
| gcgttgttgg caggactata aactggagca gccctacgg acaacagtag cccgggctcc | 1020 |
| tctcctccat ctccctgggg agcctgagcc ttgagacgct ggggcaagtg cacggcatgc | 1080 |
| tgcctcacgt ggggccccgg tgaaaacacg tggcagctgg ggaagaatc gta | 1133 |

<210> SEQ ID NO 57
<211> LENGTH: 735
<212> TYPE: DNA
<213> ORGANISM: Sus scrofa

<400> SEQUENCE: 57

| | |
|---|---|
| tactgcctgt ctctatggac ttgactcctc tcgggacttc atgcgaggga tcttacagaa | 60 |
| tttgtccttt tgcatctggc ttgtttcact gagcatcgtg tccccaaggt ccatccatgt | 120 |
| tgcagcctgt gtcaggattt ccttcctttt caaggctgaa tagtactcca ctctgcggat | 180 |
| ggaccacgtt ttgattatcc atactagtaa atccatacta ataacttgtt cactgaagcc | 240 |
| cacagcttat gctaccttcc gtgggctcct ccctgccctg tctctacgcc ttctgctata | 300 |
| gccccatccc ctctcatcca ggccacgcct cctgtcccct ggacactgtc ccagaagcca | 360 |
| actgccctct gactgctgct ctcgcgtgac ggaggacaag gcaggctcag gggtccacgg | 420 |
| gctgggccc cagggctccc catggctggt gccccttcct gattccagaa gtacagtggc | 480 |
| agcaccagct ttccagctgc cccaccttct gtccgcaggc tgctcgggtg ggggcaggtg | 540 |
| ggcagtgatg tcacctgctg taaccaccct accgtcgctc atccctgtcc aggaggtcac | 600 |
| ggtgaccttg gcaaacattc tgaacaacac acacctccct ctgcttagag gccggggcc | 660 |
| tccccgggtg actgggggca caggctgacc ccagcctgtc tctgttctct gaaggacatg | 720 |
| ataagtactg caaca | 735 |

<210> SEQ ID NO 58
<211> LENGTH: 500
<212> TYPE: DNA
<213> ORGANISM: Sus scrofa

<400> SEQUENCE: 58

| | |
|---|---|
| aggaagaaca gggaaacaacg gggttgagga gaagaaacgg gtgtctggca ggggcacgtg | 60 |
| ccaacggtcc accgggtgct gccgcgctgc ggcctggcgc cagaggggc agctccgccc | 120 |
| ctcgggccgc gccctgccgc ttgtgctggc tcgcggctgg gctctgcttg gctgggttac | 180 |
| agctgggtgc agccgcaggc tgtggtgggt gccgccgggt cagccagccc ggccccaccc | 240 |
| ggcccgtctc gccggcctgg cccgggcagc cctcctgcag tcgaggagtc gccctgacgg | 300 |
| gctgattggt ccacagcctc agatgcaaac cagccccacg tgcctggagc cagccagccc | 360 |
| gggacaccct ggtggaggca ggaaggcagc agcctggaga gccgcgccgg atgatgctgc | 420 |
| ggggaaaccg ggctcccgcc gggggcgccc tggctctggc caggcttggc ttgaatgctg | 480 |
| acgtgagcgg tggccctata | 500 |

<210> SEQ ID NO 59
<211> LENGTH: 500
<212> TYPE: DNA
<213> ORGANISM: Sus scrofa

<400> SEQUENCE: 59

| | |
|---|---|
| tggcgttgca gtggctctgg cggaggccgg cggctacagc tccgattgga cccctaggct | 60 |
| gggaacctcc ataagctgtg ggtgcagccc taaaaagcaa aaacccaa catatatata | 120 |

| | |
|---|---:|
| tatatatata tataattatg gtaaaataca cataaaatag aatttacctt cttaataatt | 180 |
| ttcagtgcac aattcagtgg cactaagcac attcatgcgg ccgtgtcacc tgctccagaa | 240 |
| cttccatct acccaaacgg actctccgcc catggaaca cgccctgc cctcccccg | 300 |
| gccctgcccc gccagctcct ccctgtgtct gtggatccgg ctcctccagg accccgtgc | 360 |
| gtgggctcac agagtgtgtg tccctctgtg accgatcgtc gtgtcccga ggcccgttct | 420 |
| gtggcagctg cgttatgacc gactaccttc gaatgctcag tgactgccgt gcattggaca | 480 |
| cgcagtccgc tacccttttc | 500 |

<210> SEQ ID NO 60
<211> LENGTH: 550
<212> TYPE: DNA
<213> ORGANISM: Sus scrofa

<400> SEQUENCE: 60

| | |
|---|---:|
| tgctttctgt gccccctcc agcttgggac cccagcaggg caaggggtgt atagggctta | 60 |
| aggaggcagg gggcgtctcc tcccgctggc tgcccagagc accccagcc ccgcctgccc | 120 |
| ctcgtccatc tccagcctgt cctttcctgt gccctccctg tcccgggcgg ccgcacact | 180 |
| ggcttccacc tccccaccca actggcggcc cggtccttcc tgctgaggca ccccgaggtc | 240 |
| cccgctgctg ggaccagct ggcaggtggg tcccactgct ttctcagcgt gggctttgga | 300 |
| gggggatct gcacatacca tcccttcagg cccccgtgggg agcctgggga ccatccggga | 360 |
| ccctgtggg caggcccaga ggactgccag gaagagaccc aggggaccag gcagctccca | 420 |
| ggcctctcag cttcaggcca ggggagccca ccccaggtg gcaggtgaag ccaggccccc | 480 |
| aacccacaaa actgcccgca gggaagtagg agggacagga ggaggggagg ccaggcccgg | 540 |
| gccgcccttg | 550 |

<210> SEQ ID NO 61
<211> LENGTH: 819
<212> TYPE: DNA
<213> ORGANISM: Sus scrofa

<400> SEQUENCE: 61

| | |
|---|---:|
| tgaggagcgc aggcccaggc ctgagtgtgc ccagcttaca cccctggcag cttcgtccct | 60 |
| cctggcccta accccatcc taccccagca gcaggggctc cccccggtggg gcctggtgag | 120 |
| cgtctgactg ggtttggag tcaggtctgc tccaggctca gccccatcc caagggtgc | 180 |
| cctgcagcac tgctgcccac ccctagcgc cccagacct tcgcccctcc agcctggatg | 240 |
| tacccacgga ccctgaaaag tggggctgag caggtgccct ggctggagtc ccctgactt | 300 |
| ggggctggcc aggctgccct ggaggggctg tgggggcaca gcctgcccca ggggcccgct | 360 |
| gggcactggc tctggagctg acgacaggca ggccctctct tcctggcggg ccacacccct | 420 |
| gccctggggt ttggggccaa ggcggcacg cccccatgtca ggcgggggcg aaccaggtaa | 480 |
| ttacagcctg gcagcccgct ccccagaccc cagccccgg agggccccca ccaggctgt | 540 |
| gccaccaaga cctggcatcc agggcccaaa gcaggtcaag ggcagctgct acagattctt | 600 |
| ttaagttgag acagaatcga cacatgacaa gttcctggtt ttaggtactt cgctgccggg | 660 |
| gccgccagtc agtttagtga cccagcacac cccacacagg tacaattgct cttctcaaaa | 720 |
| gaggcccctg agagagcgcc tgtcttggct caggggtaat gagcccaatg ggtatccatg | 780 |
| aggttgcggg ttccatcccc ggcctcgccg cgttggtta | 819 |

<210> SEQ ID NO 62
<211> LENGTH: 500
<212> TYPE: DNA
<213> ORGANISM: Sus scrofa

<400> SEQUENCE: 62

```
ggctcaggaa gcgcaggggc agcgtgtggg gcgacgggaa ccatgggggt ctgtcttccc      60
gcctctcctc aagcccaccg ccctgctgcc cacctccgac tctgcagcca gcatgccggc     120
tagagcccct gtgcacccag ctggtggcct ctggctaagg gcagtgctgg ctgtggacgc     180
gtgtcccctc cccagcagcc caagggtccc atctgccagg ctggtggctg aggtctgccc     240
tgtgtggtcc ttgcaaaaac cccgccctct cctgcccctt gaggcgtgag ggagacgcgg     300
gctgggcgga tgccctcggg cacagccgcc cgcgtggcg ccctgtcgag gaggggctc      360
cgacgtgccc tgacggccct ggccgggcgg agagggtgag gccacctcct ggccacgtcc     420
acccagctgc cacgccgcct agccagtggc ccggggccaa gtcagcagag ccaggcttcc     480
gacaagcaga ggctgtaggc                                                 500
```

<210> SEQ ID NO 63
<211> LENGTH: 700
<212> TYPE: DNA
<213> ORGANISM: Sus scrofa

<400> SEQUENCE: 63

```
gatgaggaag ccgctgctcg tgctgctcgt cttcttggcc ttggcctcgt gctgctatgc      60
tgcttaccgc cccagtgaga ctctgtgcgg cggggagctg gtggacaccc tccagtttgt     120
ctgcggggac cgcggcttct acttcagtaa gtagctcagc ggggcacggg ggcggggcgg     180
acacagcagg tgctccatcg gtgctgcccc ggtacctgtg cgggtccttc gggatggatg     240
gtgtggggga cgggggggcgg gggcggggcca agggaggacc tctcctccga gggtctgaga    300
cttcagaccg ggggcgccct ggccgtgcgc attgattggc acctgccatg tgcctggctg     360
gggctcacac ccctgacgt tcctgcagcg tgactcgaaa cgggaaaccg aagggacggg     420
tggcacgggg tggggaggca gaccgtgagt ggcaggcgtg cgaggggttc tttcgggcgg     480
ggtggcccag gcaggcccca caggatgaca gcctgtcccc tcctgctcct ccttgacctg     540
cccacagcca gggctgcagg cactgacatt cacccatggt attgtggtgc cttgacgtct     600
tggcagtggg cattgggttc atggactgtt tggattgaaa agtgggaata agatgggggtt    660
tgaaaaaccc aattaagaaa taaaagggcg ccctgtgggc                           700
```

<210> SEQ ID NO 64
<211> LENGTH: 300
<212> TYPE: DNA
<213> ORGANISM: Sus scrofa

<400> SEQUENCE: 64

```
tttgaaaaat tttgagtcag tgcagaattc gcatctattc cgcattcagg ctctcctgtt      60
ctcaccttgc cttagtgcgg atcttctata accaccacgt tgacgttttc aaggtactttt    120
attgaataat aagaaaaaag tgcacacaat catgtagtta actttctgtg ctctttgcca     180
gtttgaaggg accctctttt tttccttttt agggcttcgc cgacggaagt tcccgggcta     240
ggggttgagt cagagctgca gctgctggcc tacagcacag ctcttggcgg cgatggatcc     300
```

<210> SEQ ID NO 65
<211> LENGTH: 450

<212> TYPE: DNA
<213> ORGANISM: Sus scrofa

<400> SEQUENCE: 65

```
tcctgggcca caggctgcag cagctcacct gggggctggg gtctcgctct gcggatggac    60
ccatgaaggc cggagccagg tgggggccga cggcaggg caaagggtct gcacacacag   120
cgtcccccccg acccggcttc tctggttct tgggggttg gcgaggcttc tctcagtctg    180
ggtttcctgg ggaactttca agaactggga agtcttccag aaagttgggg tgaggggagg   240
taccccaaa gtgctgctcc tgtccccatc ccccacccg ctgtccatcg gcgagacccc    300
ggaccgccgt ctccctgccg aggtgtgggg tccccccctc tgccggccag ctgggcagg    360
ggtgagcgcc cctgctctg cactcgggac tcagcctggg gaaggcgggc cccaggaggt   420
cctggcctgg acggcagtga ccttccaccg                                    450
```

<210> SEQ ID NO 66
<211> LENGTH: 500
<212> TYPE: DNA
<213> ORGANISM: Sus scrofa

<400> SEQUENCE: 66

```
tgtgcatcca accccagtgg ccacgggggg tgaccctcgg ccggtcagcc gcccgcgtct    60
cccacggaac cgggccttgg cctgaggcag aaggacccag gactccatcc ctgccccgga   120
ctctgccgga gggtgcggtc tgcacagaga ccctctgggg gtgaggccgg tcggggctgg   180
ggttgagatg ggatggtcag gcggccccc gcgggcctgc aggaggctgg gtgaaggagg   240
gggcccagct cagacgcccc caaacctagc ttgggagagc tgcagcccg ccccgtcaat    300
cgcgacagcc tgcccacaga aggcattcaa atgagagaca aatatttggg cttgaagact   360
atacccagcc acgtctcttt gggagcccaa gctgctccca ggcctcatt tgggtattaa    420
ttggttttcg tttagagatt tgcatgctta tcaatggcca ctgggcggct gggcctggat   480
gcggtcccag gctttgtatg                                               500
```

<210> SEQ ID NO 67
<211> LENGTH: 661
<212> TYPE: DNA
<213> ORGANISM: Sus scrofa

<400> SEQUENCE: 67

```
tcccacgacc tgcccctcca gggccacatc tggcgacacc gtcgcaagag ttggaccggc    60
ctggtgtggc cacagcctca ggccttgtct ggccgcccag gccggctcca ggctccaagg   120
agctcctgcc tgccctccgg aaccccagca ccccgggccc gcttccccac cagacctgtt   180
tttccaggtc aaggtcacag ctaatttggg cttaaactgg acaaggaggc cttatctgga   240
gcaggctccc ggccctttgg cctctgccct ggtggggagg ccttcccaga ggctgtgtgt   300
tggcgctgac cgtgcagccc tgagcttgaa cccggataag gaggaccccc acctgggctg   360
gagccagaga gccctcgttc ccagctccg cagggttctc acagtcccgc cctgccctg    420
gggaccctgg acgtccccag caggtgaaag gtccagatgc cctctgacta gaggctcctc   480
cgctgtcaga catgctccct tcccgcaccg aggacgagac ctcagcagcc tgcgtggcc    540
tgggggtgcgg accccaaggc gtctctgagt gtgttctaat ggggagccgt ggggcctcaa   600
cagtgggggt ggcacttgga ggggagcctc cccacagctg ccccaagatg ggccctggac   660
t                                                                   661
```

<210> SEQ ID NO 68
<211> LENGTH: 500
<212> TYPE: DNA
<213> ORGANISM: Sus scrofa

<400> SEQUENCE: 68

| | | | | | |
|---|---|---|---|---|---|
| tttgttggat | gaatgaaatc | atgagaaagt | gattggaccg | ccccgttcgt | ccagctgctt | 60 |
| gccagctgct | ttgtaaagat | gacctctcac | cttctcagag | gcctggccgg | cccgaggtgg | 120 |
| cagtcagctg | agatgccatg | cttgtttggc | acgtgggagg | ccctgtcca | cggcgtgggt | 180 |
| gcctcttgtg | tctaatcagg | gtcaggggga | gcagcaggtg | cagggacat | gtggggccgg | 240 |
| ggccgatgtc | tggggagggc | gggaggaggg | ggtgtgcgga | ggccgttgtg | ggggtgcagg | 300 |
| ggacagaccc | cagcgagacc | ctccctggcc | aggcaccagg | acaggtgatg | ggggccgcc | 360 |
| tccggggcgt | gtgacagaag | cctctcagag | gaggccctcc | cacggtctct | ggaccatcaa | 420 |
| gggaccgggg | gcgctgggcc | tggggtcac | acccagctgg | ccggccagcc | cgggtggggt | 480 |
| cggaggcccg | ggcagttcac | | | | | 500 |

<210> SEQ ID NO 69
<211> LENGTH: 550
<212> TYPE: DNA
<213> ORGANISM: Sus scrofa

<400> SEQUENCE: 69

| | | | | | |
|---|---|---|---|---|---|
| gggcaggagg | ggcccggggc | tggtgcggag | ggtggaggtg | gtgcaggagg | gtgtgaggca | 60 |
| gggctcactg | agcgtgcgcg | gctggctgtg | ccctagagtg | gttagcacgt | gccccacccc | 120 |
| tccagtgtcg | ctctgttcac | ctgtgcctgg | ctcacaggtg | tggaaactga | gactcgggtg | 180 |
| ttgcatgagc | ttccaggatg | agaatcagca | ggcttcccag | gcagggctgt | gtccggggct | 240 |
| ctgggctctt | accaaggagg | ggacaccag | ggacagccct | gcttggggt | gtcgggctgg | 300 |
| ccaggctggg | tggtccttcc | tgtggctggc | agcccttggc | agtcacccc | ttaccctcaa | 360 |
| ctgcccctca | gctgagacac | gacctccctg | cagagccctg | tccacccaga | cactcactcg | 420 |
| cctcctccag | gaagccttcc | agggctgcct | cgccctggtc | tcagcaggag | acagagagag | 480 |
| agggtgggcc | caggagcaga | ggcaggcagc | cagaggggaa | gcccaggggc | cctcactcac | 540 |
| ccctggggcc | | | | | | 550 |

<210> SEQ ID NO 70
<211> LENGTH: 500
<212> TYPE: DNA
<213> ORGANISM: Sus scrofa

<400> SEQUENCE: 70

| | | | | | |
|---|---|---|---|---|---|
| tttgcattca | gctcgtaccc | gggatccttc | ccgggggctc | tgggggtggg | ggaatggggg | 60 |
| tcagaggcag | ctgtcatctg | cctgtcctac | ctgtctcac | aggctggccc | tggagccctg | 120 |
| gcctcctcct | aggggcacat | caggttttgg | gggaggccca | gcccaccgtc | ccacctccaa | 180 |
| gaccacagct | gggagcctgc | ccccaagcc | tagacctagt | ggggctcctg | ccagccaggc | 240 |
| ccccaccttc | atgctgccac | ccaccaaggt | gggacagtgc | agccaggaca | tccagcttct | 300 |
| ggagctgccc | gaggctcagc | acaggctggt | accctaggga | gcaggtcacc | cagggccgcc | 360 |
| tggcgaggcc | tgcggggacg | gggggtaggg | tgggcagcaa | agaacctct | gagctgggcc | 420 |
| gggcggggtc | ggtgagggcc | cggggccgcg | ggctgtgtgc | gtggccctg | agcccgtgca | 480 |
| gacgcagacc | ctgggtgggt | | | | | 500 |

<210> SEQ ID NO 71
<211> LENGTH: 550
<212> TYPE: DNA
<213> ORGANISM: Sus scrofa

<400> SEQUENCE: 71

```
tgtgctgctg tggctgtggt gtaggccgcc agctgcagct ctgattcgga ctcctagcct      60
gcgaacctcc atatgctgct ctaaaaagac aaacataaaa taaaatgggt gcgctgttaa     120
tttgaacact ctgcctcctc cagagacgag gccgaaacag gcctctctga aggtcccacc     180
tggcagggag gaggaggcca gccccgtggg gggcagagag aagcccgatg tccccagaca     240
cacacgcaca gggaccgtgg ccccggctgc cagcccgcg ggggagggc aaggccagag       300
actcccagca gcccacagga ccttggtggc acaggacac aaacacaggt gacggtgggt      360
gaggcctggc cttteccccc ctgggcacga gcacaggaca cacaagagcc ccagcgtgct     420
gaccgccacg ccaaggagcc tggatgaagc tggacaccga gagtccacac tgtgtgatta     480
ggctgacgtg aagtttaaga acaagcgggt ggctcagcgc ttgaaggcca gaacaaggcc     540
gggagggcag                                                            550
```

<210> SEQ ID NO 72
<211> LENGTH: 1300
<212> TYPE: DNA
<213> ORGANISM: Sus scrofa

<400> SEQUENCE: 72

```
atgtcaggat agtaacctgg ggtgctgcag tgacaatgcc agatccttaa ccactgtgcc      60
acaagggaac tccttgacct agaatcctat acccactgca aatatatttc aaaaaaggta     120
aagtcctgag cagaaaagca aaatgggat aattcatttc tggaagacct tccttgttaa      180
aggaagtttt ttggacgtga tgaaggtaga aactcggagg cacacaaaga aagaaagaaa     240
gaaagagcac tggaaacgga gcaaataaag gtaaaaataa agttcatctc tttctcattt     300
tttaattgct ccaaaagata gctgacctct aaagtaaaaa atagtggaaa tgtagcatat     360
gtctctagcg taatttaaag tataacttat agcaatgata gcccaaataa aggaggaatt     420
gagaatatac agttgctgtg ttcccattgt ggctcagcag taatgaacct ggctaatatc     480
catgaggatg caggttcaat ccctggcctc actcagtggg ttaaaggatc cagggttgca     540
gtgagatgtg acgtatgtca cagacgtggc tcggatctgg catttctgtg actgtggctg     600
tggtgtaggc cagcatctgc acctccgatt tgacccctag cctgggaacc accatatgct     660
gctggtgtgg ccctaacaga cacaaaataa aataaaaata aagagagag agaatatacc     720
attgtaaatt tcctcacatg acacaaagag caatgtgata ttatttggta tatggtgatt     780
gattcaagat gtatatcata atattgattc aagatgtata tattccttt ctaaaaagaa     840
gatttataca ataaggcaag agtgaaaata aagtggaatg ctaaagaata gttaatccaa     900
aagaaggcag aaaatgggga aaagacatat aacagatgga acaaataaaa aagagctaat     960
gagattgtaa aatttaatcc aaacatacag ataatcccat taaatttaaa cactctcaac    1020
acattgatta aaagaaattg tcaaattgaa taaacaaagc aagacccaac tagatgcaga    1080
ctatgaaaaa cccacttcat ataaagacat gggtaggttt agagcagaat gatggggaaa    1140
ccatgtcacg caaacatttg tcaaaataaa gctggtgtgg ctgtattcat ctcagacaca    1200
gcagacttca gaacaagaaa cactgcaaag gatgaaagag atactgcata atgataaagg    1260
```

```
gatcaatttt ccaagtgcag gctccaaaca acagaggttt                    1300

<210> SEQ ID NO 73
<211> LENGTH: 500
<212> TYPE: DNA
<213> ORGANISM: Sus scrofa

<400> SEQUENCE: 73
atgacctcat actgaatcga gctcggtatc aggggatctc tcagctgggg gggagggcaa     60
tggggcattt gtctgaggat gccccagggc aggcccattg gctggtttgg tgcccatgcc    120 cccccacac cccggcagtg cccctgctg agcctgggac cccctctggg agttagggat     180
tgggggtggg aaccaggctt tgcagtaatt ccagccccca gggcccttcc ctccccgccc    240
tcaggacccc cagccccgcc ccacacagtc tccactgtga cagcctcacc ccttgggtca    300
agtcctgtcc tctccggccc ccgctgggca gtggagccag ctaggtgaga ggcacaggcc    360
actagggcgg tgggcactgc tgaggacaga ggggcctggg tggccttgga cgaggcccag    420
cgacgctgag acagtgagcc aggctccagg ctttcccagg gagggtccct gaatgtccac    480
ttcttgtgac atcgggtgac                                                500

<210> SEQ ID NO 74
<211> LENGTH: 550
<212> TYPE: DNA
<213> ORGANISM: Sus scrofa

<400> SEQUENCE: 74
aagtccatta gggaagggat tgtgcaaac acagagacag gtgcagggct gggccagctg      60
ctgggctggg ggctcctcaa ggcgcccgta aaccctccc tgccagccgc ctgccgccaa     120
ggtctgctgt ccaccccggc cgggctgctg tgttcccggc gtgtgtcctg cgaacccgac    180
tcccgttcac ccctgagcac tgcctggagg ccggctgccc aggcgggacg ggccctcagg    240
gctgggctgg ctcttggcct gtgtttcatt tctgagcagg tccttctcag tggggggggc    300
cttgggtgaa gcaggcatgt gcaccactgg ggccctgtcc ccagtgggca tcctgggcgc    360
ttgtctggcc cccaaacccc caggccgtgt gcatcatacc ttcaccctga gccccagccg    420
aaccccggac atgtgctggg ggaccctggg cacaggggtg agggagcagt ggccttggtg    480
gaagcccagc cttggcacct ggggaggggg tgcatctggc atgctctgct gtaaccaagc    540
ccagggcagg                                                           550

<210> SEQ ID NO 75
<211> LENGTH: 950
<212> TYPE: DNA
<213> ORGANISM: Sus scrofa

<400> SEQUENCE: 75
gacgtgcagt agccatgacc tctacggccc ccactgacca gcccgtgtcc ttgtcccgag     60
accgacccct aagcaatagg atgcagcaga agtgacagaa cggcctccgc gatgaggtcg    120
cagagggctc tggctctgac tcaggcccct catccctcgc tctcctggag cagggccagg    180
taggggcccc ccagagacgc cctagaggag gtgacgggca gccagcccgc cccagggaag    240
gcctggggac accagggaac agaacggcac aggctcctgg cacagtctcc caggagcccc    300
ctggtggcac agaaatcctg accggcccag tgggggggc tgggcgggg ctcggggagg     360 agggactggg tgaggccgtc tgactcctgg ctgagcgccg catacttgct gcctgcccac    420
gatgccgggc caggccttcc gcacggaccc aggctcacat tcgccctaca tgccactgtg    480
```

| | |
|---|---|
| tgggagtttg ggatggtgtg cccgctgggc ccggggtca gggcacgctt cccagaggag | 540 |
| cgggttccag aaggcccagg tggagaggcg ataggagggc tccaggggc ttcccaggcc | 600 |
| acctgcgagg accctcctgg ggggaaggga gcggagggag acagccgggt cccttaggcc | 660 |
| aaggctgagt tgtgaccgca gggagaggag agaaggagca cccacagcag ggcaggggct | 720 |
| gcgggaggct gtgctgggtg gccgggtggt gggtctgggg gccaggaccg tgggaggcct | 780 |
| cgagggggga gcaggcacgg gaggggcccc tggacggcag agtccctgct ccagctgccg | 840 |
| ccccgacccc aggtccacct tcatttcaca gcctggcccc cggccgctct gaccggccct | 900 |
| gcccatgcag gtgtagcggg gcagtgaggg ccaggctccg gccgtcccaa | 950 |

<210> SEQ ID NO 76
<211> LENGTH: 450
<212> TYPE: DNA
<213> ORGANISM: Sus scrofa

<400> SEQUENCE: 76

| | |
|---|---|
| gcaggcctgg cagcagggaa atgatccaga aagtgccacc tcagccccca gccatctgcc | 60 |
| acccacctgg aggccctcag gggccgggcg ccgggggca ggcgctataa agccggccgg | 120 |
| gcccagccgc ccccagccct ctgggaccag ctgcgttccc aggccgccgg caagcaggtc | 180 |
| tgtccccctg ggctcccgtc agctgggtct gggctgtcct gctggggcca gggcatctcg | 240 |
| gcaggaggac gtgggctcct ctctcggagc ccttgggggg tgaggctggt gggggctgca | 300 |
| ggtgcccctg ggctggcctc aacgccgccc ggtcccgcag gtcctcaccc ccgccatgg | 360 |
| gccctgtgga cgcgcctcct gccccaggct gggcccttgc tggcccctct ggagcacccc | 420 |
| gcccccgggg cccaaagcct ttcatgaaca | 450 |

<210> SEQ ID NO 77
<211> LENGTH: 1363
<212> TYPE: DNA
<213> ORGANISM: Sus scrofa
<220> FEATURE:
<221> NAME/KEY: misc_feature
<222> LOCATION: (206)..(206)
<223> OTHER INFORMATION: n is a, c, g, or t

<400> SEQUENCE: 77

| | |
|---|---|
| cctccagctg ggcccggcag ggcaccgtgc ccctcagggg acaccacggg gggccacagt | 60 |
| ggcctctcct gctccaggct ctgctcccgc ctggggcccc ctgggccgcc cgcccatggc | 120 |
| cagggcaaac tcccagtgcg gctgcccgtc tgggcaaaga ggccgccagg ccccgcgtgg | 180 |
| tcttagcagg cactggcgga tgccgntaac taaccatttc ttccgcagga gtccgaatct | 240 |
| gctctgacca cgggccctaa aaatcgctcc tggcccgcag aggatccccg aacagcgggg | 300 |
| ctgcctcctg ctcctcctgc cgggccggca ctcggcaggc acgtgccctc gtcgtcccca | 360 |
| gtctgtcaac cgtcccgtcg ttacgatccc cagagtccca cgcgcgggca gctctttcca | 420 |
| caccccgcac ggccccggag ctgcctgggc acccagatcg ccctgacgc ctttgctcct | 480 |
| aattctgctg aaatacacat aacgtctcct tgaacgtttg tccattttca cggggacaat | 540 |
| tctgtggccg taggtacact ccccttgggg cgcagccatc gcaccatccg cttccaggag | 600 |
| gtcccgtcgt cccagatgga cactgtcccc actgatccct aattccctgt cccccccagc | 660 |
| cctgcccttc ctgtctctgt ggccctggcc cctccaggga gccctgtgc gtgggatcac | 720 |
| aaaacgtgtg tcccttttgcg tccggtgtgt gtctctgagc atccggagct tggggtgctt | 780 |

| ccacgctgcg cctgtgtcag gacgtccttc ccttttgcgg ctgcgcgatg ctccccgtgg | 840 |
| ggctgcccca cactgcgcgt gttcgctcat ccatccacta aggctgagtt acttttggcg | 900 |
| gttgtgaata ctgctgtgtg aacacgggcg tgcaaatacc tgctggaggc catgctctta | 960 |
| ggcctctcgg ggggcacacc cagagcggat atgctcaata aggtaattct gtgtttagct | 1020 |
| tttgggggaa ccatcaggct ggtctccaga gtgacggagc atgcgtcgca ttcacaggaa | 1080 |
| tggtgctcga ggctttgagg tctccaccac tcgcttccta ttttctgtgc gtcacagccg | 1140 |
| tcggaacggc tgggtggtgc ctctgtgtgg cttcaatgtg cttttctttt tcctggctat | 1200 |
| gaggttgagc gttttttatg tacttgctgg ccattcgcag ggttttgggg gtttcttttc | 1260 |
| ttttttgcct ttggggacgg cgcccagagc gtatagaagt ccctggctg gggactgaat | 1320 |
| cagagctgca gctgccagcc tagcccacag ccgcagcaac gca | 1363 |

<210> SEQ ID NO 78
<211> LENGTH: 500
<212> TYPE: DNA
<213> ORGANISM: Sus scrofa

<400> SEQUENCE: 78

| tcatgccatc gccaccgccc cccacccga cgtttcaaac accagaacca cccctcgggc | 60 |
| ggcagagaga ggaccggaag gagagacagc ctggtcccaa ggcctcgccc ggtcctgtgt | 120 |
| ctccgagcga catttctttc tgtttccctc ctccgcggtc caagtttcac ccatcagagg | 180 |
| cgcattgttt tcatcatctg aaaaaaaaat ctctgtctct taataaaaca caagaaaaag | 240 |
| tagccttcga aagaaagcac atgaatgata tgtgctggcg acagtgctgg cggcctctga | 300 |
| gccgtggtgg gaggtgggag ccagcggagc ccctgaccga tcacgtgacc cacgtctctc | 360 |
| ctgcacagct ggctgcacct gcacgcggtg acacagggac ccagcctcct gccagcaggt | 420 |
| cacccccaccc cgtccgtctc ctgtggaagg ggcagcgttg ccttctgagg gtgggctgct | 480 |
| ctgaggggcg tcctttggcc | 500 |

<210> SEQ ID NO 79
<211> LENGTH: 626
<212> TYPE: DNA
<213> ORGANISM: Sus scrofa

<400> SEQUENCE: 79

| gccatgggct gcggcggttc acgcggcttg ccggcctgcc tggaagtccc acaggaccaa | 60 |
| ggggagggca cgtcagcaca ggggcccgg gcacggacgt tgcccccagc cgccccggcc | 120 |
| cccgccctcc agacaggacg cccggtcacc ttgcggggac agccagcctc gtggcctcga | 180 |
| gcagaagaag tgagagtggg gtgcacaggg gccccccggg gaaggagagg ggacagcggg | 240 |
| ggtgagcggg tgcgggcgtg ctcgggacca gcccctggcc tcttggcgcc tccctccccg | 300 |
| tccttaaacc gggcccagcc tcttgggcct cgacccaagg ctgtttggaa aataggtgga | 360 |
| ccgtggccct gacccgaagg ccagcgggga cccgagtgcg gtccccaatg gatcagcagg | 420 |
| cgcctgggca gcctgcggcc ccgggacccg gagacacagg tgggaatggg aggaggagga | 480 |
| ggaagacggg aggagaggag tgaggaccag cagaaaccac gccctcctct cttcccgtcc | 540 |
| tcgccctcgc ctccgacagc tccgactcgg ctgcaaggaa aaggccccag cccagcccgc | 600 |
| cgccaccggg gggggggggg gggggg | 626 |

<210> SEQ ID NO 80
<211> LENGTH: 500

```
<212> TYPE: DNA
<213> ORGANISM: Sus scrofa

<400> SEQUENCE: 80
tactcgggtt tgttaccact gagccacaaa gggagctcct aaaaataata attttcttaa      60
agccaatgac atggagagca gttagggtgg aggctggtgg gtggtggggc cgcggcaggc     120
gccctgaagg tcctgagtgg cacccttggc cggggaggt gggtgggcga ggggtgttga      180 gaagggcag ggcctcgtgg gggcaggaag gaagagccag tggctcccag tccctgacc      240 ttgctgcctt gagcctggtt ctccccaaaa ttctgtctgt gtcccttcac ttcacggaag     300
cttggggccc gttgccaggg agacagatgg gctggtgaca cccaaaatga gccaccagga    360
ggggggcact gactttagcc agccggtcac atcaagaagc aaacaggccc ccgctgctg     420 taaaggcagc ttgggctgg gtccgggag cacccctgg gctggggaaa gggggtcctc      480
tcaggccccc ggggaggatg                                                 500

<210> SEQ ID NO 81
<211> LENGTH: 427
<212> TYPE: DNA
<213> ORGANISM: Sus scrofa

<400> SEQUENCE: 81
tctattcgcc gtggccggaa gaggctaacc gtacattgac cgggcatctg gcgatgtatc     60
acttctctcc aaccgaaact tcccggcaaa acttgctgcg tgaaaacgtt gcggatagcc    120
gaatcttcat taccggtaat acagtcattg atgcactgtt atgggtgcgt gaccaggtga    180
tgagcagcga caagctgcgt tcagaactgg cggcaaatta cccgtttatc gaccccgata    240 aaagatgat tctggtgacc ggtcacaggc gtgagagttt cggtcgtggc tttgaagaaa    300
tctgccacgc gctggcagac atcgccacca cgcaccagga catccagatt gtctatccgg    360
tgcatctcaa cccgaacgtc agagaaccgg tcaatcgcat tctggggcat gtgaaaaatg    420
tcattct                                                              427

<210> SEQ ID NO 82
<211> LENGTH: 650
<212> TYPE: DNA
<213> ORGANISM: Sus scrofa

<400> SEQUENCE: 82
ggcgttgccg tgagctgtgg tgcgggtcac agatggggct cagatcccgc gtggctgtgg     60
ctctggccta ggccggtggc tgcagctccg attcgacccc tggcctggga gcctccatat    120
gctgcgggag cagccctaaa aaaaaaaaa aaaaaagga agaaaagaga agaaagaaaa       180
gaaaagacaa aagtcaaaag gagctcccct gagcgatgtc tgtctacgag caggtccctg    240
ggagcctgag gcagggtgag cctggacccc tgagggccac tccagactca gtgctctcac   300
tggccaaggt ctttggggac cggctggggg cgcgcgcagg ctaaggagga ggtcagagga   360
ggggcttcag gctgcaggc cagcggcagc tctgggcccg gggcggggg gagatggcct     420 gagggccttg cggggctgg agggtggggg gcttcctgga gtgggaagac gggaagccag   480
gtcagaggag aggagcgagg gctgaagctc ctgaaggcg ctggctaccc ccagctggcc     540
cgccccgctg ccacattcaa cagccacccg gcctgtggtc ctggcagggt cctgcagaa    600 aagccccaag ggcccagcc tggccctctg ggcctaaaga gccaagcccc                 650

<210> SEQ ID NO 83
```

```
<211> LENGTH: 550
<212> TYPE: DNA
<213> ORGANISM: Sus scrofa

<400> SEQUENCE: 83
ttaacccacg gagcaaggct ggggatcgaa cctgtaacct cgtggctcct cgtcggattc      60
gttaaccact gcgccacgac ggggaccccc cagggctggc gtttccctct gtgtgcacac     120
agtggacctg agccaaccag cagggccttc accaccacgg cgcaagagtc ggcagcaaga     180
gagcagtgtc tcatggctca ctttctcccc cttccccgga gtggtgacaa aaccccgccg     240
ccaccggact cggttagaca aggcggtgcc cagtgccccc gtctgtcacc cgcacggcac     300
ggcgctctcc tttctttctc ggggctccac cacgtgtcct cagtttccgc atgagagtac     360
cgcggctggc ggggtggtgg ctctgggggtc ggggccgtg agggcagggc tgggctgggg     420
gaggcaggtc ttggcccatt acgcgggggg cagactccac atcacacgct ctctgtgcct     480
cttggctgcc tgacaccatg gacttcaaac aggaacagcc gtggaggcat gcagcccag     540 ggcccgggtt                                                           550

<210> SEQ ID NO 84
<211> LENGTH: 550
<212> TYPE: DNA
<213> ORGANISM: Sus scrofa

<400> SEQUENCE: 84
tgacacctcc aggcaggagg gtgcaggctg gggtcccagg taatggtgtg ctggcctgtg      60
gggcgtgggc tcagctctta ggatggtggg ctgggcgccg acccagcaag gacagggtga     120
tggcaggtcg tgggctcagc aaatgagtgc ccaggttgtg ggggtgggca ttgggggctc     180
aggggaagct catcagcttg gagagggacg ggggagggag ggggccttgg ccagctggcc     240
cagatgcctg gatgtgagca ctcacgtgcc ccggggtcca cctcccctcc agtgccatct     300
gggcaggagg ctccgatgcc tgtccctggg accgctgtc ctgaaatgag gttcacttgg      360
tgccttcccc agagatgctc ggtccggaag ctgacgaggc aggagtgcac aagggtctgg     420
ggaaatggag cagagtgcgg ctggggcaca gaggctgccc ccagcctggg aagatgggga     480
gctttgcagg ggtaccccgc cagcttgtgg ggccctggat acccaagggt gtgaagaggc     540
tgaagagcga                                                           550

<210> SEQ ID NO 85
<211> LENGTH: 984
<212> TYPE: DNA
<213> ORGANISM: Sus scrofa
<220> FEATURE:
<221> NAME/KEY: misc_feature
<222> LOCATION: (679)..(679)
<223> OTHER INFORMATION: n is a, c, g, or t

<400> SEQUENCE: 85
ctgagcccag ctatgtagat tagaccccgg tccgtcccaa attcttctca aagctgtccc      60
gagatgagag atgaggtttt cgtgtcctgt gctctcctcg cttcccctgg gatgtgccct     120
agggtgggag agggtgtgtc ccagggctca gcaggcggtc ccatcttccc gagacgggag     180
agatcccctc cttctcggcg cctgtcccca cggccccac agacacccc ccccccggca       240 tggcacccat gcacctgcca tcgtgccag tagggatgg gtttggcgag actggagatg       300
gctgtagcca gtgagacatg ccctgccacg tagcctgacc cctgggtgt gctctgtgag      360 atctggggac ccccagcaca cctagggatc atctttgcca gcctcctggg gagcctctca     420
```

```
gaaatggggg ccccagaag gctggcaaag gtgatgggga gcgtgggaag tctggcggtt      480
ggcggggtgg gtgggggca gtgcgggctg ggtgggggt gctccggggt cggaagtggt       540
ccagcaaggt tttggacaca aagtcaggag aaggagtga cgaggagact tgcagaatta      600
caggtagaat caggaaccca catcgacgcc aattgatcta tccccccctt tgattgtttt    660
ctcctggggc ttttttccnt tttttttttt ttttttttt ttaatccctc cttagctttt      720
tacgcgctca acaccaaatt aaacgtactc cccaccccac gtaacagggg ggcggtgacc    780
cgaaggacga ggagcacacg aagccaccat ccgtcacctt ggcggcacca gccgctgtcc    840
tgccctccgc ccatttatcg cccttgaatt gattttgtt ttgctctgtc cctgtcgctt     900
gggtagagtg aaaagggaa cctctgtggg ggtgccagcc actgggcccc ccaaagattt     960
caggggaatg aaacggctgc cgcc                                            984
```

```
<210> SEQ ID NO 86
<211> LENGTH: 550
<212> TYPE: DNA
<213> ORGANISM: Sus scrofa

<400> SEQUENCE: 86
tgcccctgac aaccctgccc tgttagccac actcgcgact aataaggcga gaggtcagcg    60
ggcagcccca cggggagaaa gtgcctccgt gccccccacc cctggctctg atggcccagc    120
ctggcacccc aaggtggcct cggccttcct acctccaagg tccaggcgca tgtccaagca    180
ccagcagaag cttctccagg gttggtgcct gctcagggca gaaagcaggg gtgaggctcc    240
ccaaagggcc actggcacca atgccccag gcagccccag cgaaggggac agcccacccc    300
cagcccgggg acgcaggcct gaggggacat ggggaaccca gagcagggcc aaggggagca    360
gagcccctcc tccgggactt gaaatctttc ccgggggggcc cagggagctg ggtctgcag     420 agggcacttt caaaatacgg cccaccccca aattgccacg tggccacag agcaaggagt    480 cgctgccaaa gtggcctggc ttcagcgcag gaagttcccc tcctggggcc tcccctccta    540
taggcacagg                                                             550
```

```
<210> SEQ ID NO 87
<211> LENGTH: 500
<212> TYPE: DNA
<213> ORGANISM: Sus scrofa

<400> SEQUENCE: 87
tgagccaggg cctggcccag ctaagcccct ggagccctcc cggcctgttt cctgcctccc    60
atgctggcgg agctcggctt actgagcggg ggccaggcca gtgtgcgtgt ggaggtagat   120
tccactcagc tggaggttga ggtgggcagg gggccgcaga ccctcaggcc agctctggcc    180
ggccaggtcc ctgaagctcc cccggctggc ctccccgtcc ctgcctctgg ccttgtcctg    240
gcccttgcct gacaagcttc tgtggctctg cctgcaggag agacactggc tccccgctc    300 tcggatgagg acgggctttt ctgcacaag tcctgcccca gaatgtttgg ggcgccagca    360
gctgagccca gcacgtctcc ccctgcccct ggctggacac gaatcccggc atcgaggcgg    420
gaagggggat ggagggatgg ggcctaccca cccctgctcc ccacccagaa tagctgggcg    480
gcccccatgg gaggccgccc                                                 500
```

```
<210> SEQ ID NO 88
<211> LENGTH: 913
<212> TYPE: DNA
```

<213> ORGANISM: Sus scrofa

<400> SEQUENCE: 88

| | | | | | |
|---|---|---|---|---|---|
| ctgttttcac | gtcttctgag | gacacaccca | gaagaggggc | tgcaggcgcc | catggtgact | 60 |
| ccatgtgttc | actgctgagg | cctctgcaga | ccgtctcccg | cagcagccgc | acccgtttcc | 120 |
| atgccaccaa | cagcgtgcga | ggccgcactg | tccccacggc | tgtgcaactg | ttttgaatct | 180 |
| gagttatata | agcaacagac | gctccttcaa | acacactcac | gtgcacacgt | gcgcacaggc | 240 |
| gcacagacac | acacacggag | taataggcct | ccccccccctc | cctgagccca | gaggggcct | 300 |
| ggggccctgg | agcctgtgct | tagggcctt | ttaggaaagc | tggtgcctcc | cagaggggcc | 360 |
| gccccgagcg | ttggcttccc | aagtccccac | caaccctcga | cagactcaaa | cgttggtttc | 420 |
| tttcgtgctt | ttgcccaagg | gatgggcccg | aggtggccct | gcctgaggtt | tcagcccagc | 480 |
| gccccaggca | ccctttctct | cccggtcccc | ggccacttca | tgggacagcg | ggccttcccc | 540 |
| cacgttgtcc | cctgggttgt | cgtgcttttc | gtaatgagac | ggaggcaggt | gcacctgtcc | 600 |
| tggggtgaat | tctcttctgc | aggaactcgc | ttccccggcg | cctggtctgt | ctgttcctcg | 660 |
| gttgttggaa | cctctcgtca | ccagaaaggg | tggctctgac | gtcgcccttt | cctccgtgg | 720 |
| cttttgcagt | ctgggtcttg | tcggggaacc | tgccccaaag | aggggagtga | cccccacga | 780 |
| gggagacgta | gctcctgtgg | cgacagcacc | gggggccccc | agattcatgg | ggttcacgct | 840 |
| cacagtcgca | tgacgctgcc | tttggacgag | ggcagctcaa | gggaagcttg | tttcctgcca | 900 |
| cgagccacag | gca | | | | | 913 |

<210> SEQ ID NO 89
<211> LENGTH: 650
<212> TYPE: DNA
<213> ORGANISM: Sus scrofa

<400> SEQUENCE: 89

| | | | | | |
|---|---|---|---|---|---|
| tccacacctg | tggagccgct | gcctcgctga | tgccctctgc | ccagctgatg | gtcaggtgcc | 60 |
| cagacttggg | gctcagtcca | aacaggggcc | cacaggtgct | gcacctgggc | aagggagcct | 120 |
| gtgcgcaggg | cctcaggtgt | cccaggctcg | ctgggaccga | agcgcactgg | gtcctggact | 180 |
| ccgggcttcc | ccaggggctg | ctcggggcca | cctggaaatg | aagccccacc | tggctcatag | 240 |
| ggtccacgtg | agggccctga | ggccaccaag | ccaccaaaca | actcagttaa | gggaggggag | 300 |
| cttggggctg | ctaagctcca | agcgggaagc | ggccgcactc | agcactgcct | ctctgccagc | 360 |
| cagccgccca | gcttgctgac | gtcccaacca | ggccagggac | cctgtcccac | agatgctggg | 420 |
| cccttccagt | ctctgctccc | tggaggcgct | gggcactgtg | tgggcacaca | gcccgcaccc | 480 |
| gcctgtaagg | aagggaaagg | ccccatcctc | aaaaaagccg | tgggcaggtg | ggccatgatg | 540 |
| gtcctccgag | gcaggtcctc | ctgggacccc | ttgctccctc | gggctcgccc | aggagccgcc | 600 |
| aggtctgccc | tggattaact | ctgccccgca | tgtcatttc | aaactggctt | | 650 |

<210> SEQ ID NO 90
<211> LENGTH: 700
<212> TYPE: DNA
<213> ORGANISM: Sus scrofa

<400> SEQUENCE: 90

| | | | | | |
|---|---|---|---|---|---|
| tgggggcctt | tggggccgga | gcggccagtc | tgctgggccc | gggagcaggg | ggtctctgtc | 60 |
| cgcaggagg | gggcctggtc | tcaggggagg | agaggaggca | ggtctcacct | gaaaggatct | 120 |
| gccttctcct | caggcctctg | ggatgcctgg | gcagagaaac | cagaaggaaa | ggcccaactt | 180 |

```
gctggctggt gggatgggg ccggggtcg ctcccggcac accccccca aaccccacct      240 tagtggccaa agtgggtgtc atgatggcca ctgacctcac gggggcgcag agacaacaa      300 aatttcagcc actcttgggg aaggacact tgtggcctga gtcttagggg ctgagtttcg      360 gggggaccc ccagctctcc ccccagtatg agacaccctg cccactcctc ccagctgctc      420
cccaaaccca gtgcttctgg acgggcatct ccccgctgcc cctgcagccg ctgtcctctg      480
accatgtccc ctccccacct ccctctgca gggccaggcc tcagggagc agagccgagg      540 cccaccccta gactgagctg ggaccgaga ccccaagtcg ccacccggtc tctgcgttag      600 agaggggtt ccggggggca ccctggggcg gcactggggg gcgggaagga gagccctggg      660
ccgttctggg aaaggtctgg gagggaggga ggggttttgc                         700

<210> SEQ ID NO 91
<211> LENGTH: 1400
<212> TYPE: DNA
<213> ORGANISM: Sus scrofa

<400> SEQUENCE: 91
gcacacccgg agaacagagg gaggggtcct taccagtctc agggttttt tggggatttc       60 tttgaacttg ccctattggt ttcgaggctt ctgttctctc aatcccccc ttctgaaccc      120 ccccaaaaat gggttcagcc cccaccccag ccagaggaaa ccaattgggg gattgggggg      180
aggcggggcc agcaaaagcc ttgggccccc agccccctg gctttggcct ctggcctgcc      240 aggtagggg agggacgcgg tgacctccgg gggcctggcc acggactctg cccccacccc      300
cagggcagac gtgcacagga ggggagaggc tccgaggaat gaggccatca aagggacagg      360
tgaggccacg agccgtggga cctggaagtg tttaggggcct gggggacgag gctgcggcct      420
gcgggctccg tggtcaggag gccctctgcc cactgagcag ctcccaccac tggcacacga      480
gcctctctgg ggtccggctg gtctccggca ggggtgggct ctgaacgtcc agctccgcag      540
acaaatcaga ttcccccgag ccctgagaaa gccccctccc ccagcccgtc tccccacctg      600
tcggtggaca gagtgacccc tgctgacccc ctgcccgggc tcccgcagga gatgtgagag      660
agtaagaggc ggtacaggac ggccggggcg gcccgggcga ggtgcaggtg tgtgggtgtg      720
aggctgggca caggctggca cagcctccct ggcccagtcc cttgggcacc tctgggcacc      780
tcggtgtgcc tgcctcctga agggatccac cctccagcca cctcctctcg ggccagcccc      840
caccccaccc ccgagctaca gatgcctgcg cattcgcccc aagtgtcctg gaccctggag      900
ccaggcagcc cacccgctca gcctggccag accagcgtt gcccttcacg ccctcctccc      960
tcccgccggg tcctcgcgct cgtctcctca ggttggaagc cccttcccac ctgccatctt     1020
gcctgcgccc aggatacacg gctcaactca aggcctcact cctcgccctc tccaaggctc     1080
tgtccaggcc cctctctgac ctggcaccac ctgccgcctc ctggcagccc cagcaaaccc     1140
cctgccacag tccacgacag tcctcttctg gctctgcccc caggatgctt ctagaactgg     1200
ggggggggtc cttccagccc acgcagcatc cactgggccc tggctcccct ccccaggtgc     1260
ccctcagagc ttgcagctgg tgcagacggc tctgctccga acccatgctc cctgcgccct     1320
tggacctggt gagatgttgc aggtcatttg gctgcaccca aaagagtggc ccctcagggt     1380 ccccccctgcg cccctccatc                                             1400

<210> SEQ ID NO 92
<211> LENGTH: 391
<212> TYPE: DNA
```

<213> ORGANISM: Sus scrofa

<400> SEQUENCE: 92

```
gtactgtagg gcctcattcg aatagcctac taggtcacag ctgatccaca ccttaggcca      60
tcacaacttc ccagaggtag tgccgctcct gtcgttgaac aagacggtag tgactgctgt     120
gagagctcag atctgtgggg tcactgaccg agtgtggaac cctgggggaa ggctgtgggg     180
tgtccccggc tgggtggcca tgtcatgtgc cctttctat cccttggacg aggctggttc      240
actcggctct agagcccaa gccccagctg ctctgccaac ccccaagcc tgagcctcat       300
cagacccacc accccatcgc catggctacg caggacacac cgctctccac ccccaccagc     360
cgccccacct ccccgaggtt ccaaagcttg a                                    391
```

<210> SEQ ID NO 93
<211> LENGTH: 1464
<212> TYPE: DNA
<213> ORGANISM: Sus scrofa

<400> SEQUENCE: 93

```
tccaggacct gatgcagcag ccacgtcgcg aggcccctcc cacgaggccc cttgttgacc      60
agcgctaggg aagggaccca gggagatgct gagaacgggg ccttccgagg gggcaggtgg    120
gactgactgt gacccaacac tccccacccc cctctcccgc tccagagggt gccagcctgg    180
aagctggcaa agtccaatcc acaggtgggc tcacgtgggg aggctggtgg cccccacctg    240
gtggggcccc aagctgcctc tgggcggggt ggggctgct  cccagcaggg tcccatccag    300
cttctccctg gggagactca cagttctggg agaagggtcc tgactgcacc gcagcgcccg    360
cccccctcccc agactcaccc aagttctctc tctgcatcgg tgactggtct ccgcatttgc    420
ccaggctggg catctgccca aggatacgt ccaaaggcag ggcaaagccg ggcccgtccc      480
ccggagctcc ccacaggcgc tgagggctgg gctggatctc gggggggtgg aggggaggac    540
tcagaaggtg cagcggggtg gagcgaggct gagccaaggt gcacgcgagg ccagagaag     600
gccgaggcgg gcaggaggag agagcgccag cctggagggg ggtgggtgcc ctgggcaggt    660
ctggggctca agaagaagag agtgtgtgtg caggggggctg tccaagctgc ccgggaggct   720
gcctgcccac ctccagggag caaagcaggg aggctgcagc tggcccggcc ggccgctctc    780
caggaccacg cgtggcccag gcctcaacgc tcctcccaca gcccaggaga cccagggcac    840
cgggtccatt taccgcgggc tccgggtccg tttgcctgcg ccctgggatg gactgtgggg    900
gcggggcgct gtctggggag gagggaggtg tctgaggctg gacaccttga aggcaggtga    960
gagtgacagg tccgtgcgca ggagccttcg gctctggatt ctggccctga gcgagggggct  1020
ggctggaaac tgggccgggg ctgccgcagg agagtgtgca gggagaggag acggggtttg    1080
gccccggagg tgccggggtg gtgccctgga gtgcggctga gcgggaagtg ggtgttggcg    1140
tctggagacg ggggtcgtg ggcttgggat ggtgacaaga cccccaggt ggaggcggcc     1200
gcagaggagg cagagaagcc aggccccagc ccacggcgg gaggcctggg agtcaggagg    1260
gaccagcaga gccctgggct cagtgtcacc ggtcctggca cctcgccgac ggatgtcctg    1320
gccgtgcagt ggttgtcccc tcaccctgag ccctgagaac catgcaggat gctggtgtca    1380
cagcaggaga gggccagggc ctggggagga gtcttactgg aaggccttct ccttccgttt    1440
gcagcaggcg ggaatgactg gggg                                           1464
```

<210> SEQ ID NO 94
<211> LENGTH: 694

<212> TYPE: DNA
<213> ORGANISM: Sus scrofa

<400> SEQUENCE: 94

| | | | | | |
|---|---|---|---|---|---|
| tggagccagg | gcacggcaga | gcggtcccga | ggccgtgcgt | gctgacccgg | gggatgggcg | 60 |
| gacctggggg | tgggctgtga | gcccaggcat | agggaccccg | acttgggcac | ggccaggtgg | 120 |
| ggccgggcaa | gggggaacaa | ggacgctggc | ctccaagggc | cccacgtggg | cacagaggaa | 180 |
| gagccgaccc | aggttgtggg | cgcatggaac | cccccactct | ggggggccagg | aggccgaacg | 240 |
| tcccaagggc | tgaggctggg | agggaagagt | ccctttgggg | gtcagtcagt | gtcccttgtg | 300 |
| ggtgcccccc | tgccactggc | ggcacctctg | accccaactc | cttgcgggtg | gacggtggat | 360 |
| ggatttcctg | cagcctttct | tctggaatag | tctctgccat | cctcggggaa | gcagtgattg | 420 |
| ctctgcccaa | gtccaggccc | cgccctgcaa | ggtgcctccc | accccaatga | gccccggac | 480 |
| agttcgaggg | cttctcacgc | tactgagggg | tatgaacagc | tgtcccccctc | ggaaagtggg | 540 |
| ggacaggccc | ctgccactcc | atcctcggga | cgcccggtct | agtcagcact | tgtctccctg | 600 |
| ccttgtgccc | ccctgacctt | ttttgaggac | catcaaaacc | tcagcctctg | ccccaggagg | 660 |
| tcaagccccc | cgtcccccag | cccccagacc | agca | | | 694 |

<210> SEQ ID NO 95
<211> LENGTH: 900
<212> TYPE: DNA
<213> ORGANISM: Sus scrofa

<400> SEQUENCE: 95

| | | | | | |
|---|---|---|---|---|---|
| ccagccccat | cccccggctg | gtcccccacc | acacagagcc | cccgtttccc | agggacagc | 60 |
| acagcctgcc | cccaggtctt | acataaagtc | accttctcag | agctcctgtc | gcggctcagg | 120 |
| ggaatgaatc | tgaccagcat | ccatgaggac | acaggtttga | tcccaggccc | cgctcagcag | 180 |
| gttaaggatc | tggcgttgcc | gtgagctgtg | gtggaggtcg | caagacgtgg | ctcagatctg | 240 |
| gtgtggctgt | gactgaggtg | gcggccagca | gctgcagctc | tgattggacc | cctagcctgg | 300 |
| gaacctccat | atgccgcggg | tgcagccctg | aaaggacaaa | aataaataaa | taaataaaag | 360 |
| aagtaaacac | accttctcta | gccataacca | cctgcctagg | ggcggagggc | caggaagcgg | 420 |
| cacccccgc | cccaggctgc | ccgtgcgccc | cgggcaggcg | gctcagcctg | cttttgtct | 480 |
| gtgatgtgag | ccgccccagc | cccacatgga | ggggctgggc | tgcgcagtaa | ctgctttaac | 540 |
| tgacgggagc | ttcgaccagc | aattcaccag | cgggcatgca | gccgggaagg | gaagttattc | 600 |
| gtgtgtagct | attaggcgcc | ggagtgaggg | tgtgcctcgc | cctgggccca | ccctgggg | 660 |
| gaggcatcac | agggggttttg | aacacctgcc | catgaacacg | gggcaaaagc | cagccaaggg | 720 |
| ggcaggtgcc | tgaggctggg | aaccaacccg | tgtctctgaa | atccggggaa | tgcccactgc | 780 |
| aggcatgttc | aaagggtcaa | gaccggggct | ctgcctgaga | aggactggcg | aaggccaact | 840 |
| acaaaagcgc | acccctctgt | gcaaacccccc | aaccaatgga | acaaaactcc | agaggggcca | 900 |

<210> SEQ ID NO 96
<211> LENGTH: 550
<212> TYPE: DNA
<213> ORGANISM: Sus scrofa

<400> SEQUENCE: 96

| | | | | | |
|---|---|---|---|---|---|
| agtctgggct | gtgtccatgg | ggttgccaag | gtgccaggca | gagaccttgg | ggacaaaggt | 60 |
| cctgtgagca | gaaggacatg | gccacgtccc | ctgctcagca | ggtgcccagg | ctgggggtctg | 120 |

| | |
|---|---|
| atgccctcgc tggggtgggg gcgggttgag gggccaggcc cagacaccct tcgtccctgc | 180 |
| cggagttgtt tgcccttctg ttcctggaag gccccctgc aggtacagga ggcccctggg | 240 |
| gctgacgctg caccttctga cacctgtggt cttggggatg ggacaggaca gggagacccc | 300 |
| ggggctggac ggagcgggta agacagagag ttgactctgt cctcgagtct gtgcagggct | 360 |
| gtccccggct tgggcttcgt ctgcaggggcc tttcgggtca gggtggcctc aaggtgacga | 420 |
| agacctggtc ctcgggagtc tgcaggcgca aaagttggag cccaccccc cggggagggg | 480 |
| gcgccaagga caggagggcc cagggaagtc tggggcctgc aaggccgtcc gggctgggga | 540 |
| aggccaaggt | 550 |

<210> SEQ ID NO 97
<211> LENGTH: 1200
<212> TYPE: DNA
<213> ORGANISM: Sus scrofa

<400> SEQUENCE: 97

| | |
|---|---|
| gtttgctctc agcaggcaag ggcctccgag gccttaatag cccataatga cagcgcccgc | 60 |
| tcctggcatg gggccccgcc tggcatgggg cagggcaggg cagagcaagc agcatgcagc | 120 |
| ttctaccttc ttcctgacct cgtggcccct tccgaggcct caggggggtcc cccgagtggg | 180 |
| accccagccc tggctctcct ctccagagcc aggcccaagg ctgggagtgg cccagagatg | 240 |
| agggtgcccg agcagggcac tgccttggcg tccccatccc tggcgcctca gggccgtact | 300 |
| gtccaaaacc aaaagaaagc agtcagcaaa acttctccca gcaagctggg gtcaaaggtc | 360 |
| gcttccgagg cgtgatcagg gtggcctttg ctactgtcac cgtgtgccct gggagaggca | 420 |
| cagggacaca gacacacacc tccgagaacc tggggcttcc agggcgtcag gctgcctggg | 480 |
| ccatcccggg ccctgtggt cccaggatct gccgggaccg tgaggcctgc gtcccaccct | 540 |
| ctgcctggga caggccccac agagctcaca gccaggggac cggggacagg gccccgcctg | 600 |
| ggccacctgc ctccagcctc acccagcctg ggccccaggc ctgtgcctgc gacaccctga | 660 |
| gtctcaggac gggcgcggga caaagccgcc cggcccctcc ccggctgggg aggagacccg | 720 |
| cgtggccctg acgtgtgggc ctgtcagagc tgaaatgtca cagcaattag ccctaacgag | 780 |
| gccgagggag ggagcggcgg ggaggccggc ggaggggatc cacgagccga gggcccggag | 840 |
| ctggccaccc caccggtcga ttccaggcac tcagggataa ttgggtgttt agaagtcagg | 900 |
| cggcagcaga gagcgggcca ggcgggctgt gccccccctc ccaccgcccc ttaacaggtg | 960 |
| cccgaacacg caggtctggg gagatgctga ggtcgccaag ggcaccctg gccgtgccgc | 1020 |
| gggtgctatg ctggttcggc accatgggag ctgcacctgc agctgtattg gtctgtgtgt | 1080 |
| gtgtgtgtgt gcacgcgtgt gcgtgtgtac gtgtgtgtgt gtgtgtgtgt gtgtgtgtgt | 1140 |
| gtgtacgtgg ggggggggg caagcccgtg cgtgtggtgc acagtagaca tttagaaggt | 1200 |

<210> SEQ ID NO 98
<211> LENGTH: 600
<212> TYPE: DNA
<213> ORGANISM: Sus scrofa

<400> SEQUENCE: 98

| | |
|---|---|
| ggggaccagg gcccagccct ccagctccca cgcatacctg ctaggagctt gcaacctgcg | 60 |
| agagctttgt ggaccccctg ccgggtgacc cctgaagctg gcagctctcc ttggctctgc | 120 |
| agcggctctc tacactaccc cctctccagc ggcctcgggc ccagacatca cccacccgca | 180 |
| agggaagcag caagcatcca ccagctgggc cctttccccc cagcctgtga ccggccccgc | 240 |

```
gcccccctcac acctctgcgg tccaagaccc ctctctggct gggccctggt gctgcccttg      300
ccgtgcacat ctggggtcca taccccacca acaggcccca ctttttctgtc tcccagtgtc      360 cccctcagct gccctgatgg gcccacacct ggcttctctg ctgcccccct tgaccgcaaa      420
aagactgggg tccaggaccc cctgccccat gactgccctg aagacctca agcctctcct       480 ctcaatcctg accctttaag gctcttgcca cggagaaagc ggctgggtt ggggagggt        540 gtgggtccca aagcagcttg catacttctc ctgactggga gctcattcct ccacagcgtg      600
```

<210> SEQ ID NO 99
<211> LENGTH: 1350
<212> TYPE: DNA
<213> ORGANISM: Sus scrofa

<400> SEQUENCE: 99

```
cccgccttat ttttaaattt ccgaaaacaa aaccacacc tctcccgtcc ccgaaattat        60
tttggtatag tcttattcaa agaagtcctg ccactgaagc ccacttgtcc tgtcccgggc      120
tgctttggcc aagggccctg acgggcccag ggtggctcat tcccgcatcc ccgcagaggc      180
cgccttcaca tcccatgcgg gagcctggct tccggcaccc ggctgtgccc tcgctgtggc      240
catggactgc tttcgcagaa gcatagggc cacaacatgg dacagcctcg ctctgctcgc       300
tgtggttccg ctgaacctct cagctggaca tctgggcagc aagcacccca gctttgcttc      360
aggctctggt tccaggctgg gccctcctcg gccctgcccg ctgggtgcca agcagggctg      420
gtccggctgt gcccccgggt ctatagaagc ctctgcaggg cttcctacag ccaggctggg      480
attcggcggc tgcccgggac tgaggccccc tctgagtctg acccccccat ccttccctcc      540
cacacagccc cccgccccg cttctgcttc agtgaggccc caccctgcct cactcgctga      600
catttccaga acaggggtt ccaggaagcc ctgagcctgc aggggactca gtgaccagcc      660
gcatctgaat tttccctcct tctgatctct ggagacacgt ctggctcagc ctggctcgag      720
tgccctgagc tggggaccag acagacctg cagatggagg tctgagcctg gcagggcag       780 ggcccaaggc tcaggagaa attgcaggtg tgagatcaat gaccggagcc tggatggggc      840
cgccctggcc agggcagctt tctccctgca gctccctgcc actgtccccc ccaactctgg      900
gctcctgctc tggacccagt tgtgtgttcc cctcctccca gccgagccac cctcccccat      960
tctgcccccc ccaatccaac accctatcgt gggaaccagt ggagctgaaa gaaggacccc     1020
ccaagggccc cccagccgct gtaatccttg ggggcctctg cccaggtgcc aggtctcggg     1080 caggagggc cgcgggcaca gccgtggcag atgcgccccc caagcctggg ctcggaggag     1140
ccccgccccc actgacattt ccaggccgcc cgctgcagac ccggctggcc gtgatattta     1200
gacagggctt attgccgtg actggttttt gatgactttg gggcccagga tgagctcagc      1260
cgagcccgcg ttggcccacc ttggtctcag cttgggtttg ataatataac gcgttcaact    1320
gaaccgctga cgcctgcgtg ggccgaggcc                                      1350
```

<210> SEQ ID NO 100
<211> LENGTH: 1354
<212> TYPE: DNA
<213> ORGANISM: Sus scrofa

<400> SEQUENCE: 100

```
gcttgcagta gttcatcaga ttggacgact cataaatgtc aagacatcta aagattggtg       60
catccaatca tttcccacca ggttgttttt ttgtagatgt caagaagctg acccaaaaac     120
```

-continued

```
tcacgtggaa atgcacgtca actgggagag ttgaaacaat ttctaaaaag aagaaggacg    180
tcgtgggagg actcttcgcg ctctttggtt tcgcttcact ttatattatt agttactgat    240
tttcctaaaa gctgcagtag tccagacagt gggcctctat aagggaggg gctcagagat    300
ggttgggaca gaatagaaag cccagaaacg accccccgca aatgtggtca attgagtttg    360
ggcaaggatg tgaaagcggt tcagtggaga agagtctttt caagaaatct ctggtcctgg    420
atccactgct catccaggcc caagagtgaa cttggcgcac atttctcaca gtgtatacaa    480
aaactgactc aaaataattc acataccgtc gtgtagcgta tgaagccatg aaacatccag    540
aagaaaatct cggtaacctc agggcatctg ggcctccac cctcagcacc actggccttg    600
gggccagata cttacgtgtt ctcctgtgca ctgtgggacg tgcagccaaa ccccaacaag    660
gtgaccatca gaaatgtctc cagacgtcgc caaataactg ccagagagca caggagcccc    720
tcactgagaa ccacagggtg gggcagagag atctcagaca tgacacgatt aggggaaaac    780
aatctgacac actggctttg ttaaatttaa aacttttccc ctgtaaaagg caatggtaag    840
acattaagag gcgaagtggc agactgggag aaaatatttg caaatcatgt atcagatacg    900
aagaagatgc aggaaatcct caaagttcag tcacaagaaa acccaattca aaaaccagca    960
gagcagacat acgatggcaa ataaccacga gaaagtcagc acccgctgtc cctggggga   1020
cgcgagtcaa agccaggagg acaccaggat atgcccactg ccaaggctac ggataacggg   1080
aagcaagaga cacagacaga aaggatgctt cggtgctggg gagggtgggg tggggcgggg   1140
ggtcccccccc tggagcagga tgtgaaggca cttggggggg gctctgcact cctgggggcc   1200
tttggcacag gcggagggcc cgggaaggct ctagggcac ggagagggt gccaggcttc     1260
cttacccagc ccaggcagac caggccctgt catgaagcct gacgtgcagc agcaagagca   1320
acatgctaca gacatgtgtc tgtgtgtgtg tgtg                               1354
```

<210> SEQ ID NO 101
<211> LENGTH: 1000
<212> TYPE: DNA
<213> ORGANISM: Sus scrofa

<400> SEQUENCE: 101

```
ggttctcagg cgcacggggc agaggctgag ggtccgaggg gctttgggtg ctggaaagcc     60
tgagtttgaa tcccagctcg gtttcttaaa gctgtgtctc cacggccaag gaatggggcc    120
tctctgggaa aggtctgggg tgaggctggc gggacctgcc agcccggag gcatctgac     180
cagacagctt ctcaagctca cagggcttca tggcaggatg gggaaggctg tggtggggag    240
tggggagcac tcgacaccct gtccaggcct cttgagtcac ggtggcctct gaaaagggt    300
tctctgtgtc caatgagcaa gtcttttgtcc ggggcaggat tactaagtcc aagggtgtct    360
gccccctccgt ggggcacaga gcaggggccc cagatcacgt ggctgtaact gccaggttgc    420
aaagcctgcc accatgtccc actgggttct ccagttacct tgggaggtgc agggtggggt    480
gatgggaaa ctgaggcaga gagctggcaa aagagtgccg gcagggactg cgggcgccag     540
acccagctaa ccgaccctca cacgagctg cttctacttt gcagcctgga cgtgggaaaa    600
ggttacccca cagcagcgtg tgcaggcacg ctggtatgtc tgtgtactta tgcatatgtt    660
ctacgtgcat gcacgtgagt gtgctgtgtg cattgtgcct gtgtgtgtgt gcatgtgtgt    720
gtgcactcat gtgtctatac gtgtgtgtag tgaatgcttg tgcatgtgta tttgcatgtg    780
tatgtttgta cgtgtgcagt gaatgcatgt gtgtgcagtg gcgcatgtg cgtgtgtgcg    840
catgtgtctg tttatacctg tgtgtagtga atgcatgtgc atgtgtgtgt ttacatgtgc    900
```

```
acgtgagaat gtgcactcgt gcatgtttgc atgtgagttt catgtacaca tgcttttaac    960
gtgtgcacgt gtgcacatgt gtttctgtgt cccttgcacg                         1000
```

<210> SEQ ID NO 102
<211> LENGTH: 1500
<212> TYPE: DNA
<213> ORGANISM: Sus scrofa

<400> SEQUENCE: 102

```
cgtataaata tattaatata gaataaaata gattgataat atagataaac taaacccatt     60
atcaataccg ggtggcccca gcaaaggata ctagccagtt tatcaaggtg ctaagtcagc    120
acatagaatg ccacaaacg aaaacctgta ctgcctatgt ccactctaat ggagtatgcc    180
actgacatca gtggtaggtg agctgagtcc atctgggctc ccagttcggg cccggcttgt    240
cccccaacgg aggttccttc cagggttccc caaacccaac cgggccccca ggtctccctg    300
tcttgactcg tttctggagt cttctggggc tctgcagtcc tcccttgttg gggcttctgt    360
cccctgccc ctggccttgc gggctcggcc ctgccctggg tcccgggcct gcgggctcac    420
cctccttctt tccctggaag agagggagcc aggctgggcc gggccaggag ggaatgcgcc    480
tgactctgct ccagatggac aggtcggac atgcagtggc ctcgccttgg gctgctgagc    540
caagagcagg acgggttctt tctggaatgt ggggccagcc aggttcagcg tgtgggtggg    600
cagccgccag catctgtcag ggccgctgca ggcgcgggga atgacctcga cttctgcttg    660
gcacccagct ctggaacagc ccctgcggga gcctccgccc agagctgggc cagagggtcc    720
cctgtgccgg ggaccccagc agggcccctc cctgactctc caacccacct gcctgggagg    780
agtggccccc tggcctccgt ggatctctgg gtcgggctc agccggcttg acagcctggg    840
aacagccaat gcacatcccc aggcctggcc acacccttcc accgggagcg ggcggatctg    900
catttcgcca ggctctgcgg gcagctctga gagccccggg tctcggagcc cagccgtggc    960
cgttgtacgc cctgggggct gtggacagcg tgtcctcatt gcccctccga ggtccggccc   1020
aggtcccctc ccacctgctc gcccagagcc ctctccccac caaccacact tcctgctgtt   1080
ctgcaagcgg gacacacact ccggtttcag gacctttgca cgtgccgctt cctctgcaga   1140
gaaatgcctg gagcagatgt ttgtccgcac ggctgctccg cgaggcctac cgagagcccc   1200
tcacctaaac ggccgggcct cagcagcccg ggggccctgtc ccaccgccc aggtggtggg   1260
ttctcctgtg ccagtgtggg catctctgta agatacctgt ttatctgctc atcgtctggt   1320
ctccccaga aggtagagca gggcccggca cagccgtcct cggggtggcc actcgccctt   1380
ggggctcagc ctccatgcag ggagggacgc ctggtgacac gagagcccg tgtgagtgtg   1440
ccggccgcc agcctgcctt aggtcacagc caaagccggc attaaccacc aggccctcga   1500
```

<210> SEQ ID NO 103
<211> LENGTH: 600
<212> TYPE: DNA
<213> ORGANISM: Sus scrofa

<400> SEQUENCE: 103

```
tctagaatac ctggccctcc agggacgtgt cctgtagctg cggctttcag ggcaaagtgt     60
aattaaacat ccccaggctt cccttccagt tggcacaggg cacccacatg aggagcagcc    120
tctgggtgcc aaagggccca ctggtgccag gcgctgggct gagtgcaccc ccgcatgctt    180
cccgcccact caccctgctgg ccccacccct gaccacagca cctgtgggaa cactaggcct    240
```

| | |
|---|---|
| ggcagccaca cgctgctctc actggaggcc agtgccaggc agcctgcttg gctacgctag | 300 |
| cagatgcccg ctcgcctctg cccctgcccc tagcccatga aggagcccag ggtggggcac | 360 |
| aggaaggacg attggggccc caggtcaggc acatccaggc cacagccgtg ccacacgaa | 420 |
| ggcggccctg aggggcgtt gggggcaga ccctgccccc ccgctgccgc cccagctcca | 480 |
| ggcattaatt cccagggacc tgttgcactg ggtggccgcc agcctgcccc cttgccttcc | 540 |
| aaggcctcta aaatgccccct cttttcgtaa actaggactt accaagctca gcgagccctc | 600 |

<210> SEQ ID NO 104
<211> LENGTH: 1867
<212> TYPE: DNA
<213> ORGANISM: Sus scrofa

<400> SEQUENCE: 104

| | |
|---|---|
| agtatatcgg gtgagactgg ggaccggtct gccgggaagc ccaccataa aggccacgtt | 60 |
| gggccacagt ccgggccacg tgagtgtggg cgggtccgcg ggtctgctct tggaacacca | 120 |
| ggatctctaa gaggtaccag ccgaggccaa gttcacgtga gcaagtgagc aaatgactga | 180 |
| atgagagcgt gagcgaatga gtgaggggtg agtccgtcca ccacgcagcc taggctcagc | 240 |
| caaccgctgt ccccgcgtct ccactggtga ccagaacgga aagagtgggg aaagagtggt | 300 |
| tgtctcccac aacccagtcc caaccccccc tggacgcccc accctccag gggtgccggg | 360 |
| cctggcctgt gggccccagt ctggaggctc tggcaccttc ctcatccgtt ctcccagcac | 420 |
| cccaggttcg tgctgagccc tcctggccca caggcctcgg ggacaaagag gccacctgg | 480 |
| aggctcaggg agcctcacct gcctcgtggt cctggcggag gcgggtctgg acatgtgata | 540 |
| gaccggcctg ggctcagcag ctcctgctgg aagatgtcag ggacagcctg gccactctc | 600 |
| ccaccaggag aacttattcc tcggtggggt ccccccgggg aagggatggg atcccagcgg | 660 |
| ggaccccaga gcgtccagca cacggacctg tccctccagc ccctgcccca cacggatgct | 720 |
| cacagctcag cctcgaacac gcacctgttg gactttgcct cctgaggctg tcttctcagc | 780 |
| cgacgcgggc ctccgctgca tggtctggaa gcccagtggg actcggtggt gacagggaac | 840 |
| aggggctctt ggagtggggt gccggggag ccccgaggga gctgcttggg cctttgatgg | 900 |
| ctgagtgggc tgaagtcagg caggctcccc cagggctccc tgaccccccc cacctcaaaa | 960 |
| aatccagagc atcctttgct ttgggtctgg tgaggctctc tgaggtcaga ccctgcgtgg | 1020 |
| ctgggccagt ggggctggag caggaagaaa gcaggacagc cccgccccct ggcccagact | 1080 |
| ccccaaaccc agcaggagac acctgaaacg ggatggaacc atcctgaaaa gagccacctc | 1140 |
| ctcctcctta tgcatcagct gccggggtct ggggcccgc ccaggcccc agatgtccgg | 1200 |
| gctgctcccg tctcacatcc aggggtttct gggcccagga ctctgtcccc caagcatgc | 1260 |
| agagggtcca ggctggggtc ttcatgcctg cccgtgtgca tggtggggaa ggaaggggac | 1320 |
| agtctgagaa ccccccgccc tccccatgcg tggcgccggg ggacaaagcc ggctggggtc | 1380 |
| tcaggttttgg gttcagagca aacgttgatc tgacctggtt ctgagatgct cggcccgatg | 1440 |
| ctgcgttgtc cgctcgcatt ttcctgttt ctctgggagg cgctgcgtgc gctgtggctt | 1500 |
| ccggccagcc ccacggaggg acgcagggtg gctggcgggg tctgggggcc cctgcccgca | 1560 |
| ccagaacgtc tggctcaggt ttttgtcctc gtgacccatc actaagggcc accctctgac | 1620 |
| ccggagccct gtctccgagg tgggaattgg gggctgtccc tggcgtcata ggacctggtt | 1680 |
| gggggcatcc agggctgtgt catgcccctc cccagaagac tctgggggct gcgggagggt | 1740 |
| ttccccagct tcgggccagc ctggggaggg cggaaggcgc tggaggcctt gcctgtccca | 1800 |

```
gggagcatgg cttcgctgca gactggggcc ccgcacaccc agccaccact ggccgtctgg   1860
aagcact                                                              1867

<210> SEQ ID NO 105
<211> LENGTH: 650
<212> TYPE: DNA
<213> ORGANISM: Sus scrofa

<400> SEQUENCE: 105
gttgaggatt cctcggcaat ttcctcgtca ctggcgctcc aatcgcctcg atgggcttct     60
cctccagata cagctgcaga tcctgggcgg gcacaccgtt gagcgtcacc tcgtagtgca    120
gattgcactc gttgtcaatg acatccagg ccatgccgac ggcatgtgga ttctgtgcat    180
ccgtgtgctc ctgtcgcttc agcagaatgg gttccgccga gtcccgagca tcggccactg    240
gacggggcac taggcggcca cggatcaggc tcgtctcatg ctcggtggcc acattaacgc    300
ccagttcgcc ggcatacagc gactcgagga ccttgggacc caacttctcc acactaccaa    360
tggcctggtt gaagttgaag ctcggcgtca gatcctccag cttggccttc cgcttgccct    420
gctcctcaat caaactgatg ttgggcctat cccgggtgtt cacgtgctcc gtttcgatgt    480
tgtaggccag agatccatcg gtgttcaagt agacccacgc caaaccgctg ctcttggtcg    540
aggattcggc actgtgcggc gccagcaggg tctggaagat ttcgcagctg gctcgggtca    600
cgatgtgtcc ctggatgcgc agatgtgggt acttcttgga ctccacggtc              650

<210> SEQ ID NO 106
<211> LENGTH: 1630
<212> TYPE: DNA
<213> ORGANISM: Sus scrofa

<400> SEQUENCE: 106
ggtgttgtca ctgctgtggc tcagacccct gctgtggcac agggtccatc cttagcccag     60
aaacttgcac atgccacagg tgcagccaaa agaaaattct tactaataag ttgttcattt    120
gcctttacgt agagtggcat caaacagcaa atttaaaaca ccatctatca atacatagac    180
cgcggtcaaa gggaaagaac tttctatttc agcacctta acatggcttt gcccgaattt    240
gggaccaggt gctgtgtttt tcatctctcc ctgcaggtgg tccccagatg accaggccgg    300
tcctgggcgg gaggagccgg actgtggatc cagttgcttc ccaagacagg ctgacaggag    360
agcagcaagg gccacccca accgaaacca aagccagaac gagcagaaag atgccgtctt    420
ccaagtgggg gctgggagct tcctcccatc ctccggagcc gtgaggctgc cctggagctg    480
gcaggagcca cagaggaccc ggctttgacc gcccctctgg gacccacaat caggaccctg    540
actcagatgc tgagggggct ggacaacacc ccaggaccct gctgcttccc cagaaccgct    600
gtgtccatca aggtccagat ggcacccgtg tccccactgg agcacgcact ccgtggggca    660
ggctttccct tgggcaccga tgcaccttga gggcagagac ggggcccaat aaacgtttcc    720
aaaccagtgg gtgagggacc cgaccggccc gacacggcag cccggatgca gggactccgt    780
gcttggccca gcctcccttg gggtggtcct gtgtcctcag gggtggatag ccatcatgt    840 gggtggcctc tggggacatc cgttctctga ttgggtgagt ttcagccaca gagatattcc    900
caggactaca aagctgggtc ccttgggca cctgctgtca caaaaagaca aggccctgac    960
ccccagtagc caagttcccc caggggctcc ccagggtctg gtcatccaga ctgtgccagc   1020
cgtgctgccc gccccagtcc tgcctgaccc gagtctctgt aaacatcccc cggccccacc   1080
```

```
cagctttacc ccaaggccga aagcaccagc cccccctgcac cacagatgag gcccccatgg    1140
ctccccgacc taacttctgt ctgcagttgg ctttcagcct cgggtgggg caaggcctgc      1200 atctcaggct cccgggagaa gttgctgcct ccacagcaga gccaggggcc tgctgaccac    1260
ctgggccggg tcggatctgg tctagaatgc tgctaaggtg tccttgcagg cagccccggg    1320 cggcccccgcc ctccaggaag gaaggggaca ttgccaggac tcaggaatga agccatccca   1380
ggttttgaat ccccggtccc accaccttcc acctctgacc tcaggcacct cggctttcag    1440
agctgccctt tctgactctg ggacacgggg ctgtgaggcg ctctcggtgt gtgacagctg    1500 gggggggca ctctctaacg agggtgggcg tgcccaggtg actgaccaca gccctttcct     1560
ctctcaaaaa cgcccgcccg agtgacctca cgggaggcag ggccaggaac cccaaaccaa    1620
accagaatca                                                           1630

<210> SEQ ID NO 107
<211> LENGTH: 1820
<212> TYPE: DNA
<213> ORGANISM: Sus scrofa

<400> SEQUENCE: 107
agtgagccct gcaggacagt ctgctgaggg gtgtctgggc tcctcagagg ctcatggcca      60
cgggcactgg gaggatagca ggtggacccc tgcatccagg tcccaggtcc caggtcccag    120 accccccggac aggctttcta tctgcaggag gggggctcct ggggcagcag ggatgtggct   180
gtgaggcctc gtcagtctcc ctgtttctat ctctctctgt atcacacaca cacacacaca   240
cacacacaca cacacacaca cgcacgcacg cacacacaca gaggcgtgac cagggctgca   300
gacagggcca tgggaggact gcccggcagt gcacccagat ggccacacgg tggggccctc   360
gtcccacttt tgctgctgat gcttccgccc aggctgctgg gagcaagcac tagcttccca   420
gggctctgac cagagaggga tgggaggggt catgggtcaa caggcgccag ggaatgggga   480
ataggatctg aggggcgggg gcaaggggcc caggcgaggc tgcagtgccc agagctccct   540
gcacctgcag gaccagccac aggccaacag ctgcaggcag agcagggctg ctcctgtccc   600
cagaagctgg cacagcacat ggggtctgac agccccaccc cgggcctccc acagagggc    660 gggtccccca aactcctccc ccgtcccacc tcacagctca gcatctccac tgcctgagga   720
cgagcccaac acacgggcac acacacacat gcacgcacac acatgaatgc acctgcaagc   780
acacactcac acgtaagcag gtacacacat gcatgcacac aatgaacaca catgcacgca   840
cacacgcatg cacacacgca cacacactca aacacgtaca tgcaagcaca tgctggtcct   900
ttgtccccgt ggagggagg atggaggccc agcccgtggg gagggcatgt ggagtgttgg    960
ggggctggct ccaacgccct cgctcaacag gcaccaacgc tggactgaga taagccgggg   1020
cgctggctcc cttggggccg ctcagcaggt ttgacgccca ccacaggtgg cactgcctct   1080
ttcagaagac ggatgtggcc atgccaccct cacagcctca ccagtccccc ctcagcttta   1140
gtggtgtccc tgtcactgta cccggggcct tccttcttcc agggccaaaa gcgagttcag   1200
gggacagtgg cgcccccata attactcacc cagggtgctg tcctctgtgg tggccttgag   1260
gccaaggtgc tcccatgggg gcccacaggg ctggcagggt cacttcctga gagcacccag   1320 ggccagggg gtgccccagg cctggccggt ccccatctgg aatgagggcc ttgcgcagag    1380
gcggtgcacc cctcttttaca gcagccccgg gggagagtga ctcctgcgtc atggacctgg   1440
gggctgacct gtcacgtgtc tcgcccagtt gcacccatc catttccggg tggaagggac    1500
aaagccatcc tggtcgtctc agaggacctc tggagcctct tggccccagc agcccagccc   1560
```

```
ctcccgggcc cgcatcctct gcccacccaa aatcacctgt gcccacaggg tccccttctg    1620
ggtgtccagg gcgacccaga actgccctg cagacacacc cagcccagga catggccgcc    1680
ttgccgggcc tgtctgcctg gggcagcctg actgccacag acaggccgct tggaggacca    1740
tctgcctgag cccccaaggc catcccacg gggcccacac agccagcgcc tgtagacgat    1800
gccacttggg gtgggggag                                                 1820
```

<210> SEQ ID NO 108
<211> LENGTH: 1500
<212> TYPE: DNA
<213> ORGANISM: Sus scrofa

<400> SEQUENCE: 108

```
tgccgaatag aggtggaaac caagacccga aaaaatgtcc acattttca attattagaa      60 atttagaaaa atattttaca ggagttaaaa ggtattccat tctggggggcg ggtgggcatg   120 cccacggcat gcaggcattc cccgaccagc gactgaactc gagccacggc agtcaccatg   180
ctggatcctt aacctgctga gccctgggc aactccagac actccatatt catgtaaact    240
attttttaac caaaaaaatg acaaagcttt tcaaaacaaa acacatttca tgggaagagt    300
ggcattgctt cacgcctgga tggtcgctgc ggcttgcggg acgacgaggg ccccgcggg    360 agcgcctccg cacggcgcat caggacgtgg tgtccaggga agcggggtca cttcacggcc   420
tctcgggtgc gcgtgggttt cctttttcggc accacacccg gactcagcac ttggggggttc  480 ttaaacgtga gaggcactgc ggggctcgaa gcccatcac tgacctcctc agactctgtt     540
atgtgaaaac ccatccgtcc acgagaccaa agagacagac gaacaaacgc aaggtggcgc   600
ctaggttggg cacagcatga gggcagagcg gaaaccttgg cgaaatcccg gcgaagcctg   660
gacgtcgcca gctcttactt gacgcaaaca tagggggatt caggaactct ctttaccgca    720
tttgcaatta atttgctgca aatctaaaat cgttccaagc acaatgctca ctgcatggaa    780
aaacccaggg gtaggtctcg cccgatcagg atgttttccc gtgccctctg tgcgggtgct    840
gccccctgcg ctggtcagtg agaagtgtcc ctccaccgac gacatgaaac ttcccaggtc    900
cacgctctct gctgtcctgg acgaaaactc atctctgtga atctcccgcc agctccgcgg    960
gagccttcca gggctggaag gacggccgtc ccgttccagg gggcaggtgc acgcttccca  1020
aagctccgcg tcctgctagg acgctcagac ggcatcaccc acaaacccca cgaactgttt  1080
ccctcgaggc gacaggctcg cccttctccg agaaagcagc ccgcacacgt cagcaagggg  1140
ccagctgcgt ttgtaactca aatggccaca tagagtttgt cctggaggca cggggtctgt  1200
ctgggccgca ccactgcaca cgcagaatat gctgggacac gctccgggt ccagcttcat   1260 ggaattaata aagtttactg cttcaccaag tacattctta agtgtagctg gccgccagcc  1320
tgggcgtccg ctccgaggct gcctctctgc ctggaaccct tgtgctgggg gaccctctct   1380
ccagccccac cccagccccg agcccaggca acatccttct tgtaagacac ccgctaccct   1440
gccctcccgc ttctccttct ctggatccaa tctcctccgc ttctaagctc tcttgaggct  1500
```

<210> SEQ ID NO 109
<211> LENGTH: 550
<212> TYPE: DNA
<213> ORGANISM: Sus scrofa

<400> SEQUENCE: 109

```
atggcactcg cggttgtgac tgagctaccg gacggcgcga gcagggccac gagggcgaca      60
```

| | |
|---|---|
| agcgcggggc tgagaacctg tgcgagggca ggtccctgcg gctgcagaca agcctctatc | 120 |
| gcaggcccac agacaggagc cccgtgtga ccctcaggct gcgagaccaa agtcacggct | 180 |
| ctgctgggaa aacctcgaac ctgatgactg ggtgggtgac cccaggacct tgaattccgg | 240 |
| cctctgcaga acgtctgag cctacgggag tggccaccct ctcggttagg gcctgtgtcc | 300 |
| ttccctggct tccagcctag agcaaaagca ttaaatcaca gtgtggccca gcccggaccg | 360 |
| tgcaggacct tagacaaaag aggagggaga gagagatgag gcagagaggc agagagacag | 420 |
| aggtggagag acagatagac agagacagag gcagagagag agacagacag acagagacag | 480 |
| aggcggagag acagacagag acagaggtgg agagacaggc agacagagac agaggccgag | 540 |
| agagagacag | 550 |

<210> SEQ ID NO 110
<211> LENGTH: 900
<212> TYPE: DNA
<213> ORGANISM: Sus scrofa

<400> SEQUENCE: 110

| | |
|---|---|
| tttctaaact ctcttactag ttctagtttt ctattgtttt ctgggggggt tctatataaa | 60 |
| cattcgtgtc gtgattggag atggttttgt ttttcctct ccaaactgta tgccatgtgt | 120 |
| ttcttttct tgtcttatca cactggctag gacttccagt aaaacactag atatgaacaa | 180 |
| tgagaggaga gccaggcctt cttctcagtc ttggaggaaa cagtcagtct ttcctcattt | 240 |
| agaatgagag cttttctttt cttttctttc tttcttctt ttttttttt ttaataggtt | 300 |
| aaggaacttc tcttgtattc ttatttttt agagttgtta ttttttttt ctctcttttt | 360 |
| agggctgcac ccgaggcata tggaggttct aaggctgggg tcgaattgga gctacagtcg | 420 |
| atggcctacg ccacagcaat gtgagatctg agccacatct gcgacctata ccacagctca | 480 |
| cagcaatgtc agatggttaa cccactgaac aaggccaggg attgagcccg catcctcatg | 540 |
| gatgccagtc agtttcgtga ccgctgagcc atgaagggaa cttccaataa tgcaccaatt | 600 |
| ttaaatgaaa aagacaaagc atccagccca cagcctgagt aaggagtttg gaggcctgac | 660 |
| ccctgcgtgg tcctgggcct gggcctgggc tggtcggggt ggggggggt gggggggacc | 720 |
| ctgtggaccc tccctcctca gccaggcctg cccctccatc cctagctgtc ggggctcgg | 780 |
| aggaaggcgg gtggatgacg gtccctggga ccctcctca tatgtatctg ggtccctggt | 840 |
| ccctctgagg cccaggtcag gtcatgggag tcaaaggtca gccaaggggg tagcccagag | 900 |

<210> SEQ ID NO 111
<211> LENGTH: 950
<212> TYPE: DNA
<213> ORGANISM: Sus scrofa

<400> SEQUENCE: 111

| | |
|---|---|
| taacccactg accgaggcca gggatcaaac ctgcaacctc atgcttccta gtcggttcgg | 60 |
| taaccactgc gccacaacgg gaactccttt gcttttgttt ttaggatttc acatacacgt | 120 |
| gataacgtgc cgtatttatc tttctcatct gaattatttc acttagccta agcccttcag | 180 |
| ggtccatcca tggtgctggg agtggcagga tttgcttctt tttttttttt tttttgtggc | 240 |
| tgaaaatcag tccaggatta tcttcttttt ctgttcatct gtggaggaca caggctgcgt | 300 |
| ccgtgtgacg ctctgccggg aatacggggg ccgatcgctt tctgagccag tgttctcatt | 360 |
| ttcttgggag aagtacccgg agtggaacgg ctgggtcgtc ctgcagttct gtgctgcatt | 420 |
| ttttgaagac gctcggagcg cttccacag tggctgcacc gactgacatt cccaccgaag | 480 |

```
tgcacggatt tccccatcct tttccacgt ttccccgca cttgctattt ttgccctgtg      540
gatgtcggcc tctccgtcag gtgtgagggg agtctccgtg cggcccaggc gaggagcgac      600
cgtgagcgtc gtttcacgtt cctgttgggc cacctgcgtg gcttctccgg aaaaagggct      660
gttcaggctt cttgcccatt tctcagtctg attgtttggg gggtttgctg ttgagttgtg      720
tgagttccgc acgtatgggg ggcatcaacc ctttatcagc tatgcgattg gcaagtccgt      780
tctcccatgt tccgccggcc gccttggcac gtgtgggcgg tctccttggc tcttccttgg      840
tgcagaaggc ttcggtctga tgtgggccca tttgtttatc ttcttttctt tcctcaccgt      900
tgttttgatg tcagatgcaa aaatccattg ccagggtctg tgccgagaac               950
```

<210> SEQ ID NO 112
<211> LENGTH: 306
<212> TYPE: DNA
<213> ORGANISM: Sus scrofa

<400> SEQUENCE: 112

```
cgccacctca atcgccggtt tgttctgcaa cacggtccag ataaccagcg cacctaacag       60
gtcgaacact gccagaactg cgaacagcgg gctgaagccg atggtgtcag ccagtgcacc      120
gacaaccagc gcaaacagcg tacttgccag ccatgcggac atcccggtta aaccgtttgc      180
cgttgccact tcgttacgac caaacacatc ggaagagagc gtaatcagcg cgccagacag      240
tgcctggtgg gcaaaaccac cgatacacag cagcataatt gcgacatacg gttggtgaa      300 caggcc                                                               306
```

<210> SEQ ID NO 113
<211> LENGTH: 800
<212> TYPE: DNA
<213> ORGANISM: Sus scrofa

<400> SEQUENCE: 113

```
gttttccatg atgcaccagg ggggccggga ccgcagcagg gaaggctcca tcctggctct       60
gtaagacctt gaaaacacct cattcctctg gtcttggcct gctcttcggt acgccaagtt      120
gctgagactg atgtggggat cagtggggag caggaatctt tctgattcag ccgtttcaaa      180
gtgtcccaag cagaagctgt gatggcaatg ccaaggctat ccatggaggt ggctgtgcca      240
ggggccccat ttcctgggag cccattccag gaaaggaatc ttgtagcccc aggctccagc      300
agccagtgca cggcccctgg gactatccgg gtagatcaga gggaggaaca gagctgtgga      360
tggtaagcag gtggcccaag tccaatttat gtctgtggtc ccagcagggt gcccaggagg      420
cccctcgtaa ctcttaagaa tcttggtctg gtcagctaaa ttgtatgacc attgtactga      480
gcacacatcc cgtttaagta gaattttcaa ggatgactag gagtttgcca cctgaaggca      540
ggaagggcat tccaggcaga gggtacagag gtgagaggga ggctctgaca ctttgggcgt      600
gcagggggtt tgatgtgact gcagctggca cacagtgtat gcccaggcct ggcacggctg      660
tgttggtgtt tggagaggaa gggagaggtg agttgagccc aaggtcttcc aggccaaaag      720
actgaaggtg accgcggctg tccggggctg gcccgcagac caggagggag caggtgggag      780
ctggctcttg ttccggggac                                                800
```

<210> SEQ ID NO 114
<211> LENGTH: 3062
<212> TYPE: DNA
<213> ORGANISM: Sus scrofa

<400> SEQUENCE: 114

```
cacaccccag gagaggaaag acccacacag tcctgatgac agcttggctc ggggctggag       60
ccccgagtta taaatgtcca tcacgagctg tgttctgtca gagccatcag tgggaaggcc      120
aggccagctc agcagcccaa aaatgaagag ctaggtctgg gattgggccc aagcagaggg      180
cacaggaaag ccacataaac aaggcaccca accccctgt catccaccaa tgtcacattc       240
aggtcacacc cctggtcttc gggggaggtc ccctaagatc cggtggcagg gggaggaaaa      300
gtctgactgg attccttgac aggtgtatca gcggaaggcc aggaggagtg ctcgggcact      360
gccacctccc aggggcatga tggtcatgga ccagatggca gttatgggag gaacctcccc      420
cgtggtcaga gctctgggtg ctgtacctgg tcatgcattt cgagtggaag gaaaagaaaa      480
catacaactc cacccccagc agctttaggc tgttggtcta aaggtcctgc ctcctggaag      540
agacacgcct ctgtcagcgg acactgctaa acctaaagga gaactgcca cctggtcacg       600
ggacttccta ggccaaccaa cctacaggtg acggcccgga gcatcacgag gaggtagggg      660
acgggaaggg atgcatttgc tgctcagcgg atccactggg gcgtttctgg agcccccacg      720
cccacacttt actgcaaatg cacaagcccc aggcagcagg acaagtcaca gtagctctgg      780
gttatccaag gagtcaggga cctacctgga agagtctaga acaggtgaca gaggagggag      840
aggatggtac cagcagtata gggagaatca gaaatctgac ccaccctggg ggcctgactg      900
actcccagac caaatgccac actcaggttc cccgtctgcc tgcacttcca gggctgggcc      960
acgggagtta tgggcccag gtagcatcag aggctcccag gtacaggcac aagcagcaac      1020
cacaggaggg atccaggcca gggagcatcc aagaagcagc agaagctcca ccttaggtac     1080
agttctggca cctccaagtt gagaacatgt cctagacagt gcctgacccc aacccaatgg     1140
agtgtctggg actagactag gcacgccatt ttggtcccag gttgccccat ctgtacaaag     1200
ggtgtgcggc cccaggggg acacaatgag ctcccatggg aagggtcttg cgaatctcct     1260
tagaagcaga tgtaagaggt gacgtccagc ttgtgcctgg gatgtagaag tggaaaaagc     1320
accctcccc cgacaaggat gaaagcaaga ggcacaaaac aacctgaaat tcccaacgcc     1380
cctggagatc cttggagaac tgggattctc cacctgtagg ggcacctgtg aggagaggct     1440
gtgtgagcac ctgctgacct ggcacagagg atgcccaata ctaagaagca tcagctaaaa     1500
gtctccagga attcctggaa gctgaggaag ggctcaggag agggtacaga agccctgggg     1560
ctatagatat aagggacgtg cacacccact tgcaggtccc catggacccc agggacattc     1620
acagtgatgg gcaagattcc caaaatgcac cccttgtgtg tgggcctggt tcggtgggtc     1680
agcagacacc acaccaaagg cacaaagcac acccctcag gctactctcc tccctctccc     1740
ttgtggaaca tgagccttga gatgctgggg cacgtgaaaa acactgtcac acttaggtcc     1800
tggtgaaaac tgactgcggc cagcggaaag aatcataaag accctacacc cacacacagc     1860
cttaattaca gctgtgagtg gggctggagc cccaagaatg tctacaccca taagacatag     1920
cgttaatcag aaaaacaaga acagccccaa ccccaccacc aggctgacaa ctaacaggtc     1980
atgttggaat atcactggga atgttctagg agtgtagaaa gacacaccaa ctagggcatg     2040
atgcaaagat aatacttcag cctgggagtg gatgtgacac agggaaaagc ataaagtgat     2100
ggcagaggac tttgatgtca gtgatggaag ccacaaaaac ttctagctta gctccattcc     2160
caacaagatt gactgcaaac cccatgctaa acaacagca aaagaaaga atcctcattt       2220
ccaggcataa aatttttccc ccagtctctg ctgtcctcca taagatgtct gatttcaaca     2280
ggaattacga ggctataaga aaggcaagaa aaaactacac actgtcaaga gaaagccatc     2340
```

```
agaataacca gactcgtagc acagacactg gaattgtcag gatatttaa ataaccgtga    2400 caaatacatt aaagattcta atgagaaggg ggtagacatg taagatcaca tagatttcag    2460
caaagagatg aaactcgaag gaaaattaaa tgggagccct agagtgaaaa acactgtagc    2520
agagaagatg ggttcatccg taaacatgac acagcttagg aaagaatcag tgaacttgaa    2580
gacagggcca cagaaaatat ccaaactgaa atgcaaggag gaaaaataat gaaaggggga    2640
gagagaaaaa ataaaagaac aaagcatcca agagctggag ggtgacactg aagaagagag    2700
cataggcata gctggaatct cagaaagaga gaaagaaata acccaagatg taatggatga    2760
gaatttcaca gaagcgttgt caagcaacaa accatacatc caagaagctc agagaacacc    2820
aagcaaggta agtactgtaa aaaaatagcc cgaggtatac ctcattcagg ctgctgaaaa    2880
tccatgacaa aagaagtctt gaaagtagcc agaaacagaa ggcgtgttcc attcagaggg    2940
aaaagacacc attgttgcca gaaaccaaat aaaccagggc tgaaagggta aaactttttt    3000
tttttttttt tttttttgg ccatgcctgt ggcatgtgga ggtttcccga tcagggatca    3060
ac                                                                  3062
```

<210> SEQ ID NO 115
<211> LENGTH: 1300
<212> TYPE: DNA
<213> ORGANISM: Sus scrofa

<400> SEQUENCE: 115

```
aaacggataa atacaggtga cccacaggca gaagctgaag tacaaacagt tcacaacggc      60
acccaaaaaa taccgaaggc tcaagggtaa atctgacccc agatgaaagg ccttctcacg     120
gaaaatggca aagtggcgct gagaggcatg agaggttcga atagatggag ggctccgccg     180
ttttcccggg tccgaggatt cagtgacgtc acgacgccaa ttcctctgaa acgcctctct     240
aggttcagtg cagcccagac ccactggcag ccgccctcgc tgcagagaca gcccagctgg     300
gtcttgaggt tcctacagcg aagcaaaggg tctagaaaaa gcagacgtct ctggaaaggg     360
agaagcagcc gatggattgg catacggcga caggagattc ctcggacagt ggcaccagga     420
gaggggtgga cagagactgg tgcaaccgag cgggcccagg aataagtcca caccacacg     480 taccatctcg ttgtttatttt atttttttcct tttcagggcc actcctgggg catgtggagg     540
ctccccagcc aggagtcgaa tcggagctgc agctacaagc ctaccccaca gccacagcga     600
cacaggatct gagccatgtc tgcagcctac accacagctc ccggcaatat tggatcctta     660
acccactgag caaggccagg gactgaaccc acgtgctcat ggatactagt tgggtttgtt     720
accactgagt cacagtggga actccttaa ttttaatttt tgaaggttca gaactcttta     780
attttttagt gaggtataga ttatattacg caccatttct ttctgacttc ggtgcacggc     840
ttttcaacaa atgggtgctg gacctgctgg gtgccttctt caaatgaacc acaagccctc     900
cctcgcgccg tatgcaaaat ttaactcgag gggctcatag acataaacgt aaactctaaa     960
gctataaaat ttccagaaga aaacgtaagg aaaaccttt gggtcttggg caaagatttc    1020
ttacccatga cagcaaaatt acaatctaca gaagaactgg tggcctttat cggcatttaa    1080
aacacctgcc ctttgaatga tgctgtcgca aaaccgaaca tgcagcaaaa cggatgcaac    1140
tagcaggtct cacactcagt gacccacgtc agaaagggaa agacacgcca cgtgacatcc    1200
cttagatgca gaatgtaaaa cacggccccc gtgaaccgac ctcaagagag agacagacct    1260
acagacgcag caaatttggg gttgccgagg gggatgccgg                           1300
```

<210> SEQ ID NO 116
<211> LENGTH: 3000
<212> TYPE: DNA
<213> ORGANISM: Sus scrofa

<400> SEQUENCE: 116

```
tgtgagaccc cttggcgggc caggacccc caaggtgacc gaaggcctca gcgccccag      60
ccgcccatc cccctctttc cgacacagg attttttcc caccaagctc tgttcccttg     120
gtcacgctct cacttgagca gcctcagggt ctcccggtgc ctgtatccac gacagcgtga   180
ccttcttggt gtgtcaaccc aggacccac gctggccagc cacgccttcc cagagcaccc    240
ccgcccatcc tcagagtcca gaggaaaggc ccccattgac cccagaaacc aaaacgcaga   300
gactctggga cgccagcaag aacgtacact gactcccacc tgcttcaggc acggaggcag   360
gggtgggtta tgagcgaccc cgtggaaggg ccttcttgtc catcgagggg cttccagggg   420
ctcctagacg gggatgagtg tggcaacatg tcgccgcatt acaaaagacc ctgcagtgct   480
gctgggatgg gtccccggc tagaaaagca aggattcca gcccagtcga gtaggaggcg    540
gcctcggagg ctgcagaggc gcgggggcg ctgaccacca ctcggcaagc ccgtgttgg    600
aggggacgcc cggcccggct gcagccggtg cgcctccgga taagctccta agaggccgcg   660
tgccccatgc acgcgcgtgc acacactcgc tgcccgaggg tccttcagca cagaccttgt   720
ggggacggag gacctggcag gggtgtggct ctggggaagg ggtctgtccc aggaaccctg   780
ttctggattt gggggtgggc gtggatatcc cgtcccaacc tacagaaggg aggggcttaa   840
aaagagcccc tttggtgtga ggggccagca atcctttggc ttttcttgg cccacttgga    900
gcttgacgtc tggtcagtga ctgggagcca gggccagagg gggcagccg ggctgaggca    960
ggttcaggcc aaccatctct cggccacact cccgaggtcg ggcagctacg ggcccccag   1020
agacacaagc cccaggggtc cttccccccc gccccctgcc ccagatcacc aggagaccca   1080
agcagctctg cctccccgtg cctgagaaat gccccatctg ggtacccaaa tcaccctccc   1140
agaaggtaga gtggggggcc caggacaggg ggaccccagt tacagagccc caggcaggct   1200
tcccaggggc gaggggactc cgtttggggc acagacggag gcagagcggg ctgatggatt   1260
ctcccccggt tcagggatgc tggctgcctg gcctccagga gccggcgtg ccatctgatc    1320
tgattaaggc ctgcagtccc agctgggcgg gcacagcctg ggggctcggc gggcagggaa   1380
gaaggcgctg tcgccccagc cggtcaggct cgctttctct tcatttcctc tccattaaaa   1440
gtgtcagaac catttattga ttttttaaat caggacgtgt tgtccgtgac acagcaaagt   1500
gaacaaaatc agagcaaaga gaggccaggg ctgaagcccc agagggcggc gcctccaatc   1560
cgggttgtgc ccggggctc caagccctt cttcttctgg ggtcctgggc gtagtggcca    1620
gggcagaatg cacctgccgt catcctggga ggcttggcca tcgctggctt ctgtctcatg   1680
acgcaccgtc gttccatatc tacgaaaca gcttcgcatt aacaggcagg ggaggcggtt   1740
gtttctcctt tatctgccca ccatcggcgc tggggccacg tggagcccag ccggctgact   1800
tcccgctcgc acgcagggca ctgattgcag gaacgaggac atccagcccc cgcctctcaa   1860
tgccccgggt gctgagagca tttcgcccaa acggcttggg tgggacaagg gatggagctg   1920
tgcgccaggg gcctggctgg ggcagaaggg ggcctgcccg tgtctgcccg tggcctccag   1980
cacctcggc tgccaggctg ctctggagag gtgcccgggg gccgagggcc aggggcaccc    2040
tgttctgccc cacgtctctc tgtcctgctg aaagttccac cagacgcgtg ctataccctg   2100
ggagtcagga ggatggggga tagttggggc ttgacgtctg tttctgaaaa acaccgtttc  2160
```

```
tccctgaaat atatatgtat taattttcg tcaagataaa actgtgtata gttttcgtg    2220 atgagaaaac gcatccatct tccttagaaa gcctgaagag gtacaggagc ctataaagga    2280
caagatgaca gatgcctcta acgcacacca aatgtgcggt ggcccccagg ggaccgcata    2340
gacggggcgg ctccagatgg ccaccgtgtg cgagggacac ggttcagggt ggcagagtat    2400 tcctggggg gggggctca gcggttccca tttccccctc ccttccttcc ttcatttctt     2460
tccttctttc tttcttttg tggttttagg gccgcacccg cggcgtgtgg aggttcccag    2520
cctaggggtc taatcagagc tacagctgcc ggcctccacc acagctcacg gcaacgccgg    2580
atccttaacc cacggagcga gaccagggat ggaacctggg acctcatgga tcttagttgg    2640
gtttgttccc gctgagccac aacgggaact ccagccattc ccatttcttg ctccagttcc    2700
aagaattcca attcttattc ctgttctta aggccagagg cgacagccac gccgagtccc     2760
agaagcaggg ctcaaggatg ctgctgttga ctgtgtccgt gggcggggg agttgataag    2820 aaccccccaac acagggtggt ggccagcaac ggggagggg ggaggggggc tggtggggaa    2880
aagtcccctg aacccatgg gctgccccct ccaggctggg gcacgacccc gagccccatg    2940
gcccgaggag aaacggtccc agcccaggc tgggctcccg cacccctgcc ctgacccgc     3000

<210> SEQ ID NO 117
<211> LENGTH: 1895
<212> TYPE: DNA
<213> ORGANISM: Sus scrofa

<400> SEQUENCE: 117
tcatggaagc ccttatcaca acctcggatc caaaacccac tgcgcgagtc cagggataga    60
actcgcatcc ccacagaccc tatgttgggg tcttaaccag ctgagccaca tggaaactgg    120
gtaatctatt tttagatgtt cctagggttt ttggccttgc ctgtacgtgg ggacgctgct    180
gggccaggga tcaaacccgc gccacagctg tgacccaagc agagcagtga cagcaccgga    240
tccttaagca cgaggccagc agggagcccc tgtgtttaga ttttggtgag gatactgcgt    300
gggattcagg atattcactt tggggctgtt ggaattgccc gtcgctgttt aagcaaagag    360
aaatcccttc actctgtgta actgtgggga aatcctttag tctcttgaaa ccattgcgtg    420
tgtttaagag tggtaactct gccaccataa atgcccagac cagcgccttc ctgagatccg    480
cttttgttgc aaatatctgg tttgaatgct ttgatcgccc gcaccagacc agggtgggcg    540
gacgccgccg ggaccccgac gtgaccatcg tgcttctgta tccgcccttt ctccggcacg    600
cgccccctgg ttgcctctgg ctgcttttag tggaggaact gaagcctcgc cacccagacc    660
ccgagaccgc aggacccaca atgcttcaaa cacctgccct ctgacttta caggtcaagt    720 tcgccaacgc cgaatttgca ccgattggct acagagagca cggtggcgcc aagcctccac    780 ttggagttt ataaggtctc cctccagctc gcaatgaaaa tgagctgtga taaggcaaag    840
acaaaattag tatgaaatcc agatgcttca tctacaatac aatgaccgcg ggatttgggt    900
ctgagcgact gaaatcaagg tgggcttccg gagggaggct gttagaggaa aggcattcac    960
ggaggctcag gtccgagagg cttccacacc cctaagaggg ctgagacggc aagtagggac    1020
caagccccgc agtcgggaga gctgggcagg aaggaagtct gaggtcaccc ccacctgggg    1080
aggaactgcc tagagaagcg ggggcgggaa gcaggggatg cccagtccca agacagggac    1140
agggcggaaa gggctctctg caggcccctca atgctgccac agtgtcctcg taagaggag    1200 gcagagagaa ttgacaccgg ggagaccacg ggaccacgga ggtggagacc gggctgcccg    1260
```

| | |
|---|---:|
| cgcgtgccag ttgctcccga agccggcccc tcccccagag cctttgggaa gaggcgccaa | 1320 |
| cctgcagttc tgctactcgg ggacagggac agggacagcc ccctggagcc gcctcttagg | 1380 |
| ggcagcatcc cccagaacct tccttaacag accatctgga gagagatggg tctgggctgc | 1440 |
| agctcctgga actgttttgc ccacccggcg agcaccagtg ggtgccagcc tgggctgccc | 1500 |
| agcctcaggg ccggggaggg ctgagggcac tggggcccgg ctctgggact cccctgcctc | 1560 |
| ctgcccgtgc aggacagcca cctcccagca tctgcttcct gccacccaca tccccaggac | 1620 |
| cgtcagccca ggcatgcccc tggcgtcggc cactcacacc acaggccagg aacccaaggg | 1680 |
| ggcaacacag aagggcagtt gccatctgca gatggaatgg acaaactggg gtccgtgatg | 1740 |
| atggcaggct ctgggcgccc gggctggcag gggagccagg actgtgcggc catcacagga | 1800 |
| agggcatgac ggggtgaaag caagagtgga aacctctgcc acccgcctgg gcgcacatac | 1860 |
| cggccaccct gcagccccac ccccatttgt ttgct | 1895 |

<210> SEQ ID NO 118
<211> LENGTH: 1040
<212> TYPE: DNA
<213> ORGANISM: Sus scrofa

<400> SEQUENCE: 118

| | |
|---|---:|
| gcgcgccgga tccttaatta agtctgagag atctgcggcc gcggccaggg tctgcttctg | 60 |
| gccaagtgtg gggctctgct ccatcctggc tcggaggtcc acccatggca aagcctgggg | 120 |
| tcctccccact gaatatttgg gggtccactc gtgccaaagg ctgggtgtcc agtgtgccaa | 180 |
| cggtacatgg aagcaatgtc ttcccaagga ccgtccaagg tgtggtcagg cctggacagc | 240 |
| tgtgagtccc ttcgggacta gacttggtgg ccgaacccta gggaccgtgc ccagggcccc | 300 |
| ccacgaggcc aggtgtttgc cccagggaca gaacggccaa gggtggccga gggttctttt | 360 |
| tgtttgtttt ttcttctttc tctttttctt tggccgaggg ttcttaaagc gctctctctg | 420 |
| ctctttgtcc cgatcctgag cgggcagtgt cctggtcggt ggggtgctgg gcagccgcag | 480 |
| cagggctgag agagcccggc ttgtcactag ggcgcgccgg tgagcccagc gggcatgccg | 540 |
| tgtccagacg ttggatgggg cagcgagggg actggggtgc cccagccccc gtgggaagcc | 600 |
| cgccctgtgg aagccgctgt gctcgccaca acaagcaccg tcgactagct ggtgaatcag | 660 |
| cgcccgtcgc ccgcgtaatc ccaggcgctt tctgcccaac ctgagccctg accccacacc | 720 |
| ccttgcgacc gctccgtgga ccctggggcg atgaggtgaa ccgtgggctt ggccatcgtg | 780 |
| gtggcagacg gtgcacacc cgtgcgcctg tcggcccccc tccatccagg agcagagtgc | 840 |
| gcacccagtg ggggctgggc agggagccgc ctccacctcc gccctgaggg gacgggactc | 900 |
| tttcgacccg gagtgggaag ggacatatgc ggacgatgcc agaccctgtc tgtgggggga | 960 |
| gggggagaag gccctctttg gagaattcca ggacgggtga ggaacgtgtg ctggaccggc | 1020 |
| cgggtcggag gtgggccttg | 1040 |

<210> SEQ ID NO 119
<211> LENGTH: 9236
<212> TYPE: DNA
<213> ORGANISM: Sus scrofa

<400> SEQUENCE: 119

| | |
|---|---:|
| ggcaaccagg ggaagatggg gaagcggggt gcaggggcgt ttgcgcgggc caaggaccac | 60 |
| cttggaaatc tggagcctgg caggagcggc gcagggttga ggggctggct tgggcagggc | 120 |
| tggctggcac ctgggagcct ggcggggttg aggtccgggc tcccaggtgc cctataggca | 180 |

-continued

```
gggcaacatc ggcatggggg gtgacaggcc cgagctgggg tgcggaggga agagggggga    240
gccaggcatt catcccggtc aattttggtt tcaggtcgtg gcggctggtg gtcagggggga   300
gttggagaga ggttcgcccc ggggcctggg gcagcggagg tgtagctggc agctgtgggc   360
aggtgaggac agccgtctgc cgggccaggt gagtccccct ccctcccag gccttgtttc    420
tctggcctcc tgcatccgga ggttctgggg agcgagggcc ggcgaggcga agcggctgac   480
cccccggcag agtggcggcg gacgacaggc aaggcgggca gaacaggtga cacgtctcag   540
ggggagctgg gaccgggcgg ggctgggggg ccggggccgt cccaggtgga aagagcatct   600
caagcgagtc tggtgggaga cgaggcaggg ctgccagcag ggaggagacg caacaggcgg   660
ggggcattcc aggcccgggt cggacaggac ccgtcggggg tgtcaggaca gtggggtccc   720
cagccgccac ttcacccact gcaattcatt tagtagcagg tacaggagcg gctctggccg   780
ggcctcttga ggcctgagct ggagcctcga gggccggaga atgggaaaga aggtgcagtg   840
tgccagacag acgtcacctg gagggagcac ggccgtgggg acgggcccca gagagatttc   900
ggcagcaggg aggctgcgcg ggcccagcct gcggacgtgc gttcccacgc agcactgcgg   960
cccaggggct ggcgcggcag ggccccggt gtccttggtg gcactgtgcg ccctcgccgc   1020
tcgcccctgg gactggcacg gcagacagga cagcacccag gggagtcaag ggcactgacg   1080
agaccagact aggcgaggcg ggtggggtgg aatggatgtg acctctgggg ggagggaggt   1140
ggggacgcag gcaggggcga ggcgccggag cctggcggcg agcgaggcca aggcgggcct   1200
ctgcgggtga caactgagca catatgggta cctttgcgct cgcaccggag acaggtgagt   1260
gtctggcccc ggcctgccgc cctcccggcc ccgccactgc ctctgccctc cccctcgacc   1320
agggccctct gcttccccac agcctcgtct ccagtggggg tggacacact gccagcacca   1380
caggccggac gccaggatgt gcttggaggg acatgacaca gtccggtgtg acggagaggg   1440
acagacgtga cgccgtccgg ccttcctggt gagcgcaggt ccaggccttg ccccccaggc   1500
cagccgcccc accccccacc cctcatggcc gtcttctgtc ccgcagaaca ctctcggctg   1560
gccccgcggg ggagctgcca cacccagcgt ctgttccttt gccttcctga aggagcacgt   1620
gcatgactgc tgctctctgg accccagaac cctcaaacga caaggtgagg caggtcccgc   1680
ctcgccccac acgtggaagg ggcgtgggcg agagccgggc gctcacggtg ccccccctccc  1740
cctgcagaga tggtgctacc cagctcatgc ctgggccttg gacccggact tcttcaagtc   1800
ctcctagctc tgactcaaga atatgctgca ttctggagcc actacactac ttgactcagg   1860
aatcagctct ggaaggtggg cgcgcgctcc tcccgctccc ggagccccgc ccgctgcccg   1920
ctccccgctc acgtcctgtc tctgtcctcg tccgcaggtt gagccaaagg aacagacgtc   1980
ccacaccacc ggaccaacgg caccgcgggg gttccccacc cccgcccgg ccactccacc    2040
tcggcggcca cccctgctg cgccctggag acaccaccag cctccctctc tcccttcct    2100
cctttttttc ctctgtcttt tctcttctct tctttcctct cctttgctca gaagactcgg   2160
ggcatccagg actctgtgtc cccgtccttc ctgaattaat ttgcactaag tcgtttgcac   2220
tggtttggag tcctggaacc agccccgggt ctcggagcgg gtgtgtgagc tgccgagtgg   2280
cctggcctcc tcggcccgcg ccccctcagc acctgccatt gtccatctct gtctgggggt   2340
gactgggtgg gggcctgagt gtgtggggcc ccgccctccc ctctcctagt ctggaagctc   2400
cgaccaccga gcagacctca aacgctgcac tgagtgtcca tctcgtcatg tgcccctcct   2460
cgccagggcc accccagagc cctggactca tcaataaact cagttaccgg aatctgtctc   2520
```

```
agggggctttg caattgggct ggggggtgcgc cggggaaggg gggggatgaga tggggaacat    2580 gcaaggaagg gcctgtgggc tgggggacac agaatgggtg gggaggggggc tcacaggact      2640 cggggggtaa tgaacgtggg gctgggcgca aaggggagtg ggacgtgggg atcagggcgg      2700
ggggcctgga ggatgcaggg tccctgcagg gaaagggggc cgagggcgtg aggcatgtcc      2760
tcagccctga gaggccctac cccacaaagc acagcctgcg cgcgacctcc aggcccccaa      2820 accccgccc cagaccctga agccctggtc cagggcagtg ggtctgactg gcggaaggaa      2880
catgccaccc aggctggcca caccactggg acgcccatgg gcggccactt tcatcaagag      2940
cctggcaggc cctgagtgct gggctggagg gcacagaggg tccccctccc ctcacgcttt      3000
gcggtgctgg ggcaccgcag gagtgcccaa caggagaccc caggaagtct gctgggctgc      3060
agcgaagggc agggtagggg ggcggcccac aggggcccag ctcagtaggc aggtggcagt      3120
gggaggcggc agaaagttgg aaagggtgga ctgggcacgt caggatctcg tggcggcagc      3180 cccgagcca cggccttggg tgcactgcag ccccacggt tggtgtcccg gtcccaggca      3240
gcagctgggc tggtgacgcc cctctgcctc tgcccacccc cccaccgcc ccccgccag      3300 cctcccagcc cctgggcgcc tggcgtgacg ctgggaacgc gagggagcag gcctcggaaa      3360
cagggctggg tccttgaccc cttcctctgc tcagggcagt caggaaatgc ctagcgggcc      3420
gactgaccga gaggagatag cggaggcctg ggagaccccg cgctcgtgcc gttcccagcg      3480
tccggccgcg tggcccttgg ctggcctggt ttgggcccca tgagctcacc ccccgccccc      3540
cacagcctcc ccgcgtctgg tctcctctct gggccctgct gtccctcctg acggggggaca    3600 gagccctcca gggcccggg gggacggtcc cgggtcagca gggcgggtgg gcagcacagc      3660
tgcgtttggt gaagcccctg cccaaagcac cctcagcgtt tcctctgcgc gtccggccgc      3720 cccggaggc tttcccaagt ccacgggcaa ctcgcaggcg agcccactcc acctccatca      3780
cgcgggtttg gccagcggca gaagcactcg cccttcaggc gtcaggagtt aagcccctcc      3840
aaggcccggt gctaatcagc tgcctctcct ggagcttcgc aaagcgggct ctcagagccc      3900
agcttcccgg gggctcaccg tggtggcatg ggcaccacag gtggccggag gggcaccgag      3960
cacgacgggg ctgtgggggg tggaggaggg aggttggtga ctccgaacct ctactgaggc      4020
acacagagga cacggccgct tccaggggag tcagcctgcg aagggcagag gggctgtagc      4080
ctcccggtca cgccctcgcc tctgccctgg attcctcctg ggggcccgcg gctcgtcggg      4140
gaggtgagtg cccctggatg ggcgtaggct ggggggggcag ggagtggggg agccccgagg    4200
ccctgggccc acagccctgt cttgcccac acacagggct gtctacactg ggtgcccact      4260
tgctctgctt ctaggctgtt ccctgggcag ctgcctggag ggccgtgggc acagtgcggg      4320
cagccagtgg ggaggccggg gatggggccg gggataggga cccctgcccc tgggtgagcc      4380
ccacctgggc tgggaagaca gcagcagcgc cccttcaggt ccatggacca ggggacccag      4440
ggtggactgt gtttaccttc agcccaggcc agtttcctgc ttgagaaagc ccggaggggg      4500
gtgcgggaca ggcccgggcc ccccacgcaa aggcagtttc gcaatgtccc tgcgctgact      4560
gaaatgtcac caggcacacg gcttgaattt ctccccaga cctggcaggg gcgggggtgg      4620
gggcaccggg ctgctgggat cttggcccct gaacctcccc cggccctgcg gccagggagg      4680
gtttaggctg agtgacagcc cacggaaacc tggacccgac atgtctgtgt gtccatgtgt      4740
gtctgtgtgt gcgtccacct atgcgtctgc gtgtgtgtcc atgtgtgtcc acatatctgt      4800
gtccacgtgt ctgtgtccac gtgtctgtgt ccacgtgtgt gtccacgtgt gtccatgtgt      4860
ctatgagtcc ttgtgtgcat ctgtgtgccc gtgtgtctgt gtgtctgtcc cctgcagtcc      4920
```

```
ccgtggacct gtctcttata cacatctcaa cctggcagcg ccccttcagg tccatggacc    4980
aggggaccca gggtggactg tgtttacctt cagcccaggc cagtttcctg cttgagaaag    5040
cccgggaggg ggtgcgggac aggcccgggc cccccacgca aaggcagttt cgcaatgtcc    5100
ctgcgctgac tgaaatgtca ccaggcacac ggcttgaatt tctcccccag acctggcagg    5160
ggcggggtg ggggcaccgg gctgctggga tcttggcccc tgaacctccc ccggccctgc     5220
ggccagggag ggtttaggct gagtgacagc ccacggaaac ctggacccga catgtctgtg    5280
tgtccatgtg tgtctgtgtg tgcgtccacc tatgcgtctg cgtgtgtgtc catgtgtgtc    5340
cacatatctg tgtccacgtg tctgtgtcca cgtgtctgtg tccacgtgtg tgtccacgtg    5400
tgtccatgtg tctatgagtc cttgtgtgca tctgtgtgcc cgtgtgtctg tgtgtctgtc    5460
ccctgcagtc cccgtggacc tgtgtggtct ctggtgtgca gccctagccg cggcccgtcc    5520
caggctgagt gtccccaggg tgcagcacag ctgtgacgag ggtgtgggtc ccgctggccg    5580
tgtcgctggg ctgtgggccc tatcctcttt gtggctgctc tgcaaggcct gatggctttt    5640
gtgtggcctg gccgttcggg tccatgcccc tggaagagc aacgtctgag ctagctccac     5700
gcgtgggtcc atctcggccc aggtttaatg agccactttc aggcagggat tgcacaggag    5760
gcagggtggg aagtggctct gctcagaccc ctgaacaggg tctggagatt ctccaagggc    5820
acaaaagaac ggacgatgcc cctggggtca gcgacaatgc tccctgagaa atcttggcac    5880
acagggctgg gcctgcgagg tggcccctcg ccccacccca gcctcctgga ggacaaccgt    5940
cgccctgctc ccagagctgg ggggcgccac acgtggggca cagggagcat gggcccgatt    6000
ccaggcctgg gctccctctc gtgtccagga tctccccgtg tcttgtctca caagcccct    6060
gacttggagg ccccagggtg acccctttaaa ggggaacag aaggttctag aaggagcgtg    6120
gccagctttg gcttccctag ggctgtggtg accacactgg gccacggccc aggccacccc    6180
acccgcctcc ttcccctggg ccccctccct tcccgcacc tctccctggc ctgcacctgg     6240
tgacacggct ggctcccagc cagggctgag ggggaccagc ggggccccctt cctggaagcc    6300
cacctgcagg ccggccttgct gggaaggggc ctgctcctcg ccggcccac ccgcccgggg     6360
ccgtttcctg gaagcggtca ctggatattt tgttccttgt cagcgccgag cttgcataaa    6420
gcagacactg agctccttgt cctccgggag cacgcgctcc atcaccgaac acctggccgg    6480
acacaggcgg gcagccgggc ctgggggagc agcgcgggcc tggggccgga ccagcaaacg    6540
atcacggcgc cgagcgcagg gcccgcgccg cttctgcagg ccgcccccac gtgcccaggc    6600
ccagcggtgc ccatcctgca ggctgggagg aggctgtggg cgcagagctg agaaggggc     6660
agaggcactg ggggggaca gccgtgttcc cacactttgc agaaaccttg gccggcctgg     6720
atgtcttgct gggagagctg ggggagggga cagggcagga agccggtccc cccgagcggg    6780
gtaggaagag gcctcggccc tggaggagg aggaggggag ggcagtgaga tggaaagagc     6840
accagggct cgaggcttct ttctggaaca aggactagaa ggaggaggcc gggcagctgc     6900
ttgggatgct tggaacaggc cggccccagt gctgacaggg acgtgacctg ggggccggtc    6960
ccgggcccag gcgggctggg agggcgcctg gtgggtcagc gccactcaga gccctggcag    7020
caggggggcct gggcacggct gcaggacaga gctcaggaca cagatggggg cgaggactga    7080
gtggggcacc acagatgctc ccaggaggtg gccaaggagt ggccttggga tcccaggatg    7140
gccctggtcc cagaagatgc ggcagcccaa gggaccaggc cagggccgca ggggccaca     7200
atctgagcag ggctcaggcc cagggcagag gcccctccc acccagccct ccctgggccc     7260
```

```
gcctctccgt gcaggcagtg ggctcagatg gggcagacat gagaccaggt ccagggagaa    7320
gcggggcccc ttggcttcat tcaggtggct ttcagaccgc gccccgtgcg tggcaaggcc    7380
cacagcgctc aggagcacac agaccccccac acgggctcc cccaggttgg gcggtgacat    7440
cagccctgtg tcaacagcag gagctggcag ctccccaccg gggcttaggg agcggggacc    7500
ctgagccacc ctgccaccgc cccaccccac cgtggcccac acgagggccc gctgctctgg    7560
gtctggggcc aaggcccccc aggcgcctgg cactgtctgc ccctcccgct ggctctccgt    7620
ctccagtgtc cccgcagag agcatggggc cacaggcctg aatgccaccc tcttcctccc    7680
tctgaggggg gcctgaggtt ttgggggttc acagagtggc ctccggggtg gtccaggcc    7740
cagcgaggca aagcggaccc cagggagtcc cgcggaatgt gggacagccc ccccgtagat    7800
ctcgggggg ccaagctctg gttgacctcc atcctgggc tgtgggcctt tggtcagtgg    7860
ggagggtcat gacacccagc ccaccagctg gtgacagccc tggacgtgcc ggctcagggc    7920
tggcctgccc ctgcagcctt gaaccctgt tctctgggag tgggggcgca ggggcgccg    7980
gggcagggtg agagacgaga gcctctcttc ccagaacttc tgcctgcgat gaggacccag    8040
caggggcctc tcctcaccag agggcctctg ccggctgcag ggcccagag aggcccagag    8100
gctggaggcc gggccttggg aagaggccgg acttccagaa accagctgcc cgctccgcag    8160
cacccagcgc ccacttggga gggggcgcg ccccgtgcc ccgcccgggt ccactgctgg    8220
ggccgccaca ataaagtttg tccctgctgg ttactgtccg tgtctgagag gttctggag    8280
cctgccaca atgggcgtca ggatgcggct gggagggagc ctcgcgagtc agagtgtgct    8340
ggtctcggac aggccccggc gccccccagcc cgtgctctgt ggacagatgg gtgggtgggt    8400
gggtgtcgga gggggttgga gagggtgggc gggacgaggg gcttcctgca ctctgtccca    8460
gggaagcggg gaccaaggag gggacagccc ccggtcacca ggagggtcct gtccctctca    8520
cccccccggga caggtgagct ccccggagcc gcccttctgg gacaggaccc cacggccagg    8580
ccacggcccc cccacccccg tggtccctcc gtcccacggc cggcctgggg ggccacgggc    8640
ccagggcccc cgctcccccgt tggccctccg agggtgaacg acctcgcctg ggacgtgggg    8700
cagagggcag gcgccaagag tgaccccctg ggacacgtgg ctgtttgcag ttctggaggc    8760
agccgagata aagcggctgt tttcccagtg ggctcagggc cagagggggg cgaggggcag    8820
ccccagtcaa ggccgggccg ctgcctcggg ctcccctctg tgcggaggga ggggccggt    8880
tgcacagcag cccctgcccg ccgcccgccc gccggcgcag gcaccgtggg acccggcctg    8940
gtgcccctcc cccgcccctg ctcaggggcc agccctctct ggttcccagg acgccccgc    9000
cccgcaggcg gccagagagt cccagagtgt tagcctccca cgtgtgggat cctgtcatat    9060
gcgacagctt aactcaggcc gaatttcatg ggtcctggat ttgggtgggc acggcccctg    9120
cacagcgggg ctggaagcct aaggcggtgg gcgtgggggt gagaggcccg cagacaacag    9180
gagggaggct gggacacttc aagggttgac atgctatgcc tgtcacggat aaatgc         9236
```

<210> SEQ ID NO 120
<211> LENGTH: 5349
<212> TYPE: DNA
<213> ORGANISM: Sus scrofa

<400> SEQUENCE: 120

```
agatgtgtat aagagacagg ggctgggtgg gaaggacaga gggtggggcc ggaggaaatg      60
ggatgcagag cccaccgtgc acgctctgct ggcctttgag cctcgctgag tcgcaagaag     120
ccctcgggcc tggaaacaga cccccggccc ccacccccac cccggccccc ggattacccc     180
```

-continued

```
ggcatggctg gagggcccga gaagccaccc aggcttcccg tgccgagctg ggtgctgggc      240
ccagccgagc gggcttgacg ccacgcttag ccctccccag ggagcccagg gtcggaagga      300
agaggccggc cggagggccg tggccgctca ggctggaggg ggcccccggg tcaggatggg      360
ccccagacgt ccccgctccc cggccatccg tcacggagct gtcacccagg aacgtgctcc      420
agacgtgctt tcctgccgcc gaggcccccga gcaggctcca ggcgccccca ccccgaacg      480 cccacgcaca ccctcggtct gcgaacaccc tgccgtcatc cggtggcccc ggttcccgcc      540
gcccgcgcca tccgggtgcc ccttcctccc tgggtcgggg gccatgccct cagcgggcac      600
gcaggcctgt gcaggtctgt tctgactctt ccccaaagac gcaggccggc tgcgggcgcc      660
ccgacctcgt ctgaggcccg tttgtgctca ctggctgtct cagaaagggg tgcccacggg      720
aagcgcgtgt tccttgggcc gcaaggcaag ggagcccacc ccaaggtggc tgagggcaaa      780
tggcccaggg cctctaagga gtccctgggg gccgggccgg cctgcagctt gaggaggaga      840
gccctggctc tgctcccccg ggcaggtgag cccacggcag ggggctcccc agcagccttg      900
gcaggaagca gtgaggaagg ggtgaggatg aaggcaaggg ggcctgcggg gacttgggca      960
aagcccctga agaactgagt tcctcggaaa ggccggagcc ctcagccgag cctcggcctc     1020
cgagcgatgg aggcggccca cctgcggccc cagggtgcag ctgtgcatcc gtcccctcg     1080 ggcctccccc tgccccccg ccaccacac tctcccctt ttgcctttga tcacttgagt      1140
gcgacagctt gtgcgcctg agccccagag accgctgccc cctgccgcc agccccacgg      1200 gagcgtccac ctgggcctgg cctgggcact catccctccc ggatgaggcc tttctagcct     1260
gggccgcccc gggagcggca gaccccagccc ctcgccccc tccccagtg aaggtgctgc      1320 ctggtggtct ggggaagccc ctggaacagg gggcgcaggt cccacacggg tgctctggcc     1380
tccagctgcc agggagggcc gcgctcaggc cagggtcccc tccaccagaa ccgccagggc     1440
cctggggaaa acctgtctgt gctaacaggg ccgctccccg ggactccacg gagaggtgcg     1500 agggaccccct gagcacccac cgccactaag gggcccagcc agctcgcggg tgcaggcagc     1560 cggctggggcg ctcacatgca tactgctctc tggctttgtg tgtgcgcctg ggttggggtg     1620
agcggaggtg cccgaaggcg gaagagccca ccctccactc ggggacctat ttcagcaaga     1680
agacggatgg gactgccggg catggacaaa ggaacaggat gaaccttctg gaacgcacaa     1740
ggcttccacg gctgaccggt cataggaagg cgcgtctcta ggccaatcca ccgtccaccg     1800
tccattcccc agccctcgag aggggggcagg atggaccgct gcagcgtgag agagctctgg     1860
ggcgctccca cagggcaaag tcccagggca ctgacctcag agcccaacca ggccaccggg     1920
gctgggccca ccagggagcc ggggccaggg tcagggtcag ggcccagagt gcgggaaagg     1980
gtggcgtgtt gcttggggcg gcgggcgcgc agacggcccc tcgcaccccc cgacagccct     2040
ggagctgagt gaagcccgcg ggtcaccttg gctggggttg gggtctcctg cgaccggcac     2100
cccagctcag gtcatccttg ctgtaccgca gaggggcagg ggttctgagc agggacaggg     2160
tgggccgcgc aggaagcccc cttctctctg aggctgcccc ggcctggag cctctctggg      2220 gcatgccacc cctctcacag acgcctccca ggagccccca ctttcctgct gcgtggtgag     2280
ggtgtctctc acccgattcc tggccctgc aggtcgagtg agtccctgct aagcctgggg      2340
ttggagcagg tgcagggcat caccacacag cagcagaggc tgtgggggcc cctgagaggc     2400
gctcccaggt accctcctca ggggctgag cccggggttg accgggacc tcgcctgccc      2460 caaagccggc gccctcctcc cgcccgcccg accagggcca gagaagcagg tgtggggcgg     2520
```

```
cacaaaccca agtcagcttc cagatcctgc tggggccgcg ttgaaactcg aagcccccag    2580
gctgggaggt ctagacaccc ctgcccagac cgacagcctg ggcctggctc acagctgcct    2640
gggggcccag gggtgcacct gccctgtggg tggggtcag agggcaggga accctcggga     2700
aggtccccca gggtcaaggt tgggcctaag ctccggtgac ctctgggaag tctgggctg     2760 ggttttgttc ccagaggaga gagggccagt agcctcagag gggctgtggc acggtgggaa    2820
ggccccaggt gaccccagag cgtgcgaagc aagcccccctt gactgcaaag cgcaaagggc    2880
agaggtgggg tgggagcctc gacccccga gcccaggtac acaggggaa gggcgaggga      2940 tccggcaggg gccacacccg ccaccccagg cagcccacaa agcctttggg cccggagccc    3000
cagatgggcc cagcccagct ctgggaacag tcttcccaga attccccagc tctgggtacc    3060
aacagggctg cccggccccc agagccctcg ggcgggagc ccttcccag ggggatctcc      3120 taagtggcaa ggcctgttgg gaggggctgg tgagaggcca ctctggcggg aagaccccca    3180
gccacctgga gccctagcc actgcctgct gcggctccct agggatccag gccatcaga     3240 gaagctccag cgacactgtt tattttcaaa tgacactttt taagaaaaac agcctcaccc    3300
aaatgcttgg ccctgagtct ggaatgtgca gacagacagc tgcccctccc cagagcctgc    3360
acggccctcc gggtggggga ggagcagggg gcaccctgg gaccgggccg caggctgtca     3420
gggcacggaa cgtgtctctg ggccctgtcc tcaattcccg gtgcccagtg gccccaactt    3480
cccagcagac ccagcagggc cccagcttgt cttggcctgg ccgctggtcc tgtcacccca    3540
ggcctggagt tctggaagat tctgctcctg ctcccgtgtg cacataccac tccccggggc    3600
agccctgcac ttctgttcct gctgggctcc ctgcctgcat ccgtgaggcc tgcagcccgc    3660
ctgatcttcc aggtcctcct ccgagccccc gcctccagga agcccccag gagagctcag    3720 gagggtcggc tccctgcgcg cagctgtcag acccctgggc ccaccccgcc ggctgctagg    3780
gtccaggttc cccacaagcc ctcgggcaga ggctgggccg ctgggtccct cggagacaac    3840
tggctccgag gccttgccct agacgggttt ccgggagccc gtccccagcg cacccactg     3900 agttttgaac acttggcgcc accccacac cccaggcggt ggccaggagg cctcctgggc    3960
agcagacagt ccgtgaggtg gccctggggt ggctcctgac ctgggcgctg gcccagccct    4020
gggcacagct ttccagatct tgcctgccgc ttcctccagg ctgcctcggc ccctcccgcc    4080
tgggggtgcc cagcttttcc tggaggatgc ccacccttgc ccatggtcag ggaggggctg    4140
agaaacccca cctcgtgcct ctgcccggcc tatgccaggg gaaccaggtt ccctcccgca    4200
ggaggggacc gagtccctga cagcccactg cagaggggag gaggtgcctg gctctgcccc    4260
cagccccacc aaccccgtgg cttcctgtttt cgcagcccac aaagcactaa aggccgcagg    4320
tcctggaaca tcaaagaccc gggaagtcca ttgtattgaa ttgagtgtaa atgagcctga    4380
ggcctgtggc ttgcgtttcc cacaattacc gctgcccggg aagggctccg gaaccgacac    4440
agcccccagg gcccccttgcc catgtgggga gccaggctg gcctgaagaa gccccataag    4500 gtggaccccca ctttgagccc ccacgagagt gggccaagga ccaggtcagg ggctgcccag    4560
gctctgggcc tcctctgcct gccaggtggg ctccctcggg gccagcctg gcctgcagga    4620 ccttcccacg ctgagttccc cagcctggta tgagcgtagt ggacggcagc catgcccagc    4680
actcaggggc ctgagggaca gagcgggaac tccagccccc gggtcctcgg ccctaggat    4740 ccttctaggt ggggaagccc aagggagcag agggtgaac gcagctgtgt ggggcccag     4800 gctgccgagc agacccctcc tgctccactc ctcggccgag tgggcgccga gatgccgggg    4860
cagtgccatt tccaggcgc caccggaggc tcccagaggg agtgaggcac gagctgggag     4920
```

```
ggagggcggg ggggctgggg aggcagagag cggaggccgg aggccggtga ggaggcccgg    4980 aggggggcctg gagtcaatga cccagggatt atcgtgctgg gtctttgcaa agttggctga    5040
gcaaacgccg gagccaaggg tcagggagac gggactggcg gggccccgcg gccccctttc    5100 cccttttctgg aaaaagcctg tttcccaggt caaaatccag ctcatgatcc gccccctttg    5160
ggactgatgt tcagaggccc agtggtccca gcacctctgt ccaccgcccc cccacgctc     5220 ccggggccgc caacccctgt gggctgcgag gtgcgggcac ctctcccttc gaagcaaagc    5280
cctgccctgc gtgggcagcg tgatttcctg cttctctggg gctgcacttt gactggggtg    5340
gggggggtgg                                                           5349
```

<210> SEQ ID NO 121
<211> LENGTH: 1593
<212> TYPE: DNA
<213> ORGANISM: Sus scrofa
<220> FEATURE:
<221> NAME/KEY: misc_feature
<222> LOCATION: (1551)..(1551)
<223> OTHER INFORMATION: n is a, c, g, or t

<400> SEQUENCE: 121

```
agcccctcag cccctccgag cagctgctgg gctcagcggg ctcgccccccc gatgtgcggc     60 cctccataat caatcatgga gggcggggcc cgggggggggc gggccgacct gtcagccagc    120
tccaagggca gggacagctg ctgttccgga gggttcccag gggccagccc caccagacag    180
cggcctcggc ccccccttccc cgaggggcac ccccacggag ggcccagacc ggagggactc    240
ggggcccaga ggccagggca agagtgaagg cagcgccggt gggagcggcg gtcagcgggg    300
tccaggcttc agttcccaag gagccccatg ccctgagccc gcactgagcc ctgtgcagcc    360
tgtgggtgcc gccgaggccc gccacccccgc cccccaccag cctggggtcg aaggagggag    420
ggggtggcct gacggatggt aacagctgct ccccccacct cgccggcgtg gacagggctc    480
gcttctcctg cccgagcccc cggctgcccc atccgtcacg gcccacccag gactgtgcgt    540
ccagcctccc tccctcctaa tcccccccgca ttttccgaat tctcgggcca ctgctgcttc    600
ctcctcaaat tcctggcccc cctcgcccca tccccgccat gggaaagggc cgcgatgcca    660
ggacacttgc tcgtctcggc cgggcggggg gaggagcagc tggctgggcc cggcagctgt    720
gaggtgcggg ggtgccaggg agaagggccc agattagggg gcgtcatggg aaagctggga    780
gggaacgcta cccagagccc ctcctgccgc agcctgtgct gctccctctc cgcatttctg    840
gcctctgagt gctccctgga gggaagggac cactgtgtcc tgccggcctc tggctctgcc    900
aggaatgtcc atctgtccgg gccgggttac ctggctcaga gcgtgggtac cagctcatcc    960
agccctgacg cctgctctcg ggaacagtgg atgggccagg cgccccgtc acaccccgca    1020 gctgggctcc acagacgggc ccgggatggc acggaggtg gggggcggcc ccagggcgag   1080
gctccctcct ggaagggcta gagtgtgggc tgcgcggaga gggaggccgg acggccaggc   1140
caggtgcagc ccggggcagg tgctggtggg ggctgtgacc cacgtgtgca gctcaagggt    1200
ccaggagccc cagggacaga gcctcaggga cagaccctca gagccacagc aggaagcctg    1260
gtggcagtag ctggcggggc cgtgggtgc tcggccctgc agacagaggc agaggcaggc    1320
tccctgctga tgacaggggc tttctctgtc cctgggggg cggaggggc ccgaccatgg    1380 accccgggcc tcctctcgca cgattcccag gccagcctgg tctcaggcag tccaaggttg    1440
cacaatggtc tccatcgtcc agagttgcag agccagcact ctcccactgg acggcggccc    1500
```

```
ggggtgggct gcaccgccgc tcagggctca gggccgcggc cggccagccc nccgcaggcc    1560
ttgaccctgt ctcttataca catctcaacc ctg                                 1593

<210> SEQ ID NO 122
<211> LENGTH: 831
<212> TYPE: DNA
<213> ORGANISM: Sus scrofa

<400> SEQUENCE: 122
tgagatgtgt ataagagaca ggccttgacc ctgggcctgg ctcagctgcg cgccctcctc      60
cttgcagctc cgcctcgacc ccatccatca gccatttttcc tacccttcct gtaataaaaa    120
acccgaagcg gcgtggcccc gtgtccgctg gggtgactgc ggcctgcctg ctggtggctc    180
ccacctgggc ccggccccct gaaaacacac accccggcgat ggcttgcccg gggccctggt    240
ggaggggcgg ggggcctcgc ctgcctcttg tctgaaattt tcggtccccac atgccccgac    300 tcctctcccg gcccaccctg caggcccggc cggtgccccg gccactttcc cgaaggacgg    360
actcagcatt tcccagggca cctgctgatg gtgcccagac cccgggggcc ttcccgccgg    420
gcgcggcccc acgtcgcccc tccagtggcc acagcgggcc tgggccaagg ctgggagttc    480
tgcacgggcc tgggggagga aggcggggga gggggacag tctcctggcg ggacgaggg     540 tgggggcagc aggtggggag ttcccacagc cggggcagcg ggacgccgct tggctgccct    600
gggtctcagc cggggacagt gccccaccagg agagagacgg cagacagtac agcccacccg    660 tttttatatcc tctcaggcgg tctgtgcttt attggggtaa atatgcagga catagaaact    720
ctgccactgg acccccttggc cggggggacac agcagcggca ttgcatgctt tctgggtgca    780
gcgcagccag caccaccggc cagagcaccc catcttcccg atcaaccgga c              831

<210> SEQ ID NO 123
<211> LENGTH: 4636
<212> TYPE: DNA
<213> ORGANISM: Sus scrofa

<400> SEQUENCE: 123
ctctgggcta gcaccgtggg ggctttgcca gagtggaact gaactgggtc caccccggag      60
cccagagggc ggtgaatggg aggcagagcc catcctggga atggaccaga agaaagggag    120 cggggggtggg ggaaggggca tcagatcctg gtccttcctt gtcgcctgcg gtccctctgc    180
caccactccc cgaagctgat ctggagcaca cgcgtcgtta aagccgccat cgaggcccca    240
cttctgacag acggaagggg gcagagtgcc ttcctcaccg gcctcgccct gggaaggccc    300
ctccctgcag cccaggaagc cagcagcagg tgacagagcc aggggcccag ggccccaggg    360
acgggctcgc gcgcccgagc cggggggtccc ttggcgtccc catcctctcg tcctggagcc    420
ctcctgggtg accacaggaa tgtgcaaggc ggcagccggg tggcggccgg gaggcgggtg    480
ggaggcgggc ggggtggcct cttcacgggc gggcctgaga gatgggcgcc cgtccggccc    540
tggcgtcatc gtctccgcgt ctctacccac tgagcaaaga cacacgaaat gaagctcgaa    600
cgagcacagc caaagaacgg ccgtttctgt cctttcttct taatccccttt ggcttagggt    660 ttcccggcct ggacagcctg cccaagggca catgggcatc cgtccgggga cattcaggca    720
gtgaccaatc ccaggccacc caggctgtgc cctgcgtcgt gggccatttc ccagccggcc    780
agagatggag cagccactgc gggtccccga gtctcggtga cagtcaagg atggacctt     840 ggatggagac cggcgtgcgg ccatgtccgt gggtgaagga ggcgtgcagg ccgtgctggg    900
ggacatggtt gctgtcccct cggccaaacc atgaaaagca gccctctccc ccaaccccca    960
```

```
gcaccaaccc ggagaccacc ctcggccgga gcccagcacg gccaccgtca cgtctcggtc    1020
gtccagcttg ggacaggtca gttcccagat gtccaggctg gagctggtcc ttgaagatcc    1080 tagggggtcca gcccagcaca ggagggccag gtgagagccc cctgtggttc taaggatgca   1140
accaggggcc ggcggggtgc ctgccctaga gggggtaact cggccccctg ggaccagtc    1200 acccccaggag gtccccagag cccagctcgg agggccacag gtgcccagag tcccacctgg   1260
ggaaggctgc ccctcctgcc agccccgag ccgggcccct ggcgcccgcg tccagccgcg     1320
accccgggga gatattcacc ccctgccccc gtgaatcagg aggccccgag cccatgtttt    1380
cagtcctttt cctcccatcc cagcccccca ggagaagagg tgctgaactg ggtcccctgg    1440
aggctcctga gccccagaac agtgccctct gagcagacgg gcactctcag accagctcac    1500
gctggacaag tcagctcctg cctgccgcct gatgggccct gggagaagc agacatggtg     1560 aggaaaaggc cctgtgcccc ttcaccctaa ttccccagcc ccaagtccca ctgggttgcc    1620
agcttcaacc taagcaaata attcgtgccc tctaaacaaa cgcgcgggaa tcccacctgc    1680
ccttcccccg cccgcccccc cacccctggc cttgacctcc aaaagcactt gaggggctt     1740 tctccagaca ccctccaacc ccgaccccat gaagaagggg tgatggggct gttacccccaa   1800 caagcaagag aacgaagccc agagaggagt tggcgtggac agcaggggtc aggcccctt     1860 gccccgaggg cagggctggt gccacctggg tcaggcggca ggccctggaa aagcaccgga    1920
aatgagcaca cctgggtctc tagaaggttc ttccagacct ctgggggctg agtcatttca    1980
acactcctgg gccgggcagg gcttcttctt ggccccgagg acaaggtcc ccttcgtccg     2040 gggggtacgg cccctggacc cctgtccccc gcacccacc ctccgcctgg tgagggccgc     2100
ggccagctct ggacacagat ccctcagagc cccttctccc tccctgctcc ctcgtcttcc    2160
caagatgccc cggcctccag gtggggcagc caggcggcag aatgtggtcc aggcctctcg    2220
gccccaccca caccccctg ctctgccctg acagcctcca agacgcaggc acgtcgctgc     2280
gttctgcgtc ctgtctcctc atggcacaaa acggtgcccg cctagcttcc cccagagaag    2340
ggagatcgtg ctccccggac ggaccctgct ctgcctgtcc tcccgcccgg ccttcagggc    2400
ctctccccaa gggtggccgc gaggaggccc tcgcctccgg ccacgggggc tccatcctcc    2460
cgagcccgac aggcctccgc ctggtggtcc gacctcttcc ccaaggcccc gcccatcctc    2520
ctcgcgctcc cccaaaccct gcctcttttcc ccagcgccct tgtccccacg gaagaccctc   2580
cacccgtgcc attacacgct ctcgcccac cctcccagcc accccccctt ccccatcctc     2640
ctggaagctc ccacttcctt cccgtctccc acggcagcag agggtcagca gctcaggggt    2700 cctggggcc tggagatggc ctgccgggg gtctcgctga ccgcctccta cggaagctgt      2760 gccgggggt gggggtgtct ctgcccgaac ggctggagga cgagccacat cccagggcag    2820
ccggaacctg cgtcctggtc tgagacgag aggctgggtg caggtggctg aggggcctgc    2880
acacagcttg gcctggggtc ccctaggtga caacactggc tgaacactca ttgctgctcc    2940
ccttccaggg tgaccctggg gtccccgtgt ggccctcagg gcacacgggg gccccaccag    3000
gcctcacaga accccagtgg gactgcaccc agggcccaca gaagtgcggg ggcactgggg   3060
gtccagaaac aacccacaa ccaggccaag gtggccaagg ccttactcga gcggggctgc     3120
ccgtcccaag agactctggc cagtcgtccg gatccagctt cccggggccg ggccgccgc     3180 tgggctccag gcggttctgg ggggccctcc ccgggggtt cgccctccgc tctcagcagc    3240
aggaagagga gcgcggccag cggatgggga gaagagggcg ccctggccat cttgctcccc   3300
```

```
ctgggacttg aggagggtct cgggccgggc aggcgggacc gggagccaca gagaccctgg   3360
aggaggcagc atggcgggga ggtgaccggg gaagagggcc gtgtcccagg ctcacagccc   3420
ggcctggccg cccggccctc gggaggcgtg ccgctgaccg cctggccggg aggtttgctg   3480
cgtgtggggt ttgcagaaag tgctgagctg ctgagcccac aggccaggct cagaggggac   3540
aggaaggagg ttgctgccca gcctcgggca ctgctgaccc atctcccgtt tccagggcac   3600
cagagccacc taatctgccg gctctgtgcc agggacagg cttgcctgat ctctcaaggc   3660
cgggcgctcc gccttccctg ggagagggtt aaacatccag ccccagccag catctcgggc   3720
aggttcctgg ctcccccgc tcgtgcctcc tctgagaccc tggtcggcac acctttccct   3780
tgagaggagg aggaggagga aagcggatgg aaccagtgac cctgcagccc ctgagggcac   3840
cttcccacgt gccccgccc gccccgcgtc ctccgccccc agttctcacg gccccagtcc   3900
tgatggaggg agggcgacct ccgggctccc tggctcccgc cggctccgga agacagggcc   3960
gctcggctgg ggctgcaggg agggcccga cgcaggag agcagcccgg aggcaaaccc   4020
cgcgggtctt ccagaaggag gcctggcagg gggaggggg tgccaccact gctgtccctc   4080
tcgtgccaca gtggagggtg tgggtgggca gtgccggggt gggaagtgca gaaagaccct   4140
ggaccgtggg gctgggccgc cacggggag cggggtctgt cagggaccct gggggaggga   4200
ggcgaagggc tggggcagag gccggatcac ttccagattt gctgtgggac caagggccgg   4260
acctcggggt gacttctttt gtgtgctggc cacagggggg ccccggcgag gtcacacgga   4320
agggggcttc ggacctggcc taacaagccc actcccgagg aagatgcaag gggaggcaga   4380
cggaagggcc gaaggggcg atcggggac accgcggcag ggccggggca gagaagggag   4440
gcagagggca gagaagggag gcagagggca gagaagggag gcagagggc cacatgcttg   4500 gagggccagg gaggagcggg aacggcgtcc ggcgtccagc gccgaatcag gcccgtcagg   4560
cggagggtgc gtggacctgc ctggccttca cgagcacagt cagcaggctg tctcttatac   4620
acatctcaac catcat                                                  4636
```

```
<210> SEQ ID NO 124
<211> LENGTH: 482
<212> TYPE: DNA
<213> ORGANISM: Sus scrofa

<400> SEQUENCE: 124
```

```
agcaatgggg ccgtgaccta aggaggcagg cccaggtcag tggggtgacc tctcgtggcc     60
ccgatgtttg gaaatcccca aatcaaaatg acccatccga caagcttgca tgcctgcagg    120
tcgactctag aggatccccg ggtaccgagc tcgaattcgc cctatagtga gtcgtattac    180
aattcactgg ccgtcgtttt acaacgtcgt gactgggaaa accctggcgt tacccaactt    240
aatcgccttg cagcacatcc cccttt cgcc agctggcgta atagcgaaga ggcccgcacc    300
gatcgccctt cccaacagtt gcgcagcctg aatggcgaat ggcgcctgat gcggtatttt    360
ctccttacgc atctgtgcgg tatttcacac cgcatatggt gcactctcag tacaatctgc    420
tctgatgccg catagttaag ccagccccga cacccgccaa cacccgctga cgcgaacccc    480
tt                                                                    482
```

```
<210> SEQ ID NO 125
<211> LENGTH: 17
<212> TYPE: DNA
<213> ORGANISM: Sus scrofa

<400> SEQUENCE: 125
```

```
ggatccagcc agcagcc                                                    17

<210> SEQ ID NO 126
<211> LENGTH: 17
<212> TYPE: DNA
<213> ORGANISM: Sus scrofa

<400> SEQUENCE: 126
ggatccagcc tgcagcc                                                    17

<210> SEQ ID NO 127
<211> LENGTH: 17
<212> TYPE: DNA
<213> ORGANISM: Sus scrofa

<400> SEQUENCE: 127
acaaccccct cccacag                                                    17

<210> SEQ ID NO 128
<211> LENGTH: 18
<212> TYPE: DNA
<213> ORGANISM: Sus scrofa

<400> SEQUENCE: 128
acaacccccc tcccacag                                                   18

<210> SEQ ID NO 129
<211> LENGTH: 17
<212> TYPE: DNA
<213> ORGANISM: Sus scrofa

<400> SEQUENCE: 129
tgcggagggg agacctg                                                    17

<210> SEQ ID NO 130
<211> LENGTH: 17
<212> TYPE: DNA
<213> ORGANISM: Sus scrofa

<400> SEQUENCE: 130
tgcggagggg ggacctg                                                    17

<210> SEQ ID NO 131
<211> LENGTH: 20
<212> TYPE: DNA
<213> ORGANISM: Sus scrofa

<400> SEQUENCE: 131
aggtcaaggc caggtcgagg                                                 20

<210> SEQ ID NO 132
<211> LENGTH: 9
<212> TYPE: DNA
<213> ORGANISM: Sus scrofa

<400> SEQUENCE: 132 aggtcgagg                                                              9

<210> SEQ ID NO 133
<211> LENGTH: 15
<212> TYPE: DNA
<213> ORGANISM: Sus scrofa
```

```
<400> SEQUENCE: 133 cccccccac gccgc                                                 15

<210> SEQ ID NO 134
<211> LENGTH: 15
<212> TYPE: DNA
<213> ORGANISM: Sus scrofa

<400> SEQUENCE: 134 ccccccccc gccgc                                                 15

<210> SEQ ID NO 135
<211> LENGTH: 15
<212> TYPE: DNA
<213> ORGANISM: Sus scrofa

<400> SEQUENCE: 135 cccacccac gccgc                                                 15

<210> SEQ ID NO 136
<211> LENGTH: 15
<212> TYPE: DNA
<213> ORGANISM: Sus scrofa

<400> SEQUENCE: 136 cccaccccc gccgc                                                 15

<210> SEQ ID NO 137
<211> LENGTH: 15
<212> TYPE: DNA
<213> ORGANISM: Sus scrofa

<400> SEQUENCE: 137
cgccgcagca ggccg                                                15

<210> SEQ ID NO 138
<211> LENGTH: 15
<212> TYPE: DNA
<213> ORGANISM: Sus scrofa

<400> SEQUENCE: 138
cgccgcagca agccg                                                15

<210> SEQ ID NO 139
<211> LENGTH: 15
<212> TYPE: DNA
<213> ORGANISM: Sus scrofa

<400> SEQUENCE: 139
gcttatgggg ccggg                                                15

<210> SEQ ID NO 140
<211> LENGTH: 15
<212> TYPE: DNA
<213> ORGANISM: Sus scrofa

<400> SEQUENCE: 140
gcttatggag ccggg                                                15

<210> SEQ ID NO 141
<211> LENGTH: 15
<212> TYPE: DNA
<213> ORGANISM: Sus scrofa
```

```
<400> SEQUENCE: 141
cacggcttcg gagca                                                      15

<210> SEQ ID NO 142
<211> LENGTH: 15
<212> TYPE: DNA
<213> ORGANISM: Sus scrofa

<400> SEQUENCE: 142
cacggcttca gagca                                                      15

<210> SEQ ID NO 143
<211> LENGTH: 15
<212> TYPE: DNA
<213> ORGANISM: Sus scrofa

<400> SEQUENCE: 143
cacggcctcg gagca                                                      15

<210> SEQ ID NO 144
<211> LENGTH: 15
<212> TYPE: DNA
<213> ORGANISM: Sus scrofa

<400> SEQUENCE: 144
cacggcctca gagca                                                      15

<210> SEQ ID NO 145
<211> LENGTH: 14
<212> TYPE: DNA
<213> ORGANISM: Sus scrofa

<400> SEQUENCE: 145
gtctgcagga ggtg                                                       14

<210> SEQ ID NO 146
<211> LENGTH: 15
<212> TYPE: DNA
<213> ORGANISM: Sus scrofa

<400> SEQUENCE: 146
gtctgcgggc aggtg                                                      15

<210> SEQ ID NO 147
<211> LENGTH: 15
<212> TYPE: DNA
<213> ORGANISM: Sus scrofa

<400> SEQUENCE: 147
caagcccggg cggtt                                                      15

<210> SEQ ID NO 148
<211> LENGTH: 15
<212> TYPE: DNA
<213> ORGANISM: Sus scrofa

<400> SEQUENCE: 148
caagcccggt cggtt                                                      15

<210> SEQ ID NO 149
<211> LENGTH: 15
<212> TYPE: DNA
```

```
<213> ORGANISM: Sus scrofa

<400> SEQUENCE: 149
acctcaaggc cccca                                                  15

<210> SEQ ID NO 150
<211> LENGTH: 15
<212> TYPE: DNA
<213> ORGANISM: Sus scrofa

<400> SEQUENCE: 150
acctcgaggc cccca                                                  15

<210> SEQ ID NO 151
<211> LENGTH: 15
<212> TYPE: DNA
<213> ORGANISM: Sus scrofa

<400> SEQUENCE: 151
gccgggccca gccgc                                                  15

<210> SEQ ID NO 152
<211> LENGTH: 15
<212> TYPE: DNA
<213> ORGANISM: Sus scrofa

<400> SEQUENCE: 152
gctgggccca gccgc                                                  15

<210> SEQ ID NO 153
<211> LENGTH: 15
<212> TYPE: DNA
<213> ORGANISM: Sus scrofa

<400> SEQUENCE: 153
accagctgcg ttccc                                                  15

<210> SEQ ID NO 154
<211> LENGTH: 15
<212> TYPE: DNA
<213> ORGANISM: Sus scrofa

<400> SEQUENCE: 154
accagctgtg ttccc                                                  15

<210> SEQ ID NO 155
<211> LENGTH: 15
<212> TYPE: DNA
<213> ORGANISM: Sus scrofa

<400> SEQUENCE: 155
ggccctctgg gcgcc                                                  15

<210> SEQ ID NO 156
<211> LENGTH: 15
<212> TYPE: DNA
<213> ORGANISM: Sus scrofa

<400> SEQUENCE: 156
ggcgctctgg gcgcc                                                  15

<210> SEQ ID NO 157
<211> LENGTH: 15
```

```
<212> TYPE: DNA
<213> ORGANISM: Sus scrofa

<400> SEQUENCE: 157
gggggcgtcc cggga                                                    15

<210> SEQ ID NO 158
<211> LENGTH: 15
<212> TYPE: DNA
<213> ORGANISM: Sus scrofa

<400> SEQUENCE: 158
gggggtgtcc cggga                                                    15

<210> SEQ ID NO 159
<211> LENGTH: 15
<212> TYPE: DNA
<213> ORGANISM: Sus scrofa

<400> SEQUENCE: 159
gcggtcgggg gagtt                                                    15

<210> SEQ ID NO 160
<211> LENGTH: 15
<212> TYPE: DNA
<213> ORGANISM: Sus scrofa

<400> SEQUENCE: 160
gcggttgggg gagtt                                                    15

<210> SEQ ID NO 161
<211> LENGTH: 15
<212> TYPE: DNA
<213> ORGANISM: Sus scrofa

<400> SEQUENCE: 161
cgccccggtc ccgct                                                    15

<210> SEQ ID NO 162
<211> LENGTH: 15
<212> TYPE: DNA
<213> ORGANISM: Sus scrofa

<400> SEQUENCE: 162
cgccctggtc ccgct                                                    15

<210> SEQ ID NO 163
<211> LENGTH: 15
<212> TYPE: DNA
<213> ORGANISM: Sus scrofa

<400> SEQUENCE: 163
tcccgtctgc cggcc                                                    15

<210> SEQ ID NO 164
<211> LENGTH: 15
<212> TYPE: DNA
<213> ORGANISM: Sus scrofa

<400> SEQUENCE: 164
tcccatctgc cggcc                                                    15

<210> SEQ ID NO 165
```

```
<211> LENGTH: 15
<212> TYPE: DNA
<213> ORGANISM: Sus scrofa

<400> SEQUENCE: 165 gatgcccat ccccc                                                     15

<210> SEQ ID NO 166
<211> LENGTH: 15
<212> TYPE: DNA
<213> ORGANISM: Sus scrofa

<400> SEQUENCE: 166 gaagcccat ccccc                                                     15

<210> SEQ ID NO 167
<211> LENGTH: 15
<212> TYPE: DNA
<213> ORGANISM: Sus scrofa

<400> SEQUENCE: 167
ggcggctgct gcggc                                                    15

<210> SEQ ID NO 168
<211> LENGTH: 15
<212> TYPE: DNA
<213> ORGANISM: Sus scrofa

<400> SEQUENCE: 168
ggtggctgct gcggc                                                    15

<210> SEQ ID NO 169
<211> LENGTH: 15
<212> TYPE: DNA
<213> ORGANISM: Sus scrofa

<400> SEQUENCE: 169
tggctgcggt ctggg                                                    15

<210> SEQ ID NO 170
<211> LENGTH: 15
<212> TYPE: DNA
<213> ORGANISM: Sus scrofa

<400> SEQUENCE: 170
tggctgcagt ctggg                                                    15

<210> SEQ ID NO 171
<211> LENGTH: 15
<212> TYPE: DNA
<213> ORGANISM: Sus scrofa

<400> SEQUENCE: 171
gcgcagtgat tggca                                                    15

<210> SEQ ID NO 172
<211> LENGTH: 15
<212> TYPE: DNA
<213> ORGANISM: Sus scrofa

<400> SEQUENCE: 172
gcgcattgat tggca                                                    15
```

```
<210> SEQ ID NO 173
<211> LENGTH: 14
<212> TYPE: DNA
<213> ORGANISM: Sus scrofa

<400> SEQUENCE: 173 cgccccccc cggg                                                          14

<210> SEQ ID NO 174
<211> LENGTH: 14
<212> TYPE: DNA
<213> ORGANISM: Sus scrofa

<400> SEQUENCE: 174 cgccccccc ccgg                                                          14

<210> SEQ ID NO 175
<211> LENGTH: 15
<212> TYPE: DNA
<213> ORGANISM: Sus scrofa

<400> SEQUENCE: 175 cgccccccc ccggg                                                         15

<210> SEQ ID NO 176
<211> LENGTH: 15
<212> TYPE: DNA
<213> ORGANISM: Sus scrofa

<400> SEQUENCE: 176 cgccccccc cccgg                                                         15

<210> SEQ ID NO 177
<211> LENGTH: 15
<212> TYPE: DNA
<213> ORGANISM: Sus scrofa

<400> SEQUENCE: 177
gcagccggct cctgg                                                        15

<210> SEQ ID NO 178
<211> LENGTH: 15
<212> TYPE: DNA
<213> ORGANISM: Sus scrofa

<400> SEQUENCE: 178
gcagccggct cttgg                                                        15

<210> SEQ ID NO 179
<211> LENGTH: 15
<212> TYPE: DNA
<213> ORGANISM: Sus scrofa

<400> SEQUENCE: 179
gttgttgctc tggga                                                        15

<210> SEQ ID NO 180
<211> LENGTH: 15
<212> TYPE: DNA
<213> ORGANISM: Sus scrofa

<400> SEQUENCE: 180
gttgttgttc tggga                                                        15
```

```
<210> SEQ ID NO 181
<211> LENGTH: 22
<212> TYPE: DNA
<213> ORGANISM: Sus scrofa

<400> SEQUENCE: 181
atatatatat atatatatat at                                              22

<210> SEQ ID NO 182
<211> LENGTH: 70
<212> TYPE: DNA
<213> ORGANISM: Sus scrofa

<400> SEQUENCE: 182
gtgtgtgtgt gtgtgtgcac gcgtgtgcgt gtgtacgtgt gtgtgtgtgt gtgtgtgtgt     60
gtgtgtgtgt                                                            70

<210> SEQ ID NO 183
<211> LENGTH: 38
<212> TYPE: DNA
<213> ORGANISM: Sus scrofa

<400> SEQUENCE: 183
cacacacaca cacacacaca cacacacaca cacacaca                             38
```